US012071710B2

(12) United States Patent
Kim et al.

(10) Patent No.: US 12,071,710 B2
(45) Date of Patent: Aug. 27, 2024

(54) ANTIBODY LIBRARY AND ANTIBODY SCREENING METHOD USING SAME

(71) Applicant: MOGAM INSTITUTE FOR BIOMEDICAL RESEARCH, Gyeonggi-do (KR)

(72) Inventors: Dong-Sik Kim, Gyeonggi-do (KR); Mi Jung Lee, Gyeonggi-do (KR); Mi Young Oh, Gyeonggi-do (KR); Hye-Ji Choi, Gyeonggi-do (KR); Gil-Jung Kim, Gyeonggi-do (KR); Shin A Jang, Gyeonggi-do (KR); Ae Rin Yoon, Gyeonggi-do (KR)

(73) Assignee: MOGAM INSTITUTE FOR BIOMEDICAL RESEARCH, Gyeonggi-Do (KR)

( * ) Notice: Subject to any disclaimer, the term of this patent is extended or adjusted under 35 U.S.C. 154(b) by 871 days.

(21) Appl. No.: 17/058,124

(22) PCT Filed: May 31, 2019

(86) PCT No.: PCT/KR2019/006565
§ 371 (c)(1),
(2) Date: May 23, 2021

(87) PCT Pub. No.: WO2019/231276
PCT Pub. Date: Dec. 5, 2019

(65) Prior Publication Data
US 2022/0275360 A1    Sep. 1, 2022

(30) Foreign Application Priority Data

Jun. 1, 2018    (KR) ........................ 10-2018-0063306

(51) Int. Cl.
C40B 40/10    (2006.01)
C07K 16/00    (2006.01)
(Continued)

(52) U.S. Cl.
CPC ............ *C40B 40/10* (2013.01); *C07K 16/005* (2013.01); *C07K 16/28* (2013.01);
(Continued)

(58) Field of Classification Search
None
See application file for complete search history.

(56) References Cited

U.S. PATENT DOCUMENTS 8,921,281 B2    12/2014    Fischer et al.

FOREIGN PATENT DOCUMENTS

| JP | 2001519643 A | 10/2001 |
| JP | 2011507519 A | 3/2011 |

(Continued)

OTHER PUBLICATIONS

Aug. 3, 2022 Japanese Patent Office Action in Corresponding Japanese Patent Application JP2020-567149.

(Continued)

*Primary Examiner* — Christian C Boesen
(74) *Attorney, Agent, or Firm* — HULTQUIST, PLLC; Steven J. Hultquist

(57) ABSTRACT

The present invention relates to a novel antibody library and an antibody-screening method using same. Having a human sequence-derived specific VH or VL scaffold, the antibody library according to the present invention exhibits high thermodynamic stability and enjoys the advantages of allowing high soluble expression as well as reversible folding. In addition, the antibody according to the present invention includes a variety of rationally controlled CDRs so as to exhibit high specificity and high affinity to all antigens and thus can be advantageously used for selecting an adequate candidate antibody against a target antigen.

10 Claims, 4 Drawing Sheets
(4 of 4 Drawing Sheet(s) Filed in Color)
Specification includes a Sequence Listing.

(51) Int. Cl.
*C07K 16/28* (2006.01)
*C12N 15/10* (2006.01)

(52) U.S. Cl.
CPC ...... *C12N 15/1037* (2013.01); *C07K 2317/40* (2013.01); *C07K 2317/55* (2013.01); *C07K 2317/565* (2013.01); *C07K 2317/567* (2013.01); *C07K 2317/94* (2013.01)

(56) References Cited

FOREIGN PATENT DOCUMENTS

| JP | 5947022 | B2 | 7/2016 |
|---|---|---|---|
| KR | 1020070050927 | A | 5/2007 |
| KR | 1020070102587 | A | 10/2007 |
| KR | 1020140015274 | A | 2/2014 |
| KR | 1020150032337 | A | 3/2015 |
| KR | 2020180063306 | B1 | 6/2018 |
| WO | 8801649 | A1 | 3/1988 |
| WO | 8806630 | A1 | 9/1988 |
| WO | 8807085 | A1 | 9/1988 |
| WO | 8807086 | A1 | 9/1988 |
| WO | 8809344 | A1 | 12/1988 |
| WO | 9708320 | A1 | 3/1997 |
| WO | 9920749 | A1 | 4/1999 |
| WO | 200614498 | A2 | 2/2006 |
| WO | 2009036379 | A2 | 3/2009 |
| WO | 2010080463 | A1 | 7/2010 |
| WO | 2013046722 | A1 | 4/2013 |
| WO | 2018009499 | A1 | 1/2018 |

OTHER PUBLICATIONS

English Translation of Aug. 3, 2022 Japanese Patent Office Action in Corresponding Japanese Patent Application JP2020-567149.
Office Action issued in counterpart Australian Patent Application No. 2019279427 on Mar. 15, 2023.
Hifumi, M., et al., "New human enzyme antibody consisting of light chain or heavy chain polypeptides encoded by human germ line genee.g. L22 and Vh1-24, useful for treatment and diagnosis of infectious diseases and cancer", WPI, 2006, vol. 2006, No. 56, Publisher: Thomson.
Tiller, T., et al., "A fully synthetic human Fab antibody library based on fixed VH/VL framework pairings with favorable biophysical properties", "Landes Bioscience", 2013, pp. 445-470, vol. 5, No. 3, Publisher: www.landesbioscience.com.
Zhu, X., et al., "Identification of Internalizing Human Single-Chain Antibodies Targeting Brain Tumor Sphere Cells", "Molecular Cancer Therapeutics", Jun. 29, 2010, pp. 2131-2141, vol. 9, No. 7, Publisher: American Association for Cancer Research.

```
                          SEQUENCE LISTING

<160> NUMBER OF SEQ ID NOS: 134

<210> SEQ ID NO 1
<211> LENGTH: 92
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Xaa Trp Val Arg Gln Ala
            20                  25                  30

Pro Gly Lys Gly Leu Glu Trp Val Xaa Tyr Ala Ala Pro Val Lys Gly
        35                  40                  45

Arg Phe Thr Ile Ser Arg Asp Asp Ser Lys Asn Thr Leu Tyr Leu Gln
    50                  55                  60

Met Asn Ser Leu Lys Thr Glu Asp Thr Ala Val Tyr Tyr Cys Ala Arg
65                  70                  75                  80

Xaa Trp Gly Gln Gly Thr Leu Val Thr Val Ser Ser
                85                  90

<210> SEQ ID NO 2
<211> LENGTH: 26
<212> TYPE: PRT
<213> ORGANISM: Artificial sequence
<220> FEATURE:
<223> OTHER INFORMATION: Synthetic Construct

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly
            20                  25

<210> SEQ ID NO 3
<211> LENGTH: 13
<212> TYPE: PRT
<213> ORGANISM: Artificial sequence
<220> FEATURE:
<223> OTHER INFORMATION: Synthetic Construct

<400> SEQUENCE: 3

Trp Val Arg Gln Ala Pro Gly Lys Gly Leu Glu Trp Val
1               5                   10

<210> SEQ ID NO 4
<211> LENGTH: 39
<212> TYPE: PRT
<213> ORGANISM: Artificial sequence
```

```
<220> FEATURE:
<223> OTHER INFORMATION: Synthetic Construct

<400> SEQUENCE: 4

Tyr Ala Ala Pro Val Lys Gly Arg Phe Thr Ile Ser Arg Asp Asp Ser
1               5                   10                  15

Lys Asn Thr Leu Tyr Leu Gln Met Asn Ser Leu Lys Thr Glu Asp Thr
            20                  25                  30

Ala Val Tyr Tyr Cys Ala Arg
        35

<210> SEQ ID NO 5
<211> LENGTH: 11
<212> TYPE: PRT
<213> ORGANISM: Artificial sequence
<220> FEATURE:
<223> OTHER INFORMATION: Synthetic Construct

<400> SEQUENCE: 5

Trp Gly Gln Gly Thr Leu Val Thr Val Ser Ser
1               5                   10

<210> SEQ ID NO 6
<211> LENGTH: 92
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Xaa Trp Val Arg Gln Ala
            20                  25                  30

Pro Gly Lys Gly Leu Glu Trp Val Xaa Tyr Ala Asp Ser Val Lys Gly
        35                  40                  45

Arg Phe Thr Ile Ser Arg Asp Asn Ser Lys Asn Thr Leu Tyr Leu Gln
    50                  55                  60

Met Asn Ser Leu Arg Ala Glu Asp Thr Ala Val Tyr Tyr Cys Ala Arg
65                  70                  75                  80

Xaa Trp Gly Gln Gly Thr Leu Val Thr Val Ser Ser
                85                  90

<210> SEQ ID NO 7
<211> LENGTH: 26
<212> TYPE: PRT
<213> ORGANISM: Artificial sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly
            20                  25

<210> SEQ ID NO 8
<211> LENGTH: 13
<212> TYPE: PRT
<213> ORGANISM: Artificial sequence
<220> FEATURE:
<223> OTHER INFORMATION: Synthetic Construct

<400> SEQUENCE: 8

Trp Val Arg Gln Ala Pro Gly Lys Gly Leu Glu Trp Val
1               5                  10

<210> SEQ ID NO 9
<211> LENGTH: 39
<212> TYPE: PRT
<213> ORGANISM: Artificial sequence
<220> FEATURE:
<223> OTHER INFORMATION: Synthetic Construct

<400> SEQUENCE: 9

Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
            20                  25                  30

Ala Val Tyr Tyr Cys Ala Arg
        35

<210> SEQ ID NO 10
<211> LENGTH: 11
<212> TYPE: PRT
<213> ORGANISM: Artificial sequence
<220> FEATURE:
<223> OTHER INFORMATION: Synthetic Construct

<400> SEQUENCE: 10

Trp Gly Gln Gly Thr Leu Val Thr Val Ser Ser
1               5                   10

<210> SEQ ID NO 11
<211> LENGTH: 92
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Xaa Trp Val Arg Gln Ala
            20                  25                  30

Pro Gly Gln Gly Leu Glu Trp Met Xaa Tyr Ala Gln Lys Phe Gln Gly
        35                  40                  45
```

Arg Val Thr Ile Thr Ala Asp Glu Ser Thr Ser Thr Ala Tyr Met Glu
            50                  55                  60

Leu Ser Ser Leu Arg Ser Glu Asp Thr Ala Val Tyr Tyr Cys Ala Arg
 65                  70                  75                  80

Xaa Trp Gly Gln Gly Thr Leu Val Thr Val Ser Ser
                85                  90

<210> SEQ ID NO 12
<211> LENGTH: 26
<212> TYPE: PRT
<213> ORGANISM: Artificial sequence
<220> FEATURE:
<223> OTHER INFORMATION: Synthetic Construct

<400> SEQUENCE: 12

Gln Val Gln Leu Val Gln Ser Gly Ala Glu Val Lys Lys Pro Gly Ser
 1               5                  10                  15

Ser Val Lys Val Ser Cys Lys Ala Ser Gly
            20                  25

<210> SEQ ID NO 13
<211> LENGTH: 13
<212> TYPE: PRT
<213> ORGANISM: Artificial sequence
<220> FEATURE:
<223> OTHER INFORMATION: Synthetic Construct

<400> SEQUENCE: 13

Trp Val Arg Gln Ala Pro Gly Gln Gly Leu Glu Trp Met
 1               5                  10

<210> SEQ ID NO 14
<211> LENGTH: 39
<212> TYPE: PRT
<213> ORGANISM: Artificial sequence
<220> FEATURE:
<223> OTHER INFORMATION: Synthetic Construct

<400> SEQUENCE: 14

Tyr Ala Gln Lys Phe Gln Gly Arg Val Thr Ile Thr Ala Asp Glu Ser
 1               5                  10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 15
<211> LENGTH: 11
<212> TYPE: PRT
<213> ORGANISM: Artificial sequence
<220> FEATURE:
<223> OTHER INFORMATION: Synthetic Construct

<400> SEQUENCE: 15

Trp Gly Gln Gly Thr Leu Val Thr Val Ser Ser
 1               5                  10

<210> SEQ ID NO 16
<211> LENGTH: 90
<212> TYPE: PRT
<213> ORGANISM: Artificial sequence
<220> FEATURE:
<223> OTHER INFORMATION: Synthetic Construct
<220> FEATURE:

```
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Xaa Trp Tyr Gln Gln
            20                  25                  30

Lys Pro Gly Lys Ala Pro Lys Leu Leu Ile Tyr Xaa Gly Val Pro Ser
        35                  40                  45

Arg Phe Ser Gly Ser Gly Ser Gly Thr Asp Phe Thr Leu Thr Ile Ser
    50                  55                  60

Ser Leu Gln Pro Glu Asp Phe Ala Thr Tyr Tyr Cys Gln Gln Xaa Thr
65                  70                  75                  80

Phe Gly Gln Gly Thr Lys Val Glu Ile Lys
                85                  90

<210> SEQ ID NO 17
<211> LENGTH: 27
<212> TYPE: PRT
<213> ORGANISM: Artificial sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln
            20                  25

<210> SEQ ID NO 18
<211> LENGTH: 15
<212> TYPE: PRT
<213> ORGANISM: Artificial sequence
<220> FEATURE:
<223> OTHER INFORMATION: Synthetic Construct

<400> SEQUENCE: 18

Trp Tyr Gln Gln Lys Pro Gly Lys Ala Pro Lys Leu Leu Ile Tyr
1               5                   10                  15

<210> SEQ ID NO 19
<211> LENGTH: 34
<212> TYPE: PRT
<213> ORGANISM: Artificial sequence
<220> FEATURE:
<223> OTHER INFORMATION: Synthetic Construct

<400> SEQUENCE: 19

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln
```

```
<210> SEQ ID NO 20
<211> LENGTH: 11
<212> TYPE: PRT
<213> ORGANISM: Artificial sequence
<220> FEATURE:
<223> OTHER INFORMATION: Synthetic Construct

<400> SEQUENCE: 20

Thr Phe Gly Gln Gly Thr Lys Val Glu Ile Lys
1               5                   10

<210> SEQ ID NO 21
<211> LENGTH: 88
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Xaa Trp Tyr Gln Gln
            20                  25                  30

Lys Pro Gly Gln Ala Pro Arg Leu Leu Ile Xaa Ile Pro Asp Arg Phe
        35                  40                  45

Ser Gly Ser Gly Ser Gly Thr Asp Phe Thr Leu Thr Ile Ser Arg Leu
    50                  55                  60

Glu Pro Glu Asp Phe Ala Val Tyr Tyr Cys Gln Gln Xaa Thr Phe Gly
65                  70                  75                  80

Gln Gly Thr Lys Val Glu Ile Lys
                85

<210> SEQ ID NO 22
<211> LENGTH: 27
<212> TYPE: PRT
<213> ORGANISM: Artificial sequence
<220> FEATURE:
<223> OTHER INFORMATION: Synthetic Construct

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln
            20                  25

<210> SEQ ID NO 23
<211> LENGTH: 14
<212> TYPE: PRT
<213> ORGANISM: Artificial sequence
<220> FEATURE:
<223> OTHER INFORMATION: Synthetic Construct

<400> SEQUENCE: 23
```

```
Trp Tyr Gln Gln Lys Pro Gly Gln Ala Pro Arg Leu Leu Ile
1               5                   10
```

<210> SEQ ID NO 24
<211> LENGTH: 33
<212> TYPE: PRT
<213> ORGANISM: Artificial sequence
<220> FEATURE:
<223> OTHER INFORMATION: Synthetic Construct

<400> SEQUENCE: 24

```
Ile Pro Asp Arg Phe Ser Gly Ser Gly Ser Gly Thr Asp Phe Thr Leu
1               5                   10                  15

Thr Ile Ser Arg Leu Glu Pro Glu Asp Phe Ala Val Tyr Tyr Cys Gln
            20                  25                  30

Gln
```

<210> SEQ ID NO 25
<211> LENGTH: 11
<212> TYPE: PRT
<213> ORGANISM: Artificial sequence
<220> FEATURE:
<223> OTHER INFORMATION: Synthetic Construct

<400> SEQUENCE: 25

```
Thr Phe Gly Gln Gly Thr Lys Val Glu Ile Lys
1               5                   10
```

<210> SEQ ID NO 26
<211> LENGTH: 88
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Xaa Trp Tyr Gln Gln
            20                  25                  30

Lys Pro Gly Gln Ala Pro Arg Leu Leu Ile Xaa Ile Pro Asp Arg Phe
        35                  40                  45

Ser Gly Ser Gly Ser Gly Thr Asp Phe Thr Leu Thr Ile Ser Arg Leu
    50                  55                  60

Glu Pro Glu Asp Phe Ala Val Tyr Tyr Cys Gln Gln Xaa Thr Phe Gly
65                  70                  75                  80

Gln Gly Thr Lys Val Glu Ile Lys
                85
```

<210> SEQ ID NO 27
<211> LENGTH: 27
<212> TYPE: PRT
<213> ORGANISM: Artificial sequence

```
<220> FEATURE:
<223> OTHER INFORMATION: Synthetic Construct

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln
            20                  25

<210> SEQ ID NO 28
<211> LENGTH: 14
<212> TYPE: PRT
<213> ORGANISM: Artificial sequence
<220> FEATURE:
<223> OTHER INFORMATION: Synthetic Construct

<400> SEQUENCE: 28

Trp Tyr Gln Gln Lys Pro Gly Gln Ala Pro Arg Leu Leu Ile
1               5                   10

<210> SEQ ID NO 29
<211> LENGTH: 33
<212> TYPE: PRT
<213> ORGANISM: Artificial sequence
<220> FEATURE:
<223> OTHER INFORMATION: Synthetic Construct

<400> SEQUENCE: 29

Ile Pro Asp Arg Phe Ser Gly Ser Gly Ser Gly Thr Asp Phe Thr Leu
1               5                   10                  15

Thr Ile Ser Arg Leu Glu Pro Glu Asp Phe Ala Val Tyr Tyr Cys Gln
            20                  25                  30

Gln

<210> SEQ ID NO 30
<211> LENGTH: 11
<212> TYPE: PRT
<213> ORGANISM: Artificial sequence
<220> FEATURE:
<223> OTHER INFORMATION: Synthetic Construct

<400> SEQUENCE: 30

Thr Phe Gly Gln Gly Thr Lys Val Glu Ile Lys
1               5                   10

<210> SEQ ID NO 31
<211> LENGTH: 86
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid

<400> SEQUENCE: 31

Gln Ser Val Leu Thr Gln Pro Pro Ser Val Ser Ala Ala Pro Gly Gln
1               5                   10                  15
```

```
Lys Val Thr Ile Ser Cys Ser Gly Xaa Trp Tyr Gln Gln Leu Pro Gly
            20                  25                  30

Thr Ala Pro Lys Leu Leu Ile Xaa Arg Pro Ser Gly Ile Pro Asp Arg
            35                  40                  45

Phe Ser Gly Ser Lys Ser Gly Thr Ser Ala Thr Leu Gly Ile Thr Gly
50                  55                  60

Leu Gln Thr Gly Asp Glu Ala Asp Tyr Tyr Cys Xaa Phe Gly Gly
65                  70                  75                  80

Thr Lys Leu Thr Val Leu
                85

<210> SEQ ID NO 32
<211> LENGTH: 24
<212> TYPE: PRT
<213> ORGANISM: Artificial sequence
<220> FEATURE:
<223> OTHER INFORMATION: Synthetic Construct

<400> SEQUENCE: 32

Gln Ser Val Leu Thr Gln Pro Pro Ser Val Ser Ala Ala Pro Gly Gln
1               5                   10                  15

Lys Val Thr Ile Ser Cys Ser Gly
            20

<210> SEQ ID NO 33
<211> LENGTH: 14
<212> TYPE: PRT
<213> ORGANISM: Artificial sequence
<220> FEATURE:
<223> OTHER INFORMATION: Synthetic Construct

<400> SEQUENCE: 33

Trp Tyr Gln Gln Leu Pro Gly Thr Ala Pro Lys Leu Leu Ile
1               5                   10

<210> SEQ ID NO 34
<211> LENGTH: 35
<212> TYPE: PRT
<213> ORGANISM: Artificial sequence
<220> FEATURE:
<223> OTHER INFORMATION: Synthetic Construct

<400> SEQUENCE: 34

Arg Pro Ser Gly Ile Pro Asp Arg Phe Ser Gly Ser Lys Ser Gly Thr
1               5                   10                  15

Ser Ala Thr Leu Gly Ile Thr Gly Leu Gln Thr Gly Asp Glu Ala Asp
            20                  25                  30

Tyr Tyr Cys
        35

<210> SEQ ID NO 35
<211> LENGTH: 10
<212> TYPE: PRT
<213> ORGANISM: Artificial sequence
<220> FEATURE:
<223> OTHER INFORMATION: Synthetic Construct

<400> SEQUENCE: 35

Phe Gly Gly Gly Thr Lys Leu Thr Val Leu
1               5                   10

<210> SEQ ID NO 36
```

```
<211> LENGTH: 270
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t

<400> SEQUENCE: 36
gaagtgcaac ttgtcgaatc tggcggcggc ttagtgaaac caggcggcag ccttcgttta      60
agctgtgcag catctggtnt gggttcgtca ggcaccaggt aaaggtcttg aatgggtgnt    120
acgcagcacc ggtcaaaggt cgttttacga ttagtcgcga tgattcgaaa aacactcttt    180
acctgcagat gaattctctg aaaacagaag ataccgcagt gtattactgt gcacgtntgg    240
ggtcaaggta cactggttac cgttagctcg                                     270

<210> SEQ ID NO 37
<211> LENGTH: 78
<212> TYPE: DNA
<213> ORGANISM: Artificial sequence
<220> FEATURE:
<223> OTHER INFORMATION: Synthetic Construct

<400> SEQUENCE: 37
gaagtgcaac ttgtcgaatc tggcggcggc ttagtgaaac caggcggcag ccttcgttta     60
agctgtgcag catctggt                                                   78

<210> SEQ ID NO 38
<211> LENGTH: 39
<212> TYPE: DNA
<213> ORGANISM: Artificial sequence
<220> FEATURE:
<223> OTHER INFORMATION: Synthetic Construct

<400> SEQUENCE: 38
tgggttcgtc aggcaccagg taaaggtctt gaatgggtg                            39

<210> SEQ ID NO 39
<211> LENGTH: 117
<212> TYPE: DNA
<213> ORGANISM: Artificial sequence
<220> FEATURE:
<223> OTHER INFORMATION: Synthetic Construct

<400> SEQUENCE: 39
tacgcagcac cggtcaaagg tcgttttacg attagtcgcg atgattcgaa aacactctt      60 tacctgcaga tgaattctct gaaaacagaa gataccgcag tgtattactg tgcacgt      117

<210> SEQ ID NO 40
<211> LENGTH: 33
<212> TYPE: DNA
<213> ORGANISM: Artificial sequence
<220> FEATURE:
<223> OTHER INFORMATION: Synthetic Construct

<400> SEQUENCE: 40
```

```
tggggtcaag gtacactggt taccgttagc tcg                                33
```

<210> SEQ ID NO 41
<211> LENGTH: 270
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t

<400> SEQUENCE: 41

```
gaagtgcaac ttgtcgaatc tggcggcggc ttagtgcagc caggcggcag ccttcgttta    60
agctgtgcag catctggtnt gggttcgtca ggcaccaggt aaaggtcttg aatgggtgnt   120
atgcggatag cgttaagggt cgttttacca tcagtcgcga caactccaaa aatacccgt    180 acttacaaat gaatagctta cgtgcggaag ataccgcagt gtattactgt gcacgtntgg   240
ggtcaaggta cactggttac cgttagctcg                                    270
```

<210> SEQ ID NO 42
<211> LENGTH: 78
<212> TYPE: DNA
<213> ORGANISM: Artificial sequence
<220> FEATURE:
<223> OTHER INFORMATION: Synthetic Construct

<400> SEQUENCE: 42

```
gaagtgcaac ttgtcgaatc tggcggcggc ttagtgcagc caggcggcag ccttcgttta    60
agctgtgcag catctggt                                                  78
```

<210> SEQ ID NO 43
<211> LENGTH: 39
<212> TYPE: DNA
<213> ORGANISM: Artificial sequence
<220> FEATURE:
<223> OTHER INFORMATION: Synthetic Construct

<400> SEQUENCE: 43

```
tgggttcgtc aggcaccagg taaaggtctt gaatgggtg                           39
```

<210> SEQ ID NO 44
<211> LENGTH: 117
<212> TYPE: DNA
<213> ORGANISM: Artificial sequence
<220> FEATURE:
<223> OTHER INFORMATION: Synthetic Construct

<400> SEQUENCE: 44

```
tatgcggata gcgttaaggg tcgttttacc atcagtcgcg acaactccaa aatacccctg    60
tacttacaaa tgaatagctt acgtgcggaa gataccgcag tgtattactg tgcacgt      117
```

<210> SEQ ID NO 45
<211> LENGTH: 33
<212> TYPE: DNA

<213> ORGANISM: Artificial sequence
<220> FEATURE:
<223> OTHER INFORMATION: Synthetic Construct

<400> SEQUENCE: 45
tggggtcaag gtacactggt taccgttagc tcg    33

<210> SEQ ID NO 46
<211> LENGTH: 270
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t

<400> SEQUENCE: 46
caggtccaac tggttcagtc tggtgcggaa gttaaaaagc caggaagttc agttaaagtc    60
agttgtaaag cgtctggtnt gggttcgtca agcaccagga cagggcttag aatggatgnt    120
atgcacagaa attccaaggt cgtgttacga ttacggccga tgagtccact agtaccgcct    180
atatggaact ctccagcctt cgctctgaag ataccgcagt gtattactgt gcacgtntgg    240
ggtcaaggta cactggttac cgttagctcg    270

<210> SEQ ID NO 47
<211> LENGTH: 78
<212> TYPE: DNA
<213> ORGANISM: Artificial sequence
<220> FEATURE:
<223> OTHER INFORMATION: Synthetic Construct

<400> SEQUENCE: 47
caggtccaac tggttcagtc tggtgcggaa gttaaaaagc caggaagttc agttaaagtc    60
agttgtaaag cgtctggt    78

<210> SEQ ID NO 48
<211> LENGTH: 39
<212> TYPE: DNA
<213> ORGANISM: Artificial sequence
<220> FEATURE:
<223> OTHER INFORMATION: Synthetic Construct

<400> SEQUENCE: 48
tgggttcgtc aagcaccagg acagggctta gaatggatg    39

<210> SEQ ID NO 49
<211> LENGTH: 117
<212> TYPE: DNA
<213> ORGANISM: Artificial sequence
<220> FEATURE:
<223> OTHER INFORMATION: Synthetic Construct

<400> SEQUENCE: 49
tatgcacaga aattccaagg tcgtgttacg attacggccg atgagtccac tagtaccgcc    60
tatatggaac tctccagcct tcgctctgaa gataccgcag tgtattactg tgcacgt    117

<210> SEQ ID NO 50
<211> LENGTH: 33
<212> TYPE: DNA
<213> ORGANISM: Artificial sequence
<220> FEATURE:
<223> OTHER INFORMATION: Synthetic Construct

<400> SEQUENCE: 50
tggggtcaag gtacactggt taccgttagc tcg              33

<210> SEQ ID NO 51
<211> LENGTH: 264
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t

<400> SEQUENCE: 51
gacatccaaa tgacacagag cccttcttcc ttatccgcgt cggtaggaga tcgcgttaca      60
atcacctgcc gtgcgagtca gntggtatca gcagaaacca gggaaagcac cgaagctcct     120
gatttatngg cgttccgagc cgtttttagtg gctcggggtc cggcaccgac ttcaccctga    180
ctatctcttc gctgcagcct gaggattttg ctacctatta ctgtcaacag nacattcggg    240
cagggtacca aagtggaaat taaa                                            264

<210> SEQ ID NO 52
<211> LENGTH: 81
<212> TYPE: DNA
<213> ORGANISM: Artificial sequence
<220> FEATURE:
<223> OTHER INFORMATION: Synthetic Construct

<400> SEQUENCE: 52
gacatccaaa tgacacagag cccttcttcc ttatccgcgt cggtaggaga tcgcgttaca      60
atcacctgcc gtgcgagtca g                                                81

<210> SEQ ID NO 53
<211> LENGTH: 45
<212> TYPE: DNA
<213> ORGANISM: Artificial sequence
<220> FEATURE:
<223> OTHER INFORMATION: Synthetic Construct

<400> SEQUENCE: 53
tggtatcagc agaaaccagg gaaagcaccg aagctcctga tttat              45

<210> SEQ ID NO 54
<211> LENGTH: 102
<212> TYPE: DNA
<213> ORGANISM: Artificial sequence
<220> FEATURE:
<223> OTHER INFORMATION: Synthetic Construct

<400> SEQUENCE: 54
ggcgttccga gccgttttag tggctcgggg tccggcaccg acttcaccct gactatctct    60
tcgctgcagc ctgaggattt tgctacctat tactgtcaac ag    102

<210> SEQ ID NO 55
<211> LENGTH: 33
<212> TYPE: DNA
<213> ORGANISM: Artificial sequence
<220> FEATURE:
<223> OTHER INFORMATION: Synthetic Construct

<400> SEQUENCE: 55
acattcgggc agggtaccaa agtggaaatt aaa    33

<210> SEQ ID NO 56
<211> LENGTH: 258
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t

<400> SEQUENCE: 56
gaaattgtac tgacccaaag tcctgggaca ctgagtctga gtccaggtga acgtgctacc    60
cttagctgcc gtgcgagtca antggtacca acaaaagcct ggtcaggcac cacgtctgct    120
gatcnattcc ggaccgtttc tctggctccg gctcgggtac tgattttacc ctgactatct    180
ctcgtttaga acctgaggat tttgctgttt attactgtca acagnacatt cgggcagggt    240
accaaagtgg aaattaaa    258

<210> SEQ ID NO 57
<211> LENGTH: 81
<212> TYPE: DNA
<213> ORGANISM: Artificial sequence
<220> FEATURE:
<223> OTHER INFORMATION: Synthetic Construct

<400> SEQUENCE: 57
gaaattgtac tgacccaaag tcctgggaca ctgagtctga gtccaggtga acgtgctacc    60
cttagctgcc gtgcgagtca a    81

<210> SEQ ID NO 58
<211> LENGTH: 42
<212> TYPE: DNA
<213> ORGANISM: Artificial sequence
<220> FEATURE:
<223> OTHER INFORMATION: Synthetic Construct

<400> SEQUENCE: 58
tggtaccaac aaaagcctgg tcaggcacca cgtctgctga tc    42

<210> SEQ ID NO 59
<211> LENGTH: 99

<212> TYPE: DNA
<213> ORGANISM: Artificial sequence
<220> FEATURE:
<223> OTHER INFORMATION: Synthetic Construct

<400> SEQUENCE: 59
attccggacc gtttctctgg ctccggctcg ggtactgatt ttaccctgac tatctctcgt    60
ttagaacctg aggatttgc tgtttattac tgtcaacag                            99

<210> SEQ ID NO 60
<211> LENGTH: 33
<212> TYPE: DNA
<213> ORGANISM: Artificial sequence
<220> FEATURE:
<223> OTHER INFORMATION: Synthetic Construct

<400> SEQUENCE: 60
acattcgggc agggtaccaa agtggaaatt aaa                                 33

<210> SEQ ID NO 61
<211> LENGTH: 258
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t

<400> SEQUENCE: 61
gaaattgtac tgacccaaag tcctgggaca ctgagtctga gtccaggtga acgtgctacc    60
cttagctgcc gtgcgagtca antggtacca acaaaagcct ggtcaggcac cacgtctgct   120
gatcnattcc ggaccgtttc tctggctccg gctcgggtac tgattttacc ctgactatct   180
ctcgtttaga acctgaggat tttgctgttt attactgtca acagnacatt cgggcagggt   240
accaaagtgg aaattaaa                                                 258

<210> SEQ ID NO 62
<211> LENGTH: 81
<212> TYPE: DNA
<213> ORGANISM: Artificial sequence
<220> FEATURE:
<223> OTHER INFORMATION: Synthetic Construct

<400> SEQUENCE: 62
gaaattgtac tgacccaaag tcctgggaca ctgagtctga gtccaggtga acgtgctacc    60
cttagctgcc gtgcgagtca a                                              81

<210> SEQ ID NO 63
<211> LENGTH: 42
<212> TYPE: DNA
<213> ORGANISM: Artificial sequence
<220> FEATURE:
<223> OTHER INFORMATION: Synthetic Construct

<400> SEQUENCE: 63
tggtaccaac aaaagcctgg tcaggcacca cgtctgctga tc    42

<210> SEQ ID NO 64
<211> LENGTH: 99
<212> TYPE: DNA
<213> ORGANISM: Artificial sequence
<220> FEATURE:
<223> OTHER INFORMATION: Synthetic Construct

<400> SEQUENCE: 64
attccggacc gtttctctgg ctccggctcg ggtactgatt ttaccctgac tatctctcgt    60
ttagaacctg aggattttgc tgtttattac tgtcaacag    99

<210> SEQ ID NO 65
<211> LENGTH: 33
<212> TYPE: DNA
<213> ORGANISM: Artificial sequence
<220> FEATURE:
<223> OTHER INFORMATION: Synthetic Construct

<400> SEQUENCE: 65
acattcgggc agggtaccaa agtggaaatt aaa    33

<210> SEQ ID NO 66
<211> LENGTH: 252
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 66
caatcagttc tgacccaacc ccctctgta tccgcggcac ccggtcaaaa ggtgaccatc    60
tcgtgctctg gcntggtatc aacagcttcc aggtacagca ccgaagttat tgattncgtc    120
cttccggtat tccggatcgt ttttcgggga gtaaaagtgg cacctcagca acacttggta    180
ttaccggact gcagaccggc gacgaagccg attactactg cnttcggtgg tggcaccaaa    240
cttacggtcc tg    252

<210> SEQ ID NO 67
<211> LENGTH: 72
<212> TYPE: DNA
<213> ORGANISM: Artificial sequence
<220> FEATURE:
<223> OTHER INFORMATION: Synthetic Construct

<400> SEQUENCE: 67
caatcagttc tgacccaacc ccctctgta tccgcggcac ccggtcaaaa ggtgaccatc    60
tcgtgctctg gc    72

<210> SEQ ID NO 68
<211> LENGTH: 42
<212> TYPE: DNA
<213> ORGANISM: Artificial sequence

```
<220> FEATURE:
<223> OTHER INFORMATION: Synthetic Construct

<400> SEQUENCE: 68
tggtatcaac agcttccagg tacagcaccg aagttattga tt                    42

<210> SEQ ID NO 69
<211> LENGTH: 105
<212> TYPE: DNA
<213> ORGANISM: Artificial sequence
<220> FEATURE:
<223> OTHER INFORMATION: Synthetic Construct

<400> SEQUENCE: 69
cgtccttccg gtattccgga tcgttttcg gggagtaaaa gtggcacctc agcaacactt   60
ggtattaccg gactgcagac cggcgacgaa gccgattact actgc                105

<210> SEQ ID NO 70
<211> LENGTH: 30
<212> TYPE: DNA
<213> ORGANISM: Artificial sequence
<220> FEATURE:
<223> OTHER INFORMATION: Synthetic Construct

<400> SEQUENCE: 70
ttcggtggtg gcaccaaact tacggtcctg                                  30

<210> SEQ ID NO 71
<211> LENGTH: 23
<212> TYPE: DNA
<213> ORGANISM: Artificial sequence
<220> FEATURE:
<223> OTHER INFORMATION: Synthetic Construct

<400> SEQUENCE: 71
cargtgcagc tkgtgcagtc tgg                                         23

<210> SEQ ID NO 72
<211> LENGTH: 24
<212> TYPE: DNA
<213> ORGANISM: Artificial sequence
<220> FEATURE:
<223> OTHER INFORMATION: Synthetic Construct

<400> SEQUENCE: 72
tgaggagacg gtgaccaggg tgcc                                        24

<210> SEQ ID NO 73
<211> LENGTH: 23
<212> TYPE: DNA
<213> ORGANISM: Artificial sequence
<220> FEATURE:
<223> OTHER INFORMATION: Synthetic Construct

<400> SEQUENCE: 73
gargtgcagc tggtggagtc tgg                                         23

<210> SEQ ID NO 74
<211> LENGTH: 23
<212> TYPE: DNA
<213> ORGANISM: Artificial sequence
<220> FEATURE:
<223> OTHER INFORMATION: Synthetic Construct

<400> SEQUENCE: 74
```
gacatccaga tgacccagtc tcc                                            23

<210> SEQ ID NO 75
<211> LENGTH: 24
<212> TYPE: DNA
<213> ORGANISM: Artificial sequence
<220> FEATURE:
<223> OTHER INFORMATION: Synthetic Construct

<400> SEQUENCE: 75
acgtttgatt tccaccttgg tccc                                           24

<210> SEQ ID NO 76
<211> LENGTH: 23
<212> TYPE: DNA
<213> ORGANISM: Artificial sequence
<220> FEATURE:
<223> OTHER INFORMATION: Synthetic Construct

<400> SEQUENCE: 76
gaaatwgtgw tgacrcagtc tcc                                            23

<210> SEQ ID NO 77
<211> LENGTH: 23
<212> TYPE: DNA
<213> ORGANISM: Artificial sequence
<220> FEATURE:
<223> OTHER INFORMATION: Synthetic Construct

<400> SEQUENCE: 77
cagtctgtgy tgackcagcc gcc                                            23

<210> SEQ ID NO 78
<211> LENGTH: 24
<212> TYPE: DNA
<213> ORGANISM: Artificial sequence
<220> FEATURE:
<223> OTHER INFORMATION: Synthetic Construct

<400> SEQUENCE: 78
acctaggacg gtcagcttgg tccc                                           24

<210> SEQ ID NO 79
<211> LENGTH: 63
<212> TYPE: DNA
<213> ORGANISM: Artificial sequence
<220> FEATURE:
<223> OTHER INFORMATION: Synthetic Construct

<400> SEQUENCE: 79
ccatctcatc cctgcgtgtc tccgactcag acgagtgcgt cargtgcagc tkgtgcagtc    60
tgg                                                                  63

<210> SEQ ID NO 80
<211> LENGTH: 63
<212> TYPE: DNA
<213> ORGANISM: Artificial sequence
<220> FEATURE:
<223> OTHER INFORMATION: Synthetic Construct

<400> SEQUENCE: 80
ccatctcatc cctgcgtgtc tccgactcag acgagtgcgt cargtgcagc tkgtgcagtc    60
tgg                                                                  63

-continued

```
<210> SEQ ID NO 81
<211> LENGTH: 63
<212> TYPE: DNA
<213> ORGANISM: Artificial sequence
<220> FEATURE:
<223> OTHER INFORMATION: Synthetic Construct

<400> SEQUENCE: 81
ccatctcatc cctgcgtgtc tccgactcag acgctcgaca gargtgcagc tggtggagtc    60
tgg                                                                  63

<210> SEQ ID NO 82
<211> LENGTH: 63
<212> TYPE: DNA
<213> ORGANISM: Artificial sequence
<220> FEATURE:
<223> OTHER INFORMATION: Synthetic Construct

<400> SEQUENCE: 82
ccatctcatc cctgcgtgtc tccgactcag agacgcactc gacatccaga tgacccagtc    60
tcc                                                                  63

<210> SEQ ID NO 83
<211> LENGTH: 63
<212> TYPE: DNA
<213> ORGANISM: Artificial sequence
<220> FEATURE:
<223> OTHER INFORMATION: Synthetic Construct

<400> SEQUENCE: 83
ccatctcatc cctgcgtgtc tccgactcag agcactgtag gaaatwgtgw tgacrcagtc    60
tcc                                                                  63

<210> SEQ ID NO 84
<211> LENGTH: 63
<212> TYPE: DNA
<213> ORGANISM: Artificial sequence
<220> FEATURE:
<223> OTHER INFORMATION: Synthetic Construct

<400> SEQUENCE: 84
ccatctcatc cctgcgtgtc tccgactcag atcagacacg cagtctgtgy tgackcagcc    60
gcc                                                                  63

<210> SEQ ID NO 85
<211> LENGTH: 63
<212> TYPE: DNA
<213> ORGANISM: Artificial sequence
<220> FEATURE:
<223> OTHER INFORMATION: Synthetic Construct

<400> SEQUENCE: 85
ccatctcatc cctgcgtgtc tccgactcag atatcgcgag cargtgcagc tkgtgcagtc    60
tgg                                                                  63

<210> SEQ ID NO 86
<211> LENGTH: 63
<212> TYPE: DNA
<213> ORGANISM: Artificial sequence
<220> FEATURE:
<223> OTHER INFORMATION: Synthetic Construct

<400> SEQUENCE: 86
```

```
ccatctcatc cctgcgtgtc tccgactcag cgtgtctcta gargtgcagc tggtggagtc    60
tgg                                                                 63
```

<210> SEQ ID NO 87
<211> LENGTH: 63
<212> TYPE: DNA
<213> ORGANISM: Artificial sequence
<220> FEATURE:
<223> OTHER INFORMATION: Synthetic Construct

<400> SEQUENCE: 87

```
ccatctcatc cctgcgtgtc tccgactcag ctcgcgtgtc gacatccaga tgacccagtc    60
tcc                                                                 63
```

<210> SEQ ID NO 88
<211> LENGTH: 63
<212> TYPE: DNA
<213> ORGANISM: Artificial sequence
<220> FEATURE:
<223> OTHER INFORMATION: Synthetic Construct

<400> SEQUENCE: 88

```
ccatctcatc cctgcgtgtc tccgactcag tagtatcagc gaaatwgtgw tgacrcagtc    60
tcc                                                                 63
```

<210> SEQ ID NO 89
<211> LENGTH: 54
<212> TYPE: DNA
<213> ORGANISM: Artificial sequence
<220> FEATURE:
<223> OTHER INFORMATION: Synthetic Construct

<400> SEQUENCE: 89

```
cctatcccct gtgtgccttg gcagtctcag tgaggagacg gtgaccaggg tgcc          54
```

<210> SEQ ID NO 90
<211> LENGTH: 54
<212> TYPE: DNA
<213> ORGANISM: Artificial sequence
<220> FEATURE:
<223> OTHER INFORMATION: Synthetic Construct

<400> SEQUENCE: 90

```
cctatcccct gtgtgccttg gcagtctcag acgtttgatt tccaccttgg tccc          54
```

<210> SEQ ID NO 91
<211> LENGTH: 54
<212> TYPE: DNA
<213> ORGANISM: Artificial sequence
<220> FEATURE:
<223> OTHER INFORMATION: Synthetic Construct

<400> SEQUENCE: 91

```
cctatcccct gtgtgccttg gcagtctcag acctaggacg gtgaccttgg tccc          54
```

<210> SEQ ID NO 92
<211> LENGTH: 39
<212> TYPE: DNA
<213> ORGANISM: Artificial sequence
<220> FEATURE:
<223> OTHER INFORMATION: Synthetic Construct

<400> SEQUENCE: 92

```
gaattcagga ggaatttaaa atgaaaaaga cagctatcg                          39
```

<210> SEQ ID NO 93
<211> LENGTH: 87
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (33)..(42)
<223> OTHER INFORMATION: n is a, c, g, or t
<220> FEATURE:
<221> NAME/KEY: misc_feature
<222> LOCATION: (45)..(50)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 93
ggctttccct ggtttctgct gataccannn tannnnnnnn nntannnnnn gactcgcacn    60
gcaggtgatt gtaacgcgat ctcctac                                       87

<210> SEQ ID NO 94
<211> LENGTH: 27
<212> TYPE: DNA
<213> ORGANISM: Artificial sequence
<220> FEATURE:
<223> OTHER INFORMATION: Synthetic Construct

<400> SEQUENCE: 94
tggtatcagc agaaaccagg gaaagcc                                       27

<210> SEQ ID NO 95
<211> LENGTH: 72
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(45)
<223> OTHER INFORMATION: n is a, c, g, or t

<400> SEQUENCE: 95
gccactaaaa cggctcggaa cgccnnnnnn angnnnantn nnnnnataaa tcaggagctt    60
cggtgctttc cc                                                       72

<210> SEQ ID NO 96

```
<211> LENGTH: 24
<212> TYPE: DNA
<213> ORGANISM: Artificial sequence
<220> FEATURE:
<223> OTHER INFORMATION: Synthetic Construct

<400> SEQUENCE: 96
ggcgttccga gccgttttag tggc                                            24

<210> SEQ ID NO 97
<211> LENGTH: 90
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (40)..(52)
<223> OTHER INFORMATION: n is a, c, g, or t
<220> FEATURE:
<221> NAME/KEY: misc_feature
<222> LOCATION: (54)..(56)
<223> OTHER INFORMATION: n is a, c, g, or t

<400> SEQUENCE: 97
tttaatttcc actttggtac cctgcccgaa tgtnnncggn nnnnnnnnnn nntnnngaca     60
gtaataggta gcaaaatcct caggctgcag                                      90

<210> SEQ ID NO 98
<211> LENGTH: 93
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 98
tgcctgacca ggcttttgtt ggtaccatgc ancnnnnnnn nnnnnnnnnn nnnnntnact     60
cgcacngcag ctaagggtag cacgttcacc tgg                                  93

<210> SEQ ID NO 99
<211> LENGTH: 30
<212> TYPE: DNA
<213> ORGANISM: Artificial sequence
<220> FEATURE:
<223> OTHER INFORMATION: Synthetic Construct

<400> SEQUENCE: 99
gcatggtacc aacaaaagcc tggtcaggca                                      30
```

```
<210> SEQ ID NO 100
<211> LENGTH: 75
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (37)..(51)
<223> OTHER INFORMATION: n is a, c, g, or t

<400> SEQUENCE: 100
ggagccagag aaacggtccg gaatancagn ancacgnnnn nnnnnnnnnn ngatcagcag      60
acgtggtgcc tgacc                                                     75

<210> SEQ ID NO 101
<211> LENGTH: 24
<212> TYPE: DNA
<213> ORGANISM: Artificial sequence
<220> FEATURE:
<223> OTHER INFORMATION: Synthetic Construct

<400> SEQUENCE: 101
attccggacc gtttctctgg ctcc                                           24

<210> SEQ ID NO 102
<211> LENGTH: 93
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (40)..(52)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 102
tttaatttcc actttggtac cctgcccgaa tgtnnncggn nnnnnnnnnn nntgnngaca      60
gtaataaaca gcaaatcct caggttctaa acg                                  93

<210> SEQ ID NO 103
<211> LENGTH: 87
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: n is a, c, g, or t
<220> FEATURE:
```

<221> NAME/KEY: misc_feature
<222> LOCATION: (34)..(50)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 103
tgcctgacca ggcttttgtt ggtaccatgc ancnnnnnnn nnnnnnnnnn gactcgcacn    60
gcagctaagg gtagcacgtt cacctgg                                       87

<210> SEQ ID NO 104
<211> LENGTH: 87
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (34)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (55)..(60)
<223> OTHER INFORMATION: n is a, c, g, or t

<400> SEQUENCE: 104
tgctgtacct ggaagctgtt gataccannn cacnnnnnnn nntncaanat tagannnnnn    60
gccagagcac gagatggtca ccttttg                                       87

<210> SEQ ID NO 105
<211> LENGTH: 27
<212> TYPE: DNA
<213> ORGANISM: Artificial sequence
<220> FEATURE:
<223> OTHER INFORMATION: Synthetic Construct

<400> SEQUENCE: 105
tggtatcaac agcttccagg tacagca                                       27

<210> SEQ ID NO 106
<211> LENGTH: 66
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(39)
<223> OTHER INFORMATION: n is a, c, g, or t

<400> SEQUENCE: 106
acgatccgga ataccggaag gacgnnnnnn nnnnnnnnna atcaataact tcggtgctgt    60
acctgg                                                              66

```
<210> SEQ ID NO 107
<211> LENGTH: 24
<212> TYPE: DNA
<213> ORGANISM: Artificial sequence
<220> FEATURE:
<223> OTHER INFORMATION: Synthetic Construct

<400> SEQUENCE: 107
cgtccttccg gtattccgga tcgt                                          24

<210> SEQ ID NO 108
<211> LENGTH: 81
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(45)
<223> OTHER INFORMATION: n is a, c, g, or t
<220> FEATURE:
<221> NAME/KEY: misc_feature
<222> LOCATION: (49)..(57)
<223> OTHER INFORMATION: n is a, c, g, or t

<400> SEQUENCE: 108
cgtaagtttg gtgccaccac cgaannnnnn nnnnnnnnnn nnnnnatcnn nnnnnnngca    60
gtagtaatcg gcttcgtcgc c                                             81

<210> SEQ ID NO 109
<211> LENGTH: 54
<212> TYPE: DNA
<213> ORGANISM: Artificial sequence
<220> FEATURE:
<223> OTHER INFORMATION: Synthetic Construct

<400> SEQUENCE: 109
gggcagggta ccaaagtgga aattaaacgc acggtggctg ccccttctgt gttc          54

<210> SEQ ID NO 110
<211> LENGTH: 33
<212> TYPE: DNA
<213> ORGANISM: Artificial sequence
<220> FEATURE:
<223> OTHER INFORMATION: Synthetic Construct

<400> SEQUENCE: 110
aattatctag aactagcact cacccctgtt gaa                                33

<210> SEQ ID NO 111
<211> LENGTH: 54
<212> TYPE: DNA
<213> ORGANISM: Artificial sequence
<220> FEATURE:
<223> OTHER INFORMATION: Synthetic Construct

<400> SEQUENCE: 111
ggtggtggca ccaaacttac ggtcctaggc cagcccaagg ccaaccccac tgtc          54

<210> SEQ ID NO 112
<211> LENGTH: 40
<212> TYPE: DNA
<213> ORGANISM: Artificial sequence
<220> FEATURE:
<223> OTHER INFORMATION: Synthetic Construct

<400> SEQUENCE: 112
```
ttatctagaa ctaacattct gtaggggcca ctgtcttctc 40

<210> SEQ ID NO 113
<211> LENGTH: 36
<212> TYPE: DNA
<213> ORGANISM: Artificial sequence
<220> FEATURE:
<223> OTHER INFORMATION: Synthetic Construct

<400> SEQUENCE: 113
actagtgcgt ttaatttcca ctttggtacc ctgccc 36

<210> SEQ ID NO 114
<211> LENGTH: 30
<212> TYPE: DNA
<213> ORGANISM: Artificial sequence
<220> FEATURE:
<223> OTHER INFORMATION: Synthetic Construct

<400> SEQUENCE: 114
actagtaccc aggaccgtaa gtttggtgcc 30

<210> SEQ ID NO 115
<211> LENGTH: 48
<212> TYPE: DNA
<213> ORGANISM: Artificial sequence
<220> FEATURE:
<223> OTHER INFORMATION: Synthetic Construct

<400> SEQUENCE: 115
ttctagataa ttaattagga ggaatttaaa atgaaatacc tattgcct 48

<210> SEQ ID NO 116
<211> LENGTH: 84
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (30)..(42)
<223> OTHER INFORMATION: n is a, c, g, or t
<220> FEATURE:
<221> NAME/KEY: misc_feature
<222> LOCATION: (46)..(51)
<223> OTHER INFORMATION: n is a, c, g, or t

<400> SEQUENCE: 116
ctgtcctggt gcttgacgaa cccannnnan nnnnnnnnnn nngaannnnn naccagacgc 60
tttacaactg actttaactg aact 84

<210> SEQ ID NO 117
<211> LENGTH: 24
<212> TYPE: DNA
<213> ORGANISM: Artificial sequence
<220> FEATURE:
<223> OTHER INFORMATION: Synthetic Construct

<400> SEQUENCE: 117
tgggttcgtc aagcaccagg acag 24

<210> SEQ ID NO 118
<211> LENGTH: 87

```
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (31)..(54)
<223> OTHER INFORMATION: n is a, c, g, or t
<220> FEATURE:
<221> NAME/KEY: misc_feature
<222> LOCATION: (58)..(63)
<223> OTHER INFORMATION: n is a, c, g, or t

<400> SEQUENCE: 118
cgtaacacga ccttggaatt tctgtgcata nnnnnnnnnn nnnnnnnnnn nnnngatnnn      60
nnncatccat tctaagcctt gtccagg                                         87

<210> SEQ ID NO 119
<211> LENGTH: 33
<212> TYPE: DNA
<213> ORGANISM: Artificial sequence
<220> FEATURE:
<223> OTHER INFORMATION: Synthetic Construct

<400> SEQUENCE: 119
tatgcacaga aattccaagg tcgtgttacg att                                  33

<210> SEQ ID NO 120
<211> LENGTH: 78
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (22)..(48)
<223> OTHER INFORMATION: n is a, c, g, or t

<400> SEQUENCE: 120
caccagggtc ccctggcccc annnnnnnnn nnnnnnnnnn nnnnnnnngc gggcgcagta      60
atacactgcg gtatcttc                                                   78

<210> SEQ ID NO 121
<211> LENGTH: 87
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(57)
<223> OTHER INFORMATION: n is a, c, g, or t

<400> SEQUENCE: 121
aacggtaacc agtgtacctt gaccccannn nnnnnnnnnn nnnnnnnnn nnnnnnnacg       60 tgcacagtaa tacactgcgg tatcttc                                         87

<210> SEQ ID NO 122
<211> LENGTH: 90
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(60)
<223> OTHER INFORMATION: n is a, c, g, or t
```

<400> SEQUENCE: 122
aacggtaacc agtgtacctt gaccccannn nnnnnnnnnn nnnnnnnnnn nnnnnnnnnn    60
acgtgcacag taatacactg cggtatcttc                                     90

<210> SEQ ID NO 123
<211> LENGTH: 93
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(63)
<223> OTHER INFORMATION: n is a, c, g, or t

<400> SEQUENCE: 123
aacggtaacc agtgtacctt gaccccannn nnnnnnnnnn nnnnnnnnnn nnnnnnnnnn    60
nnnacgtgca cagtaataca ctgcggtatc ttc                                 93

<210> SEQ ID NO 124
<211> LENGTH: 96
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(66)
<223> OTHER INFORMATION: n is a, c, g, or t

<400> SEQUENCE: 124
aacggtaacc agtgtacctt gaccccannn nnnnnnnnnn nnnnnnnnnn nnnnnnnnnn    60
nnnnnnacgt gcacagtaat acactgcggt atcttc                              96

<210> SEQ ID NO 125
<211> LENGTH: 99
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (28)..(69)
<223> OTHER INFORMATION: n is a, c, g, or t

<400> SEQUENCE: 125
aacggtaacc agtgtacctt gaccccannn nnnnnnnnnn nnnnnnnnnn nnnnnnnnnn    60
nnnnnnnnna cgtgcacagt aatacactgc ggtatcttc                           99

<210> SEQ ID NO 126
<211> LENGTH: 78
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (30)..(42)
<223> OTHER INFORMATION: n is a, c, g, or t
<220> FEATURE:
<221> NAME/KEY: misc_feature
<222> LOCATION: (46)..(48)
<223> OTHER INFORMATION: n is a, c, g, or t

```
<220> FEATURE:
<221> NAME/KEY: misc_feature
<222> LOCATION: (50)..(50)
<223> OTHER INFORMATION: n is a, c, g, or t

<400> SEQUENCE: 126
tttacctggt gcctgacgaa cccannnnan nnnnnnnnnn nngaannnan aaccagatgc        60
tgcacagctt aaacgaag                                                    78

<210> SEQ ID NO 127
<211> LENGTH: 24
<212> TYPE: DNA
<213> ORGANISM: Artificial sequence
<220> FEATURE:
<223> OTHER INFORMATION: Synthetic Construct

<400> SEQUENCE: 127
tgggttcgtc aggcaccagg taaa                                             24

<210> SEQ ID NO 128
<211> LENGTH: 78
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (22)..(48)
<223> OTHER INFORMATION: n is a, c, g, or t

<400> SEQUENCE: 128
caccagggtc ccctggcccc annnnnnnnn nnnnnnnnnn nnnnnnnngc gggcgcagta        60
atacactgcg gtatcttc                                                    78

<210> SEQ ID NO 129
<211> LENGTH: 24
<212> TYPE: DNA
<213> ORGANISM: Artificial sequence
<220> FEATURE:
<223> OTHER INFORMATION: Synthetic Construct

<400> SEQUENCE: 129
tacgcagcac cggtcaaagg tcgt                                             24

<210> SEQ ID NO 130
<211> LENGTH: 87
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (31)..(42)
<223> OTHER INFORMATION: n is a, c, g, or t
<220> FEATURE:
<221> NAME/KEY: misc_feature
<222> LOCATION: (45)..(54)
<223> OTHER INFORMATION: n is a, c, g, or t
<220> FEATURE:
<221> NAME/KEY: misc_feature
<222> LOCATION: (58)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 130
```

```
ggtaaaacga cccttaacgc tatccgcata nnnnnnnnnn nnacnnnnnn nnnngatnnn    60
tcncacccat tcaagacctt tacctgg                                        87
```

<210> SEQ ID NO 131
<211> LENGTH: 49
<212> TYPE: DNA
<213> ORGANISM: Artificial sequence
<220> FEATURE:
<223> OTHER INFORMATION: Synthetic Construct

<400> SEQUENCE: 131

```
gctctagata attaattagg aggaatttaa aatgaaatac ctattgcct               49
```

<210> SEQ ID NO 132
<211> LENGTH: 50
<212> TYPE: DNA
<213> ORGANISM: Artificial sequence
<220> FEATURE:
<223> OTHER INFORMATION: Synthetic Construct

<400> SEQUENCE: 132

```
gggcccttgg tggaggccga gctaacggta accagtgtac cttgacccca              50
```

<210> SEQ ID NO 133
<211> LENGTH: 106
<212> TYPE: PRT
<213> ORGANISM: Artificial sequence
<220> FEATURE:
<223> OTHER INFORMATION: Synthetic Construct

<400> SEQUENCE: 133

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 134
<211> LENGTH: 104
<212> TYPE: PRT
<213> ORGANISM: Artificial sequence
<220> FEATURE:
<223> OTHER INFORMATION: Synthetic Construct

<400> SEQUENCE: 134

```
Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
```

```
            50                  55                  60
Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys
                100
```

ANTIBODY LIBRARY AND ANTIBODY SCREENING METHOD USING SAME

CROSS-REFERENCE TO RELATED APPLICATIONS

This application is a U.S. national phase under the provisions of 35 U.S.C. § 371 of International Patent Application No. PCT/KR2019/006565 filed May 31, 2019, which in turn claims priority of Korean Patent Application No. 10-2018-0063306 filed Jun. 1, 2018. The disclosures of such international patent application and Korean patent application are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "533_SeqListing_ST25.txt" created on Nov. 23, 2020 and is 49,290 bytes in size. The sequence listing contained in this .txt file is part of the specification and is hereby incorporated by reference herein in its entirety.

TECHNICAL FIELD

The present invention relates to a novel antibody library and an antibody-screening method using the same, wherein the antibody library according to the present invention has certain VH or VL scaffolds derived from human sequences and thus has advantages of exhibiting high thermodynamic stability and realizing high soluble expression and reversible folding.

In addition, the antibody library according to the present invention contains various CDRs that are rationally controlled to have high specificity and high affinity for all antigens and thus are useful for selection of candidate antibodies.

BACKGROUND ART

Antibodies are proteins produced by stimulation of an antigen in B cells (B lymphocytes) of leukocytes in the immune system. When an antibody meets an antigen, it recognizes the antigen through a receptor present in the cell and binds to the antigen using the receptor. Such an antibody is considered as a candidate for new protein drugs for treating diseases, and various antibody libraries are produced, and antibodies are screened from the same in order to find functional antibodies of interest.

Such an antibody library uses gene recombination technology. Genes encoding antibody proteins are extracted from B cells present in the human body to produce antibody gene libraries, and an antibody having desired antigen-binding specificity is selected from these libraries. Antibody library technology has revolutionized the production of antibodies such as human antibodies. The most outstanding feature of the antibody immune response is that no matter what kind or shape of external antigen invades the body, if the antigen is a foreign substance that is not identical to a component in the body, an antibody that specifically binds to the antigen is produced within one week.

Antibodies are produced by B lymphocytes, and one B lymphocyte produces only one type of antibody. In fact, there are a number of types of B lymphocytes in the human body, each type of B lymphocyte expressing an antibody having its own unique antigen-binding specificity on the cell membrane, and it is known that approximately 108 kinds of antigen-binding diversity exist in the human body. When an antigen invades, only the B lymphocyte expressing an antibody that specifically binds to the antigen proliferates rapidly and produces a large amount of antibodies. As a result, the concentration of this specific antibody in the serum increases rapidly, and performs the function of quickly removing the invading antigen. Therefore, there are hundreds of millions of antibody diversity in the human body, and this diversity of antibodies is referred to as an "antibody repertoire".

Therefore, a sufficient number of B lymphocytes from the human body is obtained through blood collection, mRNA is isolated from these cells, and then cDNA encoding the variable regions of the antibody heavy and light chains is obtained through RT-PCR (reverse transcriptase-polymerase chain reaction). As a result, an antibody repertoire in the human body can be acquired in vitro in the form of a gene in a relatively simple manner. The core of antibody library technology is that this human antibody gene repertoire is expressed (or displayed) as a protein, the gene encoding the antibody protein is linked through any means, which is so-called genotype-phenotype linkage, and based thereon, an antibody that binds to a specific antigen is selected from the antibody library, and at the same time, a gene encoding the specific antibody is obtained.

Here, complete immunity is not required and the form of Fab of an antibody having antigen-binding function is expressed, or an antibody fragment called a "scFv (single-chain variable fragment)", in which the heavy- and light-chain variable domains (VH and VL) are linked by short peptide linkers of about 15 amino acids, is expressed. In this case, the antibody library technology is classified into phage display, ribosome display, yeast display, or the like, depending on the medium having a surface, on which the medium used for genotype-phenotype linkage of such an antibody is expressed, and antibodies having desired antigen-binding properties can be obtained without induction of immune response such as antigen administration.

However, there are disadvantages in that a lot of technical expertise is required for antibody library production and antibody screening, and antibody optimization processes such as affinity maturation after antibody screening are often performed due to the difficulty in obtaining high-affinity antibodies, and direct functional analysis in mammalian cells is disadvantageously impossible due to problems such as toxicity during primary screening. In the case of therapeutic antibodies, antibodies that do not simply bind to an antigen but have an actual therapeutic function should be selected, and thus such a disadvantage has been a barrier to the development of therapeutic antibodies.

The phage display antibody library is the most widely used antibody library. In fact, Humira (anti-TNF-alpha human monoclonal antibody), which is currently commercially available, is a therapeutic antibody produced using phage display technology. The ideal antibody library exhibits wide antibody diversity and enables high-affinity antibody clones having the desired antigen-binding specificity to be obtained at any time. For this purpose, a library having an antibody diversity of about $10^{10}$ to about $10^{11}$ should be produced. However, it is very difficult to produce a library of this size through antibody gene cloning, and this is the most difficult challenge in producing a phage display antibody library. In addition, there is a disadvantage in which the phage itself acts as a toxin, so the functional analysis cannot be performed immediately.

The greatest advantage of ribosome display is that it is a cell-free system and thus is capable of easily producing a library that is large enough to theoretically produce a library with a size of $10^{13}$ which is advantageous for obtaining high-affinity antibodies (generally, as the size of antibody libraries increases, the possibility that high-affinity antibodies are contained in the library increases), and error-prone polymerase can be used because there is a PCR amplification process, so the introduction of mutations to artificially induce molecular evolution is very easy. However, due to toxicity problems and various experimental problems, in practice, phage display technology is mainly used for production of naive antibody libraries.

Yeast display technology has many technical limitations in constructing an antibody library with a diversity of $10^9$ or more due to the process of inserting the recombinant vector into the *S. cerevisiae* strain and the large size of the yeast cells. Therefore, it is mainly used to construct a mutant library of an antigen-specific antibody that has already been secured using the advantages in the selection process, and to select high-affinity antibodies from the library.

Among them, phage display is a technology for screening antibodies by expressing antibody fragments on the surface of a bacteriophage, and has an advantage of identifying antigen-specific antibodies within a short time compared to conventionally developed antibody technology (development of chimeric/humanized antibodies using hybridomas or development of antibodies using transgenic mice). Phage display has a disadvantage in that effective antibodies can be identified only when a highly diverse library is secured. However, the recent development of gene amplification and cloning techniques has resolved the issue of securing a large library.

A synthetic antibody library refers to an antibody library that is imparted with diversity by introducing random synthetic sequences into the complementarity-determining region (CDR) of an antibody, compared to a natural library based on human genes. However, the synthetic antibody library has a lower proportion of antibody fragments that can function normally due to the influence of mutations or frameshifts compared to a natural human library. In recent years, strategies for using antibody libraries to identify novel target antigens have been diversified, and representative thereamong, novel antigen-specific antibodies have been identified through cell panning using tumor-derived primary cells (Zhu X. et al., Mol. Cancer Res. 2010).

As described above, continuous antibody candidates can be secured due to possibility of various approach strategies, and antibodies can be produced through cloning, so phage display is an efficient approach strategy. Candidate antibody drugs targeting various types of cancer identified using such phage display technology are undergoing clinical trials. In order to identify the desired antibodies to utilize phage display technology, it is necessary to produce a library from antibody variable-region genes, and it is indispensable to construct a variety of libraries.

Although various antibody libraries are currently being developed, there is still increasing demand for an antibody library that is capable of selecting an antibody having high specificity and affinity for various antigens because it has high thermodynamic stability, enables high soluble expression, and has a high diversity.

Against this technical background, as a result of intensive efforts, the present inventors found that, when extracting common sequences from cDNAs of Asian and Caucasian races and using an antibody library based on a combination of specific VH and/or VL scaffolds based on the common sequences, the selected antibodies have high thermodynamic stability, and enables high soluble expression, and reversible folding. Based on this finding, the present invention has been completed.

Moreover, the antibody library according to the present invention contains various CDRs that are rationally controlled and designed to have high specificity and high affinity for all antigens, thus exhibiting excellent diversity and a lower repetitive sequence ratio compared to a natural antibody library, and can be usefully used to select appropriate candidate antibodies for a target antigen.

The information disclosed in this Background section is provided only for better understanding of the background of the present invention, and therefore it may not include information that forms the prior art that is already obvious to those skilled in the art.

DISCLOSURE

Therefore, the present invention has been made in view of the above problems, and it is one object of the present invention to provide an antibody library for screening for human antibodies that can be effectively used for the treatment or diagnosis of diseases, and a method for screening antibodies using the same.

In accordance with one aspect of the present invention, the above and other objects can be accomplished by the provision of a set of antibodies or fragments thereof, wherein each antibody or fragment thereof includes a pair of a heavy-chain variable region and a light-chain variable region, wherein the heavy-chain variable region includes a framework region included in a heavy-chain variable region selected from the group consisting of VH3-15 (SEQ ID NO: 1), VH3-23 (SEQ ID NO: 6) and VH1-69 (SEQ ID NO: 11), and a combination of a heavy-chain complementarity-determining region 1 (CDRH1), a heavy-chain complementarity-determining region 2 (CDRH2), and a heavy-chain complementarity-determining region 3 (CDRH3), which are different for each heavy-chain variable region, and the light-chain variable region includes a framework region included in a light-chain variable region selected from the group consisting of Vκ1-39 (SEQ ID NO: 16), Vκ3-20 (SEQ ID NO: 21), Vκ3-20-2 (SEQ ID NO: 26) and Vλ1-51 (SEQ ID NO: 31), and a combination of a light-chain complementarity-determining region 1 (CDRL1), a light-chain complementarity-determining region 2 (CDRL2), and a light-chain complementarity-determining region 3 (CDRL3), which are different for each light-chain variable region.

Nucleic acids encoding individual antibodies or fragments thereof included in the set of antibodies or fragments thereof are individually included in separate phages or host cells, and the antibodies or fragments thereof are preferably each expressed on the surface of phages or host cells, but the present invention is not limited thereto.

In accordance with another aspect of the present invention, there are provided nucleic acids encoding the set of antibodies or fragments thereof. The nucleic acids encoding the set of antibodies or fragments thereof are preferably individually contained in separate phages or host cells, but the present invention is not limited thereto.

In accordance with another aspect of the present invention, there is provided a method of identifying an antibody or fragment thereof specific for an antigen including (a)

contacting an antigen with the set of antibodies, and (b) selecting one or more antibodies or antibody fragments that bind to the antigen.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In the present invention, it was found that an antibody library having high diversity and stability can be constructed when constructing an antibody library using a trimer codon in order to secure VH and VL clones with high stability of the framework region, minimize posttranslational modification (PTM), and precisely synthesize only amino acids that minimize immunogenicity.

Figure 1:
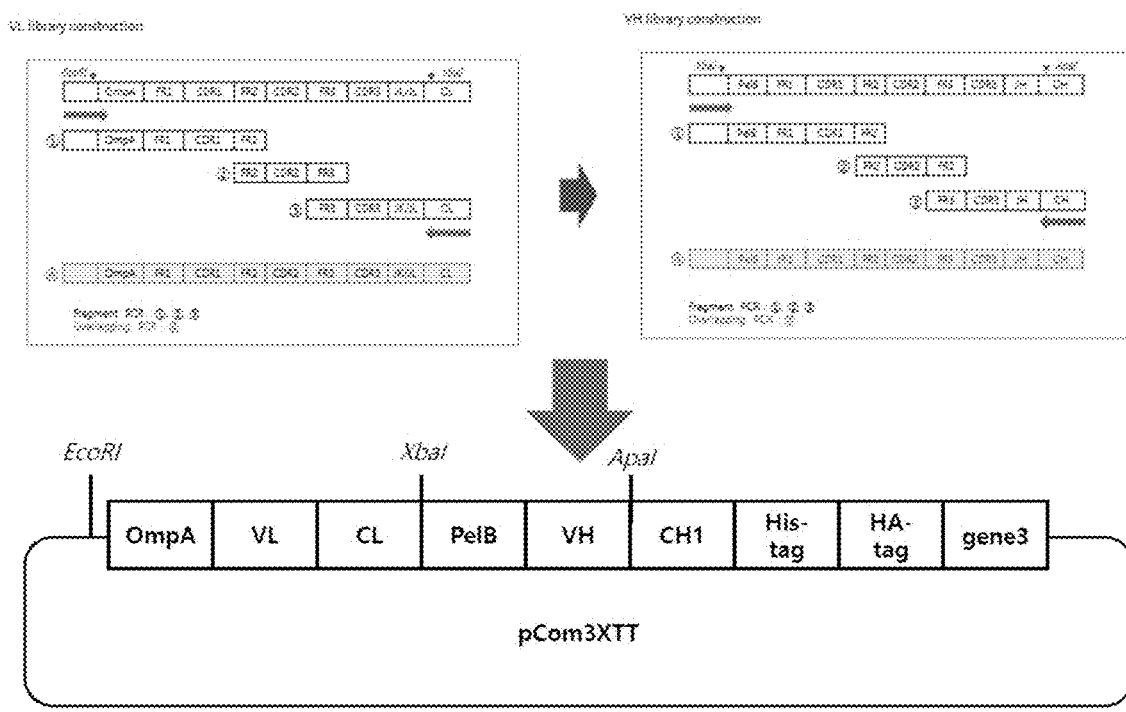
FIG. 1 is a schematic diagram showing a process of constructing a library vector according to the present invention.

That is, in one embodiment of the present invention, of the human variable region from Asian and Caucasian cDNA, VH1 and VH3 genes for the heavy-chain variable region and Vκ1, Vκ3 and Vλ1 genes for the light-chain variable region were obtained, and combinations of amino acids of the complementarity-determining region (CDR) included in the human antibody variable region were analyzed, and in particular, the heavy-chain complementarity-determining region 3 (CDRH3) was analyzed for each of 9 to 14 lengths. Asian and Caucasian variable region amino acid combinations obtained after analysis showed similarity without significant difference, and the average of the secured Asian and Caucasian combinations was calculated and then reflected in the library primer design. In the case of heavy-chain complementarity-determining region 2 (CDRH2), the possibility of occurrence of N-glycosylation sites was found to be 5% due to N-X-S/T amino acids in the analyzed combination, and the probability of occurrence of N-glycosylation sites was adjusted to 1% or less in order to prevent PTM from inhibiting the antibody-binding ability and stability in the future. Through the above method, primers for constructing a library having high diversity were designed. As a result of constructing a Fab library based on the primers, a library having a diversity of 1.54×10$^{11}$ was obtained (FIG. 1).

In one aspect, the present invention is directed to a set of antibodies or fragments thereof, wherein each antibody or fragment thereof includes a pair of a heavy-chain variable region and a light-chain variable region, wherein the heavy-chain variable region includes a framework region included in a heavy-chain variable region selected from the group consisting of VH3-15 (SEQ ID NO: 1), VH3-23 (SEQ ID NO: 6) and VH1-69 (SEQ ID NO: 11), and a combination of a heavy-chain complementarity-determining region 1 (CDRH1), a heavy-chain complementarity-determining region 2 (CDRH2), and a heavy-chain complementarity-determining region 3 (CDRH3), which are different for each heavy-chain variable region, and the light-chain variable region includes a framework region included in a light-chain variable region selected from the group consisting of Vκ1-39 (SEQ ID NO: 16), Vκ3-20 (SEQ ID NO: 21), Vκ3-20-2 (SEQ ID NO: 26) and Vλ1-51 (SEQ ID NO: 31), and a combination of a light-chain complementarity-determining region 1 (CDRL1), a light-chain complementarity-determining region 2 (CDRL2), and a light-chain complementarity-determining region 3 (CDRL3), which are different for each light-chain variable region.

Preferably, the set of antibodies or fragments thereof according to the present invention includes:
a framework region included in a pair of heavy and light-chain variable regions selected from the group consisting of VH3-15 (SEQ ID NO: 1)/Vκ1-39 (SEQ ID NO: 16), VH3-15 (SEQ ID NO: 1)/Vκ3-20 (SEQ ID NO: 21), VH3-15 (SEQ ID NO: 1)/Vκ3-20-2 (SEQ ID NO: 26), VH3-15 (SEQ ID NO: 1)/Vλ1-51 (SEQ ID NO: 31), VH3-23 (SEQ ID NO: 6)/Vκ1-39 (SEQ ID NO: 16), VH3-23 (SEQ ID NO: 6)/Vκ3-20 (SEQ ID NO: 21), VH3-23 (SEQ ID NO: 6)/Vκ3-20-2 (SEQ ID NO: 26), VH3-23 (SEQ ID NO: 6)/Vλ1-51 (SEQ ID NO: 31), VH1-69 (SEQ ID NO: 11)/Vκ1-39 (SEQ ID NO: 16), VH1-69 (SEQ ID NO: 11)/Vκ3-20 (SEQ ID NO: 21), VH1-69 (SEQ ID NO: 11)/Vκ3-20-2 (SEQ ID NO: 26) and VH1-69 (SEQ ID NO: 11)/Vλ1-51 (SEQ ID NO: 31), and
a combination of CDRH1, CDRH2 and CDRH3 different for each heavy-chain variable region and a combination of CDRL1, CDRL2 and CDRL3 different for each light-chain variable region.

In addition, in the set of antibodies or fragments thereof according to the present invention,
the framework region in the heavy-chain variable region having the sequence of VH3-15 (SEQ ID NO: 1) includes FR1 (SEQ ID NO: 2), FR2 (SEQ ID NO: 3), FR3 (SEQ ID NO: 4) and FR4 (SEQ ID NO: 5),
the framework region in the heavy-chain variable region having the sequence of VH3-23 (SEQ ID NO: 6) includes FR1 (SEQ ID NO: 7), FR2 (SEQ ID NO: 8), FR3 (SEQ ID NO: 9) and FR4 (SEQ ID NO: 10),
the framework region in the heavy-chain variable region having the sequence of VH1-69 (SEQ ID NO: 11) includes FR1 (SEQ ID NO: 12), FR2 (SEQ ID NO: 13), FR3 (SEQ ID NO: 14) and FR4 (SEQ ID NO: 15),
the framework regions in the light-chain variable region having the sequence of Vκ1-39 (SEQ ID NO: 16) includes FR1 (SEQ ID NO: 17), FR2 (SEQ ID NO: 18), FR3 (SEQ ID NO: 19) and FR4 (SEQ ID NO: 20),
the framework region in the light-chain variable region having the sequence of Vκ3-20 (SEQ ID NO: 21) includes FR1 (SEQ ID NO: 22), FR2 (SEQ ID NO: 23), FR3 (SEQ ID NO: 24) and FR4 (SEQ ID NO: 25),
the framework region in the light-chain variable region having the sequence of Vκ3-20-2 (SEQ ID NO: 26) includes FR1 (SEQ ID NO: 27), FR2 (SEQ ID NO: 28), FR3 (SEQ ID NO: 29), and FR4 (SEQ ID NO: 30), and
the framework region in the light-chain variable region having the sequence of Vλ1-51 (SEQ ID NO: 31)

includes FR1 (SEQ ID NO: 32), FR2 (SEQ ID NO: 33), FR3 (SEQ ID NO: 34) and FR4 (SEQ ID NO: 35).

The antibody or fragment thereof may be characterized in that the complementarity-determining region (CDR) included in each variable region of the pair of the heavy-chain variable region and the light-chain variable region is designed to prevent occurrence of post-traditional modification through alteration of an amino acid that has the potential to undergo post-translational modification (PTM).

In particular, regarding the CDR sequences included in the set of antibodies or fragments thereof according to the present invention, the amino acid ratio for each position in the heavy-chain complementarity-determining region 1 (CDRH1) in the heavy-chain variable region having the sequence of VH3-15 (SEQ ID NO: 1) includes the range of Table 3, the amino acid ratio for each position in the heavy-chain complementarity-determining region 2 (CDRH2) in the heavy-chain variable region having the sequence of VH3-15 (SEQ ID NO: 1) includes the range of Table 4, the amino acid ratio for each position in the heavy-chain complementarity-determining region 1 (CDRH1) in the heavy-chain variable region having the sequence of VH3-23 (SEQ ID NO: 6) includes the range of Table 3, the amino acid ratio for each position in the heavy-chain complementarity-determining region 2 (CDRH2) in the heavy-chain variable region having the sequence of VH3-23 (SEQ ID NO: 6) includes the range of Table 4, the amino acid ratio for each position in the heavy-chain complementarity-determining region 1 (CDRH1) in the heavy-chain variable region having the sequence of VH1-69 (SEQ ID NO: 11) includes the range of Table 5, the amino acid ratio for each position in the heavy-chain complementarity-determining region 2 (CDRH2) in the heavy-chain variable region having the sequence of VH1-69 (SEQ ID NO: 11) includes the range of Table 6, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 9 amino acids, the amino acid ratio for each position in the CDRH3 includes the range of Table 7, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 10 amino acids, the amino acid ratio for each position in CDRH3 includes the range of Table 8, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 11 amino acids, the amino acid ratio for each position in the CDRH3 includes the range of Table 9, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 12 amino acids, the amino acid ratio for each position in CDRH3 includes the range of Table 10, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 13 amino acids, the amino acid ratio for each position in CDRH3 includes the range of Table 11, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 14 amino acids, the amino acid ratio for each position in CDRH3 includes the range of Table 12, the amino acid ratio for each position in the light-chain complementarity-determining region 1 (CDRL1) in the light-chain variable region having the sequence of Vκ1-39 (SEQ ID NO: 16) includes the range of Table 13, the amino acid ratio for each position in the light-chain complementarity-determining region 2 (CDRL2) in the light-chain variable region having the sequence of Vκ1-39 (SEQ ID NO: 16) includes the range of Table 14, the amino acid ratio for each position in the light-chain complementarity-determining region 3 (CDRL3) in the light-chain variable region having the sequence of Vκ1-39 (SEQ ID NO: 16) includes the range of Table 15, the amino acid ratio for each position in the light-chain complementarity-determining region 1 (CDRL1) in the light-chain variable region having the sequence of Vκ3-20 (SEQ ID NO: 21) includes the range of Table 16, the amino acid ratio for each position in the light-chain complementarity-determining region 2 (CDRL2) in the light-chain variable region having the sequence of Vκ3-20 (SEQ ID NO: 21) includes the range of Table 17, the amino acid ratio for each position in the light-chain complementarity-determining region 3 (CDRL3) in the light-chain variable region having the sequence of Vκ3-20 (SEQ ID NO: 21) includes the range of Table 18, the amino acid ratio for each position in the light-chain complementarity-determining region 1 (CDRL1) in the light-chain variable region having the sequence of Vκ3-20-2 (SEQ ID NO: 26) includes the range of Table 19, the amino acid ratio for each position in the light-chain complementarity-determining region 2 (CDRL2) in the light-chain variable region having the sequence of Vκ3-20-2 (SEQ ID NO: 26) includes the range of Table 17, the amino acid ratio for each position in the light-chain complementarity-determining region 3 (CDRL3) in the light-chain variable region having the sequence of Vκ3-20-2 (SEQ ID NO: 26) includes the range of Table 18, the amino acid ratio for each position in the light-chain complementarity-determining region 1 (CDRL1) in the light-chain variable region having the sequence of Vλ1-51 (SEQ ID NO: 31) includes the range of Table 20, the amino acid ratio for each position in the light-chain complementarity-determining region 2 (CDRL2) in the light-chain variable region having the sequence of Vλ1-51 (SEQ ID NO: 31) includes the range of Table 21, and the amino acid ratio for each position in the light-chain complementarity-determining region 3 (CDRL3) in the light-chain variable region having the sequence of Vλ1-51 (SEQ ID NO: 31) includes the range of Table 22.

In particular, the set of antibodies or fragments thereof according to the present invention has one or more characteristics selected from i) to iv) below:
  i) redundancy (percentage of repetitive sequences) of 10% or less;
  ii) p-value of CDR composition >0.05;
  iii) thermal stability of 70° C. or higher; and
  iv) diversity (library size) of $10^7$ or more.

As used herein, the term "antibody" means an immunoglobulin that is selected from the group consisting of IgA, IgE, IgM, IgD, IgY and IgG and is capable of specifically binding to a target antigen. It consists of two light chains and two heavy chains, and each chain includes a variable domain having a variable amino acid sequence and a constant domain having a constant amino acid sequence. An antigen-binding site is located at the end of the three-dimensional structure of the variable domain, and this site is formed by combining three complementarity-determining regions present in each of the light and heavy chains. The complementarity-determining region is a part having particularly high variability in an amino acid sequence among the variable domains, and antibodies specific for various antigens can be found due to this high variability. The scope of the present invention includes not only a complete antibody form, but also an antigen-binding fragment of the antibody molecule.

The term "complete antibody" refers to a structure having two full-length light chains and two full-length heavy chains, wherein each light chain is linked to a corresponding heavy chain by a disulfide bond. The heavy-chain constant domain has gamma (γ), mu (μ), alpha (α), delta (δ) and epsilon (ε) types, and is subclassified into gamma 1 (γ1), gamma 2 (γ2), gamma 3 (γ3), gamma 4 (γ4), alpha 1 (α1) and alpha 2 (α2). The constant domain of the light chain has kappa (κ) and lambda (λ) types.

The term "antigen-binding fragment" according to the present invention refers to a fragment of an antibody that has antigen-binding capacity, and includes Fab, Fab', F(ab')$_2$, scFv (scFv)$_2$, scFv-Fc, Fv and the like. In the present specification, the term "antigen-binding fragment" is used interchangeably with "antibody fragment", and has the same meaning.

Among the antibody fragments, Fab refers to a structure including a variable domain of each of the heavy chain and the light chain, the constant domain of the light chain, and the first constant domain (CH1) of the heavy chain, each having one antigen-binding site. Fab' is different from Fab in that it further includes a hinge region including at least one cysteine residue at the C-terminus of the CH1 domain of the heavy chain. F(ab')$_2$ is created by a disulfide bond between cysteine residues in the hinge region of Fab'. Fv is the minimal antibody fragment having only a heavy-chain variable domain and a light-chain variable domain, and recombinant technology for producing Fv is disclosed in PCT International Publications such as WO 88/10649, WO 88/106630, WO 88/07085, WO 88/07086 and WO 88/09344. A two-chain Fv is a fragment wherein the variable domain of the heavy chain and the variable domain of the light chain are linked by a non-covalent bond, and a single-chain Fv (scFv) is a fragment wherein the variable domain of the heavy chain and the variable domain of the light chain are generally linked by a covalent bond via a peptide linker therebetween, or are directly linked at the C-terminus, forming a dimer-shaped structure, like the two-chain Fv. Such antibody fragments may be obtained using proteases (e.g., Fab can be obtained by restriction-cleaving a whole antibody with papain, and the F(ab')$_2$ fragment can be obtained by restriction-cleaving a whole antibody with pepsin), and may be produced using genetic recombination techniques.

As used herein, the term "ScFv" (single-chain Fv, single-chain fragment antibody or antibody fragment) refers to an antibody in which the variable domains of the light and heavy chains are linked. In some cases, an ScFv may include a linker (linking site) consisting of a peptide chain having about 15 linked amino acids, and in this case, ScFv may have a structure including a light-chain variable domain, a linking site, and a heavy-chain variable domain, or including a heavy-chain variable domain, a linking site, and a light-chain variable domain, and has antigen specificity the same as or similar to that of the original antibody.

As used herein, the term "antibody library" refers to a combination of various antibodies having different sequences, and means a set of a combination of specific heavy-chain variable-region and light-chain variable-region pairs in the present invention.

Nucleic acids encoding individual antibodies or fragments thereof included in the antibody library are individually contained in separate phage or host cells, and the antibodies or fragments thereof preferably are each expressed (displayed) on the surfaces of the phages or host cells, but the present invention is not limited thereto.

Examples of the host cells used for the surface expression (display) of the antibodies or fragments thereof according to the present invention include yeasts such as *Escherichia coli, Saccharomyces cerevisiae, Pichia pastoris*, and B cells of humans and mice, but are not limited thereto.

The library according to the present invention may be referred to as a "Fab library" or "scFv library" depending on the type of antibody or fragment thereof that is expressed on the surface of the phage or host cell.

In addition, as herein used, the term "antibody library" means not only a combination of specific heavy-chain variable-region and light-chain variable-region pairs at the protein level, but also combinations at the gene level encoding each specific heavy-chain variable-region and light-chain variable-region pair.

In order to separate antibodies specific for an antigen from the antibody library, very high diversity is required, and a library consisting of different antibody clones is constructed and used. The antibody genes constituting such an antibody library may be cloned into, for example, a phagemid vector and transformed into a transformant (host cell like *E. coli*).

As used herein, the term "nucleic acid" may be used interchangeably with "gene" or "nucleotide", and may be, for example, selected from the group consisting of natural/synthetic DNA, genomic DNA, natural/synthetic RNA, cDNA and cRNA, but is not limited thereto.

As used herein, the term "phagemid" vector refers to a plasmid DNA that is used for phage display and has a phage origin of replication, and generally has an antibiotic resistance gene as a selection marker. The phagemid vector used for phage display includes the gIII gene of the M13 phage or a portion thereof, and the ScFv gene is ligated to the 5' end of the gIII gene and is expressed through a transformant.

As used herein, the term "helper phage" refers to a phage that provides the necessary genetic information so that the phagemid is packaged into phage particles. Since only gIII of the phage genes or a portion thereof is present in the phagemid, host cells (transformants) transformed with the phagemid are infected with a helper phage to thereby supply the remaining phage genes. There are types such as M13K07 or VCSM13, and most thereof include antibiotic resistance genes such as kanamycin, so that transformants infected with the helper phage can be selected. In addition, because the packaging signal is defective, phagemid genes, rather than helper phage genes, are selectively packaged into phage particles.

As used herein, the term "signal sequence" refers to a base sequence or an amino acid sequence corresponding thereto, which is located at the 5' end of a gene and functions as a necessary signal when the protein encoded from the gene is secreted to the outside.

As used herein, the term "phage display" is a technique for displaying a mutant polypeptide as a fusion protein with at least a part of a coat protein, for example, on the surface of the particle of a phage, for example, a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for generating and screening novel proteins that bind to specific ligands (e.g., antigens). Using phage display technology, large libraries of protein mutants can be produced and sequences binding with high affinity to target antigens can be rapidly classified. A nucleic acid encoding a mutant polypeptide is fused with a nucleic acid sequence encoding a viral coat protein, e.g., a gene III or gene VIII protein. A monophasic phage display system, in which a nucleic acid sequence encoding a protein or polypeptide is fused with a nucleic acid sequence encoding a part of the gene III protein, has been developed. In the monophasic display system, a fused gene is expressed at a low level and a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody or antigen-binding polypeptides are prepared by a number of methods, for example, methods of modifying a single gene by inserting a random DNA sequence or cloning a related gene sequence. The libraries can be screened for the expression of antibody or antigen-binding proteins having desired characteristics.

Phage display technology has several advantages over conventional hybridomas and recombinant methods for producing antibodies having desired characteristics. This technique provides the production of large antibody libraries with a variety of sequences within a short time without using animals. The production of hybridomas and the production of humanized antibodies may require a production time of several months. In addition, since no immunity is required, the phage antibody libraries is capable of producing antibodies against antigens that are unsensitized toxic or have low antigenicity. The phage antibody libraries can also be used to produce and identify novel therapeutic antibodies.

Techniques for generating human antibodies from immunized humans, non-immunized humans, germline sequences, or unsensitized B-cell Ig repertoires using phage display libraries can be used. Various lymphatic tissues can be used to produce unsensitized or non-immunogenic antigen-binding libraries.

Techniques for identifying and separating high-affinity antibodies from phage display libraries are important for the separation of new therapeutic antibodies. The separation of high-affinity antibodies from the libraries depends on the size of the libraries, the production efficiency in bacterial cells, and the variety of libraries. The size of the libraries is reduced by inappropriate folding of the antibody- or antigen-binding protein and inefficient production due to the presence of a stop codon. Expression in bacterial cells can be inhibited when the antibody- or antigen-binding domain is not properly folded. Expression can be improved by alternately mutating residues on the surface of the variable/constant interfaces or the selected CDR residues. The sequence of the framework region is an element for providing appropriate folding when producing antibody phage libraries in bacterial cells.

It is important to generate various libraries of antibody- or antigen-binding proteins in the separation of high-affinity antibodies. CDR3 regions have often been found to participate in antigen binding. Since a CDR3 region on a heavy chain varies considerably in terms of size, sequence and structural/dimensional morphology, various libraries can be prepared using the same.

Also, diversity can be created by randomizing the CDR regions of variable heavy and light chains using all 20 amino acids at each position. The use of all 20 amino acids results in antibody sequences with great diversity and an increased chance of identifying new antibodies.

As used herein, the term "antibody variable domain" refers to the light- and heavy-chain regions of an antibody molecule including the amino acid sequences of a complementarity-determining region (CDR; i.e., CDR1, CDR2, and CDR3) and a framework region (FR). VH refers to a variable domain of a heavy chain. VL refers to a variable domain of a light chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

The term "framework region" (FR) refers to a variable domain residue other than a CDR residue. Each variable domain typically has four FRs, identified as FR1, FR2, FR3, and FR4.

Preferably, the set of antibodies or fragments thereof according to the present invention includes:
    a framework region included in a pair of heavy and light-chain variable regions selected from the group consisting of VH3-15 (SEQ ID NO: 1)/Vκ1-39 (SEQ ID NO: 16), VH3-15 (SEQ ID NO: 1)/Vκ3-20 (SEQ ID NO: 21), VH3-15 (SEQ ID NO: 1)/Vκ3-20-2 (SEQ ID NO: 26), VH3-15 (SEQ ID NO: 1)/Vλ1-51 (SEQ ID NO: 31), VH3-23 (SEQ ID NO: 6)/Vκ1-39 (SEQ ID NO: 16), VH3-23 (SEQ ID NO: 6)/Vκ3-20 (SEQ ID NO: 21), VH3-23 (SEQ ID NO: 6)/Vκ3-20-2 (SEQ ID NO: 26), VH3-23 (SEQ ID NO: 6)/Vλ1-51 (SEQ ID NO: 31), VH1-69 (SEQ ID NO: 11)/Vκ1-39 (SEQ ID NO: 16), VH1-69 (SEQ ID NO: 11)/Vκ3-20 (SEQ ID NO: 21), VH1-69 (SEQ ID NO: 11)/Vκ3-20-2 (SEQ ID NO: 26) and VH1-69 (SEQ ID NO: 11)/Vλ1-51 (SEQ ID NO: 31), and a combination of CDRH1, CDRH2 and CDRH3 different for each heavy-chain variable region, and a combination of CDRL1, CDRL2 and CDRL3 different for each light-chain variable region.

In the present invention, the framework region in the heavy-chain variable region having the sequence of VH3-15 (SEQ ID NO: 1) includes FR1 (SEQ ID NO: 2), FR2 (SEQ ID NO: 3), FR3 (SEQ ID NO: 4) and FR4 (SEQ ID NO: 5),
    the framework region in the heavy-chain variable region having the sequence of VH3-23 (SEQ ID NO: 6)

includes FR1 (SEQ ID NO: 7), FR2 (SEQ ID NO: 8), FR3 (SEQ ID NO: 9) and FR4 (SEQ ID NO: 10),
the framework region in the heavy-chain variable region having the sequence of VH1-69 (SEQ ID NO: 11) includes FR1 (SEQ ID NO: 12), FR2 (SEQ ID NO: 13), FR3 (SEQ ID NO: 14) and FR4 (SEQ ID NO: 15),
the framework region in the light-chain variable region having the sequence of Vκ1-39 (SEQ ID NO: 16) includes FR1 (SEQ ID NO: 17), FR2 (SEQ ID NO: 18), FR3 (SEQ ID NO: 19) and FR4 (SEQ ID NO: 20),
the framework region in the light-chain variable region having the sequence of Vκ3-20 (SEQ ID NO: 21) includes FR1 (SEQ ID NO: 22), FR2 (SEQ ID NO: 23), FR3 (SEQ ID NO: 24) and FR4 (SEQ ID NO: 25),
the framework region in the light-chain variable region having the sequence of Vκ3-20-2 (SEQ ID NO: 26) includes FR1 (SEQ ID NO: 27), FR2 (SEQ ID NO: 28), FR3 (SEQ ID NO: 29), and FR4 (SEQ ID NO: 30), and
the framework region in the light-chain variable region having the sequence of Vλ1-51 (SEQ ID NO: 31) includes FR1 (SEQ ID NO: 32), FR2 (SEQ ID NO: 33), FR3 (SEQ ID NO: 34) and FR4 (SEQ ID NO: 35).

The sequences of the heavy-chain variable region, the light-chain variable region, and the framework regions within each variable region of the present invention are summarized as follows:

TABLE 1

| | Amino acid sequences of variable regions and framework regions | |
|---|---|---|
| | Sequence information | SEQ ID NO |
| VH3-15 | EVQLVESGGGLVKPGGSLRLSCAASG-X-WVRQAPGKGLEWV-X-YAAPVKGRFTISRDDSKNTLYLQMNSLKTEDTAVYYCAR-X-WGQGTLVTVSS | 1 |
| FR1 | EVQLVESGGGLVKPGGSLRLSCAASG | 2 |
| FR2 | WVRQAPGKGLEWV | 3 |
| FR3 | YAAPVKGRFTISRDDSKNTLYLQMNSLKTEDTAVYYCAR | 4 |
| FR4 | WGQGTLVTVSS | 5 |
| VH3-23 | EVQLVESGGGLVQPGGSLRLSCAASG-X-WVRQAPGKGLEWV-X-YADSVKGRFTISRDNSKNTLYLQMNSLRAEDTAVYYCAR-X-WGQGTLVTVSS | 6 |
| FR1 | EVQLVESGGGLVQPGGSLRLSCAASG | 7 |
| FR2 | WVRQAPGKGLEWV | 8 |
| FR3 | YADSVKGRFTISRDNSKNTLYLQMNSLRAEDTAVYYCAR | 9 |
| FR4 | WGQGTLVTVSS | 10 |
| VH1-69 | QVQLVQSGAEVKKPGSSVKVSCKASG-X-WVRQAPGQGLEWM-X-YAQKFQGRVTITADESTSTAYMELSSLRSEDTAVYYCAR-X-WGQGTLVTVSS | 11 |
| FR1 | QVQLVQSGAEVKKPGSSVKVSCKASG | 12 |
| FR2 | WVRQAPGQGLEWM | 13 |
| FR3 | YAQKFQGRVTITADESTSTAYMELSSLRSEDTAVYYCAR | 14 |
| FR4 | WGQGTLVTVSS | 15 |
| Vκ1-39 | DIQMTQSPSSLSASVGDRVTITCRASQ-X-WYQQKPGKAPKLLIY-X-GVPSRFSGSGSGTDFTLTISSLQPEDFATYYCQQ-X-TFGQGTKVEIK | 16 |
| FR1 | DIQMTQSPSSLSASVGDRVTITCRASQ | 17 |
| FR2 | WYQQKPGKAPKLLIY | 18 |
| FR3 | GVPSRFSGSGSGTDFTLTISSLQPEDFATYYCQQ | 19 |
| FR4 | TFGQGTKVEIK | 20 |
| Vκ3-20 | EIVLTQSPGTLSLSPGERATLSCRASQ-X-WYQQKPGQAPRLLI-X-IPDRFSGSGSGTDFTLTISRLEPEDFAVYYCQQ-X-TFGQGTKVEIK | 21 |
| FR1 | EIVLTQSPGTLSLSPGERATLSCRASQ | 22 |

TABLE 1-continued

Amino acid sequences of variable regions and framework regions

| | Sequence information | SEQ ID NO |
|---|---|---|
| FR2 | WYQQKPGQAPRLLI | 23 |
| FR3 | IPDRFSGSGSGTDFTLTISRLEPEDFAVYYCQQ | 24 |
| FR4 | TFGQGTKVEIK | 25 |
| Vκ3-20-2 | EIVLTQSPGTLSLSPGERATLSCRASQ-X-WYQQKPGQAPRLLI-X- IPDRFSGSGSGTDFTLTISRLEPEDFAVYYCQQ-X-TFGQGTKVEIK | 26 |
| FR1 | EIVLTQSPGTLSLSPGERATLSCRASQ | 27 |
| FR2 | WYQQKPGQAPRLLI | 28 |
| FR3 | IPDRFSGSGSGTDFTLTISRLEPEDFAVYYCQQ | 29 |
| FR4 | TFGQGTKVEIK | 30 |
| Vλ1-51 | QSVLTQPPSVSAAPGQKVTISCSG-X-WYQQLPGTAPKLLI-X-RPSGIPDRFSGSKSGTSATLGITGLQTGDEADYYC-X-FGGGTKLTVL | 31 |
| FR1 | QSVLTQPPSVSAAPGQKVTISCSG | 32 |
| FR2 | WYQQLPGTAPKLLI | 33 |
| FR3 | RPSGIPDRFSGSKSGTSATLGITGLQTGDEADYYC | 34 |
| FR4 | FGGGTKLTVL | 35 |

TABLE 2

Sequences of nucleic acid encoding variable regions and framework regions

| | Sequence information | SEQ ID NO |
|---|---|---|
| VH3-15 | Gaagtgcaacttgtcgaatctggcggcggcttagtgaaaccaggcggcagccttcgtttaagctgtgcagcatctggt-N-tgggttcgtcaggcaccaggtaaaggtcttgaatgggtg-N-tacgcagcaccggtcaaaggtcgttttacgattagtcgcgatgattcgaaaaacactctttacctgcagatgaattctctgaaaacagaagataccgcagtgtattactgtgcacgt-N-tggggtcaaggtacactggttaccgttagctcg | 36 |
| FR1 | gaagtgcaacttgtcgaatctggcggcggcttagtgaaaccaggcggcagccttcgtttaagctgtgcagcatctggt | 37 |
| FR2 | tgggttcgtcaggcaccaggtaaaggtcttgaatgggtg | 38 |
| FR3 | tacgcagcaccggtcaaaggtcgttttacgattagtcgcgatgattcgaaaaacactctttacctgcagatgaattctctgaaaacagaagataccgcagtgtattactgtgcacgt | 39 |
| FR4 | tggggtcaaggtacactggttaccgttagctcg | 40 |
| VH3-23 | Gaagtgcaacttgtcgaatctggcggcggcttagtgcagccaggcggcagccttcgtttaagctgtgcagcatctggt-N-tgggttcgtcaggcaccaggtaaaggtcttgaatgggtg-N-tatgcggatagcgttaaggtgtcgttttaccatcagtcgcgacaactccaaaaatacccctgtacttacaaatgaatagcttacgtgcggaagataccgcagtgtattactgtgcacgt-N-tggggtcaaggtacactggttaccgttagctcg | 41 |
| FR1 | gaagtgcaacttgtcgaatctggcggcggcttagtgcagccaggcggcagccttcgtttaagctgtgcagcatctggt | 42 |
| FR2 | tgggttcgtcaggcaccaggtaaaggtcttgaatgggtg | 43 |
| FR3 | tatgcggatagcgttaaggtgtcgttttaccatcagtcgcgacaactccaaaaatacccctgtacttacaaatgaatagcttacgtgcggaagataccgcagtgtattactgtgcacgt | 44 |

TABLE 2-continued

Sequences of nucleic acid encoding variable regions and framework regions

| | Sequence information | SEQ ID NO |
|---|---|---|
| FR4 | tggggtcaaggtacactggttaccgttagctcg | 45 |
| VH1-69 | Caggtccaactggttcagtctggtgcggaagttaaaaagccaggaagttcagttaaagtcagttgtaa agcgtctggt-N-tgggttcgtcaagcaccaggacagggcttagaatggatg-N-tatgcacagaaattccaaggtcgtgttacgattacggccgatgagtccactagtaccgcctatatggaa ctctccagccttcgctctgaagataccgcagtgtattactgtgcacgt-N-tggggtcaaggtacactggttaccgttagctcg | 46 |
| FR1 | caggtccaactggttcagtctggtgcggaagttaaaaagccaggaagttcagttaaagtcagttgtaa gcgtctggt | 47 |
| FR2 | tgggttcgtcaagcaccaggacagggcttagaatggatg | 48 |
| FR3 | tatgcacagaaattccaaggtcgtgttacgattacggccgatgagtccactagtaccgcctatatggaa ctctccagccttcgctctgaagataccgcagtgtattactgtgcacgt | 49 |
| FR4 | tggggtcaaggtacactggttaccgttagctcg | 50 |
| Vκ-39 | Gacatccaaatgacacagagcccttcttccttatccgcgtcggtaggagatcgcgttacaatcacctgc cgtgcgagtcag-N-tggtatcagcagaaaccagggaaagcaccgaagctcctgatttat-N-ggcgttccgagccgttttagtggctcggggtccggcaccgacttcaccctgactatctcttcgctgcag cctgaggattttgctacctattactgtcaacag-N-acattcgggcagggtaccaaagtggaaattaaa | 51 |
| FR1 | gacatccaaatgacacagagcccttcttccttatccgcgtcggtaggagatcgcgttacaatcacctgc cgtgcgagtcag | 52 |
| FR2 | tggtatcagcagaaaccagggaaagcaccgaagctcctgatttat | 53 |
| FR3 | ggcgttccgagccgttttagtggctcggggtccggcaccgacttcaccctgactatctcttcgctgcag cctgaggattttgctacctattactgtcaacag | 54 |
| FR4 | acattcgggcagggtaccaaagtggaaattaaa | 55 |
| Vκ3-20 | Gaaattgtactgacccaaagtcctgggacactgagtctgagtccaggtgaacgtgctacccttagctg ccgtgcgagtcaa-N-tggtaccaacaaaagcctggtcaggcaccacgtctgctgatc-N-attccggaccgtttctctggctccggctcgggtactgattttaccctgactatctctcgtttagaacctgag gattttgctgtttattactgtcaacag-N-acattcgggcagggtaccaaagtggaaattaaa | 56 |
| FR1 | gaaattgtactgacccaaagtcctgggacactgagtctgagtccaggtgaacgtgctacccttagctgc cgtgcgagtcaa | 57 |
| FR2 | tggtaccaacaaaagcctggtcaggcaccacgtctgctgatc | 58 |
| FR3 | attccggaccgtttctctggctccggctcgggtactgattttaccctgactatctctcgtttagaacctgag gattttgctgtttattactgtcaacag | 59 |
| FR4 | acattcgggcagggtaccaaagtggaaattaaa | 60 |
| Vκ3-20-2 | Gaaattgtactgacccaaagtcctgggacactgagtctgagtccaggtgaacgtgctacccttagctg ccgtgcgagtcaa-N-tggtaccaacaaaagcctggtcaggcaccacgtctgctgatc-N-attccggaccgtttctctggctccggctcgggtactgattttaccctgactatctctcgtttagaacctgag gattttgctgtttattactgtcaacag-N-acattcgggcagggtaccaaagtggaaattaaa | 61 |
| FR1 | gaaattgtactgacccaaagtcctgggacactgagtctgagtccaggtgaacgtgctacccttagctgc cgtgcgagtcaa | 62 |
| FR2 | tggtaccaacaaaagcctggtcaggcaccacgtctgctgatc | 63 |
| FR3 | attccggaccgtttctctggctccggctcgggtactgattttaccctgactatctctcgtttagaacctgag gattttgctgtttattactgtcaacag | 64 |
| FR4 | acattcgggcagggtaccaaagtggaaattaaa | 65 |
| Vλ1-51 | Caatcagttctgacccaaccccctctgtatccgcggcacccggtcaaaaggtgaccatctcgtgctc tggc-N-tggtatcaacagcttccaggtacagcaccgaagttattgatt-N-cgtccttccggtattccggatcgttttcggggagtaaaagtggcacctcagcaacacttggtattaccg gactgcagaccggcgacgaagccgattactactgc-N-ttcggtggtggcaccaaacttacggtcctg | 66 |
| FR1 | caatcagttctgacccaaccccctctgtatccgcggcacccggtcaaaaggtgaccatctcgtgctct ggc | 67 |
| FR2 | tggtatcaacagcttccaggtacagcaccgaagttattgatt | 68 |

TABLE 2-continued

Sequences of nucleic acid encoding variable regions and framework regions

| | Sequence information | SEQ ID NO |
|---|---|---|
| FR3 | cgtccttccggtattccggatcgtttttcggggagtaaaagtggcacctcagcaacacttggtattaccg gactgcagaccggcgacgaagccgattactactgc | 69 |
| FR4 | ttcggtggtggcaccaaacttacggtcctg | 70 |

In the present invention, the antibody or fragment thereof may be characterized in that in that the complementarity-determining region (CDR) included in each variable region of the pair of the heavy-chain variable region and the light-chain variable region is designed to prevent occurrence of post-traditional modification through alteration of an amino acid that has the potential to undergo post-translational modification (PTM).

In the present invention, the amino acid ratio for each position in the heavy-chain complementarity-determining region 1 (CDRH1) in the heavy-chain variable region having the sequence of VH3-15 (SEQ ID NO: 1) includes the range of Table 3, the amino acid ratio for each position in the heavy-chain complementarity-determining region 2 (CDRH2) in the heavy-chain variable region having the sequence of VH3-15 (SEQ ID NO: 1) includes the range of Table 4, the amino acid ratio for each position in the heavy-chain complementarity-determining region 1 (CDRH1) in the heavy-chain variable region having the sequence of VH3-23 (SEQ ID NO: 6) includes the range of Table 3, the amino acid ratio for each position in the heavy-chain complementarity-determining region 2 (CDRH2) in the heavy-chain variable region having the sequence of VH3-23 (SEQ ID NO: 6) includes the range of Table 4, the amino acid ratio for each position in the heavy-chain complementarity-determining region 1 (CDRH1) in the heavy-chain variable region having the sequence of VH1-69 (SEQ ID NO: 11) includes the range of Table 5, the amino acid ratio for each position in the heavy-chain complementarity-determining region 2 (CDRH2) in the heavy-chain variable region having the sequence of VH1-69 (SEQ ID NO: 11) includes the range of Table 6, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 9 amino acids, the amino acid ratio for each position in the CDRH3 includes the range of Table 7, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 10 amino acids, the amino acid ratio for each position in CDRH3 includes the range of Table 8, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 11 amino acids, the amino acid ratio for each position in the CDRH3 includes the range of Table 9, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 12 amino acids, the amino acid ratio for each position in CDRH3 includes the range of Table 10, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 13 amino acids, the amino acid ratio for each position in CDRH3 includes the range of Table 11, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 14 amino acids, the amino acid ratio for each position in CDRH3 includes the range of Table 12, the amino acid ratio for each position in the light-chain complementarity-determining region 1 (CDRL1) in the light-chain variable region having the sequence of Vκ1-39 (SEQ ID NO: 16) includes the range of Table 13, the amino acid ratio for each position in the light-chain complementarity-determining region 2 (CDRL2) in the light-chain variable region having the sequence of Vκ1-39 (SEQ ID NO: 16) includes the range of Table 14, the amino acid ratio for each position in the light-chain complementarity-determining region 3 (CDRL3) in the light-chain variable region having the sequence of Vκ1-39 (SEQ ID NO: 16) includes the range of Table 15, the amino acid ratio for each position in the light-chain complementarity-determining region 1 (CDRL1) in the light-chain variable region having the sequence of Vκ3-20 (SEQ ID NO: 21) includes the range of Table 16, the amino acid ratio for each position in the light-chain complementarity-determining region 2 (CDRL2) in the light-chain variable region having the sequence of Vκ3-20 (SEQ ID NO: 21) includes the range of Table 17, the amino acid ratio for each position in the light-chain complementarity-determining region 3 (CDRL3) in the light-chain variable region having the sequence of Vκ3-20 (SEQ ID NO: 21) includes the range of Table 18, the amino acid ratio for each position in the light-chain complementarity-determining region 1 (CDRL1) in the light-chain variable region having the sequence of Vκ3-20-2 (SEQ ID NO: 26) includes the range of Table 19, the amino acid ratio for each position in the light-chain complementarity-determining region 2 (CDRL2) in the light-chain variable region having the sequence of Vκ3-20-2 (SEQ ID NO: 26) includes the range of Table 17, the amino acid ratio for each position in the light-chain complementarity-determining region 3 (CDRL3) in the light-chain variable region having the sequence of Vκ3-20-2 (SEQ ID NO: 26) includes the range of Table 18, the amino acid ratio for each position in the light-chain complementarity-determining region 1 (CDRL1) in the light-chain variable region having the sequence of Vλ1-51 (SEQ ID NO: 31) includes the range of Table 20, the amino acid ratio for each position in the light-chain complementarity-determining region 2 (CDRL2) in the light-chain variable region having the sequence of Vλ1-51 (SEQ ID NO: 31) includes the range of Table 21, and the amino acid ratio for each position in the light-chain complementarity-determining region 3 (CDRL3) in the light-chain variable region having the sequence of Vλ1-51 (SEQ ID NO: 31) includes the range of Table 22, but is not limited thereto.

TABLE 3

Amino acid distribution ratio for each position of amino acid(%) - VH3_CDR1

| Type of AA | 27 | 28 | 29 | 30 | 31 | 32 |
|---|---|---|---|---|---|---|
| Alanine(A) | 0-0.001 | 2-6 | 5-15 | 1-5 | 1-4 | 1-5 |
| Serine(S) | 20-30 | 0.1-0.5 | 0.01-0.1 | 0-0.001 | 0.01-0.1 | 0.01-0.1 |
| Glycine(G) | 0-0.001 | 0.5-3 | 0-0.001 | 1-5 | 10-20 | 0.5-2 |
| Phenylalanine(F) | 0-0.001 | 0.01-0.1 | 0-0.001 | 0.1-1 | 0.5-3 | 0-0.001 |
| Proline(P) | 60-70 | 0.5-3 | 80-90 | 0.1-1 | 0.5-3 | 3-8 |
| Valine(V) | 0.01-0.1 | 0.1-1 | 0.1-1 | 1-3 | 5-15 | 0-0.001 |
| Tyrosine(Y) | 0.01-0.1 | 0-0.001 | 0-0.001 | 0.5-3 | 1-3 | 5-15 |
| Methionine(M) | 0-0.001 | 5-12 | 0.1-1 | 1-4 | 0.5-3 | 0.3-2 |
| Threonine(T) | 0-0.001 | 1-5 | 0-0.001 | 0.5-3 | 1-5 | 5-15 |
| Lysine(K) | 1-4 | 0.01-0.1 | 2-6 | 1-4 | 0.3-2 | 3-8 |
| Isoleucine(I) | 0-0.001 | 0.5-2 | 0-0.001 | 0-0.001 | 0-0.001 | 0-0.001 |
| Tryptophan(W) | 0-0.001 | 0.1-1 | 0-0.001 | 10-20 | 20-30 | 3-9 |
| Aspartic acid(D) | 0-0.001 | 0.5-8 | 0-0.001 | 5-15 | 0.05-0.5 | 0.1-1 |
| Histidine(H) | 0-0.001 | 5-15 | 0-0.001 | 0.5-3 | 0.5-2 | 0.1-0.5 |
| Asparagine(N) | 5-15 | 0.5-3 | 0.01-0.1 | 1-5 | 1-4 | 0.1-1 |
| Arginine(R) | 0.1-1 | 5-15 | 0.1-1 | 30-40 | 15-25 | 2-7 |
| Glutamic acid(E) | 0-0.001 | 50-60 | 0.01-0.1 | 15-25 | 5-10 | 0.5-2 |
| Cysteine(C) | 0.01-0.1 | 0.01-0.05 | 0.05-0.5 | 0.1-1 | 0.1-2 | 0.1-0.5 |
| Leucine(L) | 0-0.001 | 0.05-0.1 | 0-0.001 | 0-0.001 | 0.01-0.1 | 0-0.001 |
| Glutamine(Q) | 0.05-0.3 | 2-6 | 0.01-0.1 | 0-0.001 | 0.5-3 | 45-55 |

| Type of AA | 33 | 34 | 35 |
|---|---|---|---|
| Alanine(A) | 20-30 | 0.01-0.1 | 1-5 |
| Serine(S) | 0.1-1 | 0-0.001 | 0.01-0.05 |
| Glycine(G) | 3-9 | 0.01-0.1 | 0.5-3 |
| Phenylalanine(F) | 0.5-3 | 0-0.001 | 5-15 |
| Proline(P) | 0.5-3 | 0.5-2 | 0-0.001 |
| Valine(V) | 15-25 | 0.1-0.5 | 1-5 |
| Tyrosine(Y) | 0.5-3 | 0-0.001 | 35-45 |
| Methionine(M) | 0.5-3 | 5-12 | 0.5-3 |
| Threonine(T) | 0.01-0.1 | 0-0.001 | 0-0.001 |
| Lysine(K) | 0.5-3 | 15-25 | 0.05-0.5 |
| Isoleucine(I) | 0-0.001 | 0-0.001 | 0-0.001 |
| Tryptophan(W) | 0.5-3 | 0-0.001 | 15-25 |
| Aspartic acid(D) | 0.5-3 | 0-0.001 | 0.1-1 |
| Histidine(H) | 0.1-0.5 | 0-0.001 | 1-4 |
| Asparagine(N) | 2-6 | 0.1-0.5 | 0.1-1 |
| Arginine(R) | 3-8 | 0.1-0.5 | 10-20 |
| Glutamic acid(E) | 1-4 | 0-0.001 | 1-4 |
| Cysteine(C) | 0.5-3 | 65-75 | 0.1-0.5 |
| Leucine(L) | 10-20 | 0-0.001 | 0-0.001 |
| Glutamine(Q) | 5-15 | 0.1-0.5 | 0.5-3 |

TABLE 4

Amino acid distribution ratio for each position of amino acid(%) - VH3_CDR2

| Type of AA | 49 | 50 | 51 | 52 | 52a | 53 | 54 | 55 |
|---|---|---|---|---|---|---|---|---|
| Alanine(A) | 35-45 | 5-15 | 0-0.001 | 0.5-3 | 2-6 | 25-35 | 0-0.01 | 3-8 |
| Serine(S) | 50-60 | 10-20 | 0.01-0.1 | 55-65 | 15-25 | 3-9 | 20-30 | 30-40 |
| Glycine(G) | 1-4 | 10-20 | 0-0.001 | 1-4 | 10-20 | 0.01-0.1 | 70-80 | 10-20 |
| Phenylalanine(F) | 0-0.001 | 3-9 | 0-0.01 | 0.05-0.1 | 1-4 | 0.01-0.1 | 0-0.001 | 0.5-3 |
| Proline(P) | 0.01-0.1 | 0.01-0.05 | 0-0.001 | 0.1-1 | 1-4 | 0.01-0.1 | 0-0.001 | 0.01-0.1 |
| Valine(V) | 0.01-0.1 | 15-25 | 0.01-0.1 | 0-0.01 | 0.5-3 | 0.01-0.1 | 0.01-0.2 | 1-4 |
| Tyrosine(Y) | 0-0.01 | 15-25 | 0-0.01 | 0.5-3 | 10-20 | 0.01-0.1 | 0-0.001 | 0.5-3 |

TABLE 4-continued

Amino acid distribution ratio for each position of amino acid(%) - VH3_CDR2

| | | | | | | | | |
|---|---|---|---|---|---|---|---|---|
| Methionine(M) | 0-0.001 | 0-0.01 | 0-0.01 | 0-0.01 | 0-0.01 | 1-4 | 0-0.01 | 0-0.01 |
| Threonine(T) | 0.01-0.1 | 3-8 | 0.1-0.5 | 2-6 | 1-5 | 0-0.01 | 0-0.001 | 5-10 |
| Lysine(K) | 0-0.001 | 0.1-1 | 0-0.001 | 15-25 | 1-4 | 0.1-1 | 0-0.01 | 0.5-2 |
| Isoleucine(I) | 0-0.001 | 1-4 | 95-99.98 | 0.1-1 | 0.5-3 | 0-0.01 | 0.01-0.05 | 0.5-3 |
| Tryptophan(W) | 0-0.01 | 0-0.001 | 0-0.001 | 3-9 | 5-15 | 50-60 | 0.01-0.1 | 0.01-0.05 |
| Aspartic acid(D) | 0-0.01 | 0.01-0.05 | 0-0.01 | 0-0.001 | 0.01-0.05 | 0.5-3 | 0.01-0.1 | 5-15 |
| Histidine(H) | 0.01-0.1 | 1-4 | 0-0.01 | 0.5-3 | 2-6 | 0.01-0.1 | 0-0.001 | 0.5-3 |
| Asparagine(N) | 0-0.001 | 0-0.01 | 0.01-0.05 | 0.01-0.005 | 4-10 | 0.3-2 | 0.01-0.05 | 5-15 |
| Arginine(R) | 0.01-0.1 | 0.05-2 | 0-0.001 | 1-4 | 0.5-3 | 0.5-2 | 0.01-0.05 | 0.5-1 |
| Glutamic acid(E) | 0.01-0.1 | 0-0.01 | 0-0.001 | 0.01-0.1 | 1-4 | 0-0.01 | 0-0.01 | 1-4 |
| Cysteine(C) | 0-0.001 | 0.01-0.05 | 0-0.001 | 0.01-0.1 | 0.01-0.1 | 0.01-0.1 | 0.01-0.1 | 0.01-0.05 |
| Leucine(L) | 0.01-0.1 | 3-8 | 0-0.03 | 1-3 | 1-4 | 0-0.01 | 0-0.01 | 1-4 |
| Glutamine(Q) | 0.01-0.1 | 0-0.01 | 0-0.001 | 0.5-2 | 5-12 | 0.5-3 | 0-0.01 | 0-0.01 |

| Type of AA | 56 | 57 | 58 | 59 | 60 |
|---|---|---|---|---|---|
| Alanine(A) | 1-5 | 0.5-3 | 1-4 | 0-0.001 | 95-99.99 |
| Serine(S) | 10-20 | 0.5-3 | 0.01-0.1 | 0-0.01 | 0-0.01 |
| Glycine(G) | 1-4 | 0-0.01 | 1-5 | 0-0.001 | 0-0.001 |
| Phenylalanine(F) | 0.5-2 | 0-0.01 | 3-9 | 0-0.01 | 0-0.0001 |
| Proline(P) | 0.1-1.5 | 0.1-1 | 0-0.01 | 0-0.001 | 0-0.01 |
| Valine(V) | 0.5-3 | 0.5-3 | 0.1-1 | 0-0.001 | 0.01-0.1 |
| Tyrosine(Y) | 3-9 | 0-0.01 | 55-65 | 95-99.99 | 0-0.001 |
| Methionine(M) | 0-0.01 | 0.5-3 | 0-0.01 | 0.01-0.1 | 0-0.001 |
| Threonine(T) | 5-15 | 20-30 | 0.01-0.1 | 0-0.001 | 0.01-0.1 |
| Lysine(K) | 2-6 | 30-40 | 0.5-3 | 0-0.001 | 0-0.001 |
| Isoleucine(I) | 1-5 | 20-30 | 0.1-2 | 0-0.01 | 0-0.501 |
| Tryptophan(W) | 0-0.01 | 0-0.001 | 0.5-2 | 0-0.001 | 0-0.001 |
| Aspartic acid(D) | 3-9 | 0-0.01 | 2-8 | 0-0.01 | 0-0.001 |
| Histidine(H) | 1-4 | 0.01-0.05 | 4-10 | 0.01-0.1 | 0-0.0051 |
| Asparagine(N) | 25-35 | 0.01-0.1 | 4-10 | 0-0.01 | 0-0.001 |
| Arginine(R) | 0.5-3 | 0.5-3 | 0.1-1 | 0-0.001 | 0.01-0.1 |
| Glutamic acid(E) | 5-12 | 3-8 | 0.5-3 | 0-0.001 | 0.01-0.1 |
| Cysteine(C) | 0.01-0.05 | 0-0.01 | 0.01-0.1 | 0.01-0.1 | 0.01-0.1 |
| Leucine(L) | 1-4 | 1-4 | 0.5-3 | 0.01-0.1 | 0-0.001 |
| Glutamine(Q) | 0.5-3 | 1-4 | 0.5-3 | 0-0.001 | 0-0.001 |

TABLE 5

Amino acid distribution ratio for each position of amino acid(%) - VH1-69_CDR1

| Type of AA | 27 | 28 | 29 | 30 | 31 | 32 | 33 | 34 | 35 |
|---|---|---|---|---|---|---|---|---|---|
| Alanine(A) | 0-0.01 | 2-5 | 0-0.001 | 1-5 | 1-4 | 2-5 | 30-40 | 0.05-0.5 | 1-7 |
| Serine(S) | 0.5-3 | 10-20 | 0.05-0.5 | 40-50 | 20-30 | 4-8 | 3-6 | 0.01-0.1 | 10-20 |
| Glycine(G) | 2-6 | 0.1-1 | 0-0.001 | 1-4 | 1-4 | 0-0.001 | 5-15 | 0.5-3 | 1-5 |
| Phenylalanine(F) | 40-50 | 0.01-0.1 | 95-99.99 | 0.01-0.1 | 0.01-0.05 | 4-8 | 0.5-3 | 0.01-0.1 | 0.01-0.05 |
| Proline(P) | 0-0.001 | 0.5-3 | 0-0.01 | 0.5-3 | 0.01-0.05 | 0.01-0.05 | 0.5-3 | 0-0.01 | 0.01-0.1 |
| Valine(V) | 0.5-2 | 0.01-0.1 | 0.01-0.05 | 0.1-1 | 0.0-0.5 | 0.1-0.5 | 0.5-3 | 80-90 | 0.1-0.5 |
| Tyrosine(Y) | 30-40 | 0.01-0.1 | 0.01-0.05 | 0.01-0.05 | 0.5-2 | 55-68 | 5-15 | 0.01-0.1 | 0.5-3 |
| Methionine(M) | 0-0.001 | 0.5-3 | 0-0.001 | 0-0.01 | 0-0.01 | 0-0.01 | 0-0.01 | 0-0.001 | 0-0.001 |
| Threonine(T) | 0.01-0.1 | 55-65 | 0.01-0.05 | 15-25 | 5-15 | 0.1-1 | 1-5 | 0.01-0.05 | 1-4 |
| Lysine(K) | 0.01-0.1 | 1-5 | 0-0.01 | 0.5-3 | 1-5 | 0.5-3 | 0-0.001 | 0-0.01 | 0.01-0.05 |
| Isoleucine(I) | 0.5-3 | 6-12 | 0.01-0.05 | 1-5 | 0.5-3 | 0.01-0.1 | 0.5-3 | 3-9 | 0.5-2 |
| Tryptophan(W) | 0-0.001 | 0-0.001 | 0-0.001 | 0-0.001 | 0-0.001 | 0-0.01 | 10-20 | 0-0.01 | 0-0.001 |
| Aspartic acid(D) | 1-5 | 0.5-3 | 0-0.001 | 3-7 | 10-20 | 0.5-3 | 4-10 | 0.01-0.05 | 0.5-3 |
| Histidine(H) | 0.5-3 | 0.01-0.1 | 0-0.001 | 0.01-0.05 | 0.5-3 | 5-15 | 0.5-3 | 0-0.01 | 40-50 |
| Asparagine(N) | 0.5-3 | 0.1-0.8 | 0-0.01 | 10-20 | 25-35 | 3-10 | 0.5-3 | 0.01-0.1 | 15-25 |
| Arginine(R) | 0-0.01 | 0.5-3 | 0-0.001 | 1-4 | 1-4 | 0.1-1 | 0.1-1 | 0.1-0.5 | 0.1-0.5 |
| Glutamic acid(E) | 0-0.001 | 0.01-0.05 | 0-0.001 | 0.1-1 | 1-4 | 0-0.01 | 1-4 | 0.01-0.1 | 0-0.01 |
| Cysteine(C) | 0.01-0.1 | 0-0.001 | 0-0.01 | 0-0.01 | 0-0.01 | 0.01-0.1 | 0.01-0.1 | 0-0.01 | 0.01-0.05 |
| Leucine(L) | 1-4 | 0.01-0.1 | 0.05-0.5 | 0.05-0.5 | 0.01-0.1 | 0.5-3 | 0.01-0.1 | 4-10 | 0.01-0.05 |
| Glutamine(Q) | 0-0.001 | 0-0.001 | 0.01-0.05 | 0.01-0.1 | 0.01-0.05 | 0.01-0.05 | 0.01-0.1 | 0-0.01 | 0.5-3 |

TABLE 6

Amino acid distribution ratio for each position of amino acid(%) - VH1-69_CDR2

| Type of AA | 49 | 50 | 51 | 52 | 52a | 53 | 54 |
|---|---|---|---|---|---|---|---|
| Alanine(A) | 35-45 | 3-10 | 0-0.001 | 0.1-0.8 | 5-15 | 0.5-3 | 1-5 |
| Serine(S) | 25-35 | 5-15 | 0.01-0.1 | 55-65 | 10-20 | 25-35 | 15-25 |
| Glycine(G) | 25-35 | 5-15 | 0-0.001 | 0.5-3 | 3-10 | 3-7 | 30-40 |
| Phenylalanine(F) | 0-0.01 | 1-5 | 0-0.01 | 0.1-1 | 1-4 | 0.5-2 | 1-7 |
| Proline(P) | 0-0.01 | 0-0.02 | 0-0.001 | 0.01-0.05 | 15-25 | 0.01-0.05 | 0.01-0.05 |
| Valine(V) | 0.01-0.1 | 5-12 | 0-0.01 | 0.5-3 | 0.5-3 | 0.5-3 | 0.5-3 |
| Tyrosine(Y) | 0-0.01 | 5-15 | 0.01-0.1 | 0.5-3 | 5-15 | 2-7 | 0.1-2 |
| Methionine(M) | 0-0.001 | 0.5-3 | 0-0.01 | 0-0.001 | 0-0.01 | 0.5-3 | 0-0.01 |
| Threonine(T) | 0.01-0.1 | 1-4 | 0-0.03 | 1-5 | 1-5 | 1-3 | 1-5 |
| Lysine(K) | 0-0.001 | 0.5-2 | 0-0.001 | 5-15 | 0.5-3 | 1-4 | 0.5-3 |
| Isoleucine(I) | 0-0.001 | 3-9 | 95-99.99 | 6-10 | 0.5-3 | 2-7 | 0.5-3 |
| Tryptophan(W) | 0-0.001 | 10-20 | 0-0.001 | 1-5 | 2-7 | 0-0.01 | 0.01-0.05 |
| Aspartic acid(D) | 0-0.01 | 0.5-3 | 0.01-0.05 | 1-5 | 1-5 | 30-40 | 2-7 |
| Histidine(H) | 0-0.01 | 0.5-3 | 0.01-0.05 | 0.5-3 | 2-7 | 1-4 | 0-0.01 |
| Asparagine(N) | 0-0.001 | 5-15 | 0-0.02 | 0.01-0.05 | 1-5 | 0.01-0.05 | 10-20 |
| Arginine(R) | 0-0.001 | 0.5-3 | 0-0.01 | 0.5-3 | 0.1-2 | 0.5-2 | 0.5-2 |
| Glutamic acid(E) | 0-0.01 | 0-0.001 | 0-0.001 | 0-0.05 | 1-4 | 1-4 | 0.5-3 |
| Cysteine(C) | 0.01-0.1 | 0.01-0.1 | 0-0.001 | 0-0.001 | 0.01-0.1 | 0.01-0.1 | 0.01-0.005 |
| Leucine(L) | 0.01-0.1 | 3-9 | 0.01-0.05 | 1-4 | 0.5-3 | 1-4 | 3-9 |
| Glutamine(Q) | 0-0.01 | 0-0.01 | 0-0.001 | 0.5-3 | 2-7 | 0-0.01 | 0-0.01 |

| Type of AA | 55 | 56 | 57 | 58 |
|---|---|---|---|---|
| Alanine(A) | 2-6 | 2-7 | 4-10 | 1-4 |
| Serine(S) | 25-35 | 5-15 | 0.5-3 | 2-6 |
| Glycine(G) | 30-40 | 1-5 | 0-0.01 | 1-5 |
| Phenylalanine(F) | 0.01-0.05 | 0.5-2 | 0-0.01 | 1-5 |
| Proline(P) | 0-0.01 | 0.1-1 | 0.5-3 | 0.01-0.05 |
| Valine(V) | 0.5-3 | 1-4 | 0.5-3 | 0.1-2 |
| Tyrosine(Y) | 0.5-3 | 2-8 | 0-0.001 | 25-35 |
| Methionine(M) | 0-0.01 | 0.1-2 | 0.5-3 | 0-0.01 |
| Threonine(T) | 3-8 | 5-15 | 30-40 | 0.5-3 |
| Lysine(K) | 0.5-3 | 3-10 | 25-35 | 5-15 |
| Isoleucine(I) | 0.5-3 | 2-6 | 15-25 | 1-4 |
| Tryptophan(W) | 0.01-0.1 | 0-0.01 | 0-0.01 | 0-0.001 |
| Aspartic acid(D) | 5-15 | 5-15 | 0-0.01 | 2-5 |
| Histidine(H) | 0.5-3 | 1-4 | 0.01-0.1 | 4-8 |
| Asparagine(N) | 4-10 | 25-35 | 0.5-3 | 15-25 |
| Arginine(R) | 0.5-3 | 0.5-3 | 0.5-3 | 0.5-3 |
| Glutamic acid(E) | 0.5-3 | 5-12 | 0-0.001 | 1-4 |
| Cysteine(C) | 0.01-0.05 | 0.01-0.05 | 0-0.01 | 0.01-0.1 |
| Leucine(L) | 0.05-0.1 | 0.5-3 | 0.5-3 | 0.5-3 |
| Glutamine(Q) | 0-0.01 | 0.5-3 | 0.5-3 | 0.5-3 |

TABLE 7

Amino acid distribution ratio for each position of amino acid(%) - VH_CDR3_9AA

| Type of AA | 96 | 97 | 98 | 99 | 100 | 100a | 100b | 101 | 102 |
|---|---|---|---|---|---|---|---|---|---|
| Alanine(A) | 3-8 | 3-8 | 3-8 | 5-15 | 4-10 | 10-20 | 0.5-3 | 0.5-3 | 0.5-3 |
| Serine(S) | 1-5 | 6-12 | 5-15 | 10-20 | 10-20 | 10-20 | 4-10 | 0.5-3 | 1-5 |
| Glycine(G) | 5-15 | 5-15 | 5-15 | 5-12 | 5-15 | 5-15 | 1-5 | 0.5-3 | 0.1-0.5 |
| Phenylalanine(F) | 0.1-0.8 | 0.5-3 | 0.5-3 | 2-5 | 0.5-3 | 1-5 | 45-55 | 0.1-0.5 | 1-5 |
| Proline(P) | 0.5-3 | 5-15 | 1-5 | 0.5-3 | 0.1-1 | 2-6 | 0.5-3 | 0.1-0.5 | 0.5-3 |
| Valine(V) | 3-8 | 3-9 | 10-20 | 3-8 | 3-7 | 3-8 | 4-10 | 1-5 | 4-10 |
| Tyrosine(Y) | 0.5-3 | 2-7 | 4-10 | 15-25 | 15-25 | 15-25 | 5-12 | 0.5-3 | 60-70 |
| Methionine(M) | 0.01-0.05 | 1-4 | 1-4 | 0.1-1 | 0.1-1 | 0.1-0.5 | 1-5 | 0.5-3 | 0.5-3 |
| Threonine(T) | 5-15 | 2-6 | 4-10 | 3-9 | 5-15 | 3-8 | 2-5 | 0.5-3 | 0.5-3 |
| Lysine(K) | 0.5-3 | 0.5-3 | 1-4 | 1-5 | 0.5-3 | 0.5-3 | 0.01-0.1 | 0.1-1 | 0-0.001 |
| Isoleucine(I) | 0.5-3 | 1-5 | 0.5-3 | 1-4 | 1-4 | 3-8 | 5-12 | 2-6 | 1-5 |
| Tryptophan(W) | 0.5-3 | 3-9 | 1-4 | 0.5-3 | 0.5-3 | 0.5-3 | 0.1-1 | 0-0.001 | 0.01-0.1 |
| Aspartic acid(D) | 25-35 | 2-7 | 3-9 | 4-10 | 4-10 | 4-10 | 0.5-3 | 70-80 | 1-5 |
| Histidine(H) | 1-5 | 0.5-3 | 1-3 | 0.5-3 | 0.5-3 | 1-5 | 0.5-3 | 0.1-0.5 | 1-5 |
| Asparagine(N) | 0.5-3 | 1-5 | 2-6 | 2-6 | 3-8 | 0.5-3 | 0.5-3 | 1-4 | 0.5-3 |
| Arginine(R) | 1-4 | 4-10 | 5-15 | 1-5 | 1-4 | 1-4 | 0.1-1 | 0.1-0.5 | 0.1-0.5 |
| Glutamic acid(E) | 5-15 | 1-4 | 1-4 | 1-5 | 1-4 | 0.5-3 | 0.5-3 | 2-5 | 0.1-0.5 |
| Cysteine(C) | 0-0.001 | 0.01-0.05 | 0.01-0.05 | 0.01-0.1 | 0.01-0.1 | 0.01-0.05 | 0-0.001 | 0-0.001 | 0.01-0.05 |
| Leucine(L) | 1-4 | 5-15 | 1-5 | 0.5-2 | 0.5-3 | 0.5-3 | 1-4 | 0.1-0.5 | 0.5-3 |
| Glutamine(Q) | 5-15 | 2-6 | 0.5-3 | 0.5-2 | 0.5-3 | 0.1-1 | 0.1-0.5 | 0.5-3 | 0.1-1 |

TABLE 8

Amino acid distribution ratio for each position of amino acid(%) - VH_CDR3_10AA

| Type of AA | 96 | 97 | 98 | 99 | 100 | 100a | 100b | 100c | 101 | 102 |
|---|---|---|---|---|---|---|---|---|---|---|
| Alanine(A) | 5-15 | 3-9 | 4-10 | 4-10 | 5-15 | 4-10 | 5-15 | 1-4 | 0.5-3 | 0.5-3 |
| Serine(S) | 3-8 | 5-15 | 10-20 | 10-20 | 10-20 | 5-15 | 5-12 | 2-6 | 0.5-3 | 2-6 |
| Glycine(G) | 5-15 | 5-15 | 5-15 | 10-20 | 5-15 | 10-20 | 10-20 | 1-4 | 1-4 | 0.01-0.1 |
| Phenylalanine(F) | 0.1-0.5 | 1-4 | 0.5-3 | 1-5 | 1-4 | 1-4 | 0.5-3 | 25-35 | 0.1-1 | 2-6 |
| Proline(P) | 0.5-3 | 2-6 | 1-5 | 1-4 | 1-4 | 0.5-3 | 2-6 | 1-4 | 0.1-1 | 3-8 |
| Valine(V) | 2-6 | 2-6 | 2-6 | 2-6 | 2-5 | 0.5-3 | 1-4 | 1-4 | 0.5-3 | 5-12 |
| Tyrosine(Y) | 1-4 | 3-8 | 5-12 | 5-15 | 5-15 | 10-20 | 15-25 | 3-8 | 0.5-3 | 45-55 |
| Methionine(M) | 0.5-2 | 0.5-3 | 1-3 | 0.5-3 | 0.1-1 | 0.5-3 | 0.01-0.1 | 10-20 | 0.01-0.1 | 0.01-0.05 |
| Threonine(T) | 1-4 | 2-6 | 3-9 | 2-8 | 3-9 | 2-6 | 1-5 | 0.5-3 | 0.5-3 | 0.1-0.5 |
| Lysine(K) | 1-4 | 2-6 | 1-4 | 0.5-3 | 0.5-3 | 0.5-3 | 0.5-3 | 0.01-0.1 | 0.01-0.05 | 0-0.001 |
| Isoleucine(I) | 1-4 | 2-6 | 1-4 | 1-4 | 1-4 | 0.5-3 | 1-4 | 3-8 | 0.1-1 | 1-5 |
| Tryptophan(W) | 0.5-3 | 0.5-3 | 1-4 | 1-4 | 3-8 | 3-8 | 3-8 | 0.1-1 | 0.01-0.05 | 0.1-1 |
| Aspartic acid(D) | 25-35 | 3-8 | 4-10 | 4-10 | 3-9 | 4-10 | 3-8 | 1-4 | 75-85 | 1-5 |
| Histidine(H) | 1-5 | 2-6 | 1-4 | 0.5-3 | 1-4 | 1-4 | 1-5 | 0.01-0.1 | 0.5-3 | 3-8 |
| Asparagine(N) | 0.5-3 | 1-5 | 1-4 | 2-6 | 1-7 | 5-12 | 1-5 | 0.5-3 | 0.5-3 | 1-5 |
| Arginine(R) | 1-4 | 2-6 | 1-4 | 1-4 | 0.5-3 | 0.5-3 | 0.5-3 | 0.5-3 | 0.1-1 | 0.01-0.05 |
| Glutamic acid(E) | 5-15 | 1-5 | 2-5 | 1-4 | 1-4 | 1-4 | 1-4 | 0.5-3 | 1-4 | 0.01-0.05 |
| Cysteine(C) | 0-0.001 | 0.01-0.05 | 0.01-0.05 | 0.01-0.1 | 0.01-0.1 | 0.01-0.05 | 0.01-0.05 | 0-0.001 | 0.01-0.05 | 0.01-0.1 |
| Leucine(L) | 3-9 | 10-20 | 5-15 | 4-10 | 5-12 | 3-9 | 4-10 | 15-25 | 2-5 | 4-10 |
| Glutamine(Q) | 0.5-3 | 1-4 | 1-4 | 1-4 | 1-4 | 1-4 | 1-4 | 0.01-0.1 | 1-4 | 0-0.001 |

TABLE 9

Amino acid distribution ratio for each position of amino acid(%) - VH_CDR3_11AA

| Type of AA | 96 | 97 | 98 | 99 | 100 | 100a | 100b |
|---|---|---|---|---|---|---|---|
| Alanine(A) | 5-12 | 3-9 | 4-10 | 5-12 | 5-15 | 5-15 | 4-10 |
| Serine(S) | 2-6 | 5-15 | 5-15 | 10-20 | 10-20 | 5-15 | 5-15 |
| Glycine(G) | 5-15 | 5-15 | 5-15 | 10-20 | 5-15 | 5-15 | 5-15 |
| Phenylalanine(F) | 0.1-1 | 1-4 | 0.5-3 | 1-4 | 0.5-3 | 1-4 | 1-4 |
| Proline(P) | 0.5-3 | 2-5 | 1-5 | 1-4 | 0.5-3 | 2-5 | 1-4 |
| Valine(V) | 2-6 | 2-6 | 2-6 | 3-8 | 2-5 | 2-5 | 2-5 |
| Tyrosine(Y) | 0.5-3 | 3-8 | 5-12 | 5-15 | 5-15 | 5-15 | 10-20 |
| Methionine(M) | 0.5-3 | 0.5-3 | 0.5-3 | 0.5-3 | 0.1-1 | 0.01-0.1 | 0.01-0.1 |
| Threonine(T) | 0.5-3 | 2-6 | 3-8 | 3-8 | 3-9 | 3-8 | 3-9 |
| Lysine(K) | 0.5-3 | 2-6 | 1-4 | 1-4 | 1-4 | 0.5-3 | 0.5-3 |
| Isoleucine(I) | 1-4 | 1-5 | 1-4 | 1-4 | 1-4 | 1-5 | 1-4 |
| Tryptophan(W) | 0.5-3 | 1-4 | 1-4 | 1-4 | 2-6 | 2-6 | 3-8 |
| Aspartic acid(D) | 25-35 | 3-8 | 4-10 | 4-10 | 4-10 | 4-10 | 3-8 |
| Histidine(H) | 1-4 | 2-6 | 1-4 | 0.5-3 | 1-4 | 1-4 | 1-6 |
| Asparagine(N) | 1-4 | 1-5 | 2-5 | 3-8 | 2-6 | 3-7 | 3-9 |
| Arginine(R) | 1-4 | 1-5 | 1-4 | 1-4 | 0.5-3 | 0.5-3 | 1-4 |
| Glutamic acid(E) | 10-20 | 1-5 | 2-6 | 1-4 | 1-4 | 1-4 | 1-4 |
| Cysteine(C) | 0.01-0.05 | 0.01-0.05 | 0-0.001 | 0-0.001 | 0.01-0.05 | 0.01-0.1 | 0.01-0.1 |
| Leucine(L) | 3-8 | 10-20 | 5-15 | 3-9 | 5-12 | 5-15 | 5-15 |
| Glutamine(Q) | 1-4 | 1-4 | 1-4 | 1-4 | 1-5 | 0.5-3 | 1-4 |

| Type of AA | 100c | 100d | 101 | 102 |
|---|---|---|---|---|
| Alanine(A) | 4-10 | 1-4 | 1-4 | 0.1-1 |
| Serine(S) | 5-12 | 2-5 | 0.5-3 | 3-8 |
| Glycine(G) | 5-15 | 1-4 | 0.5-3 | 0.5-3 |
| Phenylalanine(F) | 1-4 | 25-35 | 0.1-0.5 | 1-5 |
| Proline(P) | 2-5 | 1-4 | 0.5-3 | 1-5 |
| Valine(V) | 0.5-3 | 1-5 | 0.5-3 | 4-10 |
| Tyrosine(Y) | 15-25 | 1-5 | 0.5-3 | 45-55 |
| Methionine(M) | 0.5-3 | 5-15 | 0.05-0.2 | 0.01-0.1 |
| Threonine(T) | 2-6 | 0.5-3 | 0.1-1 | 0.5-3 |
| Lysine(K) | 1-4 | 0.01-0.05 | 0.01-0.05 | 0-0.001 |
| Isoleucine(I) | 1-4 | 3-8 | 0.1-0.5 | 1-5 |
| Tryptophan(W) | 3-8 | 0.5-3 | 0.01-0.05 | 0-0.001 |
| Aspartic acid(D) | 3-8 | 1-4 | 75-85 | 1-4 |
| Histidine(H) | 1-4 | 0.5-3 | 1-4 | 4-10 |
| Asparagine(N) | 3-8 | 1-4 | 1-4 | 2-6 |
| Arginine(R) | 1-4 | 0.5-3 | 0.5-2 | 0.01-0.1 |
| Glutamic acid(E) | 1-4 | 0.5-3 | 1-5 | 0.01-0.1 |
| Cysteine(C) | 0.01-0.1 | 0-0.001 | 0.01-0.05 | 0.01-0.1 |
| Leucine(L) | 5-15 | 20-30 | 1-4 | 5-12 |
| Glutamine(Q) | 0.5-3 | 0.5-3 | 1-4 | 0.5-3 |

TABLE 10

Amino acid distribution ratio for each position of amino acid(%) - VH_CDR3_12AA

| Type of AA | 96 | 97 | 98 | 99 | 100 | 100a | 100b |
|---|---|---|---|---|---|---|---|
| Alanine(A) | 4-10 | 3-9 | 4-10 | 5-12 | 4-10 | 5-15 | 4-10 |
| Serine(S) | 1-5 | 5-15 | 5-15 | 10-20 | 5-15 | 5-15 | 5-15 |
| Glycine(G) | 10-20 | 5-15 | 5-15 | 10-20 | 5-15 | 5-15 | 5-15 |
| Phenylalanine(F) | 0.1-1 | 1-4 | 0.5-3 | 1-4 | 1-4 | 1-5 | 1-4 |
| Proline(P) | 0.5-3 | 1-5 | 1-5 | 1-5 | 1-4 | 2-5 | 1-4 |
| Valine(V) | 1-5 | 2-6 | 2-6 | 2-6 | 2-5 | 2-5 | 2-5 |
| Tyrosine(Y) | 1-4 | 3-8 | 5-12 | 5-15 | 5-15 | 5-15 | 10-20 |
| Methionine(M) | 0.1-1 | 0.5-3 | 1-4 | 0.5-3 | 0.1-1 | 0.01-0.05 | 0.01-0.05 |
| Threonine(T) | 0.5-3 | 2-6 | 3-8 | 2-6 | 3-9 | 3-8 | 3-8 |
| Lysine(K) | 0.5-3 | 2-6 | 1-4 | 0.5-3 | 0.5-3 | 0.5-3 | 0.5-3 |
| Isoleucine(I) | 0.5-3 | 1-5 | 1-4 | 1-4 | 1-4 | 1-5 | 1-8 |
| Tryptophan(W) | 0.5-3 | 0.5-3 | 1-4 | 1-5 | 3-8 | 3-8 | 3-8 |
| Aspartic acid(D) | 35-45 | 2-6 | 4-10 | 4-10 | 4-10 | 5-12 | 3-9 |
| Histidine(H) | 1-5 | 2-6 | 1-4 | 0.5-3 | 1-4 | 1-4 | 1-5 |
| Asparagine(N) | 1-4 | 1-5 | 2-5 | 2-6 | 2-6 | 2-5 | 3-8 |
| Arginine(R) | 0.5-3 | 1-5 | 1-5 | 1-4 | 0.5-3 | 0.5-3 | 1-8 |
| Glutamic acid(E) | 5-15 | 1-4 | 2-5 | 2-5 | 1-5 | 1-4 | 1-8 |
| Cysteine(C) | 0-0.001 | 0.01-0.1 | 0.01-0.05 | 0.01-0.1 | 0.01-0.1 | 0.01-0.05 | 0.01-0.1 |
| Leucine(L) | 2-6 | 15-25 | 5-15 | 4-10 | 5-15 | 5-12 | 5-15 |
| Glutamine(Q) | 0.5-4 | 1-4 | 1-4 | 1-5 | 1-4 | 0.5-3 | 1-5 |

| Type of AA | 100c | 100d | 100e | 101 | 102 |
|---|---|---|---|---|---|
| Alanine(A) | 4-10 | 5-15 | 1-4 | 0.5-3 | 0.1-1 |
| Serine(S) | 5-15 | 3-8 | 1-4 | 0.5-3 | 2-6 |
| Glycine(G) | 5-15 | 5-15 | 0.5-3 | 0.5-3 | 0.01-0.05 |
| Phenylalanine(F) | 1-4 | 1-4 | 30-40 | 0.1-0.5 | 1-4 |
| Proline(P) | 2-5 | 2-6 | 0.5-3 | 0.1-1 | 3-8 |
| Valine(V) | 0.5-3 | 1-4 | 1-4 | 0.1-0.5 | 5-15 |
| Tyrosine(Y) | 15-25 | 20-30 | 1-4 | 0.1-1 | 45-55 |
| Methionine(M) | 0.5-4 | 0.01-0.1 | 10-20 | 0.01-0.1 | 0.01-0.05 |
| Threonine(T) | 1-5 | 1-5 | 0.5-3 | 0.5-3 | 0.5-3 |
| Lysine(K) | 1-4 | 0.5-3 | 0-0.001 | 0.01-0.05 | 0-0.001 |
| Isoleucine(I) | 1-4 | 1-5 | 3-8 | 0.1-1 | 3-8 |
| Tryptophan(W) | 2-6 | 3-8 | 0.5-3 | 0-0.001 | 0.01-0.05 |
| Aspartic acid(D) | 2-6 | 2-5 | 0.5-3 | 75-85 | 0.5-3 |
| Histidine(H) | 1-6 | 1-5 | 0.5-3 | 0.5-3 | 4-10 |
| Asparagine(N) | 3-9 | 1-5 | 0.5-3 | 1-4 | 1-5 |
| Arginine(R) | 1-4 | 0.5-3 | 0.1-1 | 0.1-1 | 0.5-3 |
| Glutamic acid(E) | 1-4 | 1-4 | 0.5-2 | 1-4 | 0.01-0.1 |
| Cysteine(C) | 0.01-0.1 | 0.01-0.1 | 0.01-0.05 | 0.01-0.05 | 0.01-0.1 |
| Leucine(L) | 5-12 | 9-15 | 20-30 | 0.5-3 | 5-12 |
| Glutamine(Q) | 0.5-3 | 0.5-3 | 0-0.001 | 1-4 | 0.01-0.05 |

TABLE 11

Amino acid distribution ratio for each position of amino acid(%) - VH_CDR3_13AA

| Type of AA | 96 | 97 | 98 | 99 | 100 | 100a | 100b | 100c |
|---|---|---|---|---|---|---|---|---|
| Alanine(A) | 4-10 | 3-9 | 3-9 | 5-12 | 5-12 | 5-15 | 4-10 | 4-10 |
| Serine(S) | 1-5 | 5-15 | 5-15 | 10-20 | 10-20 | 5-15 | 5-15 | 5-15 |
| Glycine(G) | 5-15 | 5-15 | 5-15 | 10-20 | 5-15 | 5-15 | 5-12 | 5-15 |
| Phenylalanine(F) | 0.5-3 | 1-4 | 0.5-3 | 1-4 | 0.5-3 | 1-5 | 1-5 | 1-4 |
| Proline(P) | 0.5-3 | 2-6 | 2-5 | 1-4 | 1-4 | 2-5 | 1-5 | 2-6 |
| Valine(V) | 2-6 | 1-5 | 2-6 | 2-6 | 2-5 | 2-5 | 2-5 | 0.5-3 |
| Tyrosine(Y) | 0.5-3 | 3-8 | 5-12 | 5-15 | 5-15 | 5-15 | 10-20 | 15-25 |
| Methionine(M) | 0.1-1 | 0.5-3 | 1-4 | 0.5-3 | 0.1-1 | 0.01-0.05 | 0.01-0.05 | 0.5-3 |
| Threonine(T) | 0.5-3 | 2-6 | 3-8 | 2-6 | 3-9 | 3-8 | 3-8 | 2-6 |
| Lysine(K) | 0.5-3 | 2-6 | 1-4 | 1-4 | 1-4 | 0.5-3 | 0.5-3 | 0.5-3 |
| Isoleucine(I) | 0.5-3 | 2-6 | 1-4 | 1-4 | 1-5 | 1-4 | 1-4 | 1-4 |
| Tryptophan(W) | 0.5-3 | 1-4 | 1-4 | 2-5 | 2-6 | 2-6 | 3-8 | 2-6 |
| Aspartic acid(D) | 35-45 | 2-6 | 4-10 | 4-10 | 4-10 | 4-10 | 3-9 | 3-8 |
| Histidine(H) | 1-5 | 2-6 | 1-5 | 0.5-3 | 1-4 | 0.5-3 | 1-5 | 1-5 |
| Asparagine(N) | 0.5-3 | 1-4 | 1-5 | 2-6 | 3-8 | 3-8 | 3-9 | 3-9 |
| Arginine(R) | 0.5-3 | 2-5 | 1-4 | 1-4 | 0.5-3 | 0.5-3 | 1-5 | 1-4 |
| Glutamic acid(E) | 5-15 | 2-5 | 2-6 | 1-4 | 1-4 | 1-5 | 1-4 | 1-5 |
| Cysteine(C) | 0.01-0.05 | 0-0.001 | 0.01-0.05 | 0.01-0.1 | 0.01-0.05 | 0.01-0.05 | 0.01-0.05 | 0.01-0.1 |
| Leucine(L) | 2-6 | 10-20 | 5-15 | 4-10 | 5-15 | 5-12 | 5-15 | 5-12 |
| Glutamine(Q) | 1-4 | 1-4 | 1-4 | 1-4 | 1-4 | 0.5-3 | 1-5 | 0.5-8 |

TABLE 11-continued

Amino acid distribution ratio for each position of amino acid(%) - VH_CDR3_13AA

| Type of AA | 100d | 100e | 100f | 101 | 102 |
|---|---|---|---|---|---|
| Alanine(A) | 2-6 | 5-15 | 1-4 | 0.3-1 | 0.1-1 |
| Serine(S) | 5-15 | 3-8 | 0.5-3 | 0.5-3 | 1-5 |
| Glycine(G) | 4-10 | 10-20 | 0.5-3 | 0.5-3 | 0-0.001 |
| Phenylalanine(F) | 1-4 | 1-4 | 35-45 | 0.5-3 | 1-4 |
| Proline(P) | 1-5 | 3-8 | 0.5-3 | 0.1-1 | 3-9 |
| Valine(V) | 1-4 | 0.5-3 | 1-4 | 0.1-1 | 10-20 |
| Tyrosine(Y) | 20-30 | 25-35 | 2-5 | 0.1-1 | 40-50 |
| Methionine(M) | 0.01-0.05 | 0.01-0.1 | 15-25 | 0.01-0.1 | 0.5-3 |
| Threonine(T) | 1-5 | 1-4 | 0.5-3 | 0.01-0.1 | 0.1-1 |
| Lysine(K) | 0.5-3 | 0.01-0.05 | 0-0.001 | 0-0.001 | 0-0.001 |
| Isoleucine(I) | 1-5 | 0.5-3 | 2-6 | 0.1-1 | 4-10 |
| Tryptophan(W) | 1-5 | 4-10 | 0.1-1 | 0-0.001 | 0.01-0.05 |
| Aspartic acid(D) | 4-10 | 1-5 | 0.5-3 | 85-95 | 0.5-3 |
| Histidine(H) | 1-5 | 1-5 | 0.5-3 | 0.5-3 | 4-10 |
| Asparagine(N) | 4-10 | 1-5 | 0.5-3 | 0.1-1 | 1-4 |
| Arginine(R) | 0.5-3 | 0.5-3 | 0.01-0.05 | 0.1-1 | 0.01-0.1 |
| Glutamic acid(E) | 2-6 | 0.5-3 | 0.5-3 | 0.5-3 | 0.01-0.05 |
| Cysteine(C) | 0.01-0.05 | 0.02-0.2 | 0.01-0.1 | 0-0.001 | 0.01-0.1 |
| Leucine(L) | 5-15 | 3-8 | 15-25 | 0.5-3 | 5-12 |
| Glutamine(Q) | 0.5-3 | 0.5-3 | 0-0.001 | 0.5-3 | 0.01-0.1 |

TABLE 12

Amino acid distribution ratio for each position of amino acid(%) - VH_CDR3_14AA

| Type of AA | 96 | 97 | 98 | 99 | 100 | 100a | 100b | 100c | 100d |
|---|---|---|---|---|---|---|---|---|---|
| Alanine(A) | 4-10 | 0.1-1 | 5-12 | 5-12 | 5-12 | 5-15 | 4-10 | 4-10 | 2-6 |
| Serine(S) | 2-6 | 2-6 | 5-15 | 10-20 | 10-20 | 5-15 | 5-15 | 5-15 | 5-15 |
| Glycine(G) | 5-15 | 0.05-0.5 | 10-20 | 10-20 | 5-15 | 10-20 | 5-15 | 5-15 | 5-12 |
| Phenylalanine(F) | 0.5-3 | 1-5 | 0.5-3 | 1-5 | 1-3 | 1-4 | 1-4 | 1-4 | 1-5 |
| Proline(P) | 0.5-3 | 3-8 | 1-4 | 1-4 | 1-4 | 1-5 | 1-4 | 2-6 | 1-4 |
| Valine(V) | 3-8 | 10-20 | 2-6 | 2-6 | 1-5 | 2-5 | 2-5 | 1-4 | 1-4 |
| Tyrosine(Y) | 0.1-1 | 40-50 | 4-10 | 5-15 | 5-15 | 5-15 | 10-20 | 15-25 | 20-30 |
| Methionine(M) | 0.1-1 | 0.5-3 | 1-4 | 0.5-3 | 0.1-1 | 0.01-0.05 | 0-0.001 | 0.5-3 | 0-0.001 |
| Threonine(T) | 0.5-3 | 0.05-0.5 | 3-8 | 2-6 | 3-9 | 3-8 | 3-8 | 1-5 | 1-5 |
| Lysine(K) | 0.5-3 | 0-0.001 | 1-4 | 1-4 | 0.5-3 | 0.5-3 | 1-4 | 1-4 | 0.5-3 |
| Isoleucine(I) | 0.5-3 | 4-10 | 1-4 | 1-5 | 1-4 | 2-5 | 1-4 | 1-5 | 1-5 |
| Tryptophan(W) | 0.1-1 | 0.05-0.5 | 1-4 | 1-5 | 3-8 | 3-8 | 3-8 | 2-6 | 1-5 |
| Aspartic acid(D) | 35-45 | 0.5-3 | 4-10 | 4-10 | 4-10 | 4-10 | 3-9 | 3-8 | 3-9 |
| Histidine(H) | 1-4 | 4-10 | 1-5 | 0.5-3 | 1-4 | 0.5-8 | 1-5 | 1-4 | 1-5 |
| Asparagine(N) | 1-4 | 1-4 | 1-5 | 2-6 | 3-8 | 3-8 | 3-9 | 3-8 | 3-9 |
| Arginine(R) | 0.5-3 | 0-0.001 | 1-4 | 1-4 | 0.5-3 | 0.5-3 | 1-5 | 1-5 | 1-4 |
| Glutamic acid(E) | 5-15 | 0.01-0.1 | 2-6 | 2-5 | 1-4 | 1-4 | 1-5 | 1-4 | 2-5 |
| Cysteine(C) | 0.01-0.1 | 0.05-0.5 | 0.01-0.05 | 0-0.001 | 0.01-0.1 | 0.01-0.05 | 0.01-0.05 | 0.01-0.05 | 0-0.001 |
| Leucine(L) | 3-8 | 4-10 | 5-15 | 3-9 | 5-12 | 5-15 | 5-15 | 5-15 | 5-15 |
| Glutamine(Q) | 0.5-3 | 0.01-0.1 | 1-4 | 1-4 | 1-3 | 0.5-3 | 1-5 | 0.5-3 | 0.5-3 |

| Type of AA | 100e | 100f | 100g | 101 | 102 |
|---|---|---|---|---|---|
| Alanine(A) | 1-4 | 5-15 | 1-4 | 0.5-3 | 0.5-3 |
| Serine(S) | 5-12 | 1-5 | 1-4 | 0.1-1 | 2-6 |
| Glycine(G) | 5-15 | 10-20 | 0.3-2 | 0.5-8 | 0-0.001 |
| Phenylalanine(F) | 1-4 | 1-4 | 30-40 | 0.1-1 | 0.5-3 |
| Proline(P) | 1-4 | 3-8 | 0.5-3 | 0.5-3 | 3-9 |
| Valine(V) | 0.5-3 | 1-4 | 0.5-3 | 0.1-1 | 15-25 |
| Tyrosine(Y) | 25-35 | 25-35 | 1-4 | 0.01-0.05 | 35-45 |
| Methionine(M) | 0.5-3 | 0.5-3 | 20-30 | 0.01-0.05 | 0-0.001 |
| Threonine(T) | 1-5 | 0.5-3 | 0.1-1 | 0.3-3 | 0.1-1 |
| Lysine(K) | 0.5-3 | 0-0.001 | 0-0.001 | 0-0.001 | 0-0.001 |
| Isoleucine(I) | 0.5-3 | 0.5-3 | 1-5 | 0.1-1 | 2-6 |
| Tryptophan(W) | 2-6 | 5-12 | 0.1-0.5 | 0-0.001 | 0.01-0.05 |
| Aspartic acid(D) | 4-10 | 0.5-3 | 0.1-1 | 80-90 | 0.5-3 |
| Histidine(H) | 2-6 | 1-5 | 0.5-3 | 0.5-3 | 4-10 |
| Asparagine(N) | 5-15 | 1-5 | 0.1-1 | 0.5-3 | 1-4 |
| Arginine(R) | 0.5-3 | 0.5-3 | 0.01-0.1 | 0.1-1 | 0.01-0.05 |
| Glutamic acid(E) | 1-4 | 0.5-3 | 0.1-1 | 1-4 | 0-0.001 |
| Cysteine(C) | 0.01-0.1 | 0.01-1 | 0.01-0.1 | 0-0.001 | 0.01-0.1 |
| Leucine(L) | 2-6 | 4-10 | 15-25 | 0.5-3 | 5-15 |
| Glutamine(Q) | 0.5-3 | 0.1-1 | 0-0.001 | 1-4 | 0-0.001 |

TABLE 13

Amino acid distribution ratio for each position of amino acid(%) - Vx1-39_CDR1

| Type of AA | 24 | 25 | 26 | 27 | 28 | 29 | 30 |
|---|---|---|---|---|---|---|---|
| Alanine(A) | 0-0.001 | 95-99.99 | 0-0.01 | 0-0.001 | 3-6 | 0-0.1 | 3-7 |
| Serine(S) | 90-95 | 0-0.05 | 95-99.99 | 0-0.03 | 33-38 | 0-0.05 | 30-40 |
| Glycine(G) | 4-8 | 0-0.05 | 0-0.1 | 0-0.001 | 8-12 | 0-0.001 | 4-10 |
| Phenylalanine(F) | 0-0.001 | 0-0.001 | 0-0.001 | 0-0.001 | 0.5-1.5 | 0-0.001 | 0-1 |
| Proline(P) | 0-0.001 | 0-0.01 | 0-0.001 | 0-0.001 | 0.5-1.5 | 0-0.001 | 0-0.05 |
| Valine(V) | 0-0.01 | 0-0.3 | 0-0.1 | 0-0.001 | 0.5-1.5 | 80-90 | 0-1 |
| Tyrosine(Y) | 0-0.001 | 0-0.001 | 0-0.001 | 0-0.001 | 0.5-1.5 | 0-0.09 | 1-4 |
| Methionine(M) | 0-0.03 | 0-0.001 | 0-0.001 | 0-0.001 | 0-0.05 | 0-0.001 | 0-0.001 |
| Threonine(T) | 0-0.001 | 0-0.05 | 0-0.001 | 0-0.01 | 6-10 | 0-0.001 | 3-7 |
| Lysine(K) | 0-0.01 | 0-0.001 | 0-0.001 | 0-0.01 | 0.4-1.0 | 0-0.01 | 1-5 |
| Isoleucine(I) | 0-0.05 | 0-0.001 | 0-0.08 | 0-0.001 | 0.5-1.5 | 10-15 | 1-5 |
| Tryptophan(W) | 0-0.001 | 0-0.001 | 0-0.001 | 0-0.001 | 0-0.01 | 0-0.001 | 0-0.001 |
| Aspartic acid(D) | 0-0.01 | 0-0.001 | 0-0.001 | 0-0.05 | 29-33 | 0-0.01 | 4-10 |
| Histidine(H) | 0-0.001 | 0-0.001 | 0-0.001 | 0-0.3 | 1.0-2.0 | 0-0.001 | 0.5-3 |
| Asparagine(N) | 0-0.05 | 0-0.001 | 0-0.08 | 0-0.001 | 0-0.005 | 0-0.001 | 20-25 |
| Arginine(R) | 0-0.3 | 0-0.1 | 0-0.05 | 93-96 | 0-1.0 | 0-0.03 | 2-6 |
| Glutamic acid(E) | 0-0.01 | 0-0.05 | 0-0.03 | 0-0.1 | 0-0.03 | 0-0.01 | 0.5-3 |
| Cysteine(C) | 0-0.03 | 0-0.01 | 0-0.001 | 0-0.001 | 0-0.05 | 0-0.03 | 0-0.01 |
| Leucine(L) | 0-0.001 | 0-0.001 | 0-0.001 | 0-0.8 | 0-0.1 | 1-5 | 1-3 |
| Glutamine(Q) | 0-0.01 | 0-0.001 | 0-0.001 | 1-5 | 0-0.03 | 0-0.01 | 0-0.01 |

| Type of AA | 31 | 32 | 33 | 34 |
|---|---|---|---|---|
| Alanine(A) | 0.5-3 | 0.5-3 | 0-0.01 | 40-45 |
| Serine(S) | 10-20 | 5-10 | 0-0.03 | 1-4 |
| Glycine(G) | 0.5-3 | 0.5-3 | 0-0.01 | 1-4 |
| Phenylalanine(F) | 0.1-2 | 5-10 | 0-0.001 | 0-0.01 |
| Proline(P) | 0.5-3 | 0-0.07 | 0-0.1 | 0-0.01 |
| Valine(V) | 0.05-0.3 | 0-0.05 | 0-0.03 | 0.5-2 |
| Tyrosine(Y) | 0.5-3 | 35-45 | 0-0.03 | 0-0.03 |
| Methionine(M) | 0.1-0.8 | 0-0.001 | 0-0.001 | 0-0.001 |
| Threonine(T) | 5-15 | 0-0.1 | 0-0.01 | 0-0.1 |
| Lysine(K) | 5-15 | 0-0.03 | 0-0.01 | 0-0.05 |
| Isoleucine(I) | 1-5 | 0-0.001 | 3-8 | 0-0.1 |
| Tryptophan(W) | 0-0.001 | 10-20 | 0-0.001 | 0-0.001 |
| Aspartic acid(D) | 3-8 | 3-8 | 0-0.01 | 0.5-1.5 |
| Histidine(H) | 1-4 | 5-10 | 0-0.001 | 1-3 |
| Asparagine(N) | 35-45 | 3-8 | 0-0.001 | 40-50 |
| Arginine(R) | 1-4 | 0.5-3 | 0-0.001 | 0-0.03 |
| Glutamic acid(E) | 0.1-2 | 0.5-3 | 0-0.001 | 0-0.05 |
| Cysteine(C) | 0-0.01 | 0-0.1 | 0-0.001 | 0-0.001 |
| Leucine(L) | 0.1-1 | 2-6 | 90-99.99 | 0-0.001 |
| Glutamine(Q) | 0-0.01 | 0.5-3 | 0-0.001 | 0-0.001 |

TABLE 14

Amino acid distribution ratio for each position of amino acid (%)-$V_K$1-39_CDR2

| Type of AA | 50 | 51 | 52 | 53 | 54 | 55 | 56 |
|---|---|---|---|---|---|---|---|
| Alanine (A) | 20~30 | 75~85 | 0~0.001 | 1~5 | 0~0.001 | 1~3 | 1~5 |
| Serine (S) | 5~10 | 1~5 | 0.01~0.1 | 20~30 | 0~0.001 | 0~0.03 | 60~70 |
| Glycine (G) | 3~8 | 0.5~3 | 0~0.001 | 0.1~1 | 0~0.001 | 0.5~3 | 2~6 |
| Phenylalanine (F) | 0.1~0.8 | 0~0.01 | 0~0.01 | 0.5~3 | 0.01~0.3 | 0.1~2 | 0.5~2 |
| Proline (P) | 0.1~0.5 | 0.5~2 | 0~0.001 | 0~0.01 | 0.05~0.3 | 0.1~2 | 0.5~2 |
| Valine (V) | 0.5~3 | 2~6 | 0~0.001 | 0.5~3 | 0.01~0.03 | 0.1~2 | 0.5~2 |
| Tyrosine (Y) | 0.5~3 | 0~0.01 | 0~0.001 | 1~3 | 0.01~0.03 | 0.5~3 | 0.1~1.5 |
| Methionine (M) | 0.5~3 | 0~0.001 | 0~0.001 | 0~0.001 | 0~0.01 | 0~0.03 | 0~0.03 |
| Threonine (T) | 2~6 | 4~9 | 3~7 | 15~25 | 0~0.01 | 0~0.01 | 5~15 |
| Lysine (K) | 15~25 | 0~0.01 | 0.01~0.1 | 1~5 | 0~0.001 | 1~5 | 0.1~1.5 |
| Isoleucine (I) | 0.5~3 | 0.5~3 | 0~0.03 | 3~8 | 0~0.01 | 0~0.01 | 1~3 |
| Tryptophan (W) | 1~3 | 0~0.001 | 0~0.001 | 0~0.001 | 0~0.001 | 0~0.001 | 0~0.01 |
| Aspartic acid (D) | 10~20 | 0~0.03 | 0~0.05 | 1~5 | 0~0.001 | 1~4 | 3~7 |
| Histidine (H) | 0.1~0.8 | 0~0.001 | 0~0.001 | 0.1~1 | 5~15 | 5~8 | 0~0.01 |
| Asparagine (N) | 0.01~0.03 | 0~0.001 | 90~99 | 20~30 | 0~0.03 | 0.5~3 | 0.5~3 |
| Arginine (R) | 0.5~3 | 0~0.01 | 0~0.001 | 0.5~3 | 0~0.03 | 0.5~2 | 0.5~3 |
| Glutamic acid (E) | 5~10 | 1~3 | 0~0.001 | 0.01~0.05 | 0~0.001 | 35~45 | 0~0.05 |
| Cysteine (C) | 0.01~0.08 | 0~0.03 | 0~0.001 | 0~0.01 | 0~0.001 | 0~0.01 | 0.01~0.1 |
| Leucine (L) | 0.5~3 | 0~0.001 | 0~0.001 | 0.1~1 | 85~95 | 1~3 | 1~5 |
| Glutamine (Q) | 0.5~3 | 0~0.01 | 0~0.001 | 0.01~0.03 | 0~0.001 | 33~42 | 0~0.001 |

TABLE 15

Amino acid distribution ratio for each position of amino acid (%)-$V_K$1-39_CDR3

| Type of AA | 89 | 90 | 91 | 92 | 93 | 94 | 95 | 96 |
|---|---|---|---|---|---|---|---|---|
| Alanine (A) | 0~0.001 | 0.01~0.03 | 2~6 | 0.5~1.5 | 1~5 | 8~15 | 0.01~00.5 | 0.1~1 |
| Serine (S) | 0~0.01 | 0.01~0.03 | 10~20 | 3~8 | 40~50 | 3~10 | 0.1~0.5 | 0.5~2 |
| Glycine (G) | 0.01~0.05 | 0~0.005 | 0.5~3 | 0.5~1.5 | 1~5 | 0.1~1.0 | 0~0.001 | 0.5~2 |
| Phenylalanine (F) | 0~0.001 | 0~0.001 | 1~4 | 2~6 | 0.5~1.5 | 5~13 | 0~0.001 | 3~9 |
| Proline (P) | 0.01~0.03 | 0.01~0.03 | 0.01~0.1 | 0.01~0.05 | 0.01~0.1 | 1~3 | 90~99.99 | 2~8 |
| Valine (V) | 0~0.001 | 0~0.001 | 0.5~2 | 0.1~0.5 | 0.5~1.5 | 1~4 | 0~0.001 | 0.5~3 |
| Tyrosine (Y) | 0~0.001 | 0~0.01 | 50~60 | 30~40 | 0.5~1.5 | 20~30 | 0~0.001 | 10~15 |
| Methionine (M) | 0~0.001 | 0~0.01 | 0~0.001 | 0~0.01 | 0~0.001 | 1~3 | 0~0.001 | 0.01~0.05 |
| Threonine (T) | 0~0.001 | 0~0.001 | 2~6 | 0.5~2 | 8~13 | 10~20 | 0.01~0.1 | 0.01~0.05 |
| Lysine (K) | 0~0.001 | 0.01~0.05 | 0.01~0.05 | 1~5 | 0.5~3 | 0~0.001 | 0~0.001 | 0.5~2 |
| Isoleucine (I) | 0~0.01 | 0~0.001 | 0.01~0.05 | 0.5~2 | 1~5 | 2~6 | 0~0.001 | 0.5~3 |
| Tryptophan (W) | 0.01~0.1 | 0~0.001 | 0~0.001 | 0~0.001 | 0~0.001 | 0.01~0.05 | 0~0.001 | 10~20 |
| Aspartic acid (D) | 0~0.001 | 0.1~0.5 | 1~4 | 5~15 | 3~8 | 0.5~2 | 0~0.001 | 0.1~1 |
| Histidine (H) | 0~0.001 | 6~12 | 6~10 | 3~9 | 0.5~2 | 1~3 | 0~0.001 | 1~4 |
| Asparagine (N) | 0~0.001 | 0~0.001 | 0.5~3 | 20~30 | 10~20 | 3~5 | 0~0.001 | 0.5~2 |
| Arginine (R) | 90~98 | 0.01~0.05 | 0.01~0.05 | 0.1~1.0 | 0.5~3 | 0.1~0.5 | 0.01~0.1 | 3~8 |
| Glutamic acid (E) | 0~0.001 | 1~4 | 0~0.01 | 0.5~3 | 0.5~3 | 0~0.001 | 0~0.001 | 0.1~1 |
| Cysteine (C) | 0~0.001 | 0~0.001 | 0.01~0.05 | 0.01~0.1 | 0.01~0.05 | 0.01~0.05 | 0~0.001 | 0.01~0.05 |
| Leucine (L) | 4~10 | 0.01~0.05 | 3~7 | 0.5~3 | 1~3 | 8~13 | 0.01~0.1 | 35~45 |
| Glutamine (Q) | 0.01~0.1 | 85~95 | 0~0.01 | 0.1~1.0 | 0.01~0.05 | 0~0.001 | 0.01~0.1 | 1~5 |

TABLE 16

Amino acid distribution ratio for each position of amino acid (%)-$V_K$3-20_CDR1

| Type of AA | 3 | 4 | 5 | 6 | 7 | 8 | 9 | 10 | 11 | 12 | 13 | 14 |
|---|---|---|---|---|---|---|---|---|---|---|---|---|
| Alanine (A) | 0~0.001 | 95~99.99 | 0~0.001 | 0~0.001 | 0.5~2 | 0.5~2 | 0~0.001 | 0~0.001 | 0~0.001 | 0~0.01 | 0~0.001 | 95~99.99 |
| Serine (S) | 90~99.99 | 0.01~0.05 | 95~99.99 | 0.1~0.5 | 65~75 | 0.01~0.1 | 0~0.001 | 0~0.001 | 0~0.001 | 5~15 | 0.05~0.5 | 0.01~0.1 |
| Glycine (G) | 2~10 | 0.01~0.05 | 0.05~0.5 | 0~0.001 | 0.01~0.1 | 0~0.01 | 0~0.001 | 0~0.001 | 0~0.001 | 0~0.05 | 80~90 | 0~0.01 |
| Phenylalanine (F) | 0~0.001 | 0~0.001 | 0~0.001 | 0~0.001 | 0.5~2 | 1~3 | 0~0.001 | 0~0.001 | 0~0.001 | 5~15 | 0~0.01 | 0~0.001 |
| Proline (P) | 0~0.001 | 0~0.001 | 0~0.001 | 0.01~0.1 | 0.1~0.1 | 0.01~0.1 | 0~0.001 | 0~0.001 | 0~0.001 | 0.01~0.1 | 0~0.001 | 0~0.05 |
| Valine (V) | 0.01~0.05 | 0.01~0.1 | 0.01~0.1 | 0~0.01 | 0.05~0.5 | 50~60 | 0~0.001 | 0~0.001 | 0~0.001 | 0~0.001 | 2~8 | 0.01~0.1 |
| Tyrosine (Y) | 0.005~0.03 | 0~0.001 | 0.01~0.1 | 0~0.001 | 0.5~2 | 0~0.001 | 0~0.001 | 0~0.001 | 0~0.001 | 55~65 | 0~0.001 | 0~0.001 |
| Methionine (M) | 0.005~0.03 | 0~0.001 | 0~0.001 | 0~0.001 | 0~0.001 | 0.5~1.5 | 0~0.001 | 0~0.001 | 0~0.001 | 0.01~0.1 | 0~0.05 | 0~0.001 |
| Threonine (T) | 0~0.001 | 0.01~0.1 | 0~0.01 | 0~0.05 | 5~15 | 0.01~0.05 | 0~0.001 | 0~0.001 | 0~0.001 | 0.01~0.1 | 0~0.001 | 0.01~0.1 |
| Lysine (K) | 0.01~0.05 | 0~0.001 | 0~0.001 | 2~8 | 0~0.05 | 0~0.001 | 0~0.001 | 0~0.001 | 0~0.001 | 0.5~2 | 0~0.001 | 0~0.001 |
| Isoleucine (I) | 0~0.01 | 0~0.001 | 0.01~0.1 | 0~0.001 | 1~5 | 20~30 | 0~0.001 | 0~0.001 | 0~0.001 | 0~0.001 | 0~0.01 | 0~0.001 |
| Tryptophan (W) | 0~0.001 | 0~0.001 | 0~0.001 | 0~0.001 | 0~0.001 | 0~0.05 | 0~0.001 | 0~0.001 | 0~0.001 | 0.5~1.5 | 0~0.001 | 0~0.001 |
| Aspartic acid (D) | 0~0.001 | 0~0.001 | 0~0.001 | 0~0.001 | 0.5~2 | 0~0.01 | 0~0.001 | 0~0.001 | 0~0.001 | 1~4 | 4~10 | 0~0.001 |
| Histidine (H) | 0~0.001 | 0~0.001 | 0~0.001 | 2~8 | 0.3~1.5 | 0~0.001 | 0~0.001 | 0~0.001 | 0~0.001 | 3~9 | 0~0.01 | 0~0.001 |
| Asparagine (N) | 0.01~0.1 | 0~0.001 | 0.01~0.1 | 0.1~1.0 | 3~9 | 0~0.01 | 0~0.001 | 0~0.001 | 0~0.001 | 3~9 | 0~0.05 | 0~0.001 |
| Arginine (R) | 0.01~0.1 | 0.01~0.1 | 0.01~0.1 | 0.05~0.5 | 0.5~2 | 0.01~0.05 | 0~0.001 | 0~0.001 | 0~0.001 | 0.1~1 | 0.05~0.5 | 0.01~0.1 |
| Glutamic acid (E) | 0.01~0.1 | 0~0.01 | 0.01~0.1 | 0~0.05 | 0~0.05 | 0~0.001 | 0~0.001 | 0~0.001 | 0~0.001 | 0~0.001 | 0~0.01 | 0.01~0.1 |
| Cysteine (C) | 0.01~0.05 | 0.01~0.1 | 0.01~0.1 | 0~0.001 | 0~0.05 | 0.01~0.1 | 0~0.001 | 0~0.001 | 0~0.001 | 0.01~0.1 | 0.01~0.1 | 0~0.01 |
| Leucine (L) | 0~0.001 | 0~0.001 | 0~0.001 | 0~0.05 | 0.01~0.5 | 10~20 | 0~0.001 | 0~0.001 | 0~0.001 | 0.5~3 | 0~0.05 | 0.01~0.1 |
| Glutamine (Q) | 0~0.01 | 0~0.001 | 0~0.001 | 85~95 | 0~0.001 | 0~0.01 | 0~0.001 | 0~0.001 | 0~0.001 | 0.5~3 | 0~0.001 | 0.01~0.1 |

TABLE 17

Amino acid distribution ratio for each position of amino acid (%)-$V_K$3-20 & 20-2_CDR2

| Type of AA | 3 | 4 | 5 | 6 | 7 | 8 | 9 | 10 | 11 |
|---|---|---|---|---|---|---|---|---|---|
| Alanine (A) | 0~0.001 | 5~15 | 70~80 | 0.5~2 | 0.5~3 | 0~0.001 | 90~99.99 | 60~70 | 0.01~0.05 |
| Serine (S) | 3~9 | 3~8 | 2~7 | 80~90 | 20~30 | 0.01~0.1 | 0.01~0.5 | 5~10 | 0~0.01 |
| Glycine (G) | 0~0.01 | 25~35 | 0.5~2 | 0~0.01 | 0.5~2 | 0.01~0.1 | 0~0.001 | 0~0.001 | 3~8 |
| Phenylalanine (F) | 4~10 | 0.01~0.05 | 0.01~0.1 | 2~7 | 0.5~2 | 0~0.001 | 0~0.01 | 0~0.01 | 0~0.001 |
| Proline (P) | 0.01~0.1 | 0.01~0.05 | 0.1~1 | 0.1~1 | 0.01~0.05 | 0.01~0.1 | 0~0.01 | 5~15 | 0~0.001 |
| Valine (V) | 0~0.001 | 0.5.~1.5 | 2~6 | 0.5~1.5 | 0.1~1 | 0.01~0.1 | 1~3 | 0.01~0.05 | 0~0.01 |
| Tyrosine (Y) | 65~75 | 0.1~1 | 0.01~0.1 | 1~3 | 0.5~2 | 0~0.001 | 0~0.001 | 0~0.001 | 0.01~0.05 |
| Methionine (M) | 0~0.001 | 0~0.001 | 0~0.001 | 0~0.001 | 0.1~2 | 0~0.001 | 0~0.001 | 0~0.001 | 0~0.001 |
| Threonine (T) | 0.01~0.1 | 0.5~3 | 5~15 | 1~4 | 10~20 | 0~0.01 | 0.01~0.1 | 10~20 | 0~0.01 |
| Lysine (K) | 0~0.01 | 0.01~0.01 | 0~0.001 | 0~0.001 | 4~10 | 0~0.001 | 0~0.001 | 0~0.001 | 0~0.001 |
| Isoleucine (I) | 0~0.001 | 0~0.01 | 1~4 | 0.5~1.5 | 2~7 | 0~0.001 | 0~0.001 | 0~0.01 | 0~0.001 |
| Tryptophan (W) | 0~0.001 | 0~0.01 | 0~0.001 | 0~0.001 | 0~0.001 | 0~0.001 | 0~0.001 | 0~0.001 | 0~0.001 |
| Aspartic acid (D) | 0~0.001 | 35~45 | 0.01~0.1 | 0~0.001 | 1~4 | 0~0.001 | 00.1~0.05 | 0.01~0.05 | 88~98 |

TABLE 17-continued

Amino acid distribution ratio for each position of amino acid (%)-V$_K$3-20 & 20-2_CDR2

| Type of AA | 3 | 4 | 5 | 6 | 7 | 8 | 9 | 10 | 11 |
|---|---|---|---|---|---|---|---|---|---|
| Histidine (H) | 0~0.001 | 0.5~3 | 0.01~0.1 | 0.1~0.8 | 1~4 | 0.01~0.1 | 0~0.001 | 0~0.001 | 0~0.01 |
| Asparagine (N) | 0~0.001 | 1~4 | 0.01~0.1 | 0.1~0.8 | 30~40 | 0~0.001 | 0~0.001 | 0~0.001 | 0.01~0.05 |
| Arginine (R) | 0~0.001 | 0.5~2 | 0~0.01 | 0~0.01 | 1~4 | 95~99.99 | 0~0.01 | 0~0.001 | 0~0.001 |
| Glutamic acid (E) | 0~0.001 | 1~5 | 0.5~2 | 0~0.01 | 0~0.01 | 0~0.001 | 0~0.001 | 0~0.001 | 0.01~0.05 |
| Cysteine (C) | 0~0.001 | 0.01~0.1 | 0.01~0.1 | 0~0.05 | 0~0.01 | 0.01~0.2 | 0.01~0.05 | 0.01~0.05 | 0~0.001 |
| Leucine (L) | 0~0.001 | 0.5~2 | 0.5~1.5 | 0.5~2 | 0.5~2 | 0.01~0.2 | 0.01~0.05 | 0.01~0.05 | 0~0.001 |
| Glutamine (Q) | 0~0.001 | 0.01~0.1 | 0.10~0.1 | 0~0.001 | 0~0.001 | 0~0.001 | 0~0.001 | 0~0.001 | 0~0.001 |

TABLE 18

Amino acid distribution ratio for each position of amino acid (%)-V$_K$3-20 & 20-2_CDR3

| Type of AA | 4 | 5 | 6 | 7 | 8 | 9 | 10 | 11 |
|---|---|---|---|---|---|---|---|---|
| Alanine (A) | 0~0.001 | 0.01~0.05 | 4~10 | 2~6 | 1~3 | 3~8 | 0.01~0.05 | 0.1~0.5 |
| Serine (S) | 0~0.01 | 0.01~0.05 | 4~10 | 8~18 | 20~30 | 30~40 | 0.05~0.3 | 0.5~2 |
| Glycine (G) | 0~0.01 | 0~0.001 | 1~4 | 10~20 | 2~4 | 0.1~1 | 0~0.001 | 0.5~2 |
| Phenylalanine (F) | 0~0.001 | 0~0.001 | 2~5 | 0.5~2 | 0.1~1 | 0.5~3 | 0~0.001 | 2~7 |
| Proline (P) | 0~0.001 | 0~0.001 | 0.01~0.1 | 0.01~0.1 | 0.01~0.1 | 1~4 | 95~99.99 | 2~7 |
| Valine (V) | 0~0.001 | 0~0.001 | 0.1~0.5 | 0.5~2 | 0.1~1 | 0.1~1 | 0~0.001 | 0.5~3 |
| Tyrosine (Y) | 0~0.001 | 0~0.01 | 55~65 | 10~20 | 0.5~3 | 1~5 | 0~0.001 | 5~15 |
| Methionine (M) | 0~0.001 | 0~0.001 | 0~0.001 | 0~0.001 | 0~0.001 | 0~0.001 | 0~0.001 | 0~0.01 |
| Threonine (T) | 0~0.001 | 0~0.001 | 0.5~2 | 2~6 | 4~10 | 6~15 | 0.01~0.05 | 0.01~0.05 |
| Lysine (K) | 0~0.001 | 0~0.02 | 0.01~0.05 | 0.5~2 | 1~4 | 0~0.001 | 0~0.001 | 0.1~1 |
| Isoleucine (I) | 0~0.001 | 0~0.001 | 0.01~0.05 | 1~3 | 1~4 | 0.5~3 | 0~0.001 | 0.5~2 |
| Tryptophan (W) | 0.05~0.5 | 0~0.001 | 0.1~0.5 | 0~0.02 | 0~0.001 | 20~30 | 0~0.001 | 10~20 |
| Aspartic acid (D) | 0~0.001 | 0~0.001 | 0.5~2 | 4~10 | 3~10 | 0.01~0.05 | 0~0.001 | 0.1~1 |
| Histidine (H) | 0~0.001 | 5~15 | 2~6 | 1~5 | 3~8 | 0~0.01 | 0~0.001 | 1~5 |
| Asparagine (N) | 0~0.001 | 0~0.001 | 0.5~2 | 10~20 | 20~30 | 0.5~3 | 0~0.001 | 0.1~1 |
| Arginine (R) | 88~98 | 0.03~0.3 | 4~8 | 0.1~1 | 0.5~3 | 0.1~1 | 0.02~0.1 | 3~9 |
| Glutamic acid (E) | 0~0.001 | 0~0.01 | 0~0.02 | 0.5~3 | 0.5~3 | 0~0.001 | 0~0.001 | 0.1~1 |
| Cysteine (C) | 0~0.001 | 0~0.001 | 0.1~0.5 | 0.01~0.05 | 0.01~0.05 | 0~0.01 | 0~0.001 | 0.01~0.1 |
| Leucine (L) | 2~5 | 0~0.05 | 0.5~2 | 5~15 | 1~3 | 5~10 | 0.05~0.5 | 38~48 |
| Glutamine (Q) | 0.01~0.1 | 85~95 | 0.01~0.1 | 0~0.01 | 6~10 | 0~0.001 | 0.05~0.5 | 1~6 |

TABLE 19

Amino acid distribution ratio for each position of amino acid (%)-V$_K$3-20-2_CDR1

| Type of AA | 3 | 4 | 5 | 6 | 7 | 8 | 9 | 10 | 11 | 12 |
|---|---|---|---|---|---|---|---|---|---|---|
| Alanine (A) | 0~0.001 | 95~99.99 | 0~0.001 | 0~0.001 | 0.5~3 | 0.5~3 | 2~6 | 0.5~2 | 0.1~1 | 0.01~0.1 |
| Serine (S) | 90~99.99 | 0.01~0.1 | 95~99.99 | 0.01~0.1 | 60~70 | 0.1~1 | 30~40 | 25~35 | 4~10 | 0.01~0.1 |
| Glycine (G) | 3~9 | 0.01~0.1 | 0.01~0.1 | 0~0.01 | 1~4 | 0~0.01 | 6~15 | 1~4 | 0.1~0.5 | 80~90 |
| Phenylalanine (F) | 0~0.001 | 0~0.001 | 0~0.001 | 0~0.001 | 0.01~0.1 | 0.5~3 | 0.1~1 | 0.5~2 | 3~6 | 0~0.01 |
| Proline (P) | 0~0.001 | 0~0.01 | 0~0.001 | 0.01~0.1 | 0.1~1 | 0~0.01 | 0.01~0.1 | 0.1~1 | 0.01~0.05 | 0~0.001 |
| Valine (V) | 0.01~0.05 | 0.01~0.1 | 0.01~0.1 | 0~0.01 | 0.01~0.1 | 40~50 | 0.5~2 | 0.5~2 | 0~0.001 | 2~7 |
| Tyrosine (Y) | 0~0.001 | 0~0.001 | 0~0.001 | 0~0.01 | 0.5~3 | 0.01~0.1 | 0.5~3 | 1~4 | 20~30 | 0~0.01 |
| Methionine (M) | 0.01~0.05 | 0~0.001 | 0~0.001 | 0~0.001 | 0~0.001 | 0~0.01 | 0~0.01 | 0~0.01 | 0~0.01 | 0~0.01 |
| Threonine (T) | 0~0.01 | 0.01~0.1 | 0~0.01 | 0~0.01 | 3~8 | 0.01~0.1 | 3~8 | 10~20 | 0.5~2 | 0~0.01 |
| Lysine (K) | 0~0.01 | 0~0.001 | 0~0.01 | 0~0.01 | 0.01~0.05 | 0~0.001 | 0.5~3 | 2~5 | 2~6 | 0~0.001 |
| Isoleucine (I) | 0.01~0.05 | 0~0.001 | 0.01~0.1 | 0~0.01 | 0.5~2 | 30~40 | 1~4 | 3~7 | 0.01~0.05 | 0~00.1 |
| Tryptophan (W) | 0~0.001 | 0~0.01 | 0~0.001 | 0~0.001 | 0~0.001 | 0~0.01 | 0~0.01 | 0~0.01 | 0.5~2 | 0~0.001 |
| Aspartic acid (D) | 0~0.01 | 0~0.001 | 0~0.001 | 0.01~0.1 | 1~4 | 0~0.01 | 3~10 | 2~5 | 2~6 | 4~10 |
| Histidine (H) | 0~0.001 | 0~0.001 | 0~0.001 | 0~0.001 | 0~0.01 | 0.01~0.1 | 0.5~2 | 0.5~2 | 3~7 | 0~0.001 |
| Asparagine (N) | 0.05~0.1 | 0~0.001 | 0.01~0.1 | 0~0.01 | 10~20 | 0.01~0.1 | 15~25 | 25~35 | 35~45 | 0~0.01 |
| Arginine (R) | 0.01~0.1 | 0.01~0.1 | 0.01~0.1 | 90~99.99 | 0.5~3 | 0.01~0.1 | 2~5 | 1~5 | 0.1~1 | 0.01~0.1 |
| Glutamic acid (E) | 0.01~0.1 | 0.01~0.1 | 0.01~0.1 | 0.01~0.1 | 0~0.01 | 0~0.01 | 0.5~3 | 0~0.01 | 0.5~2 | 0.01~0.1 |
| Cysteine (C) | 0~0.01 | 0.01~0.1 | 0~0.01 | 0~0.01 | 0.01~0.1 | 0.01~0.1 | 0.01~0.05 | 0.01~0.05 | 0.01~0.1 | 0.01~0.1 |
| Leucine (L) | 0~0.001 | 0~0.001 | 0~0.001 | 0.01~0.1 | 0.1~0.5 | 10~20 | 1~4 | 0.05~0.1 | 1~4 | 0.1~1 |
| Glutamine (Q) | 0~0.01 | 0~0.001 | 0~0.001 | 2~7 | 0~0.01 | 0~0.01 | 0.01~0.05 | 0.01~0.05 | 0.5~2 | 0~0.001 |

TABLE 20

Amino acid distribution ratio for each position of amino acid (%)-Vλ1-51_CDR1

| Type of AA | 3 | 4 | 5 | 6 | 7 | 8 | 9 |
|---|---|---|---|---|---|---|---|
| Alanine (A) | 0~0.01 | 0.01~0.1 | 0.5~3 | 1~3 | 0.01~0.1 | 0~0.001 | 0.1~0.5 |
| Serine (S) | 95~99.99 | 0.01~0.1 | 75~85 | 45~55 | 95~99.99 | 0.01~0.1 | 0.01~0.1 |
| Glycine (G) | 0~0.001 | 95~99.99 | 4~10 | 2~7 | 0~0.001 | 0~0.001 | 0.01~0.1 |
| Phenylalanine (F) | 0.1~0.1 | 0~0.001 | 0.01~0.1 | 0.1~1.5 | 0.1~0.5 | 0~0.001 | 0.01~0.1 |
| Proline (P) | 0.~0.5 | 0~0.001 | 0.1~0.5 | 0.01~0.1 | 0.01~0.1 | 0~0.001 | 0~0.001 |
| Valine (V) | 0~0.001 | 0.01~0.1 | 0.01~0.1 | 0.01~0.1 | 0~0.001 | 0~0.001 | 85~95 |
| Tyrosine (Y) | 0.01~0.05 | 0~0.001 | 0.01~0.1 | 0.5~2 | 0.01~0.1 | 0~0.01 | 0.01~0.1 |
| Methionine (M) | 0~0.001 | 0~0.001 | 0~0.001 | 0~0.001 | 0~0.001 | 0.1~0.5 | 0~0.001 |
| Threonine (T) | 0.01~0.05 | 0~0.001 | 3~9 | 6~15 | 0~0.01 | 0.01~0.1 | 0~0.001 |
| Lysine (K) | 0~0.001 | 0~0.001 | 0~0.01 | 0.5~3 | 0~0.001 | 0.01~0.1 | 0~0.001 |
| Isoleucine (I) | 0~0.001 | 0~0.001 | 0.5~3 | 0.5~3 | 0~0.01 | 0.01~0.1 | 5~15 |
| Tryptophan (W) | 0~0.001 | 0.01~0.1 | 0~0.001 | 0~0.01 | 0~0.001 | 0~0.001 | 0~0.001 |
| Aspartic acid (D) | 0~0.001 | 0.01~0.1 | 0.5~3 | 1~4 | 0~0.001 | 0~0.01 | 0~0.001 |
| Histidine (H) | 0~0.001 | 0~0.001 | 0~0.01 | 0.5~3 | 0~0.001 | 0~0.001 | 0~0.001 |
| Asparagine (N) | 0~0.001 | 0~0.001 | 0.5~3 | 15~25 | 0~0.001 | 95~99.99 | 0~0.001 |
| Arginine (R) | 0~0.001 | 0.01~0.1 | 0.5~3 | 1~4 | 0~0.001 | 0~0.001 | 0~0.001 |
| Glutamic acid (E) | 0~0.001 | 0~0.001 | 0~0.001 | 0~0.001 | 0~0.001 | 0~0.001 | 0~0.001 |
| Cysteine (C) | 0.01~0.1 | 0.01~0.1 | 0~0.01 | 0~0.01 | 0.01~0.1 | 0~0.01 | 0.1~0.5 |
| Leucine (L) | 0.01~0.1 | 0~0.001 | 0.1~0.5 | 0.01~0.5 | 0.1~0.5 | 0~0.001 | 0.1~0.5 |
| Glutamine (Q) | 0~0.001 | 0~0.001 | 0~0.001 | 0~0.001 | 0~0.001 | 0~0.001 | 0~0.001 |

| Type of AA | 10 | 11 | 12 | 13 | 14 | 15 |
|---|---|---|---|---|---|---|
| Alanine (A) | 3~8 | 0.5~3 | 0~0.001 | 4~10 | 0.01~0.5 | 1~4 |
| Serine (S) | 0~0.01 | 25~35 | 1~5 | 5~15 | 0~0.001 | 30~40 |
| Glycine (G) | 2~5 | 1~4 | 0.1~1 | 0.1~1 | 0~0.001 | 0~0.001 |
| Phenylalanine (F) | 0~0.001 | 0.01~0.1 | 0.5~2 | 5~15 | 0~0.001 | 0.5~3 |
| Proline (P) | 0~0.001 | 0.1~0.5 | 0.01~0.1 | 1~6 | 0~0.001 | 0.01~0.1 |
| Valine (V) | 0~0.001 | 0.3~1 | 0~0.001 | 0.5~3 | 95~99.99 | 0~0.01 |
| Tyrosine (Y) | 0~0.001 | 1~3 | 2~6 | 25~35 | 0~0.001 | 10~20 |
| Methionine (M) | 0~0.001 | 0~0.001 | 0~0.001 | 0~0.001 | 0.01~0.5 | 0~0.001 |
| Threonine (T) | 0~0.001 | 4~10 | 0.5~3 | 10~20 | 0~0.001 | 0.5~3 |
| Lysine (K) | 0.05~0.5 | 2~6 | 2~5 | 0~0.001 | 0~0.001 | 0.1~2 |
| Isoleucine (I) | 0~0.01 | 2~6 | 0.1~3 | 1~5 | 0~0.001 | 0~0.001 |
| Tryptophan (W) | 0~0.001 | 0~0.001 | 0~0.001 | 0~0.001 | 0~0.001 | 0~0.001 |
| Aspartic acid (D) | 0.01~0.1 | 4~10 | 0.5~3 | 2~6 | 0~0.001 | 0.5~3 |
| Histidine (H) | 0~0.001 | 0.5~3 | 3~7 | 3~7 | 0~0.001 | 2~6 |
| Asparagine (N) | 0.01~0.1 | 30~40 | 70~80 | 2~6 | 0~0.001 | 30~40 |
| Arginine (R) | 0~0.001 | 1~5 | 0.3~2 | 0.1~1 | 0.01~0.1 | 0.01~0.05 |
| Glutamic acid (E) | 85~95 | 0.5~1.5 | 0.5~3 | 0~0.01 | 0~0.001 | 0.01~0.05 |
| Cysteine (C) | 0.01~0.1 | 0~0.001 | 0~0.001 | 0.01~0.1 | 0.01~0.1 | 0.01~0.05 |
| Leucine (L) | 0~0.001 | 0.5~3 | 0~0.001 | 1~4 | 0.01~0.1 | 0.1~1 |
| Glutamine (Q) | 0~0.001 | 0~0.001 | 0.3~2 | 0~0.01 | 0~0.001 | 0.5~2 |

TABLE 21

Amino acid distribution ratio for each position of amino acid (%)-Vλ1-51_CDR2

| Type of AA | 49 | 50 | 51 | 52 | 53 | 54 | 55 | 56 |
|---|---|---|---|---|---|---|---|---|
| Alanine (A) | 0~0.001 | 4~10 | 0~0.001 | 0.1~1 | 0~0.001 | 0~0.001 | 0~0.001 | 0~0.001 |
| Serine (S) | 1~5 | 5~15 | 2~6 | 4~12 | 0.5~3 | 0~0.001 | 0~0.001 | 95~100 |
| Glycine (G) | 0~0.001 | 5~15 | 0.1~1 | 0.5~2 | 0~0.001 | 0~0.001 | 0~0.001 | 0~0.001 |
| Phenylalanine (F) | 5~15 | 0.1~1.5 | 0.1~2 | 0.5~2 | 0~0.001 | 0~0.001 | 0~0.001 | 0~0.001 |
| Proline (P) | 0~0.001 | 0~0.001 | 0~0.001 | 0~0.001 | 0~0.001 | 0~0.001 | 95~100 | 0~0.001 |
| Valine (V) | 0~0.001 | 0.1~1.5 | 0.5~4 | 0.1~2 | 0.1~1 | 0~0.001 | 0~0.001 | 0~0.001 |
| Tyrosine (Y) | 70~80 | 1~4 | 0.5~3 | 1~5 | 0.5~3 | 0~0.001 | 0~0.001 | 0~0.001 |
| Methionine (M) | 0~0.001 | 0.5~2 | 0~0.001 | 0~0.001 | 0.5~3 | 0~0.001 | 0~0.001 | 0~0.001 |
| Threonine (T) | 0~0.001 | 1~5 | 2~7 | 5~12 | 0~0.001 | 0~0.001 | 0~0.001 | 0~0.001 |
| Lysine (K) | 0~0.001 | 1~5 | 0.1~2 | 1~4 | 15~25 | 0~0.001 | 0~0.001 | 0~0.001 |
| Isoleucine (I) | 0~0.001 | 0.5~3 | 0.5~2 | 2~5 | 1~3 | 0~0.001 | 0~0.001 | 0~0.001 |
| Tryptophan (W) | 0~0.001 | 0.1~2 | 0~0.001 | 0~0.001 | 0~0.001 | 0~0.001 | 0~0.001 | 0~0.001 |
| Aspartic acid (D) | 0.1~2 | 20~30 | 10~20 | 10~20 | 0.5~4 | 0~0.001 | 0~0.001 | 0~0.001 |
| Histidine (H) | 2~7 | 0.5~2 | 0.5~2 | 1~5 | 1~7 | 0~0.001 | 0~0.001 | 0~0.001 |
| Asparagine (N) | 0.5~2 | 10~15 | 60~70 | 45~55 | 15~25 | 0~0.001 | 0~0.001 | 0~0.001 |
| Arginine (R) | 0.1~2 | 1~5 | 0.1~1 | 0.5~2 | 1~4 | 95~100 | 0~0.001 | 0~0.001 |
| Glutamic acid (E) | 0~0.001 | 5~15 | 0~0.001 | 0~0.001 | 0.5~2 | 2~8 | 0~0.001 | 0~0.001 |
| Cysteine (C) | 0.05~0.5 | 0~0.001 | 0~0.001 | 0~0.001 | 0~0.001 | 0~0.001 | 0~0.001 | 0~0.001 |
| Leucine (L) | 0.5~2 | 0.5~3 | 0~0.001 | 0~0.001 | 3~9 | 0~0.001 | 0~0.001 | 0~0.001 |
| Glutamine (Q) | 0.5~2 | 0.1~2 | 0~0.001 | 0~0.001 | 25~35 | 0~0.001 | 0~0.001 | 0~0.001 |

TABLE 22

Amino acid distribution ratio for each position of amino acid (%)-Vλ1-51_CDR3

| Type of AA | 4 | 5 | 6 | 7 | 8 | 9 | 10 | 11 | 12 | 13 | 14 |
|---|---|---|---|---|---|---|---|---|---|---|---|
| Alanine (A) | 40~50 | 25~35 | 0.1~1 | 0~0.001 | 2~5 | 0.5~3 | 0.01~0.1 | 0.5~3 | 25~35 | 1~7 | 1~4 |
| Serine (S) | 3~7 | 25~35 | 0~0.001 | 0~0.001 | 25~35 | 58~75 | 5~15 | 25~35 | 2~4 | 1~7 | 0.01~0.1 |
| Glycine (G) | 10~20 | 0.1~1 | 0.01~0.1 | 0.1~0.5 | 2~8 | 1~5 | 0.1~1 | 1~4 | 15~25 | 3~10 | 0.01~0.1 |
| Phenylalanine (F) | 0~0.001 | 0.01~0.1 | 0.5~3 | 0~0.001 | 0.01~0.1 | 0.05~0.5 | 0~0.01 | 0.01~0.1 | 0.5~3 | 0.5~3 | 0.5~3 |
| Proline (P) | 0.01~0.1 | 0.01~0.1 | 0~0.001 | 0~0.001 | 0.01~0.1 | 0.5~2 | 0.5~2 | 0.05~0.5 | 0.5~3 | 2~7 | 0.01~0.1 |
| Valine (V) | 0.5~3 | 10~20 | 0~0.01 | 0.01~0.05 | 0.5~2 | 0.5~2 | 0.5~2 | 0.1~1 | 2~6 | 15~25 | 55~65 |
| Tyrosine (Y) | 0.01~0.1 | 0.01~0.1 | 10~20 | 0~0.01 | 0.5~2 | 0.5~2 | 0.01~0.05 | 0.5~3 | 0.5~3 | 20~30 | 0~0.01 |
| Methionine (M) | 0~0.001 | 0~0.001 | 0.01~0.1 | 0.01~0.05 | 0~0.01 | 0~0.001 | 0.01~0.05 | 0~0.001 | 0~0.01 | 0.5~3 | 2~6 |
| Threonine (T) | 0.5~3 | 20~30 | 0.01~0.1 | 0~0.001 | 3~8 | 3~7 | 1~4 | 3~9 | 1~4 | 0.01~0.1 | 0~0.01 |
| Lysine (K) | 0~0.01 | 0~0.001 | 0~0.001 | 0~0.001 | 0.5~3 | 0.5~2 | 0~0.001 | 2~6 | 0~0.01 | 0~0.01 | 0~0.001 |
| Isoleucine (I) | 0~0.001 | 0.5~3 | 0~0.01 | 0.01~0.05 | 1~4 | 1~4 | 0.5~3 | 0.5~3 | 1~4 | 0.01~0.1 | 5~10 |
| Tryptophan (W) | 0~0.001 | 0.01~0.1 | 75~85 | 0~0.001 | 0.01~0.1 | 0~0.001 | 0.01~0.05 | 0~0.001 | 0.01~0.1 | 15~25 | 0.01~0.1 |
| Aspartic acid (D) | 0~0.01 | 0~0.001 | 0~0.01 | 95~99.999 | 25~35 | 1~4 | 0.5~2 | 10~20 | 1~5 | 0~0.01 | 0.01~0.1 |
| Histidine (H) | 0.5~3 | 0.01~0.1 | 0.5~3 | 0~0.001 | 0.5~3 | 0.01~0.5 | 0~0.01 | 1~4 | 10~20 | 1~4 | 0~0.001 |
| Asparagine (N) | 0~0.001 | 0.01~0.1 | 0~0.001 | 0.01~0.1 | 8~18 | 5~15 | 1~4 | 25~35 | 0.5~3 | 0~0.01 | 0~0.001 |
| Arginine (R) | 0.01~0.1 | 0~0.001 | 0.1~1 | 0.01~0.1 | 0.5~3 | 1~4 | 0.1~1 | 1~4 | 0.5~3 | 1~4 | 0.01~0.1 |
| Glutamic acid (E) | 0.5~3 | 0.01~0.1 | 0~0.001 | 0.01~0.1 | 0.5~3 | 0~0.01 | 0~0.01 | 0.5~3 | 0.5~3 | 0.5~3 | 0~0.001 |
| Cysteine (C) | 0~0.001 | 0~0.01 | 0.0~0.1 | 0~0.001 | 0.01~0.1 | 0.01~0.05 | 0.01~0.05 | 0~0.01 | 0.01~0.1 | 0.01~0.1 | 0.01~0.1 |
| Leucine (L) | 0.5~3 | 1~4 | 0.01~0.1 | 0~0.001 | 0.01~0.1 | 0.5~3 | 75~85 | 0.01~0.1 | 2~7 | 5~15 | 20~30 |
| Glutamine (Q) | 25~35 | 0~0.001 | 0~0.001 | 0~0.001 | 0~0.001 | 0~0.001 | 0.01~0.1 | 0~0.01 | 1~4 | 0.5~3 | 0~0.001 |

In the present invention, the amino acid ratio for each position in the heavy-chain complementarity-determining region 1 (CDRH1) in the heavy-chain variable region having the sequence of VH3-15 (SEQ ID NO: 1) includes the range of Table 23, the amino acid ratio for each position in the heavy-chain complementarity-determining region 2 (CDRH2) in the heavy-chain variable region having the sequence of VH3-15 (SEQ ID NO: 1) includes the range of Table 24, the amino acid ratio for each position in the heavy-chain complementarity-determining region 1 (CDRH1) in the heavy-chain variable region having the sequence of VH3-23 (SEQ ID NO: 6) includes the range of Table 23, the amino acid ratio for each position in the heavy-chain complementarity-determining region 2 (CDRH2) in the heavy-chain variable region having the sequence of VH3-23 (SEQ ID NO: 6) includes the range of Table 24, the amino acid ratio for each position in the heavy-chain complementarity-determining region 1 (CDRH1) in the heavy-chain variable region having the sequence of VH1-69 (SEQ ID NO: 11) includes the range of Table 25, the amino acid ratio for each position in the heavy-chain complementarity-determining region 2 (CDRH2) in the heavy-chain variable region having the sequence of VH1-69 (SEQ ID NO: 11) includes the range of Table 26, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 9 amino acids, the amino acid ratio for each position in CDRH3 includes the range of Table 27, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 10 amino acids, the amino acid ratio for each position in the CDRH3 includes the range of Table 28, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 11 amino acids, the amino acid ratio for each position in CDRH3 includes the range of Table 29, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 12 amino acids, the amino acid ratio for each position in CDRH3 includes the range of Table 30, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 13 amino acids, the amino acid ratio for each position in CDRH3 includes the range of Table 31, when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 14 amino acids, the amino acid ratio for each position in CDRH3 includes the range of Table 32, the amino acid ratio for each position in the light-chain complementarity-determining region 1 (CDRL1) in the light-chain variable region having the sequence of Vκ1-39 (SEQ ID NO: 16) includes the range of Table 33, the amino acid ratio for each position in the light-chain complementarity-determining region 2 (CDRL2) in the light-chain variable region having the sequence of Vκ1-39 (SEQ ID NO: 16) includes the range of Table 34, the amino acid ratio for each position in the light-chain complementarity-determining region 3 (CDRL3) in the light-chain variable region having the sequence of Vκ1-39 (SEQ ID NO: 16) includes the range of Table 35, the amino acid ratio for each position in the light-chain complementarity-determining region 1 (CDRL1) in the light-chain variable region having the sequence of Vκ3-20 (SEQ ID NO: 21) includes the range of Table 36, the amino acid ratio for each position in the light-chain complementarity-determining region 2 (CDRL2) in the light-chain variable region having the sequence of Vκ3-20 (SEQ ID NO: 21) includes the range of Table 37, the amino acid ratio for each position in the light-chain complementarity-determining region 3 (CDRL3) in the light-chain variable region having the sequence of Vκ3-20 (SEQ ID NO: 21) includes the range of Table 38, the amino acid ratio for each position in the light-chain complementarity-determining region 1 (CDRL1) in the light-chain variable region having the sequence of Vκ3-20-2 (SEQ ID NO: 26) includes the range of Table 39, the amino acid ratio for each position in the light-chain complementarity-determining region 2 (CDRL2) in the light-chain variable region having the sequence of Vκ3-20-2 (SEQ ID NO: 26) includes the range of Table 37, the amino acid ratio for each position in the light-chain complementarity-determining region 3 (CDRL3) in the light-chain variable region having the sequence of Vκ3-20-2 (SEQ ID NO: 26) includes the range of Table 38, the amino acid ratio for each position in the light-chain complementarity-determining region 1 (CDRL1) in the light-chain variable region having the sequence of Vλ1-51 (SEQ ID NO: 31) includes the range of Table 40, the amino acid ratio for each position in the light-chain complementarity-determining region 2 (CDRL2) in the light-chain variable region having the sequence of Vλ1-51 (SEQ ID NO: 31) includes the range of Table 41, and the amino acid ratio for each position in the light-chain complementarity-determining region 3 (CDRL3) in the light-chain variable region having the sequence of Vλ1-51 (SEQ ID NO: 31) includes the range of Table 42, but is not limited thereto.

TABLE 23

Amino acid distribution ratio for each position of amino acid (%)-VH3_CDR1

| Type of AA | 27 | 28 | 29 | 30 | 31 | 32 | 33 | 34 | 35 |
|---|---|---|---|---|---|---|---|---|---|
| Alanine (A) | 0.000 | 4.393 | 9.435 | 2.896 | 2.236 | 3.180 | 26.480 | 0.075 | 3.307 |
| Serine (S) | 23.700 | 0.261 | 0.037 | 0.000 | 0.038 | 0.075 | 0.484 | 0.000 | 0.037 |
| Glycine (G) | 0.000 | 1.303 | 0.000 | 3.528 | 14.286 | 0.736 | 5.996 | 0.075 | 1.338 |
| Phenylalanine (F) | 0.000 | 0.037 | 0.000 | 0.557 | 1.516 | 0.000 | 1.825 | 0.000 | 9.773 |
| Proline (P) | 64.116 | 1.303 | 85.215 | 0.186 | 0.872 | 4.901 | 1.601 | 0.788 | 0.000 |
| Valine (V) | 0.037 | 0.521 | 0.371 | 2.154 | 12.391 | 0.000 | 18.399 | 0.150 | 3.270 |
| Tyrosine (Y) | 0.037 | 0.000 | 0.000 | 1.560 | 2.236 | 10.587 | 1.229 | 0.000 | 40.654 |
| Methionine (M) | 0.000 | 8.191 | 0.409 | 2.414 | 0.909 | 0.673 | 0.834 | 8.483 | 1.003 |
| Threonine (T) | 0.000 | 2.978 | 0.000 | 1.448 | 3.600 | 10.251 | 0.037 | 0.000 | 0.000 |
| Lysine (K) | 2.080 | 0.074 | 3.975 | 2.599 | 0.682 | 5.686 | 1.937 | 20.371 | 0.111 |
| Isoleucine (I) | 0.000 | 0.968 | 0.000 | 0.000 | 0.000 | 0.000 | 0.000 | 0.000 | 0.000 |
| Tryptophan (W) | 0.000 | 0.223 | 0.000 | 13.554 | 27.624 | 6.510 | 1.750 | 0.000 | 17.837 |
| Aspartic acid (D) | 0.000 | 1.154 | 0.000 | 10.472 | 0.114 | 0.449 | 1.750 | 0.000 | 0.297 |
| Histidine (H) | 0.000 | 9.456 | 0.000 | 1.077 | 0.796 | 0.150 | 0.112 | 0.000 | 2.081 |
| Asparagine (N) | 9.361 | 0.894 | 0.037 | 3.453 | 2.842 | 0.486 | 3.687 | 0.150 | 0.260 |
| Arginine (R) | 0.520 | 12.249 | 0.334 | 34.831 | 20.500 | 5.163 | 5.251 | 0.225 | 15.942 |
| Glutamic acid (E) | 0.000 | 52.085 | 0.037 | 18.975 | 7.579 | 0.748 | 2.756 | 0.000 | 2.787 |
| Cysteine (C) | 0.037 | 0.037 | 0.111 | 0.297 | 0.455 | 0.187 | 1.415 | 68.806 | 0.223 |
| Leucine (L) | 0.000 | 0.074 | 0.000 | 0.000 | 0.076 | 0.000 | 13.073 | 0.000 | 0.000 |
| Glutamine (Q) | 0.111 | 3.797 | 0.037 | 0.000 | 1.250 | 50.168 | 11.322 | 0.375 | 1.078 |
| Total | 100 | 100 | 100 | 100 | 100 | 100 | 100 | 100 | 100 |

TABLE 24

Amino acid distribution ratio for each position of amino acid (%)-VH3_CDR2

| Type of AA | 49 | 50 | 51 | 52 | 52a | 53 | 54 | 55 | 56 | 57 | 55 | 59 | 60 |
|---|---|---|---|---|---|---|---|---|---|---|---|---|---|
| Alanine (A) | 41.634 | 9.651 | 0.000 | 1.428 | 4.476 | 32.427 | 0.002 | 4.974 | 3.137 | 1.835 | 2.003 | 0.000 | 99.762 |
| Serine (S) | 55.912 | 13.983 | 0.043 | 60.030 | 19.436 | 5.980 | 24.556 | 36.293 | 13.598 | 0.856 | 0.049 | 0.002 | 0.009 |
| Glycine (G) | 2.124 | 14.784 | 0.000 | 2.458 | 14.177 | 0.050 | 75.113 | 14.864 | 1.908 | 0.009 | 3.721 | 0.000 | 0.000 |
| Phenylalanine (F) | 0.000 | 6.037 | 0.009 | 0.079 | 2.710 | 0.043 | 0.002 | 0.791 | 0.800 | 0.006 | 6.355 | 0.002 | 0.000 |
| Proline (P) | 0.079 | 0.019 | 0.000 | 0.482 | 2.128 | 0.030 | 0.000 | 0.035 | 0.396 | 0.247 | 0.009 | 0.000 | 0.002 |
| Valine (V) | 0.061 | 20.375 | 0.043 | 0.005 | 1.035 | 0.069 | 0.093 | 1.966 | 1.041 | 1.570 | 0.417 | 0.000 | 0.084 |
| Tyrosine (Y) | 0.002 | 18.324 | 0.008 | 1.584 | 15.556 | 0.017 | 0.000 | 0.818 | 6.252 | 0.006 | 59.547 | 99.822 | 0.000 |
| Methionine (M) | 0.000 | 0.003 | 0.003 | 0.003 | 0.006 | 2.824 | 0.002 | 0.002 | 0.003 | 1.914 | 0.003 | 0.065 | 0.000 |
| Threonine (T) | 0.036 | 5.408 | 0.154 | 4.371 | 2.997 | 0.003 | 0.000 | 7.825 | 12.503 | 22.393 | 0.054 | 0.000 | 0.060 |
| Lysine (K) | 0.000 | 0.547 | 0.000 | 17.126 | 2.079 | 0.511 | 0.003 | 0.713 | 4.737 | 33.349 | 1.349 | 0.000 | 0.000 |
| Isoleucine (I) | 0.000 | 2.104 | 99.710 | 0.498 | 1.352 | 0.005 | 0.016 | 1.581 | 3.246 | 27.034 | 0.564 | 0.006 | 0.000 |
| Tryptophan (W) | 0.005 | 0.000 | 0.000 | 5.060 | 9.196 | 53.571 | 0.050 | 0.011 | 0.002 | 0.000 | 0.776 | 0.000 | 0.000 |
| Aspartic acid (D) | 0.002 | 0.017 | 0.002 | 0.000 | 0.017 | 1.612 | 0.058 | 12.043 | 6.328 | 0.003 | 5.561 | 0.003 | 0.000 |
| Histidine (H) | 0.020 | 2.432 | 0.006 | 0.976 | 4.554 | 0.058 | 0.000 | 1.175 | 2.146 | 0.016 | 7.310 | 0.039 | 0.000 |
| Asparagine (N) | 0.000 | 0.003 | 0.013 | 0.016 | 7.134 | 0.685 | 0.016 | 10.811 | 29.935 | 0.077 | 7.647 | 0.006 | 0.000 |
| Arginine (R) | 0.010 | 1.029 | 0.000 | 2.111 | 0.815 | 1.079 | 0.025 | 1.718 | 1.490 | 1.316 | 0.349 | 0.000 | 0.060 |

TABLE 24-continued

Amino acid distribution ratio for each position of amino acid (%)-VH3_CDR2

| Type of AA | 49 | 50 | 51 | 52 | 52a | 53 | 54 | 55 | 56 | 57 | 55 | 59 | 60 |
|---|---|---|---|---|---|---|---|---|---|---|---|---|---|
| Glutamic acid (E) | 0.016 | 0.008 | 0.000 | 0.014 | 2.517 | 0.005 | 0.003 | 2.021 | 8.581 | 5.049 | 1.063 | 0.000 | 0.011 |
| Cysteine (C) | 0.000 | 0.013 | 0.000 | 0.019 | 0.058 | 0.025 | 0.058 | 0.022 | 0.017 | 0.005 | 0.074 | 0.039 | 0.013 |
| Leucine (L) | 0.089 | 5.258 | 0.009 | 1.988 | 1.857 | 0.002 | 0.002 | 2.325 | 2.050 | 1.985 | 1.891 | 0.016 | 0.000 |
| Glutamine (Q) | 0.010 | 0.005 | 0.000 | 0.752 | 7.898 | 1.000 | 0.002 | 0.005 | 1.231 | 1.330 | 1.256 | 0.000 | 0.000 |
| Tota | 100 | 100 | 100 | 100 | 100 | 100 | 100 | 100 | 100 | 100 | 100 | 100 | 100 |

TABLE 25

Amino acid distribution ratio for each position of amino acid (%)-VH1-69_CDR1

| Type of AA | 27 | 28 | 29 | 30 | 31 | 32 | 33 | 34 | 35 |
|---|---|---|---|---|---|---|---|---|---|
| Alanine (A) | 0.002 | 4.451 | 0.000 | 3.665 | 2.686 | 3.451 | 33.086 | 0.120 | 4.249 |
| Serine (S) | 1.112 | 15.468 | 0.166 | 44.036 | 23.734 | 5.599 | 5.809 | 0.072 | 16.838 |
| Glycine (G) | 4.262 | 0.552 | 0.000 | 2.330 | 2.559 | 0.000 | 11.034 | 1.129 | 3.540 |
| Phenylalanine (F) | 45.556 | 0.024 | 99.589 | 0.041 | 0.026 | 5.060 | 1.699 | 0.034 | 0.010 |
| Proline (P) | 0.000 | 1.773 | 0.005 | 0.865 | 0.026 | 0.026 | 1.651 | 0.007 | 0.082 |
| Valine (V) | 0.723 | 0.024 | 0.019 | 0.298 | 0.276 | 0.171 | 1.293 | 84.196 | 0.293 |
| Tyrosine (Y) | 37.952 | 0.038 | 0.010 | 0.017 | 0.776 | 61.578 | 12.383 | 0.067 | 1.261 |
| Methionine (M) | 0.000 | 1.254 | 0.000 | 0.005 | 0.002 | 0.005 | 0.005 | 0.000 | 0.000 |
| Threonine (T) | 0.024 | 62.052 | 0.026 | 20.088 | 8.858 | 0.634 | 3.009 | 0.017 | 2.949 |
| Lysine (K) | 0.012 | 3.103 | 0.002 | 1.801 | 3.493 | 1.012 | 0.000 | 0.007 | 0.017 |
| Isoleucine (I) | 1.516 | 8.488 | 0.014 | 3.423 | 1.329 | 0.014 | 1.005 | 6.439 | 0.833 |
| Tryptophan (W) | 0.000 | 0.000 | 0.000 | 0.000 | 0.000 | 0.007 | 14.620 | 0.005 | 0.000 |
| Aspartic acid (D) | 3.080 | 1.489 | 0.000 | 5.520 | 17.771 | 1.266 | 7.624 | 0.026 | 1.724 |
| Histidine (H) | 1.355 | 0.062 | 0.000 | 0.024 | 1.369 | 11.752 | 1.394 | 0.007 | 43.549 |
| Asparagine (N) | 1.619 | 0.223 | 0.002 | 14.765 | 32.818 | 7.343 | 1.817 | 0.024 | 22.451 |
| Arginine (R) | 0.007 | 0.942 | 0.000 | 2.359 | 1.951 | 0.286 | 0.459 | 0.187 | 0.329 |
| Glutamic acid (E) | 0.000 | 0.017 | 0.000 | 0.600 | 2.237 | 0.002 | 2.971 | 0.062 | 0.002 |
| Cysteine (C) | 0.053 | 0.000 | 0.007 | 0.002 | 0.005 | 0.077 | 0.041 | 0.007 | 0.017 |
| Leucine (L) | 2.727 | 0.038 | 0.142 | 0.108 | 0.065 | 1.701 | 0.058 | 7.590 | 0.014 |
| Glutamine (Q) | 0.000 | 0.000 | 0.017 | 0.053 | 0.017 | 0.014 | 0.043 | 0.002 | 1.842 |
| Total | 100 | 100 | 100 | 100 | 100 | 100 | 100 | 100 | 100 |

TABLE 26

Amino acid distribution ratio for each position of amino acid (%)-VH1-69_CDR2

| Type of AA | 49 | 50 | 51 | 52 | 52a | 53 | 54 | 55 | 56 | 57 | 58 |
|---|---|---|---|---|---|---|---|---|---|---|---|
| Alanine (A) | 39.885 | 6.884 | 0.000 | 0.342 | 10.682 | 1.634 | 3.358 | 4.481 | 4.605 | 7.531 | 1.915 |
| Serine (S) | 31.804 | 9.134 | 0.091 | 61.370 | 14.430 | 32.315 | 20.509 | 29.453 | 10.842 | 1.393 | 4.114 |
| Glycine (G) | 28.366 | 11.142 | 0.000 | 1.114 | 7.420 | 5.101 | 33.106 | 37.373 | 3.287 | 0.007 | 3.404 |
| Phenylalanine (F) | 0.007 | 3.703 | 0.002 | 0.399 | 2.116 | 0.889 | 4.021 | 0.043 | 0.711 | 0.002 | 3.334 |
| Proline (P) | 0.007 | 0.009 | 0.000 | 0.025 | 21.362 | 0.016 | 0.014 | 0.005 | 0.250 | 1.886 | 0.025 |
| Valine (V) | 0.054 | 8.767 | 0.005 | 1.182 | 1.363 | 1.370 | 1.500 | 1.339 | 1.980 | 1.575 | 0.610 |
| Tyrosine (Y) | 0.002 | 12.256 | 0.032 | 1.492 | 10.791 | 5.237 | 0.511 | 1.114 | 5.528 | 0.016 | 32.149 |
| Methionine (M) | 0.000 | 1.134 | 0.002 | 0.000 | 0.005 | 1.488 | 0.009 | 0.005 | 0.641 | 1.697 | 0.002 |
| Threonine (T) | 0.011 | 2.003 | 0.009 | 3.075 | 3.301 | 1.931 | 2.987 | 4.971 | 10.142 | 33.362 | 1.423 |
| Lysine (K) | 0.000 | 1.128 | 0.000 | 10.188 | 1.277 | 2.743 | 1.162 | 1.879 | 6.905 | 26.094 | 10.454 |
| Isoleucine (I) | 0.000 | 6.437 | 99.791 | 8.462 | 1.429 | 5.089 | 1.257 | 1.212 | 3.946 | 17.676 | 2.299 |
| Tryptophan (W) | 0.000 | 16.778 | 0.000 | 3.098 | 4.501 | 0.002 | 0.027 | 0.039 | 0.005 | 0.002 | 0.000 |
| Aspartic acid (D) | 0.002 | 1.479 | 0.014 | 2.939 | 3.394 | 34.621 | 5.876 | 9.642 | 9.578 | 0.005 | 4.786 |
| Histidine (H) | 0.005 | 1.187 | 0.027 | 1.277 | 4.067 | 2.099 | 0.002 | 1.657 | 2.398 | 0.048 | 6.209 |
| Asparagine (N) | 0.000 | 9.545 | 0.009 | 0.014 | 3.609 | 0.018 | 17.021 | 7.293 | 27.837 | 0.835 | 22.172 |
| Arginine (R) | 0.000 | 1.611 | 0.002 | 1.669 | 0.594 | 0.899 | 0.842 | 1.584 | 1.546 | 1.334 | 1.393 |
| Glutamic acid (E) | 0.007 | 0.000 | 0.009 | 0.009 | 2.266 | 2.028 | 1.658 | 1.798 | 7.505 | 3.075 | 2.038 |
| Cysteine (C) | 0.034 | 0.039 | 0.000 | 0.007 | 0.032 | 0.020 | 0.016 | 0.014 | 0.018 | 0.005 | 0.045 |
| Leucine (L) | 0.014 | 6.763 | 0.016 | 2.250 | 1.874 | 2.496 | 6.097 | 0.089 | 1.332 | 1.777 | 1.813 |
| Glutamine (Q) | 0.002 | 0.002 | 0.000 | 1.089 | 5.487 | 0.002 | 0.009 | 0.009 | 0.946 | 1.681 | 1.802 |
| Total | 100 | 100 | 100 | 100 | 100 | 100 | 100 | 100 | 100 | 100 | 100 |

TABLE 27

Amino acid distribution ratio for each position of amino acid (%)-VH_CDR3_9AA

| Type of AA | 96 | 97 | 98 | 99 | 100 | 100a | 100b | 101 | 102 |
|---|---|---|---|---|---|---|---|---|---|
| Alanine (A) | 4.724 | 5.125 | 5.077 | 12.434 | 7.550 | 13.005 | 1.545 | 1.390 | 1.038 |
| Serine (S) | 2.848 | 8.858 | 12.053 | 15.040 | 16.424 | 14.097 | 7.095 | 1.214 | 3.068 |
| Glycine (G) | 12.605 | 10.095 | 9.404 | 8.679 | 12.958 | 3.059 | 3.620 | 1.854 | 0.221 |
| Phenylalanine (F) | 0.353 | 1.789 | 1.347 | 2.959 | 1.589 | 3.378 | 49.327 | 0.132 | 3.157 |
| Proline (P) | 1.545 | 9.499 | 3.885 | 1.723 | 0.309 | 4.372 | 0.949 | 0.353 | 0.971 |
| Valine (V) | 5.430 | 6.472 | 15.210 | 4.505 | 3.951 | 5.630 | 7.018 | 3.421 | 7.351 |
| Tyrosine (Y) | 1.192 | 5.743 | 7.285 | 19.545 | 19.779 | 19.607 | 8.232 | 1.810 | 67.064 |
| Methionine (M) | 0.022 | 2.275 | 2.185 | 0.420 | 0.618 | 0.243 | 2.825 | 1.015 | 1.214 |
| Threonine (T) | 9.603 | 4.352 | 7.130 | 6.338 | 9.647 | 5.365 | 3.200 | 1.986 | 1.589 |
| Lysine (K) | 1.060 | 1.568 | 2.135 | 3.821 | 1.104 | 0.949 | 0.088 | 0.453 | 0.000 |
| Isoleucine (I) | 1.523 | 3.269 | 1.398 | 2.341 | 2.075 | 5.056 | 8.144 | 3.951 | 3.642 |
| Tryptophan (W) | 0.751 | 6.119 | 2.362 | 1.458 | 1.810 | 1.501 | 0.265 | 0.000 | 0.044 |
| Aspartic acid (D) | 28.631 | 5.036 | 6.137 | 6.913 | 7.241 | 7.640 | 1.214 | 74.443 | 3.620 |
| Histidine (H) | 2.031 | 1.811 | 1.965 | 1.789 | 1.258 | 2.981 | 0.728 | 0.331 | 3.091 |
| Asparagine (N) | 1.060 | 3.225 | 4.283 | 4.064 | 5.651 | 1.744 | 1.148 | 2.516 | 1.788 |
| Arginine (R) | 2.561 | 7.356 | 11.258 | 3.202 | 2.561 | 2.782 | 0.640 | 0.221 | 0.199 |
| Glutamic acid (E) | 10.662 | 2.783 | 2.053 | 3.180 | 2.649 | 1.015 | 1.810 | 3.487 | 0.265 |
| Cysteine (C) | 0.000 | 0.022 | 0.022 | 0.044 | 0.044 | 0.022 | 0.000 | 0.000 | 0.022 |
| Leucine (L) | 2.848 | 10.139 | 2.693 | 0.817 | 1.236 | 1.921 | 2.008 | 0.331 | 1.148 |
| Glutamine (Q) | 10.552 | 4.462 | 1.567 | 0.729 | 1.545 | 0.640 | 0.154 | 1.081 | 0.508 |
| Total | 100 | 100 | 100 | 100 | 100 | 100 | 100 | 100 | 100 |

TABLE 28

Amino acid distribution ratio for each position of amino acid (%)-VH_CDR3_10AA

| Type of AA | 96 | 97 | 98 | 99 | 100 | 100a | 100b | 100c | 101 | 102 |
|---|---|---|---|---|---|---|---|---|---|---|
| Alanine (A) | 9.715 | 6.624 | 7.644 | 7.850 | 9.334 | 7.187 | 9.502 | 2.627 | 1.840 | 1.435 |
| Serine (S) | 5.155 | 11.104 | 13.885 | 15.490 | 14.590 | 9.507 | 8.179 | 3.820 | 1.000 | 4.613 |
| Glycine (G) | 10.408 | 11.233 | 12.804 | 14.168 | 12.639 | 14.212 | 13.357 | 2.305 | 2.872 | 0.081 |
| Phenylalanine (F) | 0.258 | 2.256 | 1.322 | 3.127 | 2.257 | 2.191 | 1.984 | 31.700 | 0.694 | 4.468 |
| Proline (P) | 0.967 | 3.803 | 3.096 | 2.273 | 2.031 | 1.482 | 4.339 | 2.869 | 0.323 | 5.532 |
| Valine (V) | 4.382 | 4.335 | 4.499 | 4.610 | 5.531 | 1.450 | 2.662 | 2.804 | 0.742 | 8.468 |
| Tyrosine (Y) | 2.175 | 5.205 | 8.660 | 10.364 | 10.688 | 16.951 | 21.068 | 5.270 | 0.888 | 51.048 |
| Methionine (M) | 0.709 | 1.370 | 2.000 | 1.386 | 0.451 | 1.676 | 0.048 | 13.924 | 0.032 | 0.016 |
| Threonine (T) | 2.465 | 4.819 | 6.531 | 5.271 | 6.110 | 4.431 | 3.452 | 1.257 | 0.888 | 0.161 |
| Lysine (K) | 1.949 | 3.981 | 2.629 | 1.660 | 1.757 | 1.499 | 1.484 | 0.032 | 0.016 | 0.000 |
| Isoleucine (I) | 2.691 | 3.674 | 2.629 | 2.273 | 2.289 | 1.112 | 2.194 | 5.222 | 0.549 | 3.016 |
| Tryptophan (W) | 1.337 | 1.998 | 2.177 | 2.805 | 5.078 | 5.543 | 5.435 | 0.612 | 0.032 | 0.529 |
| Aspartic acid (D) | 30.352 | 4.932 | 7.160 | 7.560 | 6.545 | 7.654 | 5.485 | 2.095 | 78.377 | 3.758 |
| Histidine (H) | 3.448 | 4.351 | 2.596 | 1.564 | 2.579 | 2.510 | 3.452 | 0.064 | 1.339 | 5.855 |
| Asparagine (N) | 1.788 | 3.175 | 2.887 | 4.803 | 4.740 | 8.701 | 3.065 | 1.450 | 1.711 | 3.048 |
| Arginine (R) | 2.175 | 4.319 | 2.435 | 2.031 | 1.548 | 1.869 | 1.678 | 0.774 | 0.500 | 0.032 |
| Glutamic acid (E) | 11.471 | 2.965 | 3.983 | 2.901 | 2.418 | 2.788 | 2.791 | 1.547 | 2.469 | 0.016 |
| Cysteine (C) | 0.000 | 0.032 | 0.016 | 0.016 | 0.016 | 0.032 | 0.016 | 0.000 | 0.016 | 0.081 |
| Leucine (L) | 6.251 | 17.035 | 10.321 | 7.028 | 8.963 | 6.445 | 7.663 | 21.595 | 3.453 | 7.742 |
| Glutamine (Q) | 1.804 | 2.788 | 2.725 | 2.821 | 2.434 | 2.559 | 2.146 | 0.032 | 2.259 | 0.000 |
| Total | 100 | 100 | 100 | 100 | 100 | 100 | 100 | 100 | 100 | 100 |

TABLE 29

Amino acid distribution ratio for each position of amino acid (%)-VH_CDR3_11AA

| Type of AA | 96 | 97 | 98 | 99 | 100 | 100a | 100b | 100c | 100d | 101 | 102 |
|---|---|---|---|---|---|---|---|---|---|---|---|
| Alanine (A) | 8.655 | 6.823 | 7.485 | 8.032 | 9.073 | 10.181 | 7.214 | 7.576 | 2.139 | 1.930 | 0.593 |
| Serine (S) | 3.818 | 10.407 | 13.451 | 14.863 | 13.762 | 12.954 | 11.448 | 8.652 | 3.518 | 0.855 | 5.265 |
| Glycine (G) | 12.638 | 10.365 | 13.479 | 15.553 | 11.900 | 12.609 | 9.683 | 9.701 | 2.359 | 1.875 | 1.158 |
| Phenylalanine (F) | 0.551 | 2.343 | 1.229 | 2.774 | 1.944 | 2.442 | 2.455 | 2.028 | 31.443 | 0.193 | 3.046 |
| Proline (P) | 1.502 | 3.735 | 3.356 | 1.987 | 1.572 | 3.173 | 2.634 | 3.808 | 2.483 | 0.717 | 3.584 |
| Valine (V) | 4.093 | 4.259 | 4.447 | 5.079 | 3.820 | 3.352 | 3.366 | 1.808 | 3.035 | 0.938 | 7.181 |
| Tyrosine (Y) | 1.475 | 5.224 | 8.383 | 9.591 | 10.576 | 11.546 | 13.683 | 21.540 | 3.739 | 0.979 | 50.172 |
| Methionine (M) | 1.378 | 1.571 | 1.878 | 1.559 | 0.579 | 0.041 | 0.028 | 1.283 | 9.437 | 0.097 | 0.041 |
| Threonine (T) | 1.888 | 4.108 | 5.400 | 5.037 | 6.371 | 5.049 | 6.262 | 4.126 | 1.007 | 0.510 | 1.213 |

TABLE 29-continued

Amino acid distribution ratio for each position of amino acid (%)-VH_CDR3_11AA

| Type of AA | 96 | 97 | 98 | 99 | 100 | 100a | 100b | 100c | 100d | 101 | 102 |
|---|---|---|---|---|---|---|---|---|---|---|---|
| Lysine (K) | 1.709 | 4.714 | 2.444 | 2.139 | 2.261 | 1.904 | 1.876 | 2.042 | 0.028 | 0.014 | 0.000 |
| Isoleucine (I) | 2.040 | 3.749 | 2.555 | 2.332 | 2.537 | 3.269 | 2.317 | 2.194 | 4.939 | 0.317 | 3.432 |
| Tryptophan (W) | 1.185 | 1.943 | 2.403 | 2.332 | 4.316 | 4.732 | 5.228 | 5.271 | 1.200 | 0.014 | 0.000 |
| Aspartic acid (D) | 31.284 | 5.665 | 7.554 | 7.452 | 7.970 | 7.104 | 5.559 | 5.244 | 2.097 | 77.940 | 2.743 |
| Histidine (H) | 2.178 | 4.535 | 2.762 | 1.449 | 2.634 | 1.945 | 3.007 | 2.981 | 1.297 | 2.302 | 7.746 |
| Asparagine (N) | 2.343 | 3.487 | 3.273 | 5.341 | 4.606 | 4.428 | 6.772 | 5.933 | 2.414 | 2.606 | 4.411 |
| Arginine (R) | 1.916 | 3.515 | 2.168 | 2.139 | 1.848 | 1.614 | 2.441 | 2.318 | 0.924 | 0.703 | 0.069 |
| Glutamic acid (E) | 13.175 | 3.198 | 4.212 | 2.595 | 2.579 | 2.814 | 2.993 | 2.745 | 1.256 | 3.433 | 0.028 |
| Cysteine (C) | 0.028 | 0.028 | 0.000 | 0.000 | 0.014 | 0.028 | 0.069 | 0.041 | 0.000 | 0.028 | 0.055 |
| Leucine (L) | 5.623 | 17.629 | 10.938 | 6.859 | 8.591 | 9.063 | 10.221 | 9.093 | 25.814 | 2.537 | 8.243 |
| Glutamine (Q) | 2.522 | 2.702 | 2.583 | 2.884 | 3.047 | 1.752 | 2.745 | 1.614 | 0.869 | 2.013 | 1.020 |
| Total | 100 | 100 | 100 | 100 | 100 | 100 | 100 | 100 | 100 | 100 | 100 |

TABLE 30

Amino acid distribution ratio for each position of amino acid (%)-VH_CDR3_12AA

| Type of AA | 96 | 97 | 98 | 99 | 100 | 100a | 100b | 100c | 100d | 100e | 101 | 102 |
|---|---|---|---|---|---|---|---|---|---|---|---|---|
| Alanine (A) | 7.256 | 6.895 | 7.305 | 8.271 | 7.741 | 10.325 | 7.001 | 7.457 | 11.272 | 2.008 | 1.487 | 0.418 |
| Serine (S) | 3.794 | 9.824 | 12.906 | 15.026 | 13.475 | 12.765 | 11.995 | 9.460 | 5.159 | 2.470 | 0.953 | 4.155 |
| Glycine (G) | 13.849 | 11.194 | 13.180 | 16.152 | 12.940 | 12.693 | 10.104 | 9.200 | 12.168 | 1.719 | 1.978 | 0.014 |
| Phenylalanine (F) | 0.404 | 2.222 | 1.169 | 2.569 | 2.036 | 2.224 | 2.180 | 2.542 | 2.384 | 36.805 | 0.173 | 2.785 |
| Proline (P) | 1.269 | 3.664 | 3.118 | 2.165 | 2.065 | 3.061 | 2.945 | 3.587 | 4.653 | 1.502 | 0.419 | 5.915 |
| Valine (V) | 3.462 | 4.559 | 4.490 | 4.345 | 3.423 | 3.394 | 3.637 | 1.950 | 2.225 | 2.094 | 0.260 | 9.652 |
| Tyrosine (Y) | 2.294 | 5.770 | 8.286 | 9.094 | 10.861 | 11.711 | 13.900 | 20.971 | 24.090 | 2.788 | 0.563 | 49.950 |
| Methionine (M) | 0.505 | 1.615 | 2.165 | 1.703 | 0.520 | 0.029 | 0.014 | 1.502 | 0.029 | 13.838 | 0.058 | 0.029 |
| Threonine (T) | 1.096 | 4.284 | 5.702 | 4.561 | 6.153 | 5.040 | 5.413 | 3.928 | 3.468 | 0.881 | 0.635 | 1.241 |
| Lysine (K) | 1.717 | 4.140 | 2.599 | 1.790 | 1.853 | 1.545 | 1.833 | 2.109 | 1.488 | 0.000 | 0.029 | 0.000 |
| Isoleucine (I) | 0.938 | 3.938 | 2.685 | 2.107 | 2.383 | 2.917 | 2.136 | 2.470 | 3.295 | 5.041 | 0.419 | 4.949 |
| Tryptophan (W) | 1.010 | 1.890 | 2.396 | 3.176 | 4.939 | 5.155 | 5.124 | 4.968 | 5.419 | 1.560 | 0.000 | 0.014 |
| Aspartic acid (D) | 38.358 | 4.962 | 7.464 | 7.116 | 7.438 | 8.260 | 6.308 | 4.752 | 3.801 | 1.040 | 82.717 | 1.587 |
| Histidine (H) | 2.813 | 4.256 | 2.988 | 1.443 | 2.672 | 1.993 | 2.887 | 3.394 | 3.540 | 1.127 | 1.444 | 7.171 |
| Asparagine (N) | 2.092 | 3.563 | 3.854 | 4.590 | 4.535 | 4.202 | 6.062 | 6.384 | 3.382 | 1.560 | 2.657 | 3.116 |
| Arginine (R) | 1.616 | 3.313 | 2.353 | 2.439 | 1.704 | 1.762 | 2.223 | 2.586 | 0.708 | 0.433 | 0.404 | 0.822 |
| Glutamic acid (E) | 11.411 | 2.813 | 3.811 | 3.103 | 3.134 | 2.700 | 2.497 | 2.556 | 2.457 | 0.650 | 2.281 | 0.058 |
| Cysteine (C) | 0.000 | 0.043 | 0.014 | 0.043 | 0.029 | 0.014 | 0.058 | 0.043 | 0.072 | 0.014 | 0.014 | 0.043 |
| Leucine (L) | 4.371 | 18.191 | 11.159 | 7.289 | 9.344 | 3.433 | 10.941 | 8.579 | 9.090 | 24.469 | 1.487 | 8.051 |
| Glutamine (Q) | 1.746 | 2.856 | 2.353 | 3.017 | 2.744 | 1.776 | 2.742 | 1.473 | 1.301 | 0.000 | 2.021 | 0.029 |
| Total | 100 | 100 | 100 | 100 | 100 | 100 | 100 | 100 | 100 | 100 | 100 | 100 |

TABLE 31

Amino acid distribution ratio for each position of amino acid (%)-VH_CDR3_13AA

| Type of AA | 96 | 97 | 98 | 99 | 100 | 100a | 100b | 100c | 100d | 100e | 100f | 101 | 102 |
|---|---|---|---|---|---|---|---|---|---|---|---|---|---|
| Alanine (A) | 7.017 | 6.899 | 6.507 | 8.555 | 8.633 | 9.729 | 7.328 | 7.297 | 4.436 | 12.777 | 2.199 | 0.604 | 0.504 |
| Serine (S) | 3.408 | 10.257 | 13.215 | 15.227 | 14.137 | 13.107 | 11.765 | 9.415 | 9.141 | 5.414 | 1.762 | 0.856 | 3.509 |
| Glycine (G) | 10.912 | 10.995 | 13.635 | 15.251 | 12.689 | 12.821 | 8.571 | 9.600 | 7.747 | 13.668 | 1.225 | 1.259 | 0.000 |
| Phenylalanine (F) | 0.755 | 2.182 | 1.261 | 2.522 | 1.767 | 2.168 | 2.000 | 2.740 | 2.151 | 2.707 | 40.164 | 0.823 | 2.535 |
| Proline (P) | 0.873 | 4.163 | 3.127 | 2.235 | 2.407 | 3.175 | 2.168 | 4.085 | 2.403 | 5.145 | 1.477 | 0.369 | 6.748 |
| Valine (V) | 4.566 | 3.727 | 4.119 | 4.639 | 3.063 | 3.378 | 3.495 | 1.479 | 1.916 | 1.597 | 2.064 | 0.537 | 13.564 |
| Tyrosine (Y) | 1.880 | 5.859 | 8.356 | 9.059 | 10.266 | 11.443 | 14.773 | 20.579 | 24.298 | 28.514 | 3.122 | 0.269 | 44.234 |
| Methionine (M) | 0.621 | 1.813 | 2.236 | 1.378 | 0.421 | 0.017 | 0.017 | 1.362 | 0.034 | 0.067 | 18.966 | 0.057 | 1.276 |
| Threonine (T) | 1.276 | 4.549 | 5.767 | 4.706 | 5.614 | 5.142 | 5.445 | 4.556 | 3.210 | 2.202 | 0.705 | 0.034 | 0.201 |
| Lysine (K) | 1.528 | 4.851 | 2.506 | 2.017 | 1.986 | 1.680 | 1.855 | 1.849 | 1.496 | 0.017 | 0.000 | 0.000 | 0.000 |
| Isoleucine (I) | 1.108 | 4.700 | 2.959 | 2.336 | 2.609 | 2.554 | 1.933 | 2.288 | 3.075 | 0.773 | 4.095 | 0.235 | 7.017 |
| Tryptophan (W) | 0.890 | 1.947 | 2.219 | 3.008 | 4.275 | 4.873 | 5.176 | 4.741 | 5.562 | 7.280 | 0.369 | 0.000 | 0.017 |
| Aspartic acid (D) | 41.951 | 4.684 | 7.599 | 7.378 | 7.136 | 7.747 | 6.471 | 4.909 | 7.915 | 3.379 | 1.208 | 88.650 | 1.578 |
| Histidine (H) | 3.608 | 4.432 | 3.043 | 1.597 | 2.827 | 1.832 | 3.210 | 3.043 | 3.025 | 3.766 | 1.074 | 0.890 | 7.856 |
| Asparagine (N) | 1.494 | 2.887 | 3.161 | 4.739 | 5.015 | 5.579 | 5.655 | 6.321 | 7.814 | 3.245 | 1.343 | 0.621 | 2.417 |
| Arginine (R) | 1.142 | 3.676 | 2.757 | 2.319 | 1.531 | 1.664 | 2.739 | 2.488 | 1.882 | 0.958 | 0.017 | 0.319 | 0.050 |
| Glutamic acid (E) | 10.660 | 3.257 | 4.085 | 2.807 | 2.827 | 3.109 | 2.941 | 2.942 | 3.949 | 1.554 | 0.638 | 1.511 | 0.017 |
| Cysteine (C) | 0.017 | 0.000 | 0.017 | 0.050 | 0.034 | 0.034 | 0.017 | 0.084 | 0.034 | 0.050 | 0.050 | 0.000 | 0.050 |

TABLE 31-continued

Amino acid distribution ratio for each position of amino acid (%)-VH_CDR3_13AA

| Type of AA | 96 | 97 | 98 | 99 | 100 | 100a | 100b | 100c | 100d | 100e | 100f | 101 | 102 |
|---|---|---|---|---|---|---|---|---|---|---|---|---|---|
| Leucine (L) | 4.264 | 16.502 | 10.508 | 7.328 | 9.357 | 8.066 | 10.303 | 8.742 | 10.906 | 5.783 | 19.520 | 1.293 | 8.276 |
| Glutamine (Q) | 2.031 | 2.619 | 2.724 | 2.739 | 2.407 | 1.882 | 3.126 | 1.379 | 1.008 | 1.093 | 0.000 | 1.552 | 0.050 |
| Total | 100 | 100 | 100 | 100 | 100 | 100 | 100 | 100 | 100 | 100 | 100 | 100 | 100 |

TABLE 32

Amino acid distribution ratio for each position of amino acid (%)-VH_CDR3_14AA

| Type of AA | 96 | 97 | 98 | 99 | 100 | 100a | 100b |
|---|---|---|---|---|---|---|---|
| Alanine (A) | 6.961 | 0.545 | 8.241 | 8.018 | 8.149 | 9.300 | 7.210 |
| Serine (S) | 4.459 | 4.306 | 11.953 | 14.300 | 14.695 | 12.536 | 11.829 |
| Glycine (G) | 11.300 | 0.102 | 13.554 | 15.869 | 12.070 | 13.543 | 9.034 |
| Phenylalanine (F) | 1.157 | 3.081 | 1.498 | 3.235 | 3.080 | 2.282 | 2.846 |
| Proline (P) | 0.919 | 5.702 | 2.503 | 2.656 | 1.841 | 2.930 | 2.352 |
| Valine (V) | 4.901 | 13.838 | 4.512 | 4.494 | 3.358 | 3.832 | 3.579 |
| Tyrosine (Y) | 0.562 | 45.043 | 7.679 | 9.517 | 10.979 | 10.952 | 13.891 |
| Methionine (M) | 0.425 | 1.311 | 2.111 | 1.532 | 0.682 | 0.034 | 0.000 |
| Threonine (T) | 1.568 | 0.102 | 5.449 | 4.562 | 6.001 | 4.991 | 5.966 |
| Lysine (K) | 0.756 | 0.000 | 2.622 | 2.043 | 1.892 | 1.823 | 1.909 |
| Isoleucine (I) | 1.021 | 7.047 | 2.895 | 2.979 | 2.421 | 2.896 | 2.182 |
| Tryptophan (W) | 0.596 | 0.102 | 2.367 | 2.911 | 5.131 | 5.178 | 5.710 |
| Aspartic acid (D) | 41.899 | 1.226 | 7.815 | 7.559 | 7.450 | 7.546 | 6.847 |
| Histidine (H) | 2.791 | 7.183 | 3.048 | 1.413 | 2.711 | 1.652 | 3.170 |
| Asparagine (N) | 2.195 | 1.991 | 3.371 | 4.886 | 5.165 | 5.348 | 6.664 |
| Arginine (R) | 1.517 | 0.000 | 2.316 | 1.858 | 1.483 | 1.431 | 2.318 |
| Glutamic acid (E) | 9.973 | 0.051 | 4.393 | 2.962 | 2.745 | 2.793 | 2.454 |
| Cysteine (C) | 0.051 | 0.119 | 0.017 | 0.000 | 0.051 | 0.017 | 0.034 |
| Leucine (L) | 5.123 | 7.200 | 11.034 | 6.622 | 8.490 | 9.027 | 9.187 |
| Glutamine (Q) | 1.617 | 0.051 | 2.622 | 2.383 | 2.608 | 1.788 | 3.017 |
| Total | 100 | 100 | 100 | 100 | 100 | 100 | 100 |

| Type of AA | 100c | 100d | 100e | 100f | 100g | 101 | 102 |
|---|---|---|---|---|---|---|---|
| Alanime (A) | 7.104 | 4.873 | 2.521 | 10.729 | 1.957 | 1.022 | 1.089 |
| Serine (S) | 9.864 | 10.342 | 8.465 | 3.917 | 2.127 | 0.306 | 4.612 |
| Glycine (G) | 10.392 | 8.230 | 9.164 | 17.405 | 0.715 | 1.720 | 0.000 |
| Phenylalanine (F) | 2.061 | 2.488 | 2.044 | 2.112 | 36.164 | 0.562 | 1.378 |
| Proline (P) | 4.055 | 2.130 | 1.891 | 5.501 | 1.838 | 0.647 | 6.995 |
| Valine (V) | 2.300 | 1.976 | 1.652 | 2.044 | 1.889 | 0.306 | 18.210 |
| Tyrosine (Y) | 21.278 | 25.234 | 29.331 | 27.129 | 2.059 | 0.034 | 40.061 |
| Methionine (M) | 1.601 | 0.000 | 0.758 | 0.834 | 25.766 | 0.017 | 0.000 |
| Threonine (T) | 3.748 | 3.578 | 2.265 | 1.958 | 0.425 | 0.664 | 0.564 |
| Lysine (K) | 2.198 | 1.448 | 1.533 | 0.000 | 0.000 | 0.000 | 0.000 |
| Isoleucine (I) | 2.010 | 3.033 | 1.559 | 1.226 | 3.880 | 0.375 | 4.629 |
| Tryptophan (W) | 4.106 | 3.357 | 4.684 | 8.328 | 0.238 | 0.000 | 0.017 |
| Aspartic acid (D) | 5.196 | 6.441 | 7.852 | 1.737 | 0.596 | 85.816 | 1.361 |
| Histidine (H) | 2.564 | 2.726 | 4.258 | 3.832 | 1.055 | 1.532 | 7.369 |
| Asparagine (N) | 5.792 | 6.935 | 11.991 | 2.980 | 0.425 | 1.430 | 2.332 |
| Arginine (R) | 2.487 | 2.249 | 1.685 | 0.954 | 0.034 | 0.443 | 0.034 |
| Glutamic acid (E) | 2.368 | 3.544 | 2.510 | 1.141 | 0.442 | 2.094 | 0.000 |
| Cysteine (C) | 0.034 | 0.000 | 0.051 | 0.068 | 0.017 | 0.500 | 0.068 |
| Leucine (L) | 8.944 | 10.411 | 4.122 | 7.408 | 20.371 | 0.765 | 11.181 |
| Glutamine (Q) | 1.499 | 1.005 | 1.243 | 0.698 | 0.000 | 2.265 | 0.000 |
| Total | 100 | 100 | 100 | 100 | 100 | 100 | 100 |

TABLE 33

Amino acid distribution ratio for each position of amino acid (%)-V$_K$1-39_CDR1

| Type of AA | 24 | 25 | 26 | 27 | 28 | 29 | 30 | 31 | 32 | 33 | 34 |
|---|---|---|---|---|---|---|---|---|---|---|---|
| Alanine (A) | 0.000 | 99.639 | 0 | 0.000 | 4.354 | 0.061 | 4.726 | 1.184 | 1.885 | 0.004 | 43.094 |
| Serine (S) | 92.887 | 0.023 | 99.713 | 0.015 | 35.274 | 0.023 | 34.875 | 15.917 | 3.113 | 0.011 | 2.575 |
| Glycine (G) | 6.836 | 0.034 | 0.065 | 0.000 | 10.414 | 0.000 | 6.918 | 1.648 | 1.482 | 0.008 | 3.019 |
| Phenylalanine (F) | 0.000 | 0.000 | 0.000 | 0.000 | 1.058 | 0.000 | 0.644 | 0.678 | 6.548 | 0.000 | 0.004 |
| Proline (P) | 0.000 | 0.004 | 0.000 | 0.000 | 0.336 | 0.000 | 0.027 | 1.062 | 0.035 | 0.084 | 0.008 |
| Valine (V) | 0.008 | 0.130 | 0.080 | 0.000 | 1.433 | 83.913 | 0.498 | 0.176 | 0.012 | 0.019 | 1.264 |
| Tyrosine (Y) | 0.000 | 0.000 | 0.000 | 0.000 | 1.863 | 0.042 | 2.591 | 1.552 | 38.539 | 0.019 | 0.019 |
| Methionine (M) | 0.015 | 0.000 | 0.000 | 0.000 | 0.027 | 0.000 | 0.000 | 0.418 | 0.000 | 0.000 | 0.000 |
| Threonine(T) | 0.000 | 0.027 | 0.000 | 0.008 | 8.051 | 0.004 | 5.535 | 11.755 | 0.050 | 0.004 | 0.513 |
| Lysine (K) | 0.004 | 0.000 | 0.000 | 0.004 | 0.782 | 0.004 | 3.231 | 8.987 | 0.012 | 0.004 | 0.031 |
| Isoleucine (I) | 0.034 | 0.000 | 0.046 | 0.000 | 1.353 | 13.621 | 2.173 | 2.802 | 0.000 | 5.346 | 0.648 |
| Tryptophan (W) | 0.000 | 0.000 | 0.000 | 0.000 | 0.008 | 0.000 | 0.000 | 0.000 | 17.149 | 0.000 | 0.000 |
| Aspartic acid (D) | 0.008 | 0.000 | 0.000 | 0.031 | 31.874 | 0.004 | 6.581 | 6.404 | 5.757 | 0.004 | 0.962 |
| Histidine(H) | 0.000 | 0.000 | 0.000 | 0.169 | 1.633 | 0.000 | 1.169 | 2.422 | 7.507 | 0.000 | 2.058 |
| Asparagine (N) | 0.027 | 0.000 | 0.054 | 0.004 | 0.034 | 0.000 | 22.430 | 39.974 | 4.425 | 0.000 | 45.661 |
| Arginine (R) | 0.161 | 0.054 | 0.031 | 94.193 | 0.874 | 0.015 | 4.128 | 2.591 | 1.029 | 0.000 | 0.019 |
| Glutamic acid (E) | 0.004 | 0.031 | 0.011 | 0.069 | 0.019 | 0.004 | 1.679 | 0.851 | 1.259 | 0.000 | 0.027 |
| Cysteine (C) | 0.011 | 0.008 | 0.000 | 0.000 | 0.034 | 0.012 | 0.008 | 0.004 | 0.088 | 0.000 | 0.000 |
| Leucine (L) | 0.000 | 0.000 | 0.000 | 0.534 | 0.050 | 2.294 | 2.783 | 0.567 | 4.550 | 94.496 | 0.000 |
| Glutamine (Q) | 0.004 | 0.000 | 0.000 | 4.973 | 0.019 | 0.004 | 0.004 | 0.008 | 1.547 | 0.000 | 0.000 |
| Total | 100 | 100 | 100 | 100 | 100 | 100 | 100 | 1.00 | 100 | 100 | |

25

TABLE 34

Amino acid distribution ratio for each position of amino acid (%)-V$_K$1-39_CDR2

| Type of AA | 50 | 51 | 52 | 53 | 54 | 55 | 56 |
|---|---|---|---|---|---|---|---|
| Alanine (A) | 25.000 | 79.331 | 0.000 | 3.515 | 0.000 | 2.715 | 3.452 |
| Serine (S) | 7.092 | 3.197 | 0.056 | 27.528 | 0.000 | 0.017 | 62.585 |
| Glycine (G) | 4.588 | 1.138 | 0.000 | 0.675 | 0.000 | 1.857 | 4.228 |
| Phenylalanine (F) | 0.432 | 0.007 | 0.007 | 1.782 | 0.090 | 0.555 | 0.992 |
| Proline (P) | 0.223 | 0.741 | 0.000 | 0.007 | 0.111 | 0.307 | 1.388 |
| Valine (V) | 1.608 | 4.067 | 0.000 | 1.061 | 0.010 | 0.478 | 1.291 |
| Tyrosine (Y) | 1.483 | 0.003 | 0.000 | 2.172 | 0.014 | 1.117 | 0.466 |
| Methionine (M) | 1.076 | 0.000 | 0.000 | 0.000 | 0.003 | 0.010 | 0.010 |
| Threonine (T) | 4.529 | 7.891 | 5.066 | 20.283 | 0.007 | 0.003 | 10.678 |
| Lysine (K) | 20.408 | 0.007 | 0.059 | 3.738 | 0.000 | 3.996 | 0.449 |
| Isoleucine (I) | 1.480 | 1.573 | 0.010 | 6.898 | 0.080 | 0.003 | 2.432 |
| Tryptophan (W) | 2.078 | 0.000 | 0.000 | 0.000 | 0.000 | 0.000 | 0.007 |
| Aspartic acid (D) | 16.909 | 0.014 | 0.035 | 3.174 | 0.000 | 2.778 | 5.404 |
| Histidine (H) | 0.473 | 0.000 | 0.000 | 0.526 | 10.006 | 6.903 | 0.003 |
| Asparagine (N) | 0.010 | 0.000 | 94.763 | 26.512 | 0.010 | 1.323 | 1.962 |
| Arginine (R) | 1.166 | 0.003 | 0.000 | 1.403 | 0.010 | 0.859 | 1.569 |
| Glutamic acid (E) | 8.832 | 2.007 | 0.000 | 0.028 | 0.000 | 38.742 | 0.010 |
| Cysteine (C) | 0.045 | 0.014 | 0.000 | 0.007 | 0.000 | 0.003 | 0.038 |
| Leucine (L) | 1.379 | 0.000 | 0.003 | 0.682 | 89.657 | 2.042 | 3.034 |
| Glutamine (Q) | 1.187 | 0.007 | 0.000 | 0.010 | 0.000 | 36.292 | 0.000 |
| Total | 100 | 100 | 100 | 100 | 100 | 100 | 100 |

TABLE 35

Amino acid distribution ratio for each position of amino acid (%)-V$_K$1-39_CDR3

| Type of AA | 89 | 90 | 91 | 92 | 93 | 94 | 95 | 96 |
|---|---|---|---|---|---|---|---|---|
| Alanine (A) | 0.000 | 0.018 | 3.949 | 1.051 | 3.162 | 10.532 | 0.032 | 0.637 |
| Serine (S) | 0.011 | 0.011 | 15.171 | 5.712 | 44.687 | 7.396 | 0.156 | 1.413 |
| Glycine (G) | 0.035 | 0.004 | 1.193 | 0.848 | 3.883 | 0.604 | 0.000 | 1.057 |
| Phenylalanine (F) | 0.000 | 0.000 | 3.285 | 4.004 | 0.873 | 9.307 | 0.000 | 6.181 |
| Proline (P) | 0.018 | 0.021 | 0.053 | 0.021 | 0.050 | 2.088 | 99.613 | 4.466 |
| Valine (V) | 0.000 | 0.000 | 0.895 | 0.380 | 0.642 | 2.834 | 0.000 | 1.783 |
| Tyrosine (Y) | 0.000 | 0.004 | 53.280 | 34.031 | 1.044 | 27.512 | 0.000 | 12.675 |
| Methionine (M) | 0.000 | 0.004 | 0.000 | 0.004 | 0.000 | 2.084 | 0.000 | 0.018 |
| Threonine (T) | 0.000 | 0.000 | 4.123 | 1.452 | 11.365 | 14.935 | 0.050 | 0.032 |

TABLE 35-continued

Amino acid distribution ratio for each position of amino acid (%)-V$_K$1-39_CDR3

| Type of AA | 89 | 90 | 91 | 92 | 93 | 94 | 95 | 96 |
|---|---|---|---|---|---|---|---|---|
| Lysine (K) | 0.000 | 0.025 | 0.032 | 3.159 | 1.555 | 0.000 | 0.000 | 0.815 |
| Isoleucine (I) | 0.007 | 0.000 | 0.032 | 1.132 | 3.102 | 4.357 | 0.000 | 1.886 |
| Tryptophan (W) | 0.089 | 0.000 | 0.000 | 0.000 | 0.000 | 0.028 | 0.000 | 13.828 |
| Aspartic acid (D) | 0.000 | 0.227 | 2.891 | 10.312 | 5.814 | 1.336 | 0.000 | 0.473 |
| Histidine (H) | 0.000 | 9.127 | 7.916 | 5.768 | 1.352 | 2.056 | 0.000 | 3.260 |
| Asparagine (N) | 0.000 | 0.000 | 1.868 | 27.866 | 17.576 | 3.611 | 0.000 | 0.669 |
| Arginine (R) | 92.086 | 0.028 | 0.032 | 0.497 | 1.746 | 0.213 | 0.046 | 5.509 |
| Glutamic acid (E) | 0.000 | 2.324 | 0.007 | 1.590 | 1.214 | 0.000 | 0.000 | 0.445 |
| Cysteine (C) | 0.000 | 0.000 | 0.028 | 0.032 | 0.014 | 0.039 | 0.000 | 0.036 |
| Leucine (L) | 7.715 | 0.014 | 5.238 | 1.679 | 1.906 | 11.065 | 0.064 | 41.235 |
| Glutamine (Q) | 0.039 | 88.193 | 0.007 | 0.461 | 0.014 | 0.004 | 0.039 | 3.583 |
| Total | 100 | 100 | 100 | 100 | 100 | 100 | 100 | 100 |

TABLE 36

Amino acid distribution ratio for each position of amino acid (%)-V$_K$3-20_CDR1

| Type of AA | 3 | 4 | 5 | 6 | 7 | 8 | 9 | 10 | 11 | 12 | 13 | 14 |
|---|---|---|---|---|---|---|---|---|---|---|---|---|
| Alanine (A) | 0.000 | 99.708 | 0.000 | 0.000 | 1.078 | 1.308 | 6.955 | 1.941 | 2.488 | 0.005 | 0.000 | 99.698 |
| Serine (S) | 93.009 | 0.029 | 99.617 | 0.158 | 72.631 | 0.058 | 41.161 | 54.144 | 22.774 | 9.041 | 0.120 | 0.053 |
| Glycine (G) | 6.780 | 0.019 | 0.144 | 0.000 | 0.690 | 0.005 | 4.501 | 4.443 | 1.376 | 0.010 | 86.918 | 0.005 |
| Phenylalanine (F) | 0.000 | 0.000 | 0.000 | 0.000 | 1.136 | 2.008 | 0.753 | 0.091 | 0.374 | 10.907 | 0.005 | 0.000 |
| Proline (P) | 0.000 | 0.000 | 0.000 | 0.053 | 0.484 | 0.029 | 1.299 | 0.072 | 0.714 | 0.067 | 0.000 | 0.010 |
| Valine (V) | 0.014 | 0.077 | 0.048 | 0.005 | 0.101 | 53.659 | 0.618 | 0.556 | 0.508 | 0.000 | 5.683 | 0.062 |
| Tyrosine (Y) | 0.010 | 0.000 | 0.024 | 0.000 | 1.193 | 0.029 | 2.392 | 1.270 | 0.652 | 58.367 | 0.000 | 0.000 |
| Methionine (M) | 0.010 | 0.000 | 0.000 | 0.000 | 0.000 | 0.958 | 0.000 | 0.000 | 0.005 | 0.014 | 0.010 | 0.000 |
| Threonine (T) | 0.000 | 0.058 | 0.005 | 0.010 | 10.623 | 0.024 | 9.951 | 5.364 | 7.877 | 0.062 | 0.000 | 0.048 |
| Lysine (K) | 0.024 | 0.000 | 0.000 | 5.483 | 0.010 | 0.000 | 1.237 | 0.748 | 4.186 | 1.622 | 0.000 | 0.000 |
| Isoleucine (I) | 0.005 | 0.000 | 0.014 | 0.000 | 3.076 | 27.007 | 3.456 | 1.874 | 2.253 | 0.000 | 0.005 | 0.000 |
| Tryptophan (W) | 0.000 | 0.000 | 0.000 | 0.000 | 0.000 | 0.010 | 0.014 | 0.000 | 0.038 | 0.715 | 0.000 | 0.000 |
| Aspartic acid (D) | 0.000 | 0.000 | 0.000 | 0.000 | 1.207 | 0.005 | 6.404 | 2.483 | 4.656 | 2.591 | 7.068 | 0.000 |
| Histidine (H) | 0.000 | 0.000 | 0.000 | 4.677 | 0.609 | 0.000 | 0.000 | 0.585 | 0.729 | 5.886 | 0.005 | 0.000 |
| Asparagine (N) | 0.072 | 0.000 | 0.024 | 0.225 | 5.999 | 0.005 | 15.186 | 23.765 | 46.104 | 6.104 | 0.014 | 0.000 |
| Arginine (R) | 0.034 | 0.043 | 0.048 | 0.115 | 1.016 | 0.024 | 2.933 | 1.505 | 3.069 | 0.581 | 0.101 | 0.034 |
| Glutamic acid (E) | 0.024 | 0.005 | 0.062 | 0.010 | 0.010 | 0.000 | 0.034 | 0.000 | 0.014 | 0.000 | 0.005 | 0.014 |
| Cysteine (C) | 0.014 | 0.062 | 0.014 | 0.000 | 0.024 | 0.072 | 0.000 | 0.010 | 0.005 | 0.077 | 0.058 | 0.005 |
| Leucine (L) | 0.000 | 0.000 | 0.000 | 0.000 | 0.019 | 0.115 | 14.797 | 2.167 | 1.021 | 2.167 | 1.531 | 0.010 | 0.024 |
| Glutamine (Q) | 0.005 | 0.000 | 0.000 | 89.235 | 0.000 | 0.005 | 0.010 | 0.029 | 0.010 | 1.420 | 0.000 | 0.048 |
| Total | 100 | 100 | 100 | 100 | 100 | 100 | 100 | 100 | 100 | 100 | 100 | 100 |

TABLE 37

Amino acid distribution ratio for each position of animo acid (%)-V$_K$3-20_CDR2

| Type of AA | 3 | 4 | 5 | 6 | 7 | 8 | 9 | 10 | 11 |
|---|---|---|---|---|---|---|---|---|---|
| Alanine (A) | 0.000 | 11.374 | 73.679 | 1.717 | 1.848 | 0.000 | 97.386 | 64.191 | 0.016 |
| Serine (S) | 6.170 | 5.015 | 4.630 | 84.208 | 23.978 | 0.037 | 0.090 | 8.731 | 0.008 |
| Glycine (G) | 0.004 | 30.792 | 1.741 | 0.004 | 0.824 | 0.016 | 0.004 | 0.000 | 5.896 |
| Phenylalanine (F) | 7.860 | 0.033 | 0.012 | 5.491 | 0.824 | 0.000 | 0.008 | 0.008 | 0.000 |
| Proline (P) | 0.012 | 0.029 | 0.688 | 0.594 | 0.012 | 0.033 | 0.008 | 11.079 | 0.000 |
| Valine (V) | 0.000 | 0.733 | 4.331 | 0.701 | 0.270 | 0.049 | 2.385 | 0.029 | 0.008 |
| Tyrosine (Y) | 70.382 | 0.643 | 0.016 | 2.225 | 1.733 | 0.000 | 0.000 | 0.000 | 0.025 |
| Methionine (M) | 0.000 | 0.000 | 0.000 | 0.000 | 0.672 | 0.000 | 0.000 | 0.000 | 0.000 |
| Threonine (T) | 0.057 | 1.282 | 10.600 | 2.499 | 16.191 | 0.004 | 0.045 | 15.881 | 0.008 |
| Lysine (K) | 0.008 | 0.004 | 0.000 | 0.000 | 7.799 | 0.000 | 0.000 | 0.000 | 0.000 |
| Isoleucine (I) | 1.140 | 0.008 | 2.540 | 0.815 | 5.053 | 0.000 | 0.000 | 0.004 | 0.000 |
| Tryptophan (W) | 0.382 | 0.008 | 0.000 | 0.000 | 0.000 | 0.000 | 0.000 | 0.000 | 0.000 |
| Aspartic acid (D) | 1.809 | 40.588 | 0.078 | 0.000 | 2.270 | 0.000 | 0.016 | 0.029 | 93.964 |
| Histidine (H) | 8.077 | 1.246 | 0.025 | 0.020 | 1.947 | 0.049 | 0.000 | 0.000 | 0.004 |
| Asparagine (N) | 1.284 | 2.961 | 0.033 | 0.020 | 33.469 | 0.000 | 0.000 | 0.000 | 0.041 |
| Arginine (R) | 0.016 | 1.082 | 0.008 | 0.004 | 2.106 | 99.672 | 0.004 | 0.000 | 0.000 |
| Glutamic acid (E) | 0.000 | 3.802 | 0.906 | 0.004 | 0.004 | 0.000 | 0.000 | 0.000 | 0.029 |
| Cysteine (C) | 0.045 | 0.020 | 0.016 | 0.012 | 0.004 | 0.094 | 0.025 | 0.012 | 0.000 |

TABLE 37-continued

Amino acid distribution ratio for each position of amino acid (%)-$V_K$3-20_CDR2

| Type of AA | 3 | 4 | 5 | 6 | 7 | 8 | 9 | 10 | 11 |
|---|---|---|---|---|---|---|---|---|---|
| Leucine (L) | 2.223 | 0.766 | 0.676 | 1.684 | 0.996 | 0.045 | 0.029 | 0.037 | 0.000 |
| Glutamine (Q) | 0.529 | 0.012 | 0.020 | 0.000 | 0.000 | 0.000 | 0.000 | 0.000 | 0.000 |
| Total | 100 | 100 | 100 | 100 | 100 | 100 | 100 | 100 | 100 |

TABLE 38

Amnio acid distribution ratio for each position of amino acid (%)-$V_K$3-20 & 20-2_CDR3

| Type of AA | 4 | 5 | 6 | 7 | 8 | 9 | 10 | 11 |
|---|---|---|---|---|---|---|---|---|
| Alanine (A) | 0.000 | 0.014 | 6.618 | 4.632 | 1.944 | 5.472 | 0.018 | 0.383 |
| Serine (S) | 0.009 | 0.018 | 6.672 | 12.502 | 27.846 | 36.329 | 0.112 | 1.000 |
| Glycine (G) | 0.009 | 0.000 | 2.402 | 17.116 | 3.334 | 0.698 | 0.000 | 1.225 |
| Phenylalanine (F) | 0.000 | 0.000 | 3.082 | 1.727 | 0.787 | 1.890 | 0.000 | 5.562 |
| Proline (P) | 0.000 | 0.000 | 0.045 | 0.049 | 0.063 | 2.349 | 99.555 | 4.918 |
| Valine (V) | 0.000 | 0.000 | 0.369 | 1.691 | 0.738 | 0.675 | 0.000 | 1.464 |
| Tyrosine (Y) | 0.000 | 0.005 | 63.796 | 14.148 | 1.587 | 3.614 | 0.000 | 10.955 |
| Methionine (M) | 0.000 | 0.000 | 0.000 | 0.000 | 0.000 | 0.000 | 0.000 | 0.005 |
| Threonine (T) | 0.000 | 0.000 | 1.062 | 4.380 | 7.410 | 9.266 | 0.022 | 0.023 |
| Lysine (K) | 0.000 | 0.009 | 0.022 | 1.596 | 2.448 | 0.000 | 0.000 | 0.671 |
| Isoleucine (I) | 0.000 | 0.000 | 0.018 | 2.069 | 2.146 | 1.841 | 0.000 | 1.653 |
| Tryptophan (W) | 0.094 | 0.000 | 0.324 | 0.009 | 0.000 | 27.702 | 0.000 | 14.456 |
| Aspartic acid (D) | 0.000 | 0.000 | 1.242 | 7.159 | 5.577 | 0.018 | 0.000 | 0.491 |
| Histidine (H) | 0.000 | 10.512 | 4.639 | 2.527 | 5.278 | 0.009 | 0.000 | 3.356 |
| Asparagine (N) | 0.000 | 0.000 | 0.922 | 15.722 | 26.604 | 1.472 | 0.000 | 0.572 |
| Arginine (R) | 95.531 | 0.054 | 6.866 | 0.724 | 1.494 | 0.329 | 0.049 | 6.026 |
| Glutamic acid (E) | 0.000 | 0.005 | 0.009 | 2.019 | 1.201 | 0.000 | 0.000 | 0.387 |
| Cysteine (C) | 0.000 | 0.000 | 0.162 | 0.018 | 0.013 | 0.009 | 0.000 | 0.018 |
| Leucine (L) | 4.303 | 0.009 | 1.692 | 11.908 | 2.101 | 8.330 | 0.121 | 43.405 |
| Glutamine (Q) | 0.054 | 89.376 | 0.058 | 0.004 | 8.229 | 0.000 | 0.121 | 3.382 |
| Total | 100 | 100 | 100 | 100 | 100 | 100 | 100 | 100 |

TABLE 39

Amino acid distribution ratio for each position of amino acid (%)-$V_K$3-20-2_CDR1

| Type of AA | 3 | 4 | 5 | 6 | 7 | 8 | 9 | 10 | 11 | 12 |
|---|---|---|---|---|---|---|---|---|---|---|
| Alanine (A) | 0.000 | 99.676 | 0.000 | 0.000 | 1.581 | 1.774 | 3.895 | 1.735 | 0.440 | 0.032 |
| Serine (S) | 93.219 | 0.054 | 99.676 | 0.092 | 57.056 | 0.189 | 37.097 | 31.048 | 6.989 | 0.065 |
| Glycine (G) | 6.557 | 0.015 | 0.029 | 0.005 | 2.934 | 0.008 | 10.790 | 2.455 | 0.263 | 86.653 |
| Phenylalanine (F) | 0.000 | 0.000 | 0.000 | 0.000 | 0.060 | 1.158 | 0.585 | 0.791 | 4.513 | 0.002 |
| Proline (P) | 0.000 | 0.006 | 0.000 | 0.014 | 0.637 | 0.002 | 0.034 | 0.362 | 0.023 | 0.000 |
| Valine (V) | 0.031 | 0.074 | 0.063 | 0.005 | 0.083 | 47.528 | 0.891 | 0.805 | 0.000 | 5.508 |
| Tyrosine (V) | 0.000 | 0.000 | 0.000 | 0.002 | 0.952 | 0.025 | 1.838 | 2.175 | 26.251 | 0.006 |
| Methionine (M) | 0.012 | 0.000 | 0.000 | 0.000 | 0.000 | 0.008 | 0.002 | 0.002 | 0.008 | 0.005 |
| Threonine (T) | 0.003 | 0.049 | 0.003 | 0.008 | 5.785 | 0.028 | 5.782 | 14.453 | 0.790 | 0.005 |
| Lysine (K) | 0.002 | 0.000 | 0.006 | 0.009 | 0.017 | 0.000 | 1.709 | 3.489 | 4.066 | 0.000 |
| Isoleucine (I) | 0.029 | 0.000 | 0.054 | 0.003 | 1.492 | 36.829 | 2.438 | 4.900 | 0.011 | 0.003 |
| Tryptophan (W) | 0.000 | 0.002 | 0.000 | 0.000 | 0.000 | 0.008 | 0.002 | 0.002 | 1.093 | 0.000 |
| Aspartic acid (D) | 0.003 | 0.000 | 0.000 | 0.060 | 2.965 | 0.009 | 7.017 | 3.132 | 4.356 | 7.393 |
| Histidine (H) | 0.000 | 0.000 | 0.000 | 0.174 | 0.005 | 0.025 | 1.660 | 1.121 | 5.642 | 0.000 |
| Asparagine (N) | 0.074 | 0.000 | 0.045 | 0.005 | 15.265 | 0.032 | 19.057 | 29.809 | 40.213 | 0.005 |
| Arginine (R) | 0.037 | 0.051 | 0.058 | 93.620 | 1.012 | 0.026 | 3.649 | 3.589 | 0.510 | 0.048 |
| Glutamic acid (E) | 0.028 | 0.022 | 0.058 | 0.028 | 0.002 | 0.002 | 1.115 | 0.006 | 1.024 | 0.011 |
| Cysteine (C) | 0.002 | 0.052 | 0.008 | 0.002 | 0.015 | 0.078 | 0.025 | 0.014 | 0.037 | 0.054 |
| Leucine (L) | 0.000 | 0.000 | 0.000 | 0.961 | 0.132 | 12.267 | 2.390 | 0.088 | 2.425 | 0.212 |
| Glutamine (Q) | 0.005 | 0.000 | 0.000 | 5.014 | 0.008 | 0.003 | 0.023 | 0.025 | 1.347 | 0.000 |
| Total | 100 | 100 | 100 | 100 | 100 | 100 | 100 | 100 | 100 | 100 |

TABLE 40

Amino acid distribution ratio for each position of amino acid (%)-Vλ1-51_CDR1

| Type of AA | 3 | 4 | 5 | 6 | 7 | 8 | 9 | 10 | 11 | 12 | 13 | 14 | 15 |
|---|---|---|---|---|---|---|---|---|---|---|---|---|---|
| Alanine (A) | 0.007 | 0.092 | 1.341 | 1.946 | 0.013 | 0.000 | 0.131 | 4.889 | 1.558 | 0.000 | 7.376 | 0.092 | 2.657 |
| Serine (S) | 99.632 | 0.053 | 78.287 | 52.255 | 99.527 | 0.053 | 0.020 | 0.007 | 31.705 | 3.276 | 10.026 | 0.000 | 36.262 |
| Glycine (G) | 0.000 | 99.744 | 7.540 | 3.557 | 0.000 | 0.000 | 0.026 | 3.327 | 2.360 | 0.599 | 0.625 | 0.000 | 0.000 |
| Phenylalanine (F) | 0.072 | 0.000 | 0.059 | 0.723 | 0.138 | 0.000 | 0.026 | 0.000 | 0.026 | 0.967 | 10.512 | 0.000 | 1.920 |
| Proline (P) | 0.177 | 0.000 | 0.158 | 0.079 | 0.072 | 0.000 | 0.000 | 0.000 | 0.335 | 0.025 | 3.662 | 0.000 | 0.053 |
| Valine (V) | 0.000 | 0.020 | 0.013 | 0.020 | 0.000 | 0.000 | 89.711 | 0.000 | 0.513 | 0.000 | 1.492 | 99.658 | 0.007 |
| Tyrosine (V) | 0.020 | 0.000 | 0.033 | 0.730 | 0.020 | 0.007 | 0.020 | 0.000 | 2.005 | 3.802 | 31.990 | 0.000 | 14.244 |
| Methionine (M) | 0.000 | 0.000 | 0.000 | 0.000 | 0.000 | 0.138 | 0.000 | 0.000 | 0.000 | 0.000 | 0.000 | 0.099 | 0.000 |
| Threonine (T) | 0.020 | 0.000 | 5.923 | 11.946 | 0.007 | 0.020 | 0.000 | 0.000 | 7.139 | 1.072 | 14.042 | 0.000 | 1.420 |
| Lysine (K) | 0.000 | 0.000 | 0.007 | 1.874 | 0.000 | 0.072 | 0.000 | 0.112 | 4.372 | 3.144 | 0.000 | 0.000 | 0.638 |
| Isoleucine (I) | 0.000 | 0.000 | 1.282 | 1.729 | 0.007 | 0.026 | 9.756 | 0.007 | 4.049 | 0.724 | 2.735 | 0.000 | 0.000 |
| Tryptophan (W) | 0.000 | 0.013 | 0.000 | 0.007 | 0.000 | 0.000 | 0.000 | 0.000 | 0.000 | 0.000 | 0.000 | 0.000 | 0.000 |
| Aspartic acid (D) | 0.000 | 0.033 | 1.992 | 2.275 | 0.000 | 0.007 | 0.000 | 0.033 | 6.501 | 1.908 | 4.786 | 0.000 | 1.250 |
| Histidine (H) | 0.000 | 0.000 | 0.007 | 1.578 | 0.000 | 0.000 | 0.000 | 0.000 | 1.446 | 5.499 | 5.312 | 0.000 | 4.044 |
| Asparagine (N) | 0.000 | 0.000 | 1.972 | 19.093 | 0.000 | 99.571 | 0.000 | 0.013 | 32.369 | 76.301 | 4.615 | 0.000 | 35.953 |
| Arginine (R) | 0.000 | 0.013 | 1.269 | 2.091 | 0.000 | 0.000 | 0.000 | 0.092 | 3.543 | 0.605 | 0.552 | 0.046 | 0.013 |
| Glutamic acid (E) | 0.000 | 0.000 | 0.000 | 0.000 | 0.000 | 0.000 | 0.000 | 91.507 | 0.861 | 1.355 | 0.007 | 0.000 | 0.013 |
| Cysteine (C) | 0.026 | 0.033 | 0.007 | 0.007 | 0.020 | 0.007 | 0.138 | 0.013 | 0.000 | 0.000 | 0.053 | 0.059 | 0.039 |
| Leucine (L) | 0.046 | 0.000 | 0.112 | 0.092 | 0.197 | 0.000 | 0.171 | 0.000 | 1.216 | 0.000 | 2.209 | 0.046 | 0.526 |
| Glutamine (Q) | 0.000 | 0.000 | 0.000 | 0.000 | 0.000 | 0.000 | 0.000 | 0.000 | 0.000 | 0.724 | 0.007 | 0.000 | 0.960 |
| Total | 100 | 100 | 100 | 100 | 100 | 100 | 100 | 100 | 100 | 100 | 100 | 100 | 100 |

TABLE 41

Amino acid distribution ratio for each position of amino acid (%)-Vλ1-51_CDR2

| Type of AA | 49 | 50 | 51 | 52 | 53 | 54 | 55 | 56 |
|---|---|---|---|---|---|---|---|---|
| Alanine (A) | 0 | 7.6 | 0 | 0.2 | 0 | 0 | 0 | 0 |
| Serine (S) | 3.6 | 12.6 | 4.4 | 8.3 | 1.4 | 0 | 0 | 100 |
| Glycine (G) | 0 | 10.2 | 0.4 | 0.9 | 0 | 0 | 0 | 0 |
| Phenylalanine (F) | 9.3 | 0.6 | 0.6 | 0.8 | 0 | 0 | 0 | 0 |
| Proline (P) | 0 | 0 | 0 | 0 | 0 | 0 | 100 | 0 |
| Valine (V) | 0 | 0.6 | 2 | 0.5 | 0.4 | 0 | 0 | 0 |
| Tyrosine (V) | 77.6 | 2.6 | 1.4 | 3.6 | 1.3 | 0 | 0 | 0 |
| Methionine (M) | 0 | 1 | 0 | 0 | 1.1 | 0 | 0 | 0 |
| Threonine (T) | 0 | 3.2 | 5.6 | 8.5 | 0 | 0 | 0 | 0 |
| Lysine (K) | 0 | 3.6 | 0.8 | 2.1 | 20.2 | 0 | 0 | 0 |
| Isoleucine (I) | 0 | 1.2 | 1.2 | 3.5 | 1.9 | 0 | 0 | 0 |
| Tryptophan (W) | 0 | 0.5 | 0 | 0 | 0 | 0 | 0 | 0 |
| Aspartic acid (D) | 0.7 | 26.8 | 14.3 | 16.4 | 2 | 0 | 0 | 0 |
| Histidine (H) | 5.4 | 0.9 | 1.4 | 3.5 | 4.5 | 0 | 0 | 0 |
| Asparagine (N) | 0.9 | 13.7 | 67.5 | 49.9 | 22.9 | 0 | 0 | 0 |
| Arginine (R) | 0.4 | 3.3 | 0.4 | 1 | 2.3 | 100 | 0 | 0 |
| Glutamic acid (E) | 0 | 9.3 | 0 | 0.8 | 5.6 | 0 | 0 | 0 |
| Cysteine (C) | 0.1 | 0 | 0 | 0 | 0 | 0 | 0 | 0 |
| Leucine (L) | 0.8 | 1.6 | 0 | 0 | 5.9 | 0 | 0 | 0 |
| Glutamine (Q) | 1.2 | 0.7 | 0 | 0 | 30.5 | 0 | 0 | 0 |
| Total | 100 | 100 | 100 | 100 | 100 | 100 | 100 | 100 |

TABLE 42

Amino acid distribution ratio for each position of amino acid (%)-Vλ1-51_CDR3

| Type of AA | 4 | 5 | 6 | 7 | 8 | 9 | 10 | 11 | 12 | 13 | 14 |
|---|---|---|---|---|---|---|---|---|---|---|---|
| Alanine (A) | 43.398 | 30.048 | 0.515 | 0.000 | 3.506 | 1.570 | 0.048 | 1.262 | 25.973 | 4.082 | 2.530 |
| Serine (S) | 5.725 | 28.002 | 0.000 | 0.000 | 29.684 | 68.271 | 9.047 | 30.570 | 4.785 | 4.329 | 0.014 |
| Glycine (G) | 13.804 | 0.645 | 0.021 | 0.206 | 5.221 | 3.943 | 0.631 | 1.968 | 22.224 | 7.800 | 0.048 |
| Phenylalanine (F) | 0.000 | 0.055 | 1.785 | 0.000 | 0.062 | 0.095 | 0.007 | 0.048 | 1.104 | 1.749 | 0.843 |
| Proline (P) | 0.045 | 0.048 | 0.000 | 0.000 | 0.034 | 0.823 | 0.572 | 0.082 | 0.523 | 5.427 | 0.014 |
| Valine (V) | 1.400 | 13.175 | 0.007 | 0.014 | 0.741 | 0.720 | 1.235 | 0.446 | 4.431 | 21.350 | 57.634 |
| Tyrosine (V) | 0.021 | 0.027 | 17.221 | 0.007 | 1.358 | 1.152 | 0.034 | 1.323 | 1.145 | 16.280 | 0.007 |
| Methionine (M) | 0.000 | 0.000 | 0.014 | 0.021 | 0.007 | 0.000 | 0.014 | 0.000 | 0.007 | 1.599 | 4.039 |
| Threonine (T) | 0.796 | 24.587 | 0.021 | 0.000 | 5.734 | 4.848 | 2.138 | 6.370 | 2.483 | 0.027 | 0.007 |

TABLE 42-continued

Amino acid distribution ratio for each position of amino acid (%)-Vλ1-51_CDR3

| Type of AA | 4 | 5 | 6 | 7 | 8 | 9 | 10 | 11 | 12 | 13 | 14 |
|---|---|---|---|---|---|---|---|---|---|---|---|
| Lysine (K) | 0.007 | 0.000 | 0.000 | 0.000 | 1.694 | 0.672 | 0.000 | 4.210 | 0.007 | 0.007 | 0.000 |
| Isoleucine (I) | 0.000 | 1.234 | 0.007 | 0.021 | 2.627 | 2.489 | 1.104 | 1.125 | 2.071 | 0.059 | 8.736 |
| Tryptophan (W) | 0.000 | 0.014 | 78.605 | 0.000 | 0.027 | 0.000 | 0.027 | 0.000 | 0.021 | 20.115 | 0.027 |
| Aspartic acid (D) | 0.007 | 0.000 | 0.000 | 99.509 | 33.992 | 2.352 | 0.919 | 14.544 | 3.251 | 0.007 | 0.014 |
| Histidine (H) | 1.208 | 0.014 | 1.256 | 0.000 | 1.262 | 0.014 | 0.007 | 2.592 | 16.160 | 2.422 | 0.000 |
| Asparagine (N) | 0.000 | 0.041 | 0.000 | 0.069 | 12.129 | 9.333 | 2.778 | 31.914 | 1.454 | 0.007 | 0.000 |
| Arginine (R) | 0.055 | 0.000 | 0.419 | 0.027 | 1.056 | 2.619 | 0.247 | 2.167 | 1.063 | 2.628 | 0.027 |
| Glutamic acid (E) | 1.256 | 0.021 | 0.000 | 0.027 | 0.844 | 0.007 | 0.007 | 1.323 | 1.482 | 1.688 | 0.000 |
| Cysteine (C) | 0.000 | 0.007 | 0.048 | 0.000 | 0.034 | 0.021 | 0.021 | 0.007 | 0.041 | 0.034 | 0.021 |
| Leucine (L) | 1.311 | 2.085 | 0.082 | 0.000 | 0.027 | 1.070 | 80.988 | 0.041 | 5.823 | 9.378 | 25.989 |
| Glutamine (Q) | 30.464 | 0.000 | 0.000 | 0.000 | 0.000 | 0.000 | 0.027 | 0.007 | 2.648 | 1.002 | 0.000 |
| Total | 100 | 100 | 100 | 100 | 100 | 100 | 100 | 100 | 100 | 100 | 100 |

In the present invention, the fragment of antibody may have one or more forms selected from the group consisting of Fab, F(ab')$_2$, Fab', Fv and scFv, but is not limited thereto.

The antibody or a fragment thereof according to the present invention may have one or more characteristics selected from the group consisting of: i) redundancy (percentage of repetitive sequences) of 10% or less; ii) p-value of CDR composition >0.05; iii) thermal stability of 70° C. or higher; and iv) diversity (library size) of $10^7$ or more.

In another aspect, the present invention is directed to nucleic acids encoding a set of antibodies or fragments thereof.

In another aspect, the present invention is directed to a method of identifying an antibody or fragment thereof specific for an antigen including (a) contacting an antigen with the set of antibodies, and (b) selecting one or more antibodies or antibody fragments that bind to the antigen.

In the present invention, the set of antibodies may be expressed on the surface of the phage included in a transformant introduced with the nucleic acid encoding the set of antibodies, but is not limited thereto.

In the present invention, the identification method may include culturing the transformant and phage of the library, binding the antibody expressed on the phage surface to an antigen, and screening and selecting a transformant expressing a desired antibody. The screening and selection may be performed using various techniques known in the art.

For example, an antibody that binds to a specific antigen may be produced by isolation from the library using a panning method. The panning includes binding phages to a target antigen, removing unbound phages, recovering bound phages, infecting host cells with the phages to amplify the number of phages, and repeating this process 2 to 4 times.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1) Acquisition of Asian and Caucasian Human Variable-Region cDNAs

In order to analyze the amino acid combination of Asian and Caucasian human antibody variable-region CDRs, Asian human messenger RNA was first obtained by differentiating B-cells from PBMCs through blood donation (before IRB implementation) by a researcher in the laboratory. Caucasian messenger RNA used herein was human spleen total RNA (CAT No. 636525, Lot No. 1107171A) produced by Clontech Laboratories Inc. The obtained Asian and Caucasian messenger RNAs were converted to cDNAs using an ImProm-II Reverse Transcription System (Promega, CAT No. A3802). In order to secure the human variable-region genes from the obtained cDNA, Asian and Caucasian cDNAs were used as templates, a forward primer (Table 43: SEQ ID NO: 71) and a reverse primer (Table 43: SEQ ID NO: 72) were added to a VH1 type, a forward primer (Table 43: SEQ ID NO: 73) and a reverse primer (Table 43: SEQ ID NO: 72) were added to a VH3 type, a forward primer (Table 43: SEQ ID NO: 74) and a reverse primer (Table 43: SEQ ID NO: 75) were added to a Vk1 type, a forward primer (Table 43: SEQ ID NO: 76) and a reverse primer (Table 43: SEQ ID NO: 75) were added to a Vk3 type, and a forward primer (Table 43: SEQ ID NO: 77) and a reverse primer (Table 43: SEQ ID NO: 78 were added to a Vλ1 type, and then PCR was performed for each mixture of cDNA and primers using Platinum mix polymerase (Invitrogen, CAT No. 11306). PCR conditions were as follows: exposure at 94° C. for 3 minutes, followed by 25 repetitions of a cycle including exposure at 94° C. for 1 minute, exposure at 55° C. for 1 minute, and exposure at 72° C. for 2 minutes, and then reaction at 72° C. for 10 minutes. The amplified genes were identified as DNA bands having the expected sizes in 1% agarose gel and were each isolated using a gel extraction kit (QIAquick Gel Extraction Kit, QIAGEN, CAT. No. 28706).

TABLE 43

| Name | Sequence | SEQ ID NO |
|---|---|---|
| VH1 Fo | CARGTGCAGCTKGTGCAGTCTGG | 71 |
| JH Re_cDNA | TGAGGAGACGGTGACCAGGGTGCC | 72 |
| VH3 Fo | GARGTGCAGCTGGTGGAGTCTGG | 73 |
| Vk1 Fo | GACATCCAGATGACCCAGTCTCC | 74 |
| Jk Re_cDNA | ACGTTTGATTTCCACCTTGGTCCC | 75 |
| Vk3 Fo | GAAATWGTGWTGACRCAGTCTCC | 76 |

TABLE 43-continued

| Name | Sequence | SEQ ID NO |
|---|---|---|
| Vλ Fo | CAGTCTGTGYTGACKCAGCCGCC | 77 |
| Jλ Re_cDNA | ACCTAGGACGGTCAGCTTGGTCCC | 78 |

Example 2) Construction of Asian and Caucasian Human Antibody Variable-Region Libraries for High-Throughput Sequencing In order to perform high-throughput sequencing of Asian and Caucasian cDNAs obtained in Example 1, PCR was performed to connect barcodes to identify respective types. First, regarding Asian cDNA, a forward primer (Table 44: SEQ ID NO: 79) and a reverse primer (Table 44: SEQ ID NO: 89) were added to Asian VH1 cDNA as a template, a forward primer (Table 44: SEQ ID NO: 80) and a reverse primer (Table 44: SEQ ID NO: 89) were added to a VH3 type, a forward primer (Table 44: SEQ ID NO: 81) and a reverse primer (Table 44: SEQ ID NO: 90) were added to a Vk1 type, a forward primer (Table 44: SEQ ID NO: 81) and a reverse primer (Table 44: SEQ ID NO: 90) were added to a Vk3 type, a forward primer (Table 44: SEQ ID NO: 83) and a reverse primer (Table 44: SEQ ID NO: 91) were added to a Vλ1 type, and then PCR was performed for each mixture of cDNA and primers using a prime star mix (Takara, CAT No. R040B). PCR conditions were as follows: exposure at 94° C. for 2 minutes, followed by 10 repetitions of a cycle including exposure at 94° C. for 15 minutes, exposure at 55° C. for 15 minutes, and exposure at 72° C. for 30 minutes, and reaction at 72° C. for 5 minutes. The amplified genes were identified as DNA bands of the expected sizes in 1% agarose gel, and were individually isolated using a gel extraction kit (QIAquick Gel Extraction Kit, QIAGEN, CAT. No. 28706). Regarding Caucasian cDNA, a forward primer (Table 44: SEQ ID NO: 84) and a reverse primer (Table 44: SEQ ID NO: 89) were added to Caucasian VH1 cDNA as a template, a forward primer (Table 44: SEQ ID NO: 85) and a reverse primer (Table 44: SEQ ID NO: 89) were added to a VH3 type, a forward primer (Table 44: SEQ ID NO: 86) and a reverse primer (Table 44: SEQ ID NO: 90) were added to a Vk1 type, a forward primer (Table 44: SEQ ID NO: 87) and a reverse primer (Table 44: SEQ ID NO: 90) were added to a Vk3 type, and a forward primer (Table 44: SEQ ID NO: 88) and a reverse primer (Table 44: SEQ ID NO: 91) were added to a Vλ1 type, and then PCR was performed for each mixture of cDNA and primers using a prime star mix (Takara, CAT No. R040B). The PCR conditions were as follows: exposure at 94° C. for 2 minutes, followed by 10 repetitions of a cycle including exposure at 94° C. for 15 minutes, exposure at 55° C. for 15 minutes, and exposure at 72° C. for 30 minutes, and then reaction at 72° C. for 5 minutes. The amplified genes were identified as DNA bands of the expected sizes in 1% agarose gel and were each isolated using a gel extraction kit (QIAquick Gel Extraction Kit, QIAGEN, CAT. No. 28706).

The obtained Asian and Caucasian genes were sequenced in the numbers shown in Table 45 using a 454 sequencing (GS FLX Titanium, Roche) method by Macrogen (Guro-gu, Seoul, Korea). The composition ratio of the CDR amino acids of the sequences for CDR1, CDR2 and CDR3 based on the amino acids shown in Table 46 was analyzed.

TABLE 44

| Name | Sequence | SEQ ID NO |
|---|---|---|
| VH1 Fo Asian | CCATCTCATCCCTGCGTGTCTCCGACTCAGACGAGTGCGTC ARGTGCAGCTKGTGCAGTCTGG | 79 |
| VH3 Fo Asian | CCATCTCATCCCTGCGTGTCTCCGACTCAGACGAGTGCGTC ARGTGCAGCTKGTGCAGTCTGG | 80 |
| Vk1 Fo Asian | CCATCTCATCCCTGCGTGTCTCCGACTCAGACGCTCGACAG ARGTGCAGCTGGTGGAGTCTGG | 81 |
| Vk3 Fo Asian | CCATCTCATCCCTGCGTGTCTCCGACTCAGAGACGCACTCG ACATCCAGATGACCCAGTCTCC | 82 |
| Vλ1 Fo Asian | CCATCTCATCCCTGCGTGTCTCCGACTCAGAGCACTGTAGG AAATWGTGWTGACRCAGTCTCC | 83 |
| VH1 Fo Caucasian | CCATCTCATCCCTGCGTGTCTCCGACTCAGATCAGACACGC AGTCTGTGYTGACKCAGCCGCC | 84 |
| VH3 Fo Caucasian | CCATCTCATCCCTGCGTGTCTCCGACTCAGATATCGCGAGC ARGTGCAGCTKGTGCAGTCTGG | 85 |
| Vk1 Fo Caucasian | CCATCTCATCCCTGCGTGTCTCCGACTCAGCGTGTCTCTAG ARGTGCAGCTGGTGGAGTCTGG | 86 |
| Vk3 Fo Caucasian | CCATCTCATCCCTGCGTGTCTCCGACTCAGCTCGCGTGTCG ACATCCAGATGACCCAGTCTCC | 87 |
| Vλ1 Fo Caucasian | CCATCTCATCCCTGCGTGTCTCCGACTCAGTAGTATCAGCG AAATWGTGWTGACRCAGTCTCC | 88 |
| JH Re | CCTATCCCCTGTGTGCCTTGGCAGTCTCAGTGAGGAGACGG TGACCAGGGTGCC | 89 |
| Jk Re | CCTATCCCCTGTGTGCCTTGGCAGTCTCAGACGTTTGATTT CCACCTTGGTCCC | 90 |

TABLE 44-continued

| Name | Sequence | SEQ ID NO |
|---|---|---|
| Jλ Re | CCTATCCCTGTGTGCCTTGGCAGTCTCAGACCTAGGACGGTGACCTTGGTCCC | 91 |

Example 3) High-Throughput Sequencing Data Analysis and Primer Design Based Thereon More than 10000 human variable-region sequences were obtained for each race and type through high-throughput sequencing (Table 45). In order to detect the amino acid combinations of the CDR regions among the obtained human variable-region sequences, for the CDR1 of VH1 type, the region between serine-cysteine (Kabat numbers 22,23) and tryptophan-valine (Kabat numbers 36,37) was analyzed, for the CDR2 of VH1 type, the region between glutamic acid-tryptophan (Kabat numbers 47,48) and arginine-random-threonine (Kabat numbers 67,68,69) was analyzed and for the CDR3 of VH1 type, the region between tyrosine-tyrosine-cysteine (Kabat numbers 90, 91, 92) and glycine-threonine-leucine (Kabat numbers 103, 104, 105) was analyzed. For the CDR1 of VH3 type, the region between serine-cysteine (Kabat numbers 22,23) and tryptophan-valine (Kabat numbers 36,37) was analyzed, for the CDR2 of VH3 type, the region between glutamic acid-tryptophan (Kabat numbers 47,48) and lysine-glycine-arginine (Kabat numbers 67,68,69) was analyzed, and for the CDR3 of VH3 type, the region between tyrosine-tyrosine-cysteine (Kabat numbers 90, 91, 92) and glycine-threonine-leucine (Kabat numbers 103, 104, 105) was analyzed. For the CDR1 of Vk1 type, the region between isoleucine-random-cysteine (Kabat numbers 21, 22, 23) and tryptophan-tyrosine (Kabat numbers 35, 36) was analyzed, for the CDR2 of Vk1 type, the region between isoleucine-tyrosine (Kabat numbers 48, 49) and glycine-valine (Kabat numbers 57, 58) was analyzed, and for the CDR3 of Vk1 type, the region between tyrosine-tyrosine-cysteine (Kabat numbers 86, 87, 88) and glycine-threonine-lysine (Kabat number 101, 102, 103) was analyzed. For the CDR1 of Vk3, the region between serine-cysteine (Kabat numbers 22,23) and tryptophan-tyrosine (Kabat numbers 35,36) was analyzed, for the CDR2 of Vk3, the region between leucine-isoleucine (Kabat numbers 47,48) and isoleucine-proline (Kabat numbers 58,59) was analyzed, and for the CDR3 of Vk3, the region between tyrosine-tyrosine-cysteine (Kabat numbers 86,87, 88) and glycine-threonine-lysine (Kabat numbers 101, 102, 103) was analyzed. For the CDR1 of Vλ1, the region between serine-cysteine (Kabat numbers 22, 23) and tryptophan-tyrosine (Kabat numbers 35, 36) was analyzed, for the CDR2 of Vλ1, the region leucine-isoleucine (Kabat numbers 47, 48) and serine-glycine (Kabat number 56, 57) was analyzed, and for the CDR3 of Vλ1, the region between tyrosine-tyrosine-cysteine (Kabat numbers 86, 87, 88) and glycine-threonine-lysine (Kabat numbers 101, 102, 103) was analyzed (Table 46). VH1 and VH3 types have various lengths of CDR3, so the amino acid combinations were identified after analyzing each of 9 to 14 amino acids, which are the lengths that enable most efficient selection of antibodies when producing synthetic libraries based on conventional literature.

The result of analysis showed that no significant difference was found between Asian and Caucasian CDR amino acid combinations, i.e., that they are quite similar. CDR1 and CDR2 of VH have various amino acid combinations, but contain amino acids conserved at a higher rate than CDR3. The reason for this is that these are V-gene regions that have no V-D-J joining, so the possibility of introducing mutations is lower than in the case of CDR3, and there are amino acids that should be conserved due to the presence of residue numbers that affect structural stability. No significant difference was found between the CDR3 of VH1 and the CDR3 of VH3, and it was found that they had similar amino acid combinations. This is because the V-gene ends of VH1 and VH3 are commonly conserved as tyrosine-tyrosine-cysteine-alanine-arginine/lysine, and identical genes are applied to D and J genes during V-D-J joining.

According to the analysis result, the average of the combinations of Asian and Caucasian CDR amino acids was calculated and reflected in the primer codon design. In addition, as CDR3s of VH1 and VH3 are similar, primers constituting CDR3 were shared. In addition, there is a risk of reduction in antibody titer due to N-glycosylation, because the ratio of amino acids NXS/T of Kabat No. 52-52a-53 of CDR2 of VH1 and CDR2 of VH3 of Kabat No. 52a-53-54 is about 5%. For this reason, the possibility of N-glycosylation was eliminated by lowering the ratio of asparagine at 52 of VH1 and 52a of VH3 to 0%.

TABLE 45

| Name | Number of Sequence Analysis |
|---|---|
| VH1 Asian | 33,572 |
| VH3 Asian | 27,587 |
| Vk1 Asian | 44,113 |
| Vk3 Asian | 23,762 |
| Vλ1 Asian | 16,980 |
| VH1 Caucasian | 22,455 |
| VH3 Caucasian | 22,508 |
| Vk1 Caucasian | 28,467 |
| Vk3 Caucasian | 15,260 |
| Vλ1 Caucasian | 19,381 |

TABLE 46

| | 1 | 2 | 3 |
|---|---|---|---|
| VH1 Asian | SC-WV | EW-RXT | YYC-GTL |
| VH3 Asian | SC-WV | EW-KGR | YYC-GTL |
| Vk1 Asian | IXC-WY | IY-GV | YYC-GTK |
| Vk3 Asian | SC-WY | LI-IP | YYC-GTK |
| Vλ1 Asian | SC-WY | LI-SG | YYC-GTK |
| VH1 Caucasian | SC-WV | EW-RXT | YYC-GTL |
| VH3 Caucasian | SC-WV | EW-KGR | YYC-GTL |
| Vk1 Caucasian | IXC-WY | IY-GV | YYC-GTK |
| Vk3 Caucasian | SC-WY | LI-IP | YYC-GTK |
| Vλ1 Caucasian | SC-WY | LI-SG | YYC-GTK |

Example 4) Construction of Fab Library 4-1) Construction of Light-Chain Variable-Region Library 1) VL Frame sequence synthesis: sequences of frames 1 to 3 of human VLκ1-39, VLκ3-20, and VLλ1-51 (Table 47) were synthesized by Bioneer (http://www.bioneer.com.kr) upon request, and thus acquired.

TABLE 47

|  | Fragment 1 | Fragment 2 | Fragment 3 |
|---|---|---|---|
| VLκ 1-39 | DIQMTQSPSSLSASVGD RVTITCRASQ (SEQ ID NO: 17) | WYQQKPGKAPK LLIY (SEQ ID NO: 18) | GVPSRFSGSGSGTDFTLTISSLQP EDFATYYCQQ (SEQ ID NO: 19) |
| VLκ 3-20 | EIVLTQSPGTLSLSPGE RATLSCRASQ (SEQ ID NO: 22) | WYQQKPGQAPR LLI (SEQ ID NO: 23) | IPDRFSGSGSGTDFTLTISRLEPE DFAVYYCQQ (SEQ ID NO: 24) |
| VLλ 1-51 | QSVLTQPPSVSAAPGQK VTISCSG (SEQ ID NO: 32) | WYQQLPGTAPK LLI (SEQ ID NO: 33) | RPSGIPDRFSGSKSGTSATLGITG LQTGDEADYYC (SEQ ID NO: 34) |
| CLκ | TVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC (SEQ ID NO: 133) | | |
| CLλ | QPKANPTVTLFPPSSEELQANKATLVCLISDFYPGAVTVAWKADGSPVKAGVETT KPSKQSNNKYAASSYLSLTPEQWKSHRSYSCQVTHEGSTVEKTVAPTEC (SEQ ID NO: 134) | | |

2) Primary PCR amplification (Fragment PCR): VL CDR1 to CDR3 fragments (Fragments 1 to 3) were amplified by PCR using each frame sequence as a template (5 ng/reaction). The primer sequences used in PCR are shown in Table 48. In the above sequence, the number X means 3 bases, and in the sequence listing file, this is indicated as "NNN". The reaction was conducted using an AccuPower Pfu PCR PreMix (Bioneer, K-2025) for 30 cycles (at 95° C. for 30 seconds, at 50 to 58° C. for 30 seconds, at 72° C. for 1 minute). Each PCR product was subjected to electrophoresis and then purified using a QIAquick Gel Extraction Kit (QIAGEN, CAT. NO. 28706).

TABLE 48

| Name | Direction | Sequence | SEQ ID NO |
|---|---|---|---|
| VLκ1-39_F1 | Forward | GAATTCAGGAGGAATTTAAAATGAAAAAGACAGCTATCG | 92 |
|  | Reverse | GGCMCCCTGGTTTCTGCTGATACCAX5TAN5X4X3X2TAN4X1N3N2GACTCGCACN1GCAGGTGATTGTAACGCGATCTCCTAC | 93 |
| VLκ1-39_F2 | Forward | TGGTATCAGCAGAAACCAGGGAAAGCC | 94 |
|  | Reverse | GCCACTAAAACGGCTCGGAACGCCX21X20AN10GX19AN9TX18X17ATAAATCAGGAGCTTCGGTGCTTTCCC | 95 |
| VLK1-39_F3 | Forward | GGCGTTCCGAGCCGTTTTAGTGGC | 96 |
|  | Reverse | TTTAATTTCCACTTTGGTACCCTGCCCGAATGTX31CGGX30X29X28X27N14TN15N14N13GACAGTAATAGGTAGCAAAATCCTCAGGCTGCAG | 97 |
| VLκ3-20_F1 | Forward | GAATTCAGGAGGAATTTAAAATGAAAAAGACAGCTATCG | 92 |
|  | Reverse | TGCCTGACCAGGCTTTTGTTGGTACCATGCAN8CX11X10X9X8X7X6N7TN6ACTCGCACN1GCAGCTAAGGGTAGCACGTTCACCTGG | 98 |
| VLκ3-20_F2 | Forward | GCATGGTACCAACAAAAGCCTGGTCAGGCA | 99 |
|  | Reverse | GGAGCCAGAGAAACGGTCCGGAATAN1CAGN12AN11CACGX26X25X24X23X22GATCAGCAGACGTGGTGCCTGACC | 100 |
| VLκ3-20_F3 | Forward | ATTCCGGACCGTTTCTCTGGCTCC | 101 |
|  | Reverse | TTTAATTTCCACTTTGGTACCCTGCCCGAATGTX31CGGX35X34X33X32N16TGN7N16GACAGTAATAAACAGCAAAATCCTCAGGTTCTAAACG | 102 |
| VLκ3-20-2_F1 | Forward | GAATTCAGGAGGAATTTAAAATGAAAAAGACAGCTATCG | 92 |
|  | Reverse | TGCCTGACCAGGCTTTTGTTGGTACCATGCAN8CX16X15X14X13X12N3N2GACTCGCACN1GCAGCTAAGGGTAGCACGTTCACCTGG | 103 |
| VLλ1-51_F1 | Forward | GAATTCAGGAGGAATTTAAAATGAAAAAGACAGCTATCG | 92 |
|  | Reverse | TGCTGTACCTGGAAGCTGTTGATACCAX41CACX40X39X38TN18CAAN17ATTAGAX37X36GCCAGAGCACGAGATGGTCACCTTTTG | 104 |

TABLE 48-continued

| Name | Direction | Sequence | SEQ ID NO |
|---|---|---|---|
| VLλ1-51_F2 | Forward | TGGTATCAACAGCTTCCAGGTACAGCA | 105 |
| | Reverse | ACGATCCGGAATACCGGAAGGACGX46X45X44X43X42AATCAATAACTICGGTGCTGTACCTGG | 106 |
| VLλ1-51_F3 | Forward | CGTCCTTCCGGTATTCCGGATCGT | 107 |
| | Reverse | CGTAAGITTGGIGCCACCACCGAAX56X55X54X53X52X51X50ATCX49X48X47GCAGTAGTAATCGGCTTCGTCGCC | 108 |
| CLκ | Forward | GGGCAGGGTACCAAAGTGGAAATTAAACGCACGGTGGCTGCCCCTTCTGTGTTC | 109 |
| | Reverse | AATTATCTAGAACTAGCACTCACCCCTGTTGAA | 110 |
| CLλ | Forward | GGTGGTGGCACCAAACTTACGGTCCTAGGCCAGCCCAAGGCCAACCCCACTGTC | 111 |
| | Reverse | TTATCTAGAACTAACATTCTGTAGGGGCCACTGTCTTCTC | 112 |

N1 to N8 of SEQ ID NO: 93 (Vk1-39-F1), SEQ ID NO: (Vk3-20-F1) and SEQ ID NO: 103 (Vk3-20-2-F1) were designed to have the base ratio shown in Table 49 below, and PCR was performed.

TABLE 49

| | N1 | N2 | N3 | N4 | N5 | N6 | N7 | N8 |
|---|---|---|---|---|---|---|---|---|
| A | 0 | 1 | 5 | 0 | 0 | 0 | 5 | 6 |
| T | 10 | 95 | 0 | 85 | 0 | 0 | 95 | 88 |
| G | 0 | 0 | 0 | 3 | 92 | 95 | 0 | 0 |
| C | 90 | 4 | 95 | 12 | 8 | 5 | 0 | 6 |

X1 to X16 of SEQ ID NO: 93 (Vk1-39-F1), SEQ ID NO: 98 (Vk3-20-F1) and SEQ ID NO: 103 (Vk3-20-2-F1) were designed to have the codon ratio shown in Table 50 below, and PCR was performed.

TABLE 50

| | AA | X1 | X2 | X3 | X4 | X5 | X6 | X7 | X8 | X9 | X10 | X11 | X12 | X13 | X14 | X15 | X16 |
|---|---|---|---|---|---|---|---|---|---|---|---|---|---|---|---|---|---|
| AAC (anti-Val) | V | 1.5 | 1 | 1 | 0 | 2.5 | 0 | 68 | 1 | 0.5 | 0.5 | 0 | 0 | 63 | 1 | 1 | 0 |
| ACC (anti-Gly) | G | 20 | 12 | 4 | 1 | 5 | 3 | 0 | 7 | 9 | 4.5 | 0 | 5 | 0 | 16.5 | 5 | 1 |
| AGA (anti-Ser) | S | 32 | 37.5 | 20.5 | 8.5 | 4 | 64.5 | 0 | 43 | 54.5 | 26 | 8 | 70.5 | 0 | 39 | 34 | 8 |
| ATC (anti-Asp) | D | 22.5 | 5.5 | 5.5 | 5 | 1 | 1 | 0 | 5.5 | 2.5 | 5.5 | 2 | 2.5 | 0 | 5.5 | 3 | 4.5 |
| ATG (anti-His) | H | 1 | 1 | 2 | 4.5 | 2.5 | 0.5 | 0 | 1 | 0.5 | 0.5 | 5 | 0 | 0 | 1 | 1 | 4.5 |
| CAG (anti-Leu) | L | 0 | 1 | 0.5 | 2 | 0 | 0 | 9 | 0.5 | 0.5 | 0.5 | 1 | 0 | 6 | 1 | 0 | 1.5 |
| CAT (anti-Met) | M | 0 | 0 | 0.5 | 0 | 0 | 0 | 0.5 | 0 | 0 | 0 | 0 | 0 | 0 | 0 | 0 | 0 |
| CCA (anti-Trp) | W | 0 | 0 | 0 | 22.5 | 0 | 0 | 0 | 0 | 0 | 0 | 1 | 0 | 0 | 0 | 0 | 1 |
| CGG (anti-Pro) | P | 1 | 0 | 1 | 0 | 0 | 1 | 0 | 2.5 | 0 | 1 | 0 | 0.5 | 0 | 0 | 0.5 | 0 |
| CTG (anti-Gln) | Q | 0 | 0 | 0 | 0.5 | 0 | 0 | 0 | 0 | 0 | 0 | 1.5 | 0 | 0 | 0 | 0 | 1.5 |
| GAA (anti-Phe) | F | 1 | 1 | 1 | 8.5 | 0 | 1 | 2.5 | 1 | 0 | 1 | 13.5 | 0 | 1 | 0.5 | 1 | 7 |
| GAT (anti-Ile) | I | 1 | 2 | 4 | 0 | 1 | 3 | 19.5 | 3 | 2 | 2 | 0 | 1 | 29 | 1.5 | 4.5 | 0 |
| GCA (anti-Cys) | C | 0 | 0 | 0 | 0 | 0 | 0 | 0 | 0 | 0 | 0 | 0 | 0 | 0 | 0 | 0 | 0 |
| GCG (anti-Arg) | R | 3 | 10.5 | 7.5 | 2.5 | 0 | 5 | 0 | 8.5 | 5.5 | 7.5 | 1 | 2.5 | 0 | 8.5 | 8.5 | 1 |
| GGT (anti-Thr) | T | 11 | 7 | 16.5 | 0 | 1.5 | 14.5 | 0 | 11.5 | 6.5 | 12 | 0 | 7.5 | 0 | 6 | 18 | 1 |
| GTA (anti-Tyr) | Y | 1.5 | 2 | 2 | 39 | 0 | 1 | 0 | 2 | 1.5 | 1 | 62 | 1 | 0 | 2 | 2.5 | 33.5 |
| GTT (anti-Asn) | N | 0 | 13 | 26.5 | 3 | 38 | 4.5 | 0 | 8.5 | 14.5 | 33 | 4 | 9 | 0 | 12 | 16.5 | 31 |
| TGC (anti-Ala) | A | 4 | 3.5 | 1 | 2 | 44.5 | 1 | 0.5 | 4 | 2 | 2.5 | 0 | 0.5 | 1 | 3.5 | 2 | 0.5 |
| TTC (anti-Glu) | E | 0 | 1 | 1 | 1 | 0 | 0 | 0 | 0 | 0 | 0 | 0 | 0 | 0 | 0.5 | 0 | 0.5 |
| TTT (anti-Lys) | K | 0.5 | 2 | 5.5 | 0 | 0 | 0 | 0 | 1 | 0.5 | 2.5 | 1 | 0 | 0 | 1.5 | 2.5 | 3.5 |
| total | | 100 | 100 | 100 | 100 | 100 | 100 | 100 | 100 | 100 | 100 | 100 | 100 | 100 | 100 | 100 | 100 |

N of SEQ ID NO: 95 (Vk1-39-F2) was designed to have the base ratio shown in Table 51 below, and PCR was performed.

TABLE 51

|   | N9 | N10 |
|---|----|-----|
| A | 0  | 91  |
| T | 0  | 0   |
| G | 6  | 0   |
| C | 94 | 9   |

X of SEQ ID NO: 95 (Vk1-39-F2) was designed to have the codon ratio shown in Table 52 below, and PCR was performed.

TABLE 52

|  | AA | X17 | X18 | X19 | X20 | X21 |
|---|---|-----|-----|-----|-----|-----|
| AAC (anti-Val) | V | 2 | 7 | 2 | 1 | 1 |
| ACC (anti-Gly) | G | 12.5 | 2.5 | 2 | 2.5 | 7 |
| AGA (anti-Ser) | S | 6.5 | 4.5 | 23.5 | 0 | 50.5 |
| ATC (anti-Asp) | D | 14.5 | 0 | 2 | 3.5 | 3 |
| ATG (anti-His) | H | 1 | 0 | 1.5 | 6.5 | 0 |
| CAG (anti-Leu) | L | 2 | 0 | 0.5 | 1.5 | 0.5 |
| CAT (anti-Met) | M | 1 | 0 | 0 | 0 | 0 |
| CCA (anti-Trp) | W | 6 | 0 | 0 | 0 | 0 |
| CGG (anti-Pro) | P | 0.5 | 0.5 | 0 | 1.5 | 3.5 |
| CTG (anti-Gln) | Q | 2.5 | 0 | 0 | 38.5 | 0 |
| GAA (anti-Phe) | F | 0.5 | 0 | 1.5 | 0.5 | 1 |
| GAT (anti-Ile) | I | 0.5 | 1.5 | 6.5 | 0 | 2.5 |
| GCA (anti-Cys) | C | 0 | 0 | 0 | 0 | 0 |
| GCG (anti-Arg) | R | 5 | 0 | 5 | 3 | 5.5 |
| GGT (anti-Thr) | T | 5 | 12.5 | 28.5 | 0 | 15.5 |
| GTA (anti-Tyr) | V | 0.5 | 0 | 2 | 1 | 0.5 |
| GTT (anti-Asn) | N | 0 | 0 | 19 | 1 | 6 |
| TGC (anti-Ala) | A | 20 | 70 | 3 | 3 | 3 |
| TTC (anti-Glu) | E | 5.5 | 1.5 | 0 | 33.5 | 0 |
| TTT (anti-Lys) | K | 14.5 | 0 | 3 | 3 | 0.5 |
| total |  | 100 | 100 | 100 | 100 | 100 |

N of SEQ ID NO: 100 (Vk3-20-F2) was designed to have the base ratio shown in Table 53 below, and PCR was performed.

TABLE 53

|   | N11 | N12 | N1 |
|---|-----|-----|----|
| A | 5   | 8   | 0  |
| T | 0   | 72  | 10 |
| G | 95  | 8   | 0  |
| C | 0   | 12  | 90 |

X of SEQ ID NO: 100 (Vk3-20-F2) was designed to have the codon ratio shown in Table 54 below, and PCR was performed.

TABLE 54

|  | AA | X22 | X23 | X24 | X25 | X26 |
|---|---|-----|-----|-----|-----|-----|
| AAC (anti-Val) | V | 0 | 1 | 7 | 1 | 0.5 |
| ACC (anti-Gly) | G | 0 | 45 | 3.5 | 0 | 1.5 |
| AGA (anti-Ser) | S | 6.5 | 4.5 | 5 | 80 | 24.5 |
| ATC (anti-Asp) | D | 1 | 29.5 | 0 | 0 | 2 |
| ATG (anti-His) | H | 8 | 1.5 | 0 | 0 | 1.5 |
| CAG (anti-Leu) | L | 1 | 0.5 | 0.5 | 1 | 0.5 |
| CAT (anti-Met) | M | 0 | 0 | 0 | 0 | 0.5 |
| CCA (anti-Trp) | W | 0.5 | 0 | 0 | 0 | 0 |
| CGG (anti-Pro) | P | 0 | 0 | 1.5 | 1 | 0 |
| CTG (anti-Gln) | Q | 1 | 0 | 0 | 0 | 0 |
| GAA (anti-Phe) | F | 11 | 0 | 0 | 7 | 1 |
| GAT (anti-Ile) | I | 0.5 | 0 | 2.5 | 1 | 5.5 |
| GCA (anti-Cys) | C | 0 | 0 | 0 | 0 | 0 |
| GCG (anti-Arg) | R | 0 | 2.5 | 0 | 0 | 7.5 |
| GGT (anti-Thr) | T | 0 | 1.5 | 15 | 4 | 23.5 |
| GTA (anti-Tyr) | V | 69.5 | 0.5 | 0 | 2.5 | 2 |
| GTT (anti-Asn) | N | 1 | 1.5 | 0 | 0 | 21.5 |
| TGC (anti-Ala) | A | 0 | 9.5 | 64.5 | 2.5 | 2.5 |
| TTC (anti-Glu) | E | 0 | 2.5 | 0.5 | 0 | 0 |
| TTT (anti-Lys) | K | 0 | 0 | 0 | 0 | 5.5 |
| total |  | 100 | 100 | 100 | 100 | 100 |

N of SEQ ID NO: 97 (VLκ1-39_F3) and SEQ ID NO: 102 (VLκ3-20_F3) was designed to have the base ratio shown in Table 55 below, and PCR was performed.

TABLE 55

|   | N13 | N14 | N15 | N7 | N16 |
|---|-----|-----|-----|----|-----|
| A | 10  | 0   | 0   | 5  | 0   |
| T | 90  | 95  | 5   | 95 | 90  |
| G | 0   | 5   | 95  | 0  | 10  |
| C | 0   | 0   | 0   | 0  | 0   |

X of SEQ ID NO: 97 (VLκ1-39_F3) and SEQ ID NO: 102 (VLκ3-20_F3) was designed to have the codon ratio shown in Table 56 below, and PCR was performed.

TABLE 56

|  | AA | X27 | X28 | X29 | X30 | X31 | X32 | X23 | X34 | X35 |
|---|---|-----|-----|-----|-----|-----|-----|-----|-----|-----|
| AAC (anti-Val) | V | 1 | 0.5 | 1 | 4 | 3 | 0.5 | 2.5 | 1 | 1 |
| ACC (anti-Gly) | G | 2 | 1 | 6.5 | 1 | 2 | 4 | 25.5 | 5.5 | 1 |
| AGA (anti-Ser) | S | 17 | 6 | 45 | 7 | 1 | 5.5 | 12 | 31.5 | 34 |
| ATC (anti-Asp) | D | 2.5 | 10.5 | 5 | 1 | 0.5 | 0.5 | 6.5 | 6.5 | 0 |
| ATG (anti-His) | H | 6 | 5.5 | 1 | 1.5 | 2.5 | 3 | 2.5 | 4 | 0 |
| CAG (anti-Leu) | L | 3.5 | 1 | 1 | 7 | 23 | 1 | 6.5 | 1 | 5 |
| CAT (anti-Met) | M | 0 | 0 | 0 | 1 | 0 | 0 | 0 | 0 | 0 |
| CCA (anti-Trp) | W | 0 | 0 | 0 | 0 | 17 | 0 | 0 | 0 | 28 |
| CGG (anti-Pro) | P | 0 | 0 | 0 | 3.5 | 7.5 | 0 | 0 | 0 | 3.5 |
| CTG (anti-Gln) | Q | 0 | 0.5 | 0 | 0 | 3 | 0 | 0 | 6.5 | 0 |
| GAA (anti-Phe) | F | 4.5 | 5 | 1 | 11.5 | 8 | 3.5 | 2 | 1 | 2.5 |
| GAT (anti-Ile) | I | 0 | 1 | 3 | 4 | 2 | 0 | 2 | 2 | 2 |
| GCA (anti-Cys) | C | 0 | 0 | 0 | 0 | 0 | 0 | 0 | 0 | 0 |
| GCG (anti-Arg) | R | 0 | 1 | 4.5 | 0.5 | 13.5 | 14 | 1.5 | 4 | 1 |
| GGT (anti-Thr) | T | 5 | 1.5 | 14.5 | 19 | 0 | 1 | 5 | 11 | 12.5 |
| GTA (anti-Tyr) | V | 54 | 39 | 1 | 28.5 | 14.5 | 62 | 15 | 2 | 4 |
| GTT (anti-Asn) | N | 1 | 21.5 | 12 | 2.5 | 0.5 | 0.5 | 11.5 | 19 | 1 |

TABLE 56-continued

|  | AA | X27 | X28 | X29 | X30 | X31 | X32 | X23 | X34 | X35 |
|---|---|---|---|---|---|---|---|---|---|---|
| TGC (anti-Ala) | A | 3.5 | 1 | 2.5 | 8 | 0.5 | 4.5 | 4 | 2 | 4.5 |
| TTC (anti-Glu) | E | 0 | 1.5 | 1 | 0 | 0.5 | 0 | 2 | 1 | 0 |
| TTT (anti-Lys) | K | 0 | 3.5 | 1 | 0 | 1 | 0 | 1.5 | 2 | 0 |
| total |  | 100 | 100 | 100 | 100 | 100 | 100 | 100 | 100 | 100 |

N of SEQ ID NO: 104 (VLλ1-51_F1) was designed to have the base ratio shown in Table 57 below, and PCR was performed.

TABLE 57

|  | N17 | N18 |
|---|---|---|
| A | 0 | 0 |
| T | 90 | 5 |
| G | 0 | 5 |
| C | 10 | 90 |

X of SEQ ID NO: 104 (VLλ1-51_F1) was designed to have the codon ratio shown in Table 58 below, and PCR was performed.

TABLE 58

|  | AA | X36 | X37 | X38 | X39 | X40 | X41 |
|---|---|---|---|---|---|---|---|
| AAC (anti-Val) | V | 0 | 0 | 1.5 | 0 | 1.5 | 0 |
| ACC (anti-Gly) | G | 10.5 | 5 | 4.5 | 1 | 1 | 0 |
| AGA (anti-Ser) | S | 74 | 54 | 33 | 4.5 | 10 | 39.5 |
| ATC (anti-Asp) | D | 2 | 2.5 | 5 | 2.5 | 3.5 | 1 |
| ATG (anti-His) | H | 0 | 1 | 1 | 6.5 | 3.5 | 4.5 |
| CAG (anti-Leu) | L | 0 | 0 | 1 | 0 | 1 | 0.5 |
| CAT (anti-Met) | M | 0 | 0 | 0 | 0 | 0 | 0 |
| CCA (anti-Trp) | W | 0 | 0 | 0 | 0 | 0 | 0 |
| CGG (anti-Pro) | P | 0 | 0 | 0.5 | 0 | 5 | 0 |
| CTG (anti-Gln) | Q | 0 | 0 | 0 | 0.5 | 0 | 1 |
| GAA (anti-Phe) | F | 0 | 1 | 0 | 0.5 | 11 | 2.5 |
| GAT (anti-Ile) | I | 1 | 1.5 | 4 | 1 | 2 | 0 |
| GCA (anti-Cys) | C | 0 | 0 | 0 | 0 | 0 | 0 |
| GCG (anti-Arg) | R | 3 | 7.5 | 10 | 1 | 0.5 | 0 |
| GGT (anti-Thr) | T | 6.5 | 13 | 8.5 | 1.5 | 16 | 2 |
| GTA (anti-Tyr) | V | 0 | 1 | 2 | 6 | 36.5 | 16.5 |
| GTT (anti-Asn) | N | 2 | 11 | 22.5 | 71 | 2.5 | 29.5 |
| TGC (anti-Ala) | A | 1 | 2 | 1 | 0 | 6 | 2.5 |
| TTC (anti-Glu) | E | 0 | 0 | 0.5 | 1 | 0 | 0 |
| TTT (anti-Lys) | K | 0 | 0.5 | 5 | 3 | 0 | 0.5 |
| total |  | 100 | 100 | 100 | 100 | 100 | 100 |

X of SEQ ID NO: 106 (VLλ1-51_F2) was designed to have the codon ratio shown in Table 59 below, and PCR was performed.

TABLE 59

|  | AA | X42 | X43 | X44 | X45 | X46 |
|---|---|---|---|---|---|---|
| AAC (anti-Val) | V | 0 | 1.5 | 5.5 | 1 | 1 |
| ACC (anti-Gly) | G | 0 | 16.5 | 1 | 2 | 0 |
| AGA (anti-Ser) | S | 6.5 | 14 | 8 | 13 | 2 |
| ATC (anti-Asp) | D | 0.5 | 22 | 18 | 18.5 | 2.5 |
| ATG (anti-His) | H | 6 | 1 | 2 | 3.5 | 4 |
| CAG (anti-Leu) | L | 0.5 | 1 | 0 | 0 | 4.5 |
| CAT (anti-Met) | M | 0 | 0.5 | 0 | 0 | 1 |
| CCA (anti-Trp) | W | 0 | 0.5 | 0 | 0 | 0 |
| CGG (anti-Pro) | P | 0 | 0 | 0 | 0 | 0 |
| CTG (anti-Gln) | Q | 1 | 1 | 0 | 0 | 29.5 |
| GAA (anti-Phe) | F | 13.5 | 1 | 0.5 | 1 | 0 |
| GAT (anti-Ile) | I | 0 | 1 | 1.5 | 4 | 2 |
| GCA (anti-Cys) | C | 0 | 0 | 0 | 0 | 0 |
| GCG (anti-Arg) | R | 0.5 | 9 | 1 | 2.5 | 7 |
| GGT (anti-Thr) | T | 0 | 4 | 8.5 | 11.5 | 0 |
| GTA (anti-Tyr) | V | 71 | 3 | 2 | 4.5 | 2 |
| GTT (anti-Asn) | N | 0.5 | 8 | 51 | 34.5 | 21 |
| TGC (anti-Ala) | A | 0 | 6.5 | 0 | 0.5 | 0 |
| TTC (anti-Glu) | E | 0 | 7 | 0 | 1 | 7.5 |
| TTT (anti-Lys) | K | 0 | 2.5 | 1 | 2.5 | 16 |
| total |  | 100 | 100 | 100 | 100 | 100 |

X of SEQ ID NO: 108 (VLλ1-51_F3) was designed to have the codon ratio shown in Table 60 below, and PCR was performed.

TABLE 60

|  | AA | X47 | X48 | X49 | X50 | X51 | X52 | X53 | X54 | X55 | X56 |
|---|---|---|---|---|---|---|---|---|---|---|---|
| AAC (anti-Val) | V | 2 | 18 | 0 | 1.5 | 1 | 2.5 | 0.5 | 7.5 | 27 | 79.5 |
| ACC (anti-Gly) | G | 22 | 1 | 0 | 9.5 | 7 | 2 | 4 | 34.5 | 10 | 0 |
| AGA (anti-Ser) | S | 6 | 27 | 0 | 34 | 66 | 12 | 37 | 5 | 3.5 | 0 |
| ATC (anti-Asp) | D | 0 | 0 | 0 | 27 | 2 | 1 | 14 | 2.5 | 0 | 0 |
| ATG (anti-His) | H | 1 | 0 | 1 | 1 | 0 | 0 | 2 | 10.5 | 1 | 0 |
| CAG (anti-Leu) | L | 1 | 1 | 0 | 0 | 0.5 | 73 | 0 | 3 | 4 | 10 |
| CAT (anti-Met) | M | 0 | 0 | 0 | 0 | 0 | 0 | 0 | 1 | 2 |  |
| CCA (anti-Trp) | W | 0 | 0 | 76 | 0 | 0 | 0 | 0 | 0 | 22.5 | 0 |
| CGG (anti-Pro) | P | 0 | 0 | 0 | 0 | 0.5 | 1 | 0 | 1 | 7 | 0 |
| CTG (anti-Gln) | Q | 32.5 | 0 | 0 | 0 | 0 | 0 | 0 | 2 | 1 | 0 |
| GAA (anti-Phe) | F | 0 | 0 | 2.5 | 0 | 0 | 0 | 0 | 1.5 | 1.5 | 0.5 |
| GAT (anti-Ile) | I | 0 | 0 | 1 | 0 | 2.5 | 2 | 1 | 1 | 2 | 0 | 6 |
| GCA (anti-Cys) | C | 0 | 0 | 0 | 0 | 0 | 0 | 0 | 0 | 0 | 0 |
| GCG (anti-Arg) | R | 0 | 0 | 1 | 3.5 | 6.5 | 1 | 6.5 | 1.5 | 4 | 0 |
| GGT (anti-Thr) | T | 1 | 29 | 0 | 8 | 6.5 | 3.5 | 8 | 3 | 0 | 0 |
| GTA (anti-Tyr) | V | 0 | 0 | 19 | 1 | 0.5 | 0 | 1.5 | 1 | 13.5 | 0 |
| GTT (anti-Asn) | N | 0 | 0 | 0 | 7.5 | 6 | 3 | 21 | 1 | 0 | 0 |
| TGC (anti-Ala) | A | 33 | 23 | 0.5 | 3 | 1 | 0 | 1 | 23 | 3 | 2 |

TABLE 60-continued

| | AA | X47 | X48 | X49 | X50 | X51 | X52 | X53 | X54 | X55 | X56 |
|---|---|---|---|---|---|---|---|---|---|---|---|
| TTC (anti-Glu) | E | 1.5 | 0 | 0 | 0.5 | 0 | 0 | 1 | 1 | 1 | 0 |
| TTT (anti-Lys) | K | 0 | 0 | D | 1 | 0.5 | 0 | 2.5 | 0 | 0 | 0 |
| | total | 100 | 100 | 100 | 100 | 100 | 100 | 100 | 100 | 100 | 100 |

3) Second PCR amplification (1$^{st}$ overlapping PCR): the primary PCR products (Fragments 1 to 3) were added as templates (20 ng for each fragment/reaction) and the reaction was conducted for 16 cycles (95° C. for 30 sec, 55° C. for 30 sec, at 72° C. for 1 min). The primer sequences used for PCR are shown in Table 61. Respective PCR products (variable light chains) were subjected to electrophoresis and then purified using a QIAquick Gel Extraction Kit (QIAGEN, CAT. NO. 28706).

TABLE 61

| Name | Direction | Sequence | SEQ ID NO |
|---|---|---|---|
| VLκ1-39 | Forward | GAATTCAGGAGGAATTTAAAATGAAAAAGACAGCTATCG | 92 |
| | Reverse | ACTAGTGCGTTTAATTTCCACTTTGGTACCCTGCCC | 113 |
| VLκ3-20 | Forward | GAATTCAGGAGGAATTTAAAATGAAAAAGACAGCTATCG | 92 |
| | Reverse | ACTAGTGCGTTTAATTTCCACTTTGGTACCCTGCCC | 113 |
| VLκ3-20-2 | Forward | GAATTCAGGAGGAATTTAAAATGAAAAAGACAGCTATCG | 92 |
| | Reverse | ACTAGTGCGTTTAATTTCCACTTTGGTACCCTGCCC | 113 |
| VLλ1-51 | Forward | GAATTCAGGAGGAATTTAAAATGAAAAAGACAGCTATCG | 92 |
| | Reverse | ACTAGTACCCAGGACCGTAAGTTTGGTGCC | 114 |

4) Third PCR amplification (2$^{nd}$ overlapping PCR): the purified 1$^{st}$ overlapping PCR products were weighed and used as templates (10 ng per each product/reaction) along with CLκ (fragment PCR product) for VLκ1-39, VLκ3-20 and VLκ3-20-2, and along with CLλ (fragment PCR product) for VLλ1-51, and the reaction was conducted for 15 cycles (at 95° C. for 1 min, at 55° C. for 1 min, at 72° C. for 1 min). The primer sequences used in PCR are shown in Table 62. The respective PCR products were subjected to electrophoresis and then purified using a QIAquick Gel Extraction Kit (QIAGEN, CAT. NO. 28706).

TABLE 62

| Name | Direction | Sequence | SEQ ID NO |
|---|---|---|---|
| VLκ1-39_CLκ | Forward | GAATTCAGGAGGAATTTAAAATGAAAAAGACAGCTATCG | 92 |
| | Reverse | AATTATCTAGAACTAGCACTCACCCCTGTTGAA | 109 |
| VLκ3-20_CLκ | Forward | GAATTCAGGAGGAATTTAAAATGAAAAAGACAGCTATCG | 92 |
| | Reverse | AATTATCTAGAACTAGCACTCACCCCTGTTGAA | 109 |
| VLκ3-20-2_CLκ | Forward | GAATTCAGGAGGAATTTAAAATGAAAAAGACAGCTATCG | 92 |
| | Reverse | AATTATCTAGAACTAGCACTCACCCCTGTTGAA | 109 |
| VLλ1-51_CLλ | Forward | GAATTCAGGAGGAATTTAAAATGAAAAAGACAGCTATCG | 92 |
| | Reverse | TTATCTAGAACTAACATTCTGTAGGGGCCACTGTCTTCTC | 111 |

5) VL Library Transformation 5-a) Ligation: EcoRI (NEB, CAT. NO. R0101L) was added to the overlapping PCR products of the variable light-chain (VL) and constant light-chain (CL) regions, reaction was conducted at 37° C. overnight (O/N), and then the result was purified using a QIAquick PCR Purification Kit (QIAGEN, CAT. NO. 28106). XbaI (NEB. CAT. NO. R0145L) was added thereto, followed by reaction at 37° C. overnight (O/N) and purification using a QIAquick PCR Purification Kit (QIAGEN, CAT. NO. 28106). T4 DNA Ligase (NEB, CAT. NO. M0203S) was added to 20 μg of insert DNA fragments cut with EcoRI and XbaI and 40 μg of linearized pComb3XTT vector (EcoRI, XbaI cut), followed by reacting at 25° C. overnight (O/N).

5-b) Transformation: the ligated reaction product was purified using a QIAquick PCR Purification Kit (QIAGEN, CAT. NO. 28106). For each light-chain subtype, 1 mL of MC1061F' (SS320) Competent Cells (Lucigen, CAT. NO. 60512-1) was divided into 10 cuvettes (100 μl/cuvette) and electroporated. SB liquid media was added to adjust the total volume to 500 mL, the result was incubated with shaking at 37° C. and 200 rpm for 1 hour, and 100 μL of culture sup. was spread on an LB agar lop plate+carbenicillin (NaraeBiotech, CAT. NO. LN004CA) through serial dilution, and then incubated at 37° C. overnight to determine the pComb3XTT-Synthetic VL library size. 500 μL of carbenicillin (100 mg/mL) was added to 500 mL of the culture, which was then incubated at 37° C. (200 rpm) overnight.

4-2) Construction of Heavy-Chain Variable-Region Library

1) VH Frame sequence synthesis: sequences (Table 63) of frames 1 to 3 of human VH1-69, VH3-15 and VH3-23 were synthesized by Bioneer (http://www.bioneer.co.kr) upon request, and thus acquired.

TABLE 63

| | Fragment 1 | Fragment 2 | Fragment 3 |
|---|---|---|---|
| VH1-69 | QVQLVQSGAEVKKPG SSVKVSCKAS (SEQ ID NO: 12) | WVRQAPGQGLEW M (SEQ ID NO: 13) | YAQKFQGRVTITA DESTSTAYMELSS LRSEDTAVYYCAR (SEQ ID NO: 14) |
| VH3-15 | EVQLVESGGGLVKPG GSLRLSCAASG (SEQ ID NO: 2) | WVRQAPGKGLEW V (SEQ ID NO: 3) | YAAPVKGRFTISR DDSKNTLYLQMNS LKTEDTAVYYCAR (SEQ ID NO: 4) |
| VH3-23 | EVQLVESGGGLVQPG GSLRLSCAASG (SEQ ID NO: 7) | WVRQAPGKGLEW V (SEQ ID NO: 8) | YADSVKGRFTISR DNSKNTLYLQMNS LRAEDTAVYYCAR (SEQ ID NO: 9) |

2) Primary PCR amplification (Fragment PCR): VL CDR1 to CDR3 fragments (Fragments 1 to 3) were amplified by PCR using each frame sequence as a template (5 ng/reaction). The primer sequences used for PCR are shown in Table 64. The reaction was conducted using an AccuPower Pfu PCR PreMix (Bioneer, K-2025) for 30 cycles (at 95° C. for 30 sec, at 50 to 55° C. for 30 sec, at 72° C. for 1 min). Each PCR product was subjected to electrophoresis and then purified using a QIAquick Gel Extraction Kit (QIAGEN, CAT. NO. 28706).

TABLE 64

| Name | Direction | Sequence | SEQ ID NO |
|---|---|---|---|
| VH1-69_F1 | Forward | TTCTAGATAATTAATTAGGAGGAATTTAAAATG AAATACCTATTGCCT | 115 |
| | Reverse | CTGTCCTGGTGCTTGACGAACCCAX62N22AN2 0X61X60X59X58GAAX57X63ACCAGACGCTT TACAACTGACTTTAACTGAACT | 116 |
| VH1-69_F2 | Forward | TGGGTTCGTCAAGCACCAGGACAG | 117 |
| | Reverse | CGTAACACGACCTTGGAATTTCTGTGCATAX73 X72X71X70X69X68X67X66GATX65X64CAT CCATTCTAAGCCTTGTCCAGG | 118 |
| VH1-69_F3_CDR9 | Forward | TATGCACAGAAATTCCAAGGTCGTGTTACGATT | 119 |
| | Reverse | CACCAGGGTCCCCTGGCCCCAX98X97X96X95 X94X93X92X91X90GCGGGCGCAGTAATACAC TGCGGTATCTTC | 120 |
| VH1-69_F3_CDR10 | Forward | TATGCACAGAAATTCCAAGGTCGTGTTACGATT | 119 |
| | Reverse | AACGGTAACCAGTGTACCTTGACCCCAX108X1 07X106X105X104X103X102X101X100X99 ACGTGCACAGTAATACACTGCGGTATCTTC | 121 |
| VH1-69_F3_CDR11 | Forward | TATGCACAGAAATTCCAAGGTCGTGTTACGATT | 119 |
| | Reverse | AACGGTAACCAGTGTACCTTGACCCCAX115X1 14X113X112X111X110X103X102X101X10 0X109ACGTGCACAGTAATACACTGCGGTATCT TC | 122 |
| VH1-69_F3_CDR12 | Forward | TATGCACAGAAATTCCAAGGTCGTGTTACGATT | 119 |
| | Reverse | AACGGTAACCAGTGTACCTTGACCCCAX120X1 19X118X116X112X111X110X103X102X10 1X100X116ACGTGCACAGTAATACACTGCGGT ATCTTC | 123 |
| VH1-69_F3_CDR13 | Forward | TATGCACAGAAATTCCAAGGTCGTGTTACGATT | 119 |
| | Reverse | AACGGTAACCAGTGTACCTTGACCCCAX126X1 25X124X123X122X112X111X110X103X10 2X101X100X121ACGTGCACAGTAATACACTG CGGTATCTTC | 124 |
| VH1-69_F3_CDR14 | Forward | TATGCACAGAAATTCCAAGGTCGTGTTACGATT | 119 |
| | Reverse | AACGGTAACCAGTGTACCTTGACCCCAX132X1 31X130X129X128X122X112X111X110X10 3X102X101X100X127ACGTGCACAGTAATAC ACTGCGGTATCTTC | 125 |
| VH3-15_F1 | Forward | TTCTAGATAATTAATTAGGAGGAATTTAAAATG AAATACCTATTGCCT | 115 |
| | Reverse | TTTACCTGGTGCCTGACGAACCCAX62N21AN2 0X61X60X59X58GAAX57AN19AACCAGATGC TGCACAGCTTAAACGAAG | 126 |

TABLE 64-continued

| Name | Direction | Sequence | SEQ ID NO |
|---|---|---|---|
| VH3-15F2 | Forward | TGGGTTCGTCAGGCACCAGGTAAA | 127 |
| | Reverse | ACGACCTTTGACCGGTGCTGCGTAX81AN28N17AGN27X80ACN26X79X78X77X76TN25TX75X75AN24N23CACCCATTCAAGACCTTTACCTGG | 128 |
| VH3-15_F3_CDR9 | Forward | TACGCAGCACCGGTCAAAGGTCGT | 129 |
| | Reverse | CACCAGGGTCCCCTGGCCCCAX98X97X96X95X94X93X92X91X90GCGGGCGCAGTAATACACTGCGGTATCTTC | 120 |
| VH3-15_F3_CDR10 | Forward | TACGCAGCACCGGTCAAAGGTCGT | 129 |
| | Reverse | AACGGTAACCAGTGTACCTTGACCCCAX108X107X106X105X104X103X102X101X100X99ACGTGCACAGTAATACACTGCGGTATCTTC | 121 |
| VH3-15_F3_CDR11 | Forward | TACGCAGCACCGGTCAAAGGTCGT | 129 |
| | Reverse | AACGGTAACCAGTGTACCTTGACCCCAX115X114X113X112X111X110X103X102X101X100X109ACGTGCACAGTAATACACTGCGGTATCTTC | 122 |
| VH3-15_F3_CDR12 | Forward | TACGCAGCACCGGTCAAAGGTCGT | 129 |
| | Reverse | AACGGTAACCAGTGTACCTTGACCCCAX120X119X118X116X112X111X110X103X102X101X100X116ACGTGCACAGTAATACACTGCGGTATCTTC | 123 |
| VH3-15_F3_CDR13 | Forward | TACGCAGCACCGGTCAAAGGTCGT | 129 |
| | Reverse | AACGGTAACCAGTGTACCTTGACCCCAX126X125X124X123X122X112X111X110X103X102X101X100X121ACGTGCACAGTAATACACTGCGGTATCTTC | 124 |
| VH3-15_F3_CDR14 | Forward | TACGCAGCACCGGTCAAAGGTCGT | 129 |
| | Reverse | AACGGTAACCAGTGTACCTTGACCCCAX132X131X130X129X128X122X112X111X110X103X102X101X100X127ACGTGCACAGTAATACACTGCGGTATCTTC | 125 |
| VH3-23_F1 | Forward | TTCTAGATAATTAATTAGGAGGAATTTAAAATGAAATACCTATTGCCT | 115 |
| | Reverse | TTTACCTGGTGCCTGACGAACCCAX62N21AN20X61X60X59X58GAAX57AN19AACCAGATGCTGCACAGCTTAAACGAAG | 126 |
| VH3-23_F2 | Forward | TGGGTTCGTCAGGCACCAGGTAAA | 127 |
| | Reverse | GGTAAAACGACCCTTAACGCTATCCGCATAX89X88X87X86ACN30X85X84X83GATX82TCN29CACCCATTCAAGACCTTTACCTGG | 130 |
| VH3-23_F3_CDR9 | Forward | TATGCGGATAGCGTTAAGGGTCGTTTTACC | 129 |
| | Reverse | CACCAGGGTCCCCTGGCCCCAX98X97X96X95X94X93X92X91X90GCGGGCGCAGTAATACACTGCGGTATCTTC | 120 |
| VH3-23_F3_CDR10 | Forward | TATGCGGATAGCGTTAAGGGTCGTTTTACC | 129 |
| | Reverse | AACGGTAACCAGTGTACCTTGACCCCAX108X107X106X105X104X103X102X101X100X99ACGTGCACAGTAATACACTGCGGTATCTTC | 121 |
| VH3-23_F3_CDR11 | Forward | TATGCGGATAGCGTTAAGGGTCGTTTTACC | 129 |
| | Reverse | AACGGTAACCAGTGTACCTTGACCCCAX115X114X113X112X111X110X103X102X101X100X109ACGTGCACAGTAATACACTGCGGTATCTTC | 122 |
| VH3-23_F3_CDR12 | Forward | TATGCGGATAGCGTTAAGGGTCGTTTTACC | 129 |
| | Reverse | AACGGTAACCAGTGTACCTTGACCCCAX120X119X118X116X112X111X110X103X102X101X100X116ACGTGCACAGTAATACACTGCGGTATCTTC | 123 |

TABLE 64-continued

| Name | Direction | Sequence | SEQ ID NO |
|---|---|---|---|
| VH3-23_F3_CDR13 | Forward Reverse | TATGCGGATAGCGTTAAGGGTCGTTTTACC<br>AACGGTAACCAGTGTACCTTGACCCCAX126X125X124X123X122X112X111X110X103X102X101X100X121ACGTGCACAGTAATACACTGCGGTATCTTC | 129<br>124 |
| VH3-23_F3_CDR14 | Forward Reverse | TATGCGGATAGCGTTAAGGGTCGTTTTACC<br>AACGGTAACCAGTGTACCTTGACCCCAX132X131X130X129X128X122X112X111X110X103X102X101X100X127ACGTGCACAGTAATACACTGCGGTATCTTC | 129<br>125 |

N of SEQ ID NO: 116 (VH1-69_F1) and SEQ ID NO: 126 (VH3-15_F) was designed to have the base ratio shown in Table 65 below, and PCR was performed.

TABLE 65

|   | N19 | N20 | N21 | N22 |
|---|---|---|---|---|
| A | 70 | 0 | 30 | 40 |
| T | 30 | 90 | 0 | 0 |
| G | 0 | 5 | 0 | 0 |
| C | 0 | 5 | 70 | 60 |

X of SEQ ID NO: 116 (VH1-69_F1) and SEQ ID NO: 126 (VH3-15_F) was designed to have the codon ratio shown in Table 66 below, and PCR was performed.

TABLE 66

|   | AA | X57 | X58 | X59 | X60 | X61 | X62 | X63 |
|---|---|---|---|---|---|---|---|---|
| AAC (anti-Val) | V | 0 | 0.5 | 0.5 | 0.5 | 2 | 0.5 | 1 |
| ACC (anti-Gly) | G | 1 | 4.5 | 5.5 | 0 | 19.5 | 7.5 | 7.5 |
| AGA (anti-Ser) | S | 17 | 45.5 | 30.5 | 6 | 6 | 22 | 1 |
| ATC (anti-Asp) | D | 1 | 4 | 14 | 1 | 5 | 1.5 | 2 |
| ATG (anti-His) | H | 0 | 0 | 1 | 8 | 1 | 32.5 | 1 |
| CAG (anti-Leu) | L | 0 | 0 | 0 | 1 | 0 | 0 | 2 |
| CAT (anti-Met) | M | 1 | 0 | 0 | 0 | 0 | 0 | 0 |
| CCA (anti-Trp) | W | 0 | 0 | 0 | 0 | 20.5 | 0 | 0 |
| CGG (anti-Pro) | P | 2 | 1 | 0 | 0 | 1.5 | 0 | 0 |
| CTG (anti-Gln) | Q | 0 | 0 | 0 | 0 | 0 | 2 | 0 |
| GAA (anti-Phe) | F | 0 | 0 | 0 | 7.5 | 2 | 0 | 50.5 |
| GAT (anti-Ile) | I | 7 | 3 | 1.5 | 0 | 0.5 | 1 | 1 |
| GCA (anti-Cys) | C | 0 | 0 | 0 | 0 | 0 | 0 | 0 |
| GCG (anti-Arg) | R | 2 | 5 | 4.5 | 0.5 | 0.5 | 0.5 | 0 |
| GGT (anti-Thr) | T | 65 | 24.5 | 14 | 0.5 | 3.5 | 8 | 0 |
| GTA (anti-Tyr) | V | 0 | 0 | 1 | 66.5 | 12.5 | 2 | 33 |
| GTT (anti-Asn) | N | 0 | 8 | 21.5 | 5 | 1 | 18 | 1 |
| TGC (anti-Ala) | A | 3 | 2.5 | 2.5 | 3 | 22.5 | 4.5 | 0 |
| TTC (anti-Glu) | E | 0 | 0.5 | 1.5 | 0 | 2 | 0 | 0 |
| TTT (anti-Lys) | K | 1 | 1 | 2 | 0.5 | 0 | 0 | 0 |
| total |   | 100 | 100 | 100 | 100 | 100 | 100 | 100 |

X of SEQ ID NO: 118 (VH1-69_F2) was designed to have the codon ratio shown in Table 67 below, and PCR was performed.

TABLE 67

|   | AA | X64 | X65 | X66 | X67 | X68 | X69 | X70 | X71 | X72 | X73 |
|---|---|---|---|---|---|---|---|---|---|---|---|
| AAC (anti-Val) | V | 0 | 12 | 1.5 | 2 | 2 | 1.5 | 1.5 | 3 | 2.5 | 1 |
| ACC (anti-Gly) | G | 41.5 | 16 | 2 | 10.5 | 8.5 | 46.5 | 45.5 | 5.5 | 0 | 6 |
| AGA (anti-Ser) | S | 32 | 8 | 62.5 | 13.5 | 36 | 20 | 25 | 13 | 1.5 | 4.5 |
| ATC (anti-Asp) | D | 0 | 1 | 2.5 | 2 | 27 | 4 | 6.5 | 8.5 | 0 | 4.5 |
| ATG (anti-His) | H | 0 | 1 | 1 | 2 | 1.5 | 0 | 1 | 2 | 0 | 5 |
| CAG (anti-Leu) | L | 0 | 4 | 1 | 1 | 1.5 | 3.5 | 0 | 1 | 1 | 1 |
| CAT (anti-Met) | M | 0 | 1 | 0 | 0 | 1.5 | 0 | 0 | 0.5 | 1.5 | 0 |
| CCA (anti-Trp) | W | 0 | 20.5 | 4.5 | 6 | 0 | 0 | 0 | 0 | 0 | 0 |
| CGG (anti-Pro) | P | 0 | 0 | 0 | 28 | 0 | 0 | 0 | 0.5 | 2.5 | 0 |
| CTG (anti-Gln) | Q | 0 | 0 | 0.5 | 3.5 | 0 | 0 | 0 | 1 | 1.5 | 1 |
| GAA (anti-Phe) | F | 0 | 4.5 | 0.5 | 2.5 | 1 | 5 | 0 | 1 | 0 | 5 |
| GAT (anti-Ile) | I | 0 | 5.5 | 8.5 | 1 | 5 | 1 | 1 | 4.5 | 17 | 2 |
| GCA (anti-Cys) | C | 0 | 0 | 0 | 0 | 0 | 0 | 0 | 0 | 0 | 0 |
| GCG (anti-Arg) | R | 0 | 3.5 | 3.5 | 1.5 | 2 | 1 | 3 | 3.5 | 3 | 2.5 |
| GGT (anti-Thr) | T | 0 | 2.5 | 4.5 | 4 | 3.5 | 3.5 | 6 | 15 | 44 | 3.5 |
| GTA (anti-Tyr) | V | 0 | 10.5 | 1.5 | 11 | 6 | 0.5 | 1 | 6.5 | 0 | 36 |
| GTT (anti-Asn) | N | 0 | 5 | 0 | 2 | 0 | 10 | 4.5 | 19.5 | 0.5 | 17 |
| TGC (anti-Ala) | A | 26.5 | 4.5 | 0.5 | 7.5 | 1.5 | 2 | 3 | 4 | 6 | 1.5 |
| TTC (anti-Glu) | E | 0 | 0 | 0 | 1.5 | 1.5 | 1 | 1 | 6.5 | 2.5 | 1.5 |
| TTT (anti-Lys) | K | 0 | 0.5 | 5.5 | 0.5 | 1.5 | 0.5 | 1 | 4.5 | 16.5 | 8 |
| total |   | 100 | 100 | 100 | 100 | 100 | 100 | 100 | 100 | 100 | 100 |

N of SEQ ID NO: 128 (VH3-15_F2) was designed to have the base ratio shown in Table 68 below, and PCR was performed.

TABLE 68

|   | N23 | N24 | N25 | N26 | N27 | N17 | N28 |
|---|---|---|---|---|---|---|---|
| A | 0 | 0 | 0 | 0 | 0 | 0 | 10 |
| T | 5 | 0 | 44 | 20 | 82 | 90 | 0 |
| G | 0 | 10 | 0 | 0 | 0 | 0 | 90 |
| C | 95 | 90 | 56 | 80 | 18 | 10 | 0 |

X of SEQ ID NO: 128 (VH3-15_F2) was designed to have the codon ratio shown in Table 69 below, and PCR was performed.

TABLE 69

|  | AA | X74 | X75 | X76 | X77 | X78 | X79 | X80 | X81 |
|---|---|---|---|---|---|---|---|---|---|
| AAC (anti-Val) | V | 0.5 | 6.5 | 0 | 0.5 | 7.5 | 0 | 1 | 2 |
| ACC (anti-Gly) | G | 1.5 | 0 | 8.5 | 1 | 7.5 | 2.5 | 55 | 1 |
| AGA (anti-Ser) | S | 1 | 6 | 69.5 | 3.5 | 8 | 4.5 | 1 | 0.5 |
| ATC (anti-Asp) | D | 0 | 0 | 3.5 | 1.5 | 2 | 34 | 1.5 | 40 |
| ATG (anti-His) | H | 3.5 | 0 | 0.5 | 0 | 0 | 3.5 | 2 | 1.5 |
| CAG (anti-Leu) | L | 4.5 | 1 | 0 | 0 | 1 | 0 | 0 | 0 |
| CAT (anti-Met) | M | 0 | 2 | 0 | 0 | 0 | 0 | 0 | 0 |
| CCA (anti-Trp) | W | 0 | 0 | 0.5 | 0 | 0 | 0 | 0.5 | 0 |
| CGG (anti-Pro) | P | 0 | 0 | 0.5 | 0 | 5 | 0 | 0 | 0 |
| CTG (anti-Gln) | Q | 0.5 | 0 | 0 | 2 | 0 | 0.5 | 0 | 3 |
| GAA (anti-Phe) | F | 21 | 1.5 | 0 | 0 | 0.5 | 1.5 | 1 | 0 |
| GAT (anti-Ile) | I | 0 | 78.5 | 1 | 1 | 3 | 0 | 0 | 0.5 |
| GCA (anti-Cys) | C | 0 | 0 | 0 | 0 | 0 | 0 | 0 | 0 |
| GCG (anti-Arg) | R | 65 | 0 | 6 | 8 | 2 | 1 | 1.5 | 0 |
| GGT (anti-Thr) | T | 0.5 | 4 | 7.5 | 2 | 26.5 | 1.5 | 0.5 | 2 |
| GTA (anti-Tyr) | Y | 1 | 0 | 0 | 0 | 0 | 22 | 21.5 | 2.5 |
| GTT (anti-Asn) | N | 0 | 0 | 0 | 5 | 2 | 18 | 0 | 1.5 |
| TGC (anti-Ala) | A | 1 | 0.5 | 1 | 0 | 34 | 5 | 3.5 | 7 |
| TTC (anti-Glu) | E | 0 | 0 | 0 | 4 | 0.5 | 4.5 | 11 | 38 |
| TTT (anti-Lys) | K | 0 | 0 | 1.5 | 71.5 | 0.5 | 1.5 | 0 | 0.5 |

N of SEQ ID NO: 130 (VH3-23_F2) was designed to have the base ratio shown in Table 70 below, and PCR was performed.

TABLE 70

|   | N29 | N30 |
|---|---|---|
| A | 58 | 0 |
| T | 0 | 21 |
| G | 0 | 0 |
| C | 42 | 79 |

X of SEQ ID NO: 130 (VH3-23_F2) was designed to have the codon ratio shown in Table 71 below, and PCR was performed.

TABLE 71

|  | AA | X82 | X83 | X84 | X85 | X86 | X87 | X88 | X89 |
|---|---|---|---|---|---|---|---|---|---|
| AAC (anti-Val) | V | 18.5 | 0 | 1 | 0 | 2.5 | 2 | 2.5 | 1 |
| ACC (anti-Gly) | G | 16 | 3.5 | 19.5 | 9.5 | 22 | 4 | 0 | 5.5 |
| AGA (anti-Ser) | S | 15 | 63.5 | 19 | 39 | 36.5 | 16.5 | 1 | 0 |
| ATC (anti-Asp) | D | 0 | 0 | 0 | 41 | 8.5 | 6 | 0 | 4.5 |
| ATG (anti-His) | H | 2 | 0.5 | 3 | 1 | 1 | 2 | 0 | 5.5 |
| CAG (anti-Leu) | L | 5.5 | 1 | 1 | 0 | 1 | 1 | 1 | 1 |
| CAT (anti-Met) | M | 0 | 0 | 0 | 0 | 0 | 0 | 2 | 0 |
| CCA (anti-Trp) | W | 0 | 8 | 10.5 | 0 | 0 | 0 | 0 | 0.5 |
| CGG (anti-Pro) | P | 0 | 0.5 | 3 | 0 | 0 | 1 | 0.5 | 0 |
| CTG (anti-Gln) | Q | 0 | 0.5 | 6 | 0 | 0 | 1 | 2 | 1 |
| GAA (anti-Phe) | F | 6.5 | 0 | 3.5 | 0 | 0.5 | 1 | 0 | 8 |
| GAT (anti-Ile) | I | 2.5 | 0.5 | 1 | 0.5 | 1.5 | 3.5 | 27.5 | 0.5 |
| GCA (anti-Cys) | C | 0 | 0 | 0 | 0 | 0 | 0 | 0 | 0 |
| GCG (anti-Arg) | R | 1.5 | 5 | 2 | 2.5 | 4 | 4 | 3 | 1 |
| GGT (anti-Thr) | T | 5.5 | 5.5 | 3 | 4.5 | 9 | 16.5 | 30 | 0 |

TABLE 71-continued

| | AA | X82 | X83 | X84 | X85 | X86 | X87 | X88 | X89 |
|---|---|---|---|---|---|---|---|---|---|
| GTA (anti-Tyr) | V | 17.5 | 1.5 | 17 | 0 | 1 | 7 | 0 | 61.5 |
| GTT (anti-Asn) | N | 0 | 0 | 4 | 0 | 6.5 | 19.5 | 0 | 5.5 |
| TGC (anti-Ala) | A | 9 | 1 | 3.5 | 1 | 4 | 3 | 2 | 2 |
| TTC (anti-Glu) | E | 0 | 0 | 2 | 1 | 1 | 8 | 4.5 | 1 |
| TTT (anti-Lys) | K | 0.5 | 9 | 1 | 0 | 1 | 4 | 24 | 1.5 |
| | total | 100 | 100 | 100 | 100 | 100 | 100 | 100 | 100 |

X of SEQ ID NO: 120 (VH1-69_F3_CDR9, VH3-_F3_CDR9, VH3-23_F3_CDR9) was designed to have the codon ratio shown in Table 72 below, and PCR was performed.

TABLE 72

| | AA | X90 | X91 | X92 | X93 | X94 | X95 | X96 | X97 | X98 |
|---|---|---|---|---|---|---|---|---|---|---|
| AAC (anti-Val) | V | 5.0 | 6.0 | 10.5 | 3.0 | 2.0 | 3.5 | 5.0 | 4.0 | 7.5 |
| ACC (anti-Gly) | G | 16.0 | 14.0 | 15.0 | 16.0 | 21.0 | 15.5 | 10.5 | 4.5 | 1.0 |
| AGA (anti-Ser) | S | 5.0 | 10.0 | 13.0 | 17.0 | 19.0 | 14.0 | 8.5 | 2.0 | 6.0 |
| ATC (anti-Asp) | D | 26.0 | 5.0 | 5.0 | 4.5 | 5.0 | 6.5 | 1.0 | 69.5 | 3.5 |
| ATG (anti-His) | H | 2.0 | 1.0 | 2.0 | 3.0 | 1.5 | 2.5 | 1.0 | 0.5 | 4.5 |
| CAG (anti-Leu) | L | 4.5 | 9.5 | 4.0 | 3.0 | 2.5 | 4.0 | 13.0 | 1.0 | 3.5 |
| CAT (anti-Met) | M | 0.0 | 1.0 | 1.0 | 0.5 | 0.5 | 0.5 | 5.5 | 1.0 | 2.5 |
| CCA (anti-Trp) | W | 2.5 | 7.0 | 3.5 | 5.0 | 6.5 | 4.5 | 1.5 | 0.0 | 0.0 |
| CGG (anti-Pro) | P | 1.5 | 7.0 | 4.0 | 3.5 | 1.0 | 7.5 | 3.0 | 1.0 | 5.5 |
| CTG (anti-Gln) | Q | 7.0 | 2.5 | 1.0 | 1.5 | 1.5 | 1.0 | 0.5 | 1.0 | 1.0 |
| GAA (anti-Phe) | F | 0.5 | 2.0 | 1.0 | 2.0 | 1.0 | 3.0 | 33.5 | 0.0 | 3.5 |
| GAT (anti-Ile) | I | 1.5 | 3.0 | 1.5 | 1.5 | 1.5 | 2.5 | 4.5 | 3.0 | 3.0 |
| GCA (anti-Cys) | C | 0.0 | 0.0 | 0.0 | 0.0 | 0.0 | 0.0 | 0.0 | 0.0 | 0.0 |
| GCG (anti-Arg) | R | 4.0 | 8.5 | 13.5 | 4.5 | 3.5 | 2.5 | 0.5 | 0.5 | 0.5 |
| GGT (anti-Thr) | T | 8.5 | 5.0 | 6.0 | 5.0 | 8.0 | 3.5 | 3.0 | 2.0 | 2.0 |
| GTA (anti-Tyr) | V | 1.5 | 4.5 | 5.0 | 10.0 | 11.0 | 11.5 | 4.5 | 1.5 | 52.0 |
| GTT (anti-Asn) | N | 1.0 | 4.0 | 4.0 | 4.0 | 5.5 | 2.0 | 1.0 | 1.5 | 2.0 |
| TGC (anti-Ala) | A | 5.0 | 5.5 | 6.5 | 13.0 | 7.0 | 13.0 | 2.0 | 2.5 | 1.5 |
| TTC (anti-Glu) | E | 7.5 | 2.5 | 2.0 | 1.5 | 1.0 | 1.5 | 1.5 | 3.5 | 0.5 |
| TTT (anti-Lys) | K | 1.0 | 2.0 | 1.5 | 1.5 | 1.0 | 1.0 | 0.0 | 1.0 | 0.0 |

X of SEQ ID NO: 121 (VH1-69_F3_CDR10, VH3-15_F3_CDR10, VH3-23_F3_CDR10), SEQ ID NO: 122 (VH1-69_F3_CDR11, VH3-15_F3_CDR11, VH3-23_F3_CDR11), SEQ ID NO: 123 (VH1-69_F3_CDR12, VH3-15_F3_CDR12, VH3-23_F3_CDR12), SEQ ID NO: 124 (VH1-69_F3_CDR13, VH3-15_F3_CDR13, VH3-23_F3_CDR13) and SEQ ID NO: 125 (VH1-69_F3_CDR14, VH3-15_F3_CDR14, VH3-23_F3_CDR14) was designed to have the codon ratio shown in Table 73 below, and PCR was performed.

TABLE 73

| | AA | X99 | X100 | X101 | X102 | X103 | X104 | X105 | X106 | X107 | X108 | X109 | X110 | X111 | X112 | X113 | X114 | X115 |
|---|---|---|---|---|---|---|---|---|---|---|---|---|---|---|---|---|---|---|
| AAC (anti-Val) | V | 6.5 | 6 | 6.5 | 6.5 | 5.5 | 2 | 3.5 | 4 | 1 | 12.5 | 6.5 | 5 | 5 | 3 | 4 | 1.5 | 11.5 |
| ACC (anti-Gly) | G | 15.5 | 16 | 18.5 | 21.5 | 17.5 | 20 | 19.5 | 3.5 | 5 | 0 | 18 | 19 | 14 | 15 | 4 | 4.5 | 1 |
| AGA (anti-Ser) | S | 6 | 10.5 | 13.5 | 15.5 | 15 | 10 | 8 | 4 | 15 | 5 | 5 | 14 | 13 | 10 | 3.5 | 1 | 6.5 |
| ATC (anti-Asp) | D | 24 | 4 | 5.5 | 5.5 | 5.5 | 6.5 | 4 | 1.5 | 77 | 3 | 24.5 | 6 | 5 | 4 | 1 | 78 | 2 |
| ATG (anti-His) | H | 3.5 | 3.5 | 2 | 1 | 2 | 2 | 2.5 | 0 | 1 | 4.5 | 2.5 | 1 | 2 | 2 | 1 | 1.5 | 5.5 |
| CAG (anti-Leu) | L | 4.5 | 9 | 5.5 | 3.5 | 4.5 | 3 | 3.5 | 11 | 2 | 3.5 | 4 | 4 | 5 | 4 | 12.5 | 1 | 4 |
| CAT (anti-Met) | M | 0.5 | 1.5 | 1.5 | 1 | 0.5 | 1 | 0 | 11.5 | 0 | 0 | 1 | 0 | 0 | 1 | 9 | 0 | 0 |
| CCA (anti-Trp) | W | 1 | 2 | 2.5 | 3 | 5 | 7 | 6 | 1 | 0 | 0.5 | 1 | 5 | 6 | 5 | 1 | 0 | 0 |
| CGG (anti-Pro) | P | 2.5 | 6 | 4 | 3 | 2.5 | 2 | 5 | 3.5 | 1 | 7 | 2.5 | 4 | 3 | 5 | 3.5 | 1 | 5 |
| CTG (anti-Gln) | Q | 2 | 2.5 | 2 | 2 | 2 | 2 | 1.5 | 0 | 1.5 | 0 | 2.5 | 1 | 2 | 1 | 0.5 | 2 | 0.5 |
| GAA (anti-Phe) | F | 0.5 | 3 | 2 | 3.5 | 2.5 | 2.5 | 2.5 | 42 | 1 | 6 | 1 | 3 | 3 | 3 | 43 | 0 | 4 |
| GAT (anti-Ile) | I | 2 | 4 | 2.5 | 2 | 2.5 | 1 | 2 | 5 | 0.5 | 2.5 | 2 | 3 | 2 | 2 | 5.5 | 0 | 3 |
| GCA (anti-Cys) | C | 0 | 0 | 0 | 0 | 0 | 0 | 0 | 0 | 0 | 0 | 0 | 0 | 0 | 0 | 0 | 0 | 0 |
| GCG (anti-Arg) | R | 5.5 | 8.5 | 6 | 4.5 | 3.5 | 3.5 | 3.5 | 1.5 | 1 | 0 | 5 | 3 | 5 | 5 | 1 | 1 | 0 |
| GGT (anti-Thr) | T | 3 | 5.5 | 6.5 | 5.5 | 7.5 | 4 | 4 | 1.5 | 1 | 0 | 2.5 | 6 | 7 | 5 | 1.5 | 0.5 | 1 |
| GTA (anti-Tyr) | V | 3 | 5 | 9 | 9.5 | 11 | 19 | 20.5 | 5.5 | 1 | 52.5 | 2 | 12 | 15 | 22 | 4 | 1 | 53 |
| GTT (anti-Asn) | N | 1.5 | 2 | 2 | 3 | 3 | 5 | 2 | 1 | 1.5 | 2 | 1.5 | 3 | 4 | 4 | 1.5 | 2 | 2.5 |
| TGC (anti-Ala) | A | 8 | 6 | 6 | 6.5 | 7 | 6 | 8.5 | 2.5 | 1.5 | 1 | 7.5 | 8 | 6 | 6 | 2 | 1.5 | 0.5 |
| TTC (anti-Glu) | E | 9 | 2.5 | 3 | 2 | 2 | 2.5 | 2.5 | 1 | 2.5 | 0 | 10 | 2 | 2 | 2 | 1.5 | 3.5 | 0 |
| TTT (anti-Lys) | K | 1.5 | 2.5 | 1.5 | 1 | 1 | 1 | 1 | 0 | 0 | 0 | 1 | 1 | 1 | 1 | 0 | 0 | 0 |

TABLE 73-continued

| AA | | X116 | X117 | X118 | X119 | X120 | X121 | X122 | X123 | X124 | X125 | X126 | X127 | X128 | X129 | X130 | X131 | X132 |
|---|---|---|---|---|---|---|---|---|---|---|---|---|---|---|---|---|---|---|
| AAC (anti-Val) | V | 6 | 3 | 3 | 0.5 | 14.5 | 7 | 3 | 2 | 2.5 | 1 | 20 | 7 | 2.5 | 2.5 | 2 | 0.5 | 26 |
| ACC (anti-Gly) | G | 19.5 | 19 | 2.5 | 3.5 | 0 | 15.5 | 12 | 20.5 | 2.5 | 2.5 | 0 | 16 | 14 | 2.5 | 1.5 | 3 | 0 |
| AGA (anti-Ser) | S | 5 | 6 | 2.5 | 1.5 | 5 | 4.5 | 11 | 4.5 | 2 | 1 | 4.5 | 45 | 8.5 | 4 | 2 | 0.5 | 5.5 |
| ATC (anti-Asp) | D | 29.5 | 2.5 | 1 | 83 | 1 | 32 | 6 | 2.5 | 1 | 87 | 1 | 33.5 | 6.5 | 1.5 | 0.5 | 86 | 1 |
| ATG (anti-His) | H | 2.5 | 2.5 | 1 | 1 | 5 | 3.5 | 2 | 2.5 | 0.5 | 0.5 | 5 | 2.5 | 3 | 2.5 | 0.5 | 1.5 | 4.5 |
| CAG (anti-Leu) | L | 3 | 4 | 12 | 1 | 4.5 | 3.5 | 5 | 2.5 | 10 | 0.5 | 4 | 4 | 2 | 3.5 | 10 | 0.5 | 5 |
| CAT (anti-Met) | M | 0.5 | 0 | 12 | 0 | 0 | 0.5 | 0 | 0 | 15.5 | 0 | 0.5 | 0.5 | 0.5 | 0.5 | 22.5 | 0 | 0 |
| CCA (anti-Trp) | W | 1 | 6.5 | 1 | 0 | 0 | 1 | 4 | 8.5 | 0.5 | 0 | 0 | 0.5 | 5.5 | 8.5 | 0 | 0 | 0 |
| CGG (anti-Pro) | P | 2.5 | 6 | 2 | 0.5 | 7.5 | 2 | 3 | 7 | 2 | 0.5 | 9 | 3 | 2.5 | 6.5 | 2.5 | 0.5 | 9.5 |
| CTG (anti-Gln) | Q | 1.5 | 1 | 0 | 2 | 0 | 2 | 1 | 1 | 0 | 2 | 0 | 2 | 1 | 0.5 | 0 | 2 | 0 |
| GAA (anti-Phe) | F | 1 | 3 | 50 | 0 | 4 | 1 | 3 | 3 | 52.5 | 0.5 | 4 | 1 | 3 | 2.5 | 50 | 0.5 | 2 |
| GAT (anti-Ile) | I | 0.5 | 1 | 5 | 0 | 4.5 | 1 | 2 | 1 | 4 | 0 | 6 | 0.5 | 1.5 | 1 | 3.5 | 0 | 4.5 |
| GCA (anti-Cys) | C | 0 | 0 | 0 | 0 | 0 | 0 | 0 | 0 | 0 | 0 | 0 | 0 | 0 | 0 | 0 | 0 | 0 |
| GCG (anti-Arg) | R | 5 | 2 | 0.5 | 0.5 | 1 | 4 | 4 | 2 | 0 | 0.5 | 0 | 4.5 | 3.5 | 2 | 0 | 0.5 | 0 |
| GGT (anti-Thr) | T | 2 | 3.5 | 1 | 1 | 0.5 | 2.5 | 4 | 2.5 | 0.5 | 0 | 0 | 2 | 3 | 2 | 0.5 | 0.5 | 0.5 |
| GTA (anti-Tyr) | V | 2 | 26.5 | 3.5 | 1 | 50 | 2 | 27 | 28 | 3.5 | 0.5 | 44.5 | 1 | 30.5 | 25.5 | 2 | 0 | 39.5 |
| GTT (anti-Asn) | N | 1.5 | 2 | 1 | 1 | 2 | 1 | 5 | 2 | 1 | 0.5 | 1 | 1.5 | 7 | 2 | 0.5 | 1 | 1 |
| TGC (anti-Ala) | A | 7.5 | 8.5 | 1.5 | 1.5 | 0.5 | 7 | 4 | 9.5 | 1.5 | 1 | 0.5 | 7 | 2.5 | 9 | 1.5 | 1 | 1 |
| TTC (anti-Glu) | E | 8.5 | 2 | 0.5 | 2 | 0 | 9 | 3 | 1 | 0.5 | 2 | 0 | 8 | 2 | 1 | 0.5 | 2 | 0 |
| TTT (anti-Lys) | K | 1 | 1 | 0 | 0 | 0 | 1 | 1 | 0 | 0 | 0 | 0 | 1 | 1 | 0 | 0 | 0 | 0 |

3) Second PCR amplification (1st overlapping PCR): the primary PCR products (Fragments 1 to 3) were added as templates (40 ng for each fragment/reaction) and the reaction was conducted for 16 cycles (at 95° C. for 30 sec, to 55° C. for 30 sec, at 72° C. for 1 min). The primer sequences used in PCR are shown in Table 74. Respective PCR products (variable heavy chains) were subjected to electrophoresis and then purified using a QIAquick Gel Extraction Kit (QIAGEN, CAT. NO. 28706).

TABLE 74

| Name | Direction | Sequence | SEQ ID NO |
|---|---|---|---|
| VH1-69 | Forward | GCTCTAGATAATTAATTAGGAGGAAT TTAAAATGAAATACCTATTGCCT | 131 |
| | Reverse | GGGCCCTTGGTGGAGGCCGAGCTAAC GGTAACCAGTGTACCTTGACCCCA | 132 |
| VH3-15 | Forward | GCTCTAGATAATTAATTAGGAGGAAT TTAAAATGAAATACCTATTGCCT | 131 |
| | Reverse | GGGCCCTTGGTGGAGGCCGAGCTAAC GGTAACCAGTGTACCTTGACCCCA | 132 |
| VH3-23 | Forward | GCTCTAGATAATTAATTAGGAGGAAT TTAAAATGAAATACCTATTGCCT | 131 |
| | Reverse | GGGCCCTTGGTGGAGGCCGAGCTAAC GGTAACCAGTGTACCTTGACCCCA | 132 |

4) Fab library transformation 4-a) Ligation: XbaI (NEB. CAT. NO. R0145L) was added to PCR products of a variable heavy chain (VH), reaction was conducted at 37° C. for 6 hours, and then the result was purified using a QIAquick PCR Purification Kit (QIAGEN, CAT. NO. 28106). ApaI (NEB. CAT. NO. R0114L) added thereto, followed by reaction at 25° C. for 6 hours and purification using a QIAquick PCR Purification Kit (QIAGEN, CAT. NO. 28106). T4 DNA ligase (NEB, CAT. NO. M0203S) was added to 10 µg of insert DNA fragments cut with XbaI and apaI and 40 µg of linearized pComb3XTT vector (EcoRI, XbaI cut) and reaction was conducted at 25° C. overnight (O/N). At this time, as a proportion of the length of CDR3 with respect to the total amount of DNA, the percentage of CDR3_9AA (amino acid) lengths was adjusted to 12%, the percentage of CDR3_10AA lengths was adjusted to 14%, the percentage of CDR3_11AA lengths was adjusted to 17%, the percentage of CDR3_12AA lengths was adjusted to 22%, the percentage of CDR3_13AA lengths was adjusted to 19%, and the percentage of CDR3_14AA lengths was adjusted to 16%.

4-b) Transformation: the ligated reaction product was purified using a QIAquick PCR Purification Kit (QIAGEN, CAT. NO. 28106). For each heavy-chain subtype, 1 mL of XL1-Blue Electroporation-Competent Cells (Stratagene, CAT. NO. 200228) was divided into 10 cuvettes (100 µl/cuvette) and electroporated. SB liquid media was added to adjust the total volume to 500 mL, and the result was incubated with shaking at 37° C. and 200 rpm for 1 hour. 100 µL of culture sup. was spread on an LB agar lop plate+ carbenicillin (NaraeBiotech, CAT. NO. LN004CA) through serial dilution and then incubated at 37° C. overnight to determine the pComb3XTT-Synthetic VL library size. 500 µL of carbenicillin (100 mg/mL) was added to 500 mL of the culture, which was then incubated at 37° C. (200 rpm) overnight.

Example 5) Detection of Fab Library Performance 5-1) Determination of Library Size For a Fab library, a total of 12 libraries, each having a size of $10^{10}$ or more, was constructed using 3 VH types and 4 VL types to obtain a Fab library with a total size of $1.52 \times 10^{11}$. For a scFv library, a total of 8 libraries, each having a size of $10^{11}$ or more, was constructed using 2 VH types and 4 VL types, to obtain a scFv library with a total size of $1.27 \times 10^{12}$.

TABLE 75

| | | VL | | | | |
|---|---|---|---|---|---|---|
| | VH | Vκ1-39 | Vκ3-20 | Vκ3-20-2 | Vλ1-51 | Total |
| Fab | VH3-15 | $1.2 \times 10^{10}$ | $1.4 \times 10^{10}$ | $8.0 \times 10^{9}$ | $1.4 \times 10^{10}$ | $1.54 \times 10^{11}$ |
| | VH3-23 | $1.9 \times 10^{10}$ | $9.0 \times 10^{9}$ | $1.2 \times 10^{10}$ | $1.4 \times 10^{10}$ | |

TABLE 75-continued

| VH | | Vκ1-39 | Vκ3-20 | Vκ3-20-2 | Vλ1-51 | Total |
|---|---|---|---|---|---|---|
| scFv | VH1-69 | $1.5 \times 10^{10}$ | $1.8 \times 10^{10}$ | $4.0 \times 10^{9}$ | $1.5 \times 10^{10}$ | |
| | VH3-15 | $2.8 \times 10^{10}$ | $5.0 \times 10^{10}$ | $3.3 \times 10^{10}$ | $1.3 \times 10^{11}$ | $1.27 \times 10^{12}$ |
| | VH3-23 | $2.9 \times 10^{11}$ | $3.4 \times 10^{11}$ | $2.1 \times 10^{12}$ | $7.2 \times 10^{12}$ | |

Unit: CPU (Colony Farming Unit)

5-2) Detection of Library CDR Amino Acid Distribution

Reproducibility was analyzed by comparing the human germline CDR sequences obtained using HT-Sequencing with the CDR sequences of the actually constructed library.

Figure 2:
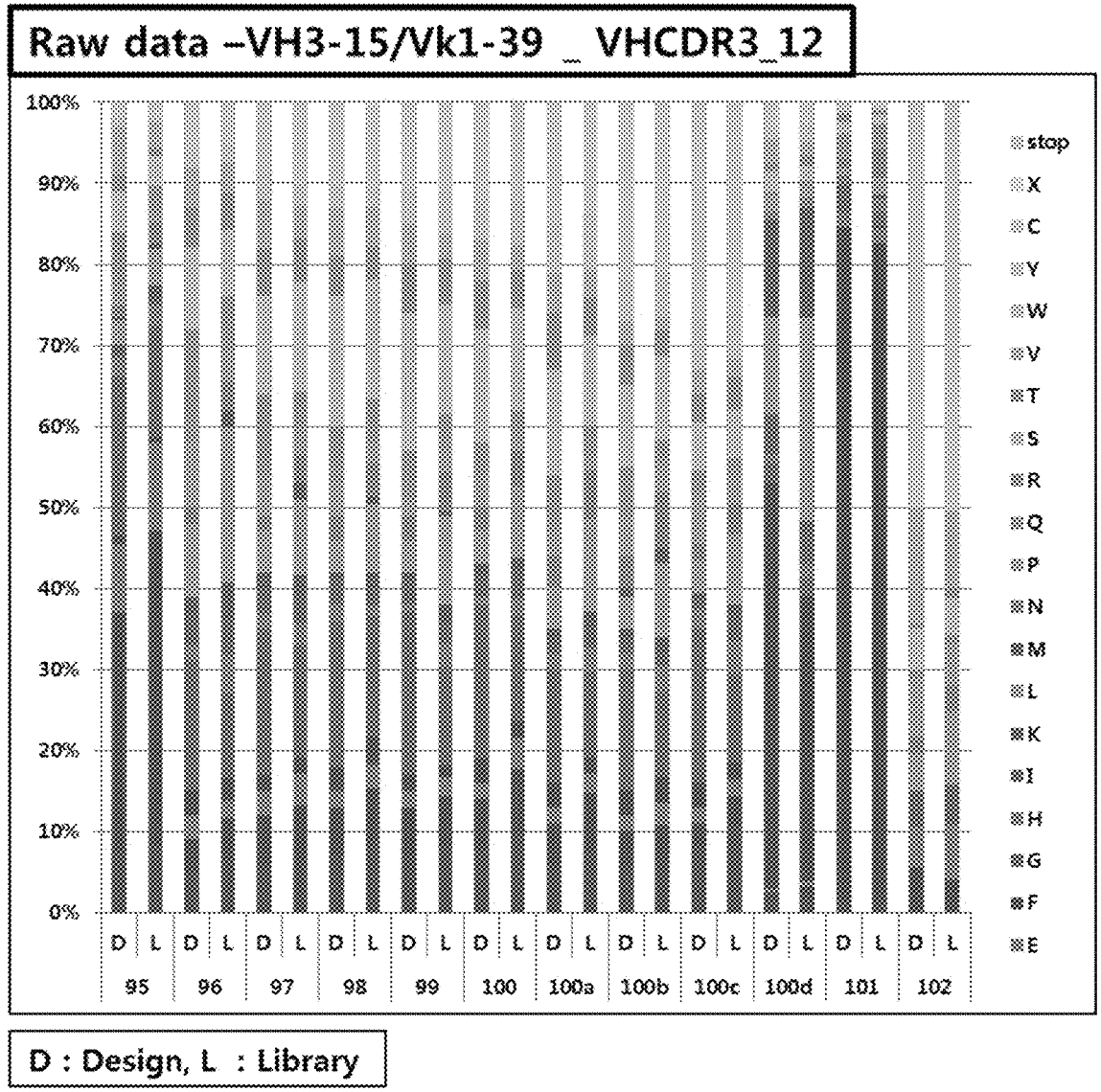
FIG. 2 is a graph showing the distribution of amino acids at different positions of the heavy-chain complementarity-determining region (CDRH3) of the library constructed in an embodiment of the present invention.

The result showed that amino acid diversity designed, as shown in FIG. 2 was obtained.

In order to quantitatively analyze the same, an analysis was conducted using a paired T-test.

The result showed that the significance levels of all library introduction sites were 5% or less, which indicates that the mutation sequence of the actual library is the same as the sequence designed based on the human germline CDR.

TABLE 76

| Paired T-test P-value Site | Equality of variances Levene test | Difference in mean Paired T-test |
|---|---|---|
| 95 | 0.956 | 0.999 |
| 96 | 0.516 | 0.999 |
| 97 | 0.663 | 0.992 |
| 98 | 0.949 | 0.963 |
| 99 | 0.821 | 0.963 |
| 100 | 0.936 | 0.983 |
| 100a | 0.948 | 0.989 |
| 100b | 0.886 | 0.984 |
| 100c | 0.869 | 0.973 |
| 100d | 0.98 | 0.994 |
| 101 | 0.994 | 0.972 |
| 102 | 0.993 | 1 |

* Significance Level (α): 5%

5-3) Detection of Redundancy (Repetitive) Sequence Distribution

The ratio of repetitive sequences was obtained by analyzing about 10000 of each library sequence using HT-sequencing.

Figure 3:
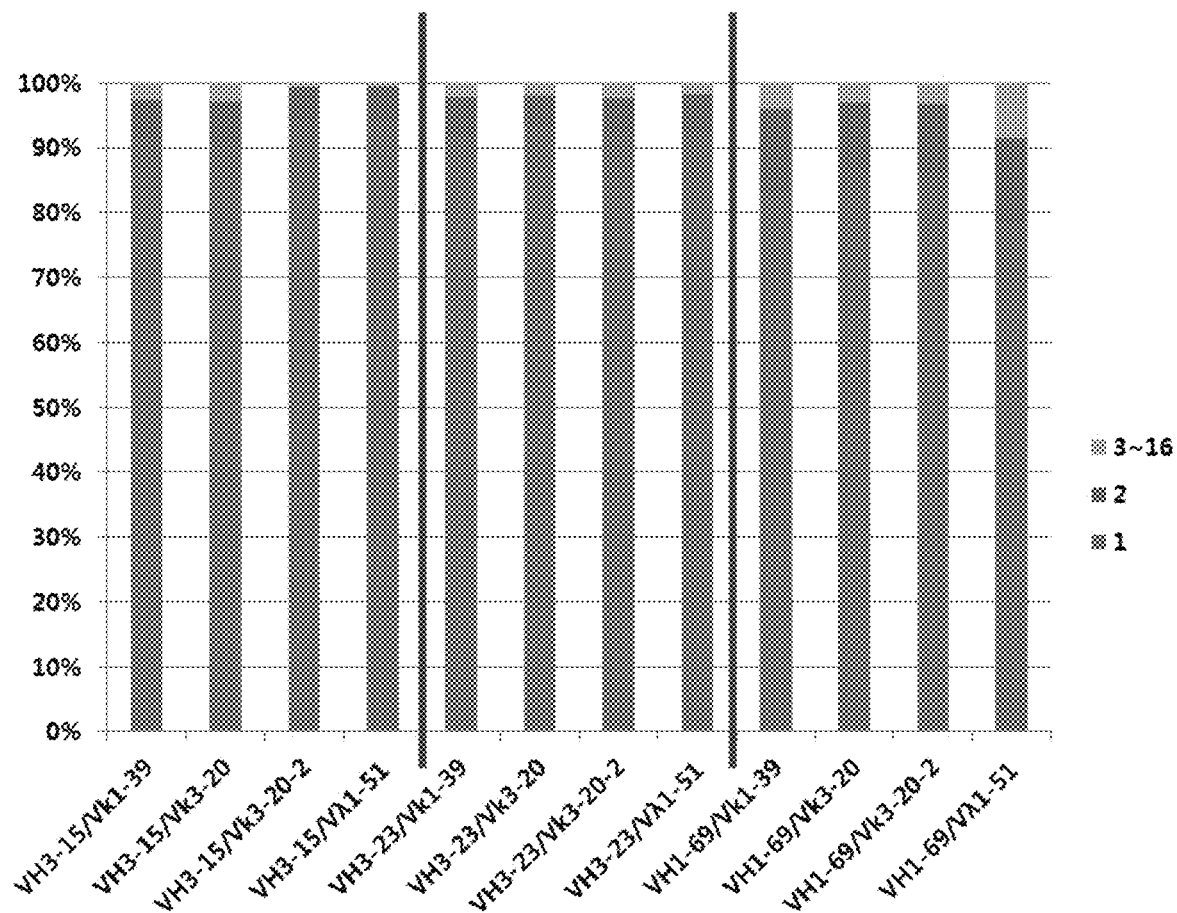
FIG. 3 is a graph showing the result of analysis of the ratio of the repetitive sequence of the library sequence constructed in an embodiment of the present invention.

The result showed that VH3-15 and VH3-23 types have a repetitive sequence ratio of 10% or less, VH1-69 has a repetitive sequence ratio of 13 to 21%, and the overall average repetitive sequence ratio is 10.5% (Table 77). As can be seen from FIG. 3, since most of the repetitive sequences were repeated twice, the effect of lowering the library quality was insignificant.

TABLE 77

| Type | % |
|---|---|
| VH3-15/Vk1-39 | 8.6 |
| VH3-15/Vk3-20 | 9.1 |
| VH3-15/Vk3-20-2 | 6.4 |
| VH3-15/Vλ1-51 | 6.6 |
| VH3-23/Vk1-39 | 8.3 |
| VH3-23/Vk3-20 | 6.8 |

TABLE 77-continued

| Type | % |
|---|---|
| VH3-23/Vk3-20-2 | 7.7 |
| VH3-23/Vλ1-51 | 7.5 |
| VH1-69/Vk1-39 | 18 |
| VH1-69/Vk3-20 | 13 |
| VH1-69/Vk3-20-2 | 13.7 |
| VH1-69/Vλ1-51 | 21 |
| Total | 10.5 |

5-4) CDR Length Analysis

The distribution of human germline VH CDR3 sequences for each length was detected through HT-sequencing, was reproduced in the library, and compared and analyzed through HT-sequencing.

Figure 4:
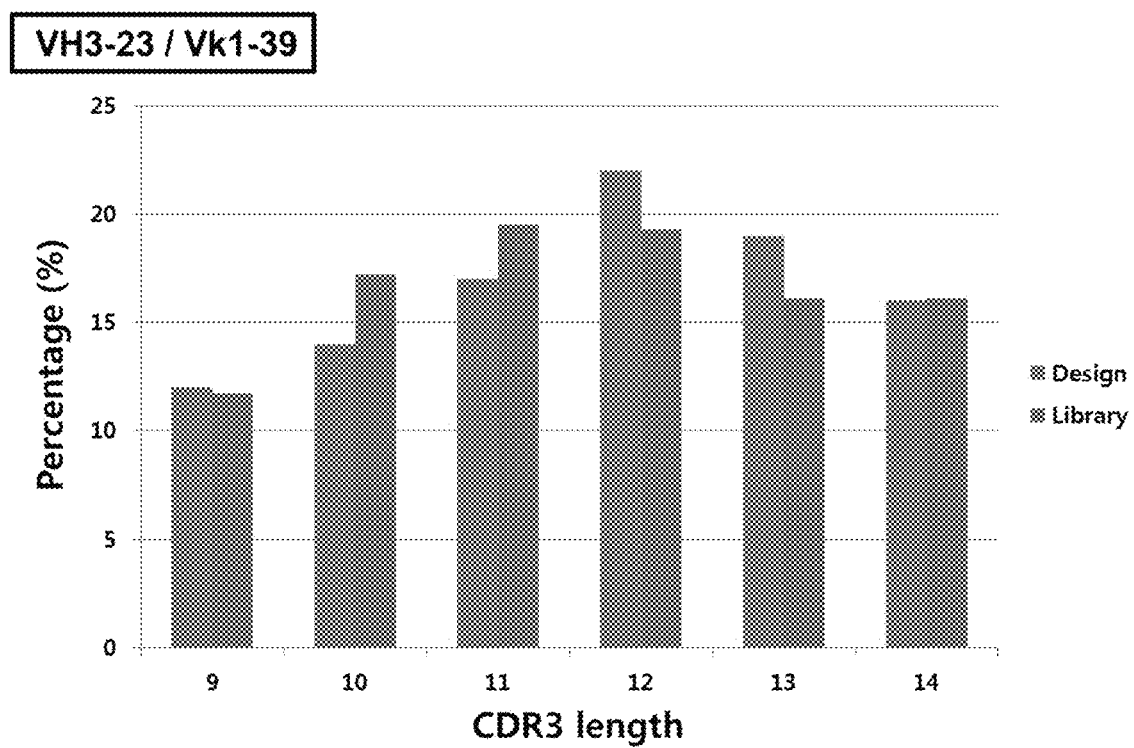
FIG. 4 shows the result of analysis of the distribution of the length of the heavy-chain complementarity-determining region (CDRH3) of the library constructed in an embodiment of the present invention.

As can be seen from FIG. 4, the distribution of the human germline sequence for each length and the CDR length of the library were similar.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

Advantageously, the antibody library according to the present invention has high thermodynamic stability and enables high soluble expression, as well as reversible folding.

Moreover, the antibody library according to the present invention contains various CDRs that are rationally controlled to have high specificity and high affinity for all antigens, and thus have a high level of diversity, and thus can be usefully used to select appropriate candidate antibodies for a desired antigen.

In addition, the antibody library according to the present invention is based on human antibody sequences and thus can be used to screen antibodies with minimal immunogenicity when administered to the human body, and to develop antibodies that can be effectively used for the treatment or diagnosis of diseases.

[Sequence List Free Text]
An electronic file was attached.

The invention claimed is:

1. A set of antibodies or fragments thereof,
wherein each antibody or fragment thereof comprises a pair of a heavy-chain variable region and a light-chain variable region,
wherein the heavy-chain variable region comprises:
a framework region included in a heavy-chain variable region selected from the group consisting of VH3-15 (SEQ ID NO: 1), VH3-23 (SEQ ID NO: 6) and VH1-69 (SEQ ID NO: 11); and
a combination of a heavy-chain complementarity-determining region 1 (CDRH1), a heavy-chain complementarity-determining region 2 (CDRH2), and a heavy-chain complementarity-determining region 3 (CDRH3), which are different for each heavy-chain variable region, and
the light-chain variable region comprises:
a framework region included in a light-chain variable region selected from the group consisting of VK1-39 (SEQ ID NO: 16), Vκ3-20 (SEQ ID NO: 21), Vκ3-20-2 (SEQ ID NO: 26) and Vλ1-51 (SEQ ID NO: 31); and
a combination of a light-chain complementarity-determining region 1 (CDRL1), a light-chain complementarity-determining region 2 (CDRL2), and a light-chain complementarity-determining region 3 (CDRL3), which are different for each light-chain variable region.

2. The set of antibodies or fragments thereof according to claim 1, wherein the set of antibodies or fragments thereof comprises:
a framework region included in a pair of heavy- and light-chain variable regions selected from the group consisting of VH3-15(SEQ ID NO: 1)/VK1-39(SEQ ID NO: 16), VH3-15(SEQ ID NO: 1)/Vκ3-20(SEQ ID NO: 21), VH3-15(SEQ ID NO: 1)/Vκ3-20-2(SEQ ID NO: 26), VH3-15 (SEQ ID NO: 1)/Vλ1-51(SEQ ID NO: 31), VH3-23(SEQ ID NO: 6)/Vκ1-39(SEQ ID NO: 16), VH3-23(SEQ ID NO: 6)/Vκ3-20(SEQ ID NO: 21), VH3-23(SEQ ID NO: 6)/Vκ3-20-2(SEQ ID NO: 26), VH3-23(SEQ ID NO: 6)/Vλ1-51(SEQ ID NO: 31), VH1-69(SEQ ID NO: 11)/Vκ1-39(SEQ ID NO: 16), VH1-69(SEQ ID NO: 11)/Vκ3-20(SEQ ID NO: 21), VH1-69(SEQ ID NO: 11)/Vκ3-20-2(SEQ ID NO: 26) and VH1-69(SEQ ID NO: 11)/Vλ1-51(SEQ ID NO: 31); and
a combination of CDRH1, CDRH2 and CDRH3 different for each heavy-chain variable region and a combination of CDRL1, CDRL2 and CDRL3 different for each light-chain variable region.

3. The set of antibodies or fragments thereof according to claim 1, wherein the framework region in the heavy-chain variable region having the sequence of VH3-15 (SEQ ID NO: 1) comprises FR1 (SEQ ID NO: 2), FR2 (SEQ ID NO: 3), FR3 (SEQ ID NO: 4) and FR4 (SEQ ID NO: 5),
the framework region in the heavy-chain variable region having the sequence of VH3-23 (SEQ ID NO: 6) comprises FR1 (SEQ ID NO: 7), FR2 (SEQ ID NO: 8), FR3 (SEQ ID NO: 9) and FR4 (SEQ ID NO: 10),
the framework region in the heavy-chain variable region having the sequence of VH1-69 (SEQ ID NO: 11) comprises FR1 (SEQ ID NO: 12), FR2 (SEQ ID NO: 13), FR3 (SEQ ID NO: 14) and FR4 (SEQ ID NO: 15),
the framework region in the light-chain variable region having the sequence of Vκ1-39 (SEQ ID NO: 16) comprises FR1 (SEQ ID NO: 17), FR2 (SEQ ID NO: 18), FR3 (SEQ ID NO: 19) and FR4 (SEQ ID NO: 20),
the framework region in the light-chain variable region having the sequence of Vκ3-20 (SEQ ID NO: 21) comprises FR1 (SEQ ID NO: 22), FR2 (SEQ ID NO: 23), FR3 (SEQ ID NO: 24) and FR4 (SEQ ID NO: 25),
the framework region in the light-chain variable region having the sequence of Vκ3-20-2 (SEQ ID NO: 26) comprises FR1 (SEQ ID NO: 27), FR2 (SEQ ID NO: 28), FR3 (SEQ ID NO: 29), and FR4 (SEQ ID NO: 30), and
the framework region in the light-chain variable region having the sequence of Vλ1-51 (SEQ ID NO: 31) comprises FR1 (SEQ ID NO: 32), FR2 (SEQ ID NO: 33), FR3 (SEQ ID NO: 34) and FR4 (SEQ ID NO: 35).

4. The set of antibodies or fragments thereof according to claim 1, wherein
the amino acid ratio for each position in the heavy-chain complementarity-determining region 1 (CDRH1) in the heavy-chain variable region having the sequence of VH3-15 (SEQ ID NO: 1) has the following distribution ratio:

| Amino acid distribution ratio for each position of amino acid(%) - VH3_CDR1 | | | | | |
|---|---|---|---|---|---|
| Type of AA | 27 | 28 | 29 | 30 | 31 |
| Alanine(A) | 0-0.001 | 2-6 | 5-15 | 1-5 | 1-4 |
| Serine(S) | 20-30 | 0.1-0.5 | 0.01-0.1 | 0-0.001 | 0.01-0.1 |
| Glycine(G) | 0-0.001 | 0.5-3 | 0-0.001 | 1-5 | 10-20 |
| Phenylalanine(F) | 0-0.001 | 0.01-0.1 | 0-0.001 | 0.1-1 | 0.5-3 |
| Proline(P) | 60-70 | 0.5-3 | 80-90 | 0.1-1 | 0.5-3 |
| Valine(V) | 0.01-0.1 | 0.1-1 | 0.1-1 | 1-3 | 5-15 |
| Tyrosine(Y) | 0.01-0.1 | 0-0.001 | 0-0.001 | 0.5-3 | 1-3 |

| Amino acid distribution ratio for each position of amino acid(%) - VH3_CDR1 | | | | | |
|---|---|---|---|---|---|
| Methionine(M) | 0-0.001 | 5-12 | 0.1-1 | 1-4 | 0.5-3 |
| Threonine(T) | 0-0.001 | 1-5 | 0-0.001 | 0.5-3 | 1-5 |
| Lysine(K) | 1-4 | 0.01-0.1 | 2-6 | 1-4 | 0.3-2 |
| Isoleucine(I) | 0-0.001 | 0.5-2 | 0-0.001 | 0-0.001 | 0-0.001 |
| Tryptophan(W) | 0-0.001 | 0.1-1 | 0-0.001 | 10-20 | 20-30 |
| Aspartic acid(D) | 0-0.001 | 0.5-8 | 0-0.001 | 5-15 | 0.05-0.5 |
| Histidine(H) | 0-0.001 | 5-15 | 0-0.001 | 0.5-3 | 0.5-2 |
| Asparagine(N) | 5-15 | 0.5-3 | 0.01-0.1 | 1-5 | 1-4 |
| Arginine(R) | 0.1-1 | 5-15 | 0.1-1 | 30-40 | 15-25 |
| Glutamic acid(E) | 0-0.001 | 50-60 | 0.01-0.1 | 15-25 | 5-10 |
| Cysteine(C) | 0.01-0.1 | 0.01-0.05 | 0.05-0.5 | 0.1-1 | 0.1-2 |
| Leucine(L) | 0-0.001 | 0.05-0.1 | 0-0.001 | 0-0.001 | 0.01-0.1 |
| Glutamine(Q) | 0.05-0.3 | 2-6 | 0.01-0.1 | 0-0.001 | 0.5-3 |

| Type of AA | 32 | 33 | 34 | 35 |
|---|---|---|---|---|
| Alanine(A) | 1-5 | 20-30 | 0.01-0.1 | 1-5 |
| Serine(S) | 0.01-0.1 | 0.1-1 | 0-0.001 | 0.01-0.05 |
| Glycine(G) | 0.5-2 | 3-9 | 0.01-0.1 | 0.5-3 |
| Phenylalanine(F) | 0-0.001 | 0.5-3 | 0-0.001 | 5-15 |
| Proline(P) | 3-8 | 0.5-3 | 0.5-2 | 0-0.001 |
| Valine(V) | 0-0.001 | 15-25 | 0.1-0.5 | 1-5 |
| Tyrosine(Y) | 5-15 | 0.5-3 | 0-0.001 | 35-45 |
| Methionine(M) | 0.3-2 | 0.5-3 | 5-12 | 0.5-3 |
| Threonine(T) | 5-15 | 0.01-0.1 | 0-0.001 | 0-0.001 |
| Lysine(K) | 3-8 | 0.5-3 | 15-25 | 0.05-0.5 |
| Isoleucine(I) | 0-0.001 | 0-0.001 | 0-0.001 | 0-0.001 |
| Tryptophan(W) | 3-9 | 0.5-3 | 0-0.001 | 15-25 |
| Aspartic acid(D) | 0.1-1 | 0.5-3 | 0-0.001 | 0.1-1 |
| Histidine(H) | 0.1-0.5 | 0.1-0.5 | 0-0.001 | 1-4 |
| Asparagine(N) | 0.1-1 | 2-6 | 0.1-0.5 | 0.1-1 |
| Arginine(R) | 2-7 | 3-8 | 0.1-0.5 | 10-20 |
| Glutamic acid(E) | 0.5-2 | 1-4 | 0-0.001 | 1-4 |
| Cysteine(C) | 0.1-0.5 | 0.5-3 | 65-75 | 0.1-0.5 |
| Leucine(L) | 0-0.001 | 10-20 | 0-0.001 | 0-0.001 |
| Glutamine(Q) | 45-55 | 5-15 | 0.1-0.5 | 0.5-3 | the amino acid ratio for each position in the heavy-chain complementarity-determining region 2 (CDRH2) in the heavy-chain variable region having the sequence of VH3-15 (SEQ ID NO: 1) has the following distribution ratio:

| Amino acid distribution ratio for each position of amino acid(%) - VH3_CDR2 | | | | | | | |
|---|---|---|---|---|---|---|---|
| Type of AA | 49 | 50 | 51 | 52 | 52a | 53 | 54 |
| Alanine(A) | 35-45 | 5-15 | 0-0.001 | 0.5-3 | 2-6 | 25-35 | 0-0.01 |
| Serine(S) | 50-60 | 10-20 | 0.01-0.1 | 55-65 | 15-25 | 3-9 | 20-30 |
| Glycine(G) | 1-4 | 10-20 | 0-0.001 | 1-4 | 10-20 | 0.01-0.1 | 70-80 |
| Phenylalanine(F) | 0-0.001 | 3-9 | 0-0.01 | 0.05-0.1 | 1-4 | 0.01-0.1 | 0-0.001 |
| Proline(P) | 0.01-0.1 | 0.01-0.05 | 0-0.001 | 0.1-1 | 1-4 | 0.01-0.1 | 0-0.001 |
| Valine(V) | 0.01-0.1 | 15-25 | 0.01-0.1 | 0-0.01 | 0.5-3 | 0.01-0.1 | 0.01-0.2 |
| Tyrosine(Y) | 0-0.01 | 15-25 | 0-0.01 | 0.5-3 | 10-20 | 0.01-0.1 | 0-0.001 |
| Methionine(M) | 0-0.001 | 0-0.01 | 0-0.01 | 0-0.01 | 0-0.01 | 1-4 | 0-0.01 |
| Threonine(T) | 0.01-0.1 | 3-8 | 0.1-0.5 | 2-6 | 1-5 | 0-0.01 | 0-0.001 |
| Lysine(K) | 0-0.001 | 0.1-1 | 0-0.001 | 15-25 | 1-4 | 0.1-1 | 0-0.01 |
| Isoleucine(I) | 0-0.001 | 1-4 | 95-99.98 | 0.1-1 | 0.5-3 | 0-0.01 | 0.01-0.05 |
| Tryptophan(W) | 0-0.01 | 0-0.001 | 0-0.001 | 3-9 | 5-15 | 50-60 | 0.01-0.1 |
| Aspartic acid(D) | 0-0.01 | 0.01-0.05 | 0-0.01 | 0-0.001 | 0.01-0.05 | 0.5-3 | 0.01-0.1 |
| Histidine(H) | 0.01-0.1 | 1-4 | 0-0.01 | 0.5-3 | 2-6 | 0.01-0.1 | 0-0.001 |
| Asparagine(N) | 0-0.001 | 0-0.01 | 0.01-0.05 | 0.01-0.005 | 4-10 | 0.3-2 | 0.01-0.05 |
| Arginine(R) | 0.01-0.1 | 0.05-2 | 0-0.001 | 1-4 | 0.5-3 | 0.5-2 | 0.01-0.05 |
| Glutamic acid(E) | 0.01-0.1 | 0-0.01 | 0-0.001 | 0.01-0.1 | 1-4 | 0-0.01 | 0-0.01 |
| Cysteine(C) | 0-0.001 | 0.01-0.05 | 0-0.001 | 0.01-0.1 | 0.01-0.1 | 0.01-0.1 | 0.01-0.1 |
| Leucine(L) | 0.01-0.1 | 3-8 | 0-0.03 | 1-3 | 1-4 | 0-0.01 | 0-0.01 |
| Glutamine(Q) | 0.01-0.1 | 0-0.01 | 0-0.001 | 0.5-2 | 5-12 | 0.5-3 | 0-0.01 |

| Type of AA | 55 | 56 | 57 | 58 | 59 | 60 |
|---|---|---|---|---|---|---|
| Alanine(A) | 3-8 | 1-5 | 0.5-3 | 1-4 | 0-0.001 | 95-99.99 |
| Serine(S) | 30-40 | 10-20 | 0.5-3 | 0.01-0.1 | 0-0.01 | 0-0.01 |
| Glycine(G) | 10-20 | 1-4 | 0-0.01 | 1-5 | 0-0.001 | 0-0.001 |

| Amino acid distribution ratio for each position of amino acid(%) - VH3_CDR2 | | | | | | |
|---|---|---|---|---|---|---|
| Phenylalanine(F) | 0.5-3 | 0.5-2 | 0-0.01 | 3-9 | 0-0.01 | 0-0.0001 |
| Proline(P) | 0.01-0.1 | 0.1-1.5 | 0.1-1 | 0-0.01 | 0-0.001 | 0-0.01 |
| Valine(V) | 1-4 | 0.5-3 | 0.5-3 | 0.1-1 | 0-0.001 | 0.01-0.1 |
| Tyrosine(Y) | 0.5-3 | 3-9 | 0-0.01 | 55-65 | 95-99.99 | 0-0.001 |
| Methionine(M) | 0-0.01 | 0-0.01 | 0.5-3 | 0-0.01 | 0.01-0.1 | 0-0.001 |
| Threonine(T) | 5-10 | 5-15 | 20-30 | 0.01-0.1 | 0-0.001 | 0.01-0.1 |
| Lysine(K) | 0.5-2 | 2-6 | 30-40 | 0.5-3 | 0-0.001 | 0-0.001 |
| Isoleucine(I) | 0.5-3 | 1-5 | 20-30 | 0.1-2 | 0-0.01 | 0-0.501 |
| Tryptophan(W) | 0.01-0.05 | 0-0.01 | 0-0.001 | 0.5-2 | 0-0.001 | 0-0.001 |
| Aspartic acid(D) | 5-15 | 3-9 | 0-0.01 | 2-8 | 0-0.01 | 0-0.001 |
| Histidine(H) | 0.5-3 | 1-4 | 0.01-0.05 | 4-10 | 0.01-0.1 | 0-0.0051 |
| Asparagine(N) | 5-15 | 25-35 | 0.01-0.1 | 4-10 | 0-0.01 | 0-0.001 |
| Arginine(R) | 0.5-1 | 0.5-3 | 0.5-3 | 0.1-1 | 0-0.001 | 0.01-0.1 |
| Glutamic acid(E) | 1-4 | 5-12 | 3-8 | 0.5-3 | 0-0.001 | 0.01-0.1 |
| Cysteine(C) | 0.01-0.05 | 0.01-0.05 | 0-0.01 | 0.01-0.1 | 0.01-0.1 | 0.01-0.1 |
| Leucine(L) | 1-4 | 1-4 | 1-4 | 0.5-3 | 0.01-0.1 | 0-0.001 |
| Glutamine(Q) | 0-0.01 | 0.5-3 | 1-4 | 0.5-3 | 0-0.001 | 0-0.001, | the amino acid ratio for each position in the heavy-chain complementarity-determining region 1 (CDRH1) in the heavy-chain variable region having the sequence of VH3-23 (SEQ ID NO: 6) has the following distribution ratio:

| Amino acid distribution ratio for each position of amino acid(%) - VH3_CDR1 | | | | | |
|---|---|---|---|---|---|
| Type of AA | 27 | 28 | 29 | 30 | 31 |
| Alanine(A) | 0-0.001 | 2-6 | 5-15 | 1-5 | 1-4 |
| Serine(S) | 20-30 | 0.1-0.5 | 0.01-0.1 | 0-0.001 | 0.01-0.1 |
| Glycine(G) | 0-0.001 | 0.5-3 | 0-0.001 | 1-5 | 10-20 |
| Phenylalanine(F) | 0-0.001 | 0.01-0.1 | 0-0.001 | 0.1-1 | 0.5-3 |
| Proline(P) | 60-70 | 0.5-3 | 80-90 | 0.1-1 | 0.5-3 |
| Valine(V) | 0.01-0.1 | 0.1-1 | 0.1-1 | 1-3 | 5-15 |
| Tyrosine(Y) | 0.01-0.1 | 0-0.001 | 0-0.001 | 0.5-3 | 1-3 |
| Methionine(M) | 0-0.001 | 5-12 | 0.1-1 | 1-4 | 0.5-3 |
| Threonine(T) | 0-0.001 | 1-5 | 0-0.001 | 0.5-3 | 1-5 |
| Lysine(K) | 1-4 | 0.01-0.1 | 2-6 | 1-4 | 0.3-2 |
| Isoleucine(I) | 0-0.001 | 0.5-2 | 0-0.001 | 0-0.001 | 0-0.001 |
| Tryptophan(W) | 0-0.001 | 0.1-1 | 0-0.001 | 10-20 | 20-30 |
| Aspartic acid(D) | 0-0.001 | 0.5-8 | 0-0.001 | 5-15 | 0.05-0.5 |
| Histidine(H) | 0-0.001 | 5-15 | 0-0.001 | 0.5-3 | 0.5-2 |
| Asparagine(N) | 5-15 | 0.5-3 | 0.01-0.1 | 1-5 | 1-4 |
| Arginine(R) | 0.1-1 | 5-15 | 0.1-1 | 30-40 | 15-25 |
| Glutamic acid(E) | 0-0.001 | 50-60 | 0.01-0.1 | 15-25 | 5-10 |
| Cysteine(C) | 0.01-0.1 | 0.01-0.05 | 0.05-0.5 | 0.1-1 | 0.1-2 |
| Leucine(L) | 0-0.001 | 0.05-0.1 | 0-0.001 | 0-0.001 | 0.01-0.1 |
| Glutamine(Q) | 0.05-0.3 | 2-6 | 0.01-0.1 | 0-0.001 | 0.5-3 |
| Type of AA | 32 | 33 | 34 | 35 | |
| Alanine(A) | 1-5 | 20-30 | 0.01-0.1 | 1-5 | |
| Serine(S) | 0.01-0.1 | 0.1-1 | 0-0.001 | 0.01-0.05 | |
| Glycine(G) | 0.5-2 | 3-9 | 0.01-0.1 | 0.5-3 | |
| Phenylalanine(F) | 0-0.001 | 0.5-3 | 0-0.001 | 5-15 | |
| Proline(P) | 3-8 | 0.5-3 | 0.5-2 | 0-0.001 | |
| Valine(V) | 0-0.001 | 15-25 | 0.1-0.5 | 1-5 | |
| Tyrosine(Y) | 5-15 | 0.5-3 | 0-0.001 | 35-45 | |
| Methionine(M) | 0.3-2 | 0.5-3 | 5-12 | 0.5-3 | |
| Threonine(T) | 5-15 | 0.01-0.1 | 0-0.001 | 0-0.001 | |
| Lysine(K) | 3-8 | 0.5-3 | 15-25 | 0.05-0.5 | |
| Isoleucine(I) | 0-0.001 | 0-0.001 | 0-0.001 | 0-0.001 | |
| Tryptophan(W) | 3-9 | 0.5-3 | 0-0.001 | 15-25 | |
| Aspartic acid(D) | 0.1-1 | 0.5-3 | 0-0.001 | 0.1-1 | |
| Histidine(H) | 0.1-0.5 | 0.1-0.5 | 0-0.001 | 1-4 | |
| Asparagine(N) | 0.1-1 | 2-6 | 0.1-0.5 | 0.1-1 | |
| Arginine(R) | 2-7 | 3-8 | 0.1-0.5 | 10-20 | |
| Glutamic acid(E) | 0.5-2 | 1-4 | 0-0.001 | 1-4 | |
| Cysteine(C) | 0.1-0.5 | 0.5-3 | 65-75 | 0.1-0.5 | |
| Leucine(L) | 0-0.001 | 10-20 | 0-0.001 | 0-0.001 | |
| Glutamine(Q) | 45-55 | 5-15 | 0.1-0.5 | 0.5-3 , | | the amino acid ratio for each position in the heavy-chain complementarity-determining region 2 (CDRH2) in the heavy-chain variable region having the sequence of VH3-23 (SEQ ID NO: 6) has the following distribution ratio:

| Amino acid distribution ratio for each position of amino acid(%) - VH3_CDR2 | | | | | | | |
|---|---|---|---|---|---|---|---|
| Type of AA | 49 | 50 | 51 | 52 | 52a | 53 | 54 |
| Alanine(A) | 35-45 | 5-15 | 0-0.001 | 0.5-3 | 2-6 | 25-35 | 0-0.01 |
| Serine(S) | 50-60 | 10-20 | 0.01-0.1 | 55-65 | 15-25 | 3-9 | 20-30 |
| Glycine(G) | 1-4 | 10-20 | 0-0.001 | 1-4 | 10-20 | 0.01-0.1 | 70-80 |
| Phenylalanine(F) | 0-0.001 | 3-9 | 0-0.01 | 0.05-0.1 | 1-4 | 0.01-0.1 | 0-0.001 |
| Proline(P) | 0.01-0.1 | 0.01-0.05 | 0-0.001 | 0.1-1 | 1-4 | 0.01-0.1 | 0-0.001 |
| Valine(V) | 0.01-0.1 | 15-25 | 0.01-0.1 | 0-0.01 | 0.5-3 | 0.01-0.1 | 0.01-0.2 |
| Tyrosine(Y) | 0-0.01 | 15-25 | 0-0.01 | 0.5-3 | 10-20 | 0.01-0.1 | 0-0.001 |
| Methionine(M) | 0-0.001 | 0-0.01 | 0-0.01 | 0-0.01 | 0-0.01 | 1-4 | 0-0.01 |
| Threonine(T) | 0.01-0.1 | 3-8 | 0.1-0.5 | 2-6 | 1-5 | 0-0.01 | 0-0.001 |
| Lysine(K) | 0-0.001 | 0.1-1 | 0-0.001 | 15-25 | 1-4 | 0.1-1 | 0-0.01 |
| Isoleucine(I) | 0-0.001 | 1-4 | 95-99.98 | 0.1-1 | 0.5-3 | 0-0.01 | 0.01-0.05 |
| Tryptophan(W) | 0-0.01 | 0-0.001 | 0-0.001 | 3-9 | 5-15 | 50-60 | 0.01-0.1 |
| Aspartic acid(D) | 0-0.01 | 0.01-0.05 | 0-0.01 | 0-0.001 | 0.01-0.05 | 0.5-3 | 0.01-0.1 |
| Histidine(H) | 0.01-0.1 | 1-4 | 0-0.01 | 0.5-3 | 2-6 | 0.01-0.1 | 0-0.001 |
| Asparagine(N) | 0-0.001 | 0-0.01 | 0.01-0.05 | 0.01-0.005 | 4-10 | 0.3-2 | 0.01-0.05 |
| Arginine(R) | 0.01-0.1 | 0.05-2 | 0-0.001 | 1-4 | 0.5-3 | 0.5-2 | 0.01-0.05 |
| Glutamic acid(E) | 0.01-0.1 | 0-0.01 | 0-0.001 | 0.01-0.1 | 1-4 | 0-0.01 | 0-0.01 |
| Cysteine(C) | 0-0.001 | 0.01-0.05 | 0-0.001 | 0.01-0.1 | 0.01-0.1 | 0.01-0.1 | 0.01-0.1 |
| Leucine(L) | 0.01-0.1 | 3-8 | 0-0.03 | 1-3 | 1-4 | 0-0.01 | 0-0.01 |
| Glutamine(Q) | 0.01-0.1 | 0-0.01 | 0-0.001 | 0.5-2 | 5-12 | 0.5-3 | 0-0.01 |
| Type of AA | 55 | 56 | 57 | 58 | 59 | 60 | |
| Alanine(A) | 3-8 | 1-5 | 0.5-3 | 1-4 | 0-0.001 | 95-99.99 | |
| Serine(S) | 30-40 | 10-20 | 0.5-3 | 0.01-0.1 | 0-0.01 | 0-0.01 | |
| Glycine(G) | 10-20 | 1-4 | 0-0.01 | 1-5 | 0-0.001 | 0-0.001 | |
| Phenylalanine(F) | 0.5-3 | 0.5-2 | 0-0.01 | 3-9 | 0-0.01 | 0-0.0001 | |
| Proline(P) | 0.01-0.1 | 0.1-1.5 | 0.1-1 | 0-0.01 | 0-0.001 | 0-0.01 | |
| Valine(V) | 1-4 | 0.5-3 | 0.5-3 | 0.1-1 | 0-0.001 | 0.01-0.1 | |
| Tyrosine(Y) | 0.5-3 | 3-9 | 0-0.01 | 55-65 | 95-99.99 | 0-0.001 | |
| Methionine(M) | 0-0.01 | 0-0.01 | 0.5-3 | 0.01-0.1 | 0-0.01 | | |
| Threonine(T) | 5-10 | 5-15 | 20-30 | 0.01-0.1 | 0-0.001 | 0.01-0.1 | |
| Lysine(K) | 0.5-2 | 2-6 | 30-40 | 0.5-3 | 0-0.001 | 0-0.001 | |
| Isoleucine(I) | 0.5-3 | 1-5 | 20-30 | 0.1-2 | 0-0.01 | 0-0.501 | |
| Tryptophan(W) | 0.01-0.05 | 0-0.01 | 0-0.001 | 0.5-2 | 0-0.001 | 0-0.001 | |
| Aspartic acid(D) | 5-15 | 3-9 | 0-0.01 | 2-8 | 0-0.01 | 0-0.001 | |
| Histidine(H) | 0.5-3 | 1-4 | 0.01-0.05 | 4-10 | 0.01-0.1 | 0-0.0051 | |
| Asparagine(N) | 5-15 | 25-35 | 0.01-0.1 | 4-10 | 0-0.01 | 0-0.001 | |
| Arginine(R) | 0.5-1 | 0.5-3 | 0.5-3 | 0.1-1 | 0-0.001 | 0.01-0.1 | |
| Glutamic acid(E) | 1-4 | 5-12 | 3-8 | 0.5-3 | 0-0.001 | 0.01-0.1 | |
| Cysteine(C) | 0.01-0.05 | 0.01-0.05 | 0-0.01 | 0.01-0.1 | 0.01-0.1 | 0.01-0.1 | |
| Leucine(L) | 1-4 | 1-4 | 1-4 | 0.5-3 | 0.01-0.1 | 0-0.001 | |
| Glutamine(Q) | 0-0.01 | 0.5-3 | 1-4 | 0.5-3 | 0-0.001 | 0-0.001, | | the amino acid ratio for each position in the heavy-chain complementarity-determining region 1 (CDRH1) in the heavy-chain variable region having the sequence of VH1-69 (SEQ ID NO: 11) has the following distribution ratio:

| Amino acid distribution ratio for each position of amino acid(%) - VH1-69_CDR1 | | | | | | | | | |
|---|---|---|---|---|---|---|---|---|---|
| Type of AA | 27 | 28 | 29 | 30 | 31 | 32 | 33 | 34 | 35 |
| Alanine(A) | 0-0.01 | 2-5 | 0-0.001 | 1-5 | 1-4 | 2-5 | 30-40 | 0.05-0.5 | 1-7 |
| Serine(S) | 0.5-3 | 10-20 | 0.05-0.5 | 40-50 | 20-30 | 4-8 | 3-6 | 0.01-0.1 | 10-20 |
| Glycine(G) | 2-6 | 0.1-1 | 0-0.001 | 1-4 | 1-4 | 0-0.001 | 5-15 | 0.5-3 | 1-5 |
| Phenylalanine(F) | 40-50 | 0.01-0.1 | 95-99.99 | 0.01-0.1 | 0.01-0.05 | 4-8 | 0.5-3 | 0.01-0.1 | 0.01-0.05 |
| Proline(P) | 0-0.001 | 0.5-3 | 0-0.01 | 0.5-3 | 0.01-0.05 | 0.01-0.05 | 0.5-3 | 0-0.01 | 0.01-0.1 |
| Valine(V) | 0.5-2 | 0.01-0.1 | 0.01-0.05 | 0.1-1 | 0.0-0.5 | 0.1-0.5 | 0.5-3 | 80-90 | 0.1-0.5 |
| Tyrosine(Y) | 30-40 | 0.01-0.1 | 0.01-0.05 | 0.01-0.05 | 0.5-2 | 55-68 | 5-15 | 0.01-0.1 | 0.5-3 |
| Methionine(M) | 0-0.001 | 0.5-3 | 0-0.001 | 0-0.01 | 0-0.01 | 0-0.01 | 0-0.01 | 0-0.001 | 0-0.001 |
| Threonine(T) | 0.01-0.1 | 55-65 | 0.01-0.05 | 15-25 | 5-15 | 0.1-1 | 1-5 | 0.01-0.05 | 1-4 |
| Lysine(K) | 0.01-0.1 | 1-5 | 0-0.01 | 0.5-3 | 1-5 | 0.5-3 | 0-0.001 | 0-0.01 | 0.01-0.05 |

| Amino acid distribution ratio for each position of amino acid(%) - VH1-69_CDR1 ||||||||||
|---|---|---|---|---|---|---|---|---|---|
| Type of AA | 27 | 28 | 29 | 30 | 31 | 32 | 33 | 34 | 35 |
| Isoleucine(I) | 0.5-3 | 6-12 | 0.01-0.05 | 1-5 | 0.5-3 | 0.01-0.1 | 0.5-3 | 3-9 | 0.5-2 |
| Tryptophan(W) | 0-0.001 | 0-0.001 | 0-0.001 | 0-0.001 | 0-0.001 | 0-0.01 | 10-20 | 0-0.01 | 0-0.001 |
| Aspartic acid(D) | 1-5 | 0.5-3 | 0-0.001 | 3-7 | 10-20 | 0.5-3 | 4-10 | 0.01-0.05 | 0.5-3 |
| Histidine(H) | 0.5-3 | 0.01-0.1 | 0-0.001 | 0.01-0.05 | 0.5-3 | 5-15 | 0.5-3 | 0-0.01 | 40-50 |
| Asparagine(N) | 0.5-3 | 0.1-0.8 | 0-0.01 | 10-20 | 25-35 | 3-10 | 0.5-3 | 0.01-0.1 | 15-25 |
| Arginine(R) | 0-0.01 | 0.5-3 | 0-0.001 | 1-4 | 1-4 | 0.1-1 | 0.1-1 | 0.1-0.5 | 0.1-0.5 |
| Glutamic acid(E) | 0-0.001 | 0.01-0.05 | 0-0.001 | 0.1-1 | 1-4 | 0-0.01 | 1-4 | 0.01-0.1 | 0-0.01 |
| Cysteine(C) | 0.01-0.1 | 0-0.001 | 0-0.01 | 0-0.01 | 0-0.01 | 0.01-0.1 | 0.01-0.1 | 0-0.01 | 0.01-0.05 |
| Leucine(L) | 1-4 | 0.01-0.1 | 0.05-0.5 | 0.05-0.5 | 0.01-0.1 | 0.5-3 | 0.01-0.1 | 4-10 | 0.01-0.05 |
| Glutamine(Q) | 0-0.001 | 0-0.001 | 0.01-0.05 | 0.01-0.1 | 0.01-0.05 | 0.01-0.05 | 0.01-0.1 | 0-0.01 | 0.5-3 , | the amino acid ratio for each position in the heavy-chain complementarity-determining region 2 (CDRH2) in the heavy-chain variable region having the sequence of VH1-69 (SEQ ID NO: 11) has the following distribution ratio:

| Amino acid distribution ratio for each position of amino acid(%) - VH1-69_CDR2 ||||||||
|---|---|---|---|---|---|---|
| Type of AA | 49 | 50 | 51 | 52 | 52a | 53 |
| Alanine(A) | 35-45 | 3-10 | 0-0.001 | 0.1-0.8 | 5-15 | 0.5-3 |
| Serine(S) | 25-35 | 5-15 | 0.01-0.1 | 55-65 | 10-20 | 25-35 |
| Glycine(G) | 25-35 | 5-15 | 0-0.001 | 0.5-3 | 3-10 | 3-7 |
| Phenylalanine(F) | 0-0.01 | 1-5 | 0-0.01 | 0.1-1 | 1-4 | 0.5-2 |
| Proline(P) | 0-0.01 | 0-0.02 | 0-0.001 | 0.01-0.05 | 15-25 | 0.01-0.05 |
| Valine(V) | 0.01-0.1 | 5-12 | 0-0.01 | 0.5-3 | 0.5-3 | 0.5-3 |
| Tyrosine(Y) | 0-0.01 | 5-15 | 0.01-0.1 | 0.5-3 | 5-15 | 2-7 |
| Methionine(M) | 0-0.001 | 0.5-3 | 0-0.01 | 0-0.001 | 0-0.01 | 0.5-3 |
| Threonine(T) | 0.01-0.1 | 1-4 | 0-0.03 | 1-5 | 1-5 | 1-3 |
| Lysine(K) | 0-0.001 | 0.5-2 | 0-0.001 | 5-15 | 0.5-3 | 1-4 |
| Isoleucine(I) | 0-0.001 | 3-9 | 95-99.99 | 6-10 | 0.5-3 | 2-7 |
| Tryptophan(W) | 0-0.001 | 10-20 | 0-0.001 | 1-5 | 2-7 | 0-0.01 |
| Aspartic acid(D) | 0-0.01 | 0.5-3 | 0.01-0.05 | 1-5 | 1-5 | 30-40 |
| Histidine(H) | 0-0.01 | 0.5-3 | 0.01-0.05 | 0.5-3 | 2-7 | 1-4 |
| Asparagine(N) | 0-0.001 | 5-15 | 0-0.02 | 0.01-0.05 | 1-5 | 0.01-0.05 |
| Arginine(R) | 0-0.001 | 0.5-3 | 0-0.01 | 0.5-3 | 0.1-2 | 0.5-2 |
| Glutamic acid(E) | 0-0.01 | 0-0.001 | 0-0.001 | 0-0.05 | 1-4 | 1-4 |
| Cysteine(C) | 0.01-0.1 | 0.01-0.1 | 0-0.001 | 0-0.001 | 0.01-0.1 | 0.01-0.1 |
| Leucine(L) | 0.01-0.1 | 3-9 | 0.01-0.05 | 1-4 | 0.5-3 | 1-4 |
| Glutamine(Q) | 0-0.01 | 0-0.01 | 0-0.001 | 0.5-3 | 2-7 | 0-0.01 |

| Type of AA | 54 | 55 | 56 | 57 | 58 |
|---|---|---|---|---|---|
| Alanine(A) | 1-5 | 2-6 | 2-7 | 4-10 | 1-4 |
| Serine(S) | 15-25 | 25-35 | 5-15 | 0.5-3 | 2-6 |
| Glycine(G) | 30-40 | 30-40 | 1-5 | 0-0.01 | 1-5 |
| Phenylalanine(F) | 1-7 | 0.01-0.05 | 0.5-2 | 0-0.01 | 1-5 |
| Proline(P) | 0.01-0.05 | 0-0.01 | 0.1-1 | 0.5-3 | 0.01-0.05 |
| Valine(V) | 0.5-3 | 0.5-3 | 1-4 | 0.5-3 | 0.1-2 |
| Tyrosine(Y) | 0.1-2 | 0.5-3 | 2-8 | 0-0.001 | 25-35 |
| Methionine(M) | 0-0.01 | 0-0.01 | 0.1-2 | 0.5-3 | 0-0.01 |
| Threonine(T) | 1-5 | 3-8 | 5-15 | 30-40 | 0.5-3 |
| Lysine(K) | 0.5-3 | 0.5-3 | 3-10 | 25-35 | 5-15 |
| Isoleucine(I) | 0.5-3 | 0.5-3 | 2-6 | 15-25 | 1-4 |
| Tryptophan(W) | 0.01-0.05 | 0.01-0.1 | 0-0.01 | 0-0.01 | 0-0.001 |
| Aspartic acid(D) | 2-7 | 5-15 | 5-15 | 0-0.01 | 2-5 |
| Histidine(H) | 0-0.01 | 0.5-3 | 1-4 | 0.01-0.1 | 4-8 |
| Asparagine(N) | 10-20 | 4-10 | 25-35 | 0.5-3 | 15-25 |
| Arginine(R) | 0.5-2 | 0.5-3 | 0.5-3 | 0.5-3 | 0.5-3 |
| Glutamic acid(E) | 0.5-3 | 0.5-3 | 5-12 | 0-0.001 | 1-4 |
| Cysteine(C) | 0.01-0.005 | 0.01-0.05 | 0.01-0.05 | 0-0.01 | 0.01-0.1 |
| Leucine(L) | 3-9 | 0.05-0.1 | 0.5-3 | 0.5-3 | 0.5-3 |
| Glutamine(Q) | 0-0.01 | 0-0.01 | 0.5-3 | 0.5-3 | 0.5-3 , | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 9 amino acids, the amino acid ratio for each position in the CDRH3 has the following distribution ratio:

| Amino acid distribution ratio for each position of amino acid(%) - VH_CDR3_9AA | | | | | | | | | |
|---|---|---|---|---|---|---|---|---|---|
| Type of AA | 96 | 97 | 98 | 99 | 100 | 100a | 100b | 101 | 102 |
| Alanine(A) | 3-8 | 3-8 | 3-8 | 5-15 | 4-10 | 10-20 | 0.5-3 | 0.5-3 | 0.5-3 |
| Serine(S) | 1-5 | 6-12 | 5-15 | 10-20 | 10-20 | 10-20 | 4-10 | 0.5-3 | 1-5 |
| Glycine(G) | 5-15 | 5-15 | 5-15 | 5-12 | 5-15 | 5-15 | 1-5 | 0.5-3 | 0.1-0.5 |
| Phenylalanine(F) | 0.1-0.8 | 0.5-3 | 0.5-3 | 2-5 | 0.5-3 | 1-5 | 45-55 | 0.1-0.5 | 1-5 |
| Proline(P) | 0.5-3 | 5-15 | 1-5 | 0.5-3 | 0.1-1 | 2-6 | 0.5-3 | 0.1-0.5 | 0.5-3 |
| Valine(V) | 3-8 | 3-9 | 10-20 | 3-8 | 3-7 | 3-8 | 4-10 | 1-5 | 4-10 |
| Tyrosine(Y) | 0.5-3 | 2-7 | 4-10 | 15-25 | 15-25 | 15-25 | 5-12 | 0.5-3 | 60-70 |
| Methionine(M) | 0.01-0.05 | 1-4 | 1-4 | 0.1-1 | 0.1-1 | 0.1-0.5 | 1-5 | 0.5-3 | 0.5-3 |
| Threonine(T) | 5-15 | 2-6 | 4-10 | 3-9 | 5-15 | 3-8 | 2-5 | 0.5-3 | 0.5-3 |
| Lysine(K) | 0.5-3 | 0.5-3 | 1-4 | 1-5 | 0.5-3 | 0.5-3 | 0.01-0.1 | 0.1-1 | 0-0.001 |
| Isoleucine(I) | 0.5-3 | 1-5 | 0.5-3 | 1-4 | 1-4 | 3-8 | 5-12 | 2-6 | 1-5 |
| Tryptophan(W) | 0.5-3 | 3-9 | 1-4 | 0.5-3 | 0.5-3 | 0.5-3 | 0.1-1 | 0-0.001 | 0.01-0.1 |
| Aspartic acid(D) | 25-35 | 2-7 | 3-9 | 4-10 | 4-10 | 4-10 | 0.5-3 | 70-80 | 1-5 |
| Histidine(H) | 1-5 | 0.5-3 | 1-3 | 0.5-3 | 0.5-3 | 1-5 | 0.5-3 | 0.1-0.5 | 1-5 |
| Asparagine(N) | 0.5-3 | 1-5 | 2-6 | 2-6 | 3-8 | 0.5-3 | 0.5-3 | 1-4 | 0.5-3 |
| Arginine(R) | 1-4 | 4-10 | 5-15 | 1-5 | 1-4 | 1-4 | 0.1-1 | 0.1-0.5 | 0.1-0.5 |
| Glutamic acid(E) | 5-15 | 1-4 | 1-4 | 1-5 | 1-4 | 0.5-3 | 0.5-3 | 2-5 | 0.1-0.5 |
| Cysteine(C) | 0-0.001 | 0.01-0.05 | 0.01-0.05 | 0.01-0.1 | 0.01-0.1 | 0.01-0.05 | 0-0.001 | 0-0.001 | 0.01-0.05 |
| Leucine(L) | 1-4 | 5-15 | 1-5 | 0.5-2 | 0.5-3 | 0.5-3 | 1-4 | 0.1-0.5 | 0.5-3 |
| Glutamine(Q) | 5-15 | 2-6 | 0.5-3 | 0.5-2 | 0.5-3 | 0.1-1 | 0.1-0.5 | 0.5-3 | 0.1-1 , | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 10 amino acids, the amino acid ratio for each position in CDRH3 has the following distribution ratio:

| Amino acid distribution ratio for each position of amino acid(%) - VH_CDR3_10AA | | | | | | | | | | |
|---|---|---|---|---|---|---|---|---|---|---|
| Type of AA | 96 | 97 | 98 | 99 | 100 | 100a | 100b | 100c | 101 | 102 |
| Alanine(A) | 5-15 | 3-9 | 4-10 | 4-10 | 5-15 | 4-10 | 5-15 | 1-4 | 0.5-3 | 0.5-3 |
| Serine(S) | 3-8 | 5-15 | 10-20 | 10-20 | 10-20 | 5-15 | 5-12 | 2-6 | 0.5-3 | 2-6 |
| Glycine(G) | 5-15 | 5-15 | 5-15 | 10-20 | 5-15 | 10-20 | 10-20 | 1-4 | 1-4 | 0.01-0.1 |
| Phenylalanine(F) | 0.1-0.5 | 1-4 | 0.5-3 | 1-5 | 1-4 | 1-4 | 0.5-3 | 25-35 | 0.1-1 | 2-6 |
| Proline(P) | 0.5-3 | 2-6 | 1-5 | 1-4 | 1-4 | 0.5-3 | 2-6 | 1-4 | 0.1-1 | 3-8 |
| Valine(V) | 2-6 | 2-6 | 2-6 | 2-6 | 2-5 | 0.5-3 | 1-4 | 1-4 | 0.5-3 | 5-12 |
| Tyrosine(Y) | 1-4 | 3-8 | 5-12 | 5-15 | 5-15 | 10-20 | 15-25 | 3-8 | 0.5-3 | 45-55 |
| Methionine(M) | 0.5-2 | 0.5-3 | 1-3 | 0.5-3 | 0.1-1 | 0.5-3 | 0.01-0.1 | 10-20 | 0.01-0.1 | 0.01-0.05 |
| Threonine(T) | 1-4 | 2-6 | 3-9 | 2-8 | 3-9 | 2-6 | 1-5 | 0.5-3 | 0.5-3 | 0.1-0.5 |
| Lysine(K) | 1-4 | 2-6 | 1-4 | 0.5-3 | 0.5-3 | 0.5-3 | 0.5-3 | 0.01-0.1 | 0.01-0.05 | 0-0.001 |
| Isoleucine(I) | 1-4 | 2-6 | 1-4 | 1-4 | 1-4 | 0.5-3 | 1-4 | 3-8 | 0.1-1 | 1-5 |
| Tryptophan(W) | 0.5-3 | 0.5-3 | 1-4 | 1-4 | 3-8 | 3-8 | 3-8 | 0.1-1 | 0.01-0.05 | 0.1-1 |
| Aspartic acid(D) | 25-35 | 3-8 | 4-10 | 4-10 | 3-9 | 4-10 | 3-8 | 1-4 | 75-85 | 1-5 |
| Histidine(H) | 1-5 | 2-6 | 1-4 | 0.5-3 | 1-4 | 1-4 | 1-5 | 0.01-0.1 | 0.5-3 | 3-8 |
| Asparagine(N) | 0.5-3 | 1-5 | 1-4 | 2-6 | 1-7 | 5-12 | 1-4 | 0.5-3 | 0.5-3 | 1-5 |
| Arginine(R) | 1-4 | 2-6 | 1-4 | 1-4 | 0.5-3 | 0.5-3 | 0.5-3 | 0.1-1 | 0.1-1 | 0.01-0.05 |
| Glutamic acid(E) | 5-15 | 1-5 | 2-5 | 1-4 | 1-4 | 1-4 | 1-4 | 0.5-3 | 1-4 | 0.01-0.05 |
| Cysteine(C) | 0-0.001 | 0.01-0.05 | 0.01-0.05 | 0.01-0.1 | 0.01-0.1 | 0.01-0.05 | 0.01-0.05 | 0-0.001 | 0.01-0.05 | 0.01-0.1 |
| Leucine(L) | 3-9 | 10-20 | 5-15 | 4-10 | 5-12 | 3-9 | 4-10 | 15-25 | 2-5 | 4-10 |
| Glutamine(Q) | 0.5-3 | 1-4 | 1-4 | 1-4 | 1-4 | 1-4 | 1-4 | 0.01-0.1 | 1-4 | 0-0.001, | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 11 amino acids, the amino acid ratio for each position in the CDRH3 has the following distribution ratio:

| Amino acid distribution ratio for each position of amino acid(%) - VH_CDR3_11AA | | | | | | |
|---|---|---|---|---|---|---|
| Type of AA | 96 | 97 | 98 | 99 | 100 | 100a |
| Alanine(A) | 5-12 | 3-9 | 4-10 | 5-12 | 5-15 | 5-15 |
| Serine(S) | 2-6 | 5-15 | 5-15 | 10-20 | 10-20 | 5-15 |
| Glycine(G) | 5-15 | 5-15 | 5-15 | 10-20 | 5-15 | 5-15 |
| Phenylalanine(F) | 0.1-1 | 1-4 | 0.5-3 | 1-4 | 0.5-3 | 1-4 |
| Proline(P) | 0.5-3 | 2-5 | 1-5 | 1-4 | 0.5-3 | 2-5 |
| Valine(V) | 2-6 | 2-6 | 2-6 | 3-8 | 2-5 | 2-5 |
| Tyrosine(Y) | 0.5-3 | 3-8 | 5-12 | 5-15 | 5-15 | 5-15 |
| Methionine(M) | 0.5-3 | 0.5-3 | 0.5-3 | 0.5-3 | 0.1-1 | 0.01-0.1 |
| Threonine(T) | 0.5-3 | 2-6 | 3-8 | 3-8 | 3-9 | 3-8 |
| Lysine(K) | 0.5-3 | 2-6 | 1-4 | 1-4 | 1-4 | 0.5-3 |
| Isoleucine(I) | 1-4 | 1-5 | 1-4 | 1-4 | 1-4 | 1-5 |
| Tryptophan(W) | 0.5-3 | 1-4 | 1-4 | 1-4 | 2-6 | 2-6 |
| Aspartic acid(D) | 25-35 | 3-8 | 4-10 | 4-10 | 4-10 | 4-10 |
| Histidine(H) | 1-4 | 2-6 | 1-4 | 0.5-3 | 1-4 | 1-4 |
| Asparagine(N) | 1-4 | 1-5 | 2-5 | 3-8 | 2-6 | 3-7 |
| Arginine(R) | 1-4 | 1-5 | 1-4 | 1-4 | 0.5-3 | 0.5-3 |
| Glutamic acid(E) | 10-20 | 1-5 | 2-6 | 1-4 | 1-4 | 1-4 |
| Cysteine(C) | 0.01-0.05 | 0.01-0.05 | 0-0.001 | 0-0.001 | 0.01-0.05 | 0.01-0.1 |
| Leucine(L) | 3-8 | 10-20 | 5-15 | 3-9 | 5-12 | 5-15 |
| Glutamine(Q) | 1-4 | 1-4 | 1-4 | 1-4 | 1-5 | 0.5-3 |

| Type of AA | 100b | 100c | 100d | 101 | 102 |
|---|---|---|---|---|---|
| Alanine(A) | 4-10 | 4-10 | 1-4 | 1-4 | 0.1-1 |
| Serine(S) | 5-15 | 5-12 | 2-5 | 0.5-3 | 3-8 |
| Glycine(G) | 5-15 | 5-15 | 1-4 | 0.5-3 | 0.5-3 |
| Phenylalanine(F) | 1-4 | 1-4 | 25-35 | 0.1-0.5 | 1-5 |
| Proline(P) | 1-4 | 2-5 | 1-4 | 0.5-3 | 1-5 |
| Valine(V) | 2-5 | 0.5-3 | 1-5 | 0.5-3 | 4-10 |
| Tyrosine(Y) | 10-20 | 15-25 | 1-5 | 0.5-3 | 45-55 |
| Methionine(M) | 0.01-0.1 | 0.5-3 | 5-15 | 0.05-0.2 | 0.01-0.1 |
| Threonine(T) | 3-9 | 2-6 | 0.5-3 | 0.1-1 | 0.5-3 |
| Lysine(K) | 0.5-3 | 1-4 | 0.01-0.05 | 0.01-0.05 | 0-0.001 |
| Isoleucine(I) | 1-4 | 1-4 | 3-8 | 0.1-0.5 | 1-5 |
| Tryptophan(W) | 3-8 | 3-8 | 0.5-3 | 0.01-0.05 | 0-0.001 |
| Aspartic acid(D) | 3-8 | 3-8 | 1-4 | 75-85 | 1-4 |
| Histidine(H) | 1-6 | 1-4 | 0.5-3 | 1-4 | 4-10 |
| Asparagine(N) | 3-9 | 3-8 | 1-4 | 1-4 | 2-6 |
| Arginine(R) | 1-4 | 1-4 | 0.5-3 | 0.5-2 | 0.01-0.1 |
| Glutamic acid(E) | 1-4 | 1-4 | 0.5-3 | 1-5 | 0.01-0.1 |
| Cysteine(C) | 0.01-0.1 | 0.01-0.1 | 0-0.001 | 0.01-0.05 | 0.01-0.1 |
| Leucine(L) | 5-15 | 5-15 | 20-30 | 1-4 | 5-12 |
| Glutamine(Q) | 1-4 | 0.5-3 | 0.5-3 | 1-4 | 0.5-3 , | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 12 amino acids, the amino acid ratio for each position in CDRH3 has the following distribution ratio:

| Amino acid distribution ratio for each position of amino acid(%) - VH_CDR3_12AA | | | | | | |
|---|---|---|---|---|---|---|
| Type of AA | 96 | 97 | 98 | 99 | 100 | 100a |
| Alanine(A) | 4-10 | 3-9 | 4-10 | 5-12 | 4-10 | 5-15 |
| Serine(S) | 1-5 | 5-15 | 5-15 | 10-20 | 5-15 | 5-15 |
| Glycine(G) | 10-20 | 5-15 | 5-15 | 10-20 | 5-15 | 5-15 |
| Phenylalanine(F) | 0.1-1 | 1-4 | 0.5-3 | 1-4 | 1-4 | 1-5 |
| Proline(P) | 0.5-3 | 1-5 | 1-5 | 1-5 | 1-4 | 2-5 |
| Valine(V) | 1-5 | 2-6 | 2-6 | 2-6 | 2-5 | 2-5 |
| Tyrosine(Y) | 1-4 | 3-8 | 5-12 | 5-15 | 5-15 | 5-15 |
| Methionine(M) | 0.1-1 | 0.5-3 | 1-4 | 0.5-3 | 0.1-1 | 0.01-0.05 |
| Threonine(T) | 0.5-3 | 2-6 | 3-8 | 2-6 | 3-9 | 3-8 |
| Lysine(K) | 0.5-3 | 2-6 | 1-4 | 0.5-3 | 0.5-3 | 0.5-3 |
| Isoleucine(I) | 0.5-3 | 1-5 | 1-4 | 1-4 | 1-4 | 1-5 |
| Tryptophan(W) | 0.5-3 | 0.5-3 | 1-4 | 1-5 | 3-8 | 3-8 |
| Aspartic acid(D) | 35-45 | 2-6 | 4-10 | 4-10 | 4-10 | 5-12 |
| Histidine(H) | 1-5 | 2-6 | 1-4 | 0.5-3 | 1-4 | 1-4 |
| Asparagine(N) | 1-4 | 1-5 | 2-5 | 2-6 | 2-6 | 2-5 |
| Arginine(R) | 0.5-3 | 1-5 | 1-5 | 1-4 | 0.5-3 | 0.5-3 |
| Glutamic acid(E) | 5-15 | 1-4 | 2-5 | 2-5 | 1-5 | 1-4 |
| Cysteine(C) | 0-0.001 | 0.01-0.1 | 0.01-0.05 | 0.01-0.1 | 0.01-0.1 | 0.01-0.05 |
| Leucine(L) | 2-6 | 15-25 | 5-15 | 4-10 | 5-15 | 5-12 |
| Glutamine(Q) | 0.5-4 | 1-4 | 1-4 | 1-5 | 1-4 | 0.5-3 |

-continued

| Amino acid distribution ratio for each position of amino acid(%) - VH_CDR3_12AA | | | | | | |
|---|---|---|---|---|---|---|
| Type of AA | 100b | 100c | 100d | 100e | 101 | 102 |
| Alanine(A) | 4-10 | 4-10 | 5-15 | 1-4 | 0.5-3 | 0.1-1 |
| Serine(S) | 5-15 | 5-15 | 3-8 | 1-4 | 0.5-3 | 2-6 |
| Glycine(G) | 5-15 | 5-15 | 5-15 | 0.5-3 | 0.5-3 | 0.01-0.05 |
| Phenylalanine(F) | 1-4 | 1-4 | 1-4 | 30-40 | 0.1-0.5 | 1-4 |
| Proline(P) | 1-4 | 2-5 | 2-6 | 0.5-3 | 0.1-1 | 3-8 |
| Valine(V) | 2-5 | 0.5-3 | 1-4 | 1-4 | 0.1-0.5 | 5-15 |
| Tyrosine(Y) | 10-20 | 15-25 | 20-30 | 1-4 | 0.1-1 | 45-55 |
| Methionine(M) | 0.01-0.05 | 0.5-4 | 0.01-0.1 | 10-20 | 0.01-0.1 | 0.01-0.05 |
| Threonine(T) | 3-8 | 1-5 | 1-5 | 0.5-3 | 0.5-3 | 0.5-3 |
| Lysine(K) | 0.5-3 | 1-4 | 0.5-3 | 0-0.001 | 0.01-0.05 | 0-0.001 |
| Isoleucine(I) | 1-8 | 1-4 | 1-5 | 3-8 | 0.1-1 | 3-8 |
| Tryptophan(W) | 3-8 | 2-6 | 3-8 | 0.5-3 | 0-0.001 | 0.01-0.05 |
| Aspartic acid(D) | 3-9 | 2-6 | 2-5 | 0.5-3 | 75-85 | 0.5-3 |
| Histidine(H) | 1-5 | 1-6 | 1-5 | 0.5-3 | 0.5-3 | 4-10 |
| Asparagine(N) | 3-8 | 3-9 | 1-5 | 0.5-3 | 1-4 | 1-5 |
| Arginine(R) | 1-8 | 1-4 | 0.5-3 | 0.1-1 | 0.1-1 | 0.5-3 |
| Glutamic acid(E) | 1-8 | 1-4 | 1-4 | 0.5-2 | 1-4 | 0.01-0.1 |
| Cysteine(C) | 0.01-0.1 | 0.01-0.1 | 0.01-0.1 | 0.01-0.05 | 0.01-0.05 | 0.01-0.1 |
| Leucine(L) | 5-15 | 5-12 | 9-15 | 20-30 | 0.5-3 | 5-12 |
| Glutamine(Q) | 1-5 | 0.5-3 | 0.5-3 | 0-0.001 | 1-4 | 0.01-0.05, | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 13 amino acids, the amino acid ratio for each position in CDRH3 has the following distribution ratio:

| Amino acid distribution ratio for each position of amino acid(%) - VH_CDR3_13AA | | | | | | | |
|---|---|---|---|---|---|---|---|
| Type of AA | 96 | 97 | 98 | 99 | 100 | 100a | 100b |
| Alanine(A) | 4-10 | 3-9 | 3-9 | 5-12 | 5-12 | 5-15 | 4-10 |
| Serine(S) | 1-5 | 5-15 | 5-15 | 10-20 | 10-20 | 5-15 | 5-15 |
| Glycine(G) | 5-15 | 5-15 | 5-15 | 10-20 | 5-15 | 5-15 | 5-12 |
| Phenylalanine(F) | 0.5-3 | 1-4 | 0.5-3 | 1-4 | 0.5-3 | 1-5 | 1-5 |
| Proline(P) | 0.5-3 | 2-6 | 2-5 | 1-4 | 1-4 | 2-5 | 1-5 |
| Valine(V) | 2-6 | 1-5 | 2-6 | 2-6 | 2-5 | 2-5 | 2-5 |
| Tyrosine(Y) | 0.5-3 | 3-8 | 5-12 | 5-15 | 5-15 | 5-15 | 10-20 |
| Methionine(M) | 0.1-1 | 0.5-3 | 1-4 | 0.5-3 | 0.1-1 | 0.01-0.05 | 0.01-0.05 |
| Threonine(T) | 0.5-3 | 2-6 | 3-8 | 2-6 | 3-9 | 3-8 | 3-8 |
| Lysine(K) | 0.5-3 | 2-6 | 1-4 | 1-4 | 1-4 | 0.5-3 | 0.5-3 |
| Isoleucine(I) | 0.5-3 | 2-6 | 1-4 | 1-4 | 1-5 | 1-4 | 1-4 |
| Tryptophan(W) | 0.5-3 | 1-4 | 1-4 | 2-5 | 2-6 | 2-6 | 3-8 |
| Aspartic acid(D) | 35-45 | 2-6 | 4-10 | 4-10 | 4-10 | 4-10 | 3-9 |
| Histidine(H) | 1-5 | 2-6 | 1-5 | 0.5-3 | 1-4 | 0.5-3 | 1-5 |
| Asparagine(N) | 0.5-3 | 1-4 | 1-5 | 2-6 | 3-8 | 3-8 | 3-9 |
| Arginine(R) | 0.5-3 | 2-5 | 1-4 | 1-4 | 0.5-3 | 0.5-3 | 1-5 |
| Glutamic acid(E) | 5-15 | 2-5 | 2-6 | 1-4 | 1-4 | 1-5 | 1-4 |
| Cysteine(C) | 0.01-0.05 | 0-0.001 | 0.01-0.05 | 0.01-0.1 | 0.01-0.05 | 0.01-0.05 | 0.01-0.05 |
| Leucine(L) | 2-6 | 10-20 | 5-15 | 4-10 | 5-15 | 5-12 | 5-15 |
| Glutamine(Q) | 1-4 | 1-4 | 1-4 | 1-4 | 1-4 | 0.5-3 | 1-5 |

| Type of AA | 100c | 100d | 100e | 100f | 101 | 102 |
|---|---|---|---|---|---|---|
| Alanine(A) | 4-10 | 2-6 | 5-15 | 1-4 | 0.3-1 | 0.1-1 |
| Serine(S) | 5-15 | 5-15 | 3-8 | 0.5-3 | 0.5-3 | 1-5 |
| Glycine(G) | 5-15 | 4-10 | 10-20 | 0.5-3 | 0.5-3 | 0-0.001 |
| Phenylalanine(F) | 1-4 | 1-4 | 1-4 | 35-45 | 0.5-3 | 1-4 |
| Proline(P) | 2-6 | 1-5 | 3-8 | 0.5-3 | 0.1-1 | 3-9 |
| Valine(V) | 0.5-3 | 1-4 | 0.5-3 | 1-4 | 0.1-1 | 10-20 |
| Tyrosine(Y) | 15-25 | 20-30 | 25-35 | 2-5 | 0.1-1 | 40-50 |
| Methionine(M) | 0.5-3 | 0.01-0.05 | 0.01-0.1 | 15-25 | 0.01-0.1 | 0.5-3 |
| Threonine(T) | 2-6 | 1-5 | 1-4 | 0.5-3 | 0.01-0.1 | 0.1-1 |
| Lysine(K) | 0.5-3 | 0.5-3 | 0.01-0.05 | 0-0.001 | 0-0.001 | 0-0.001 |
| Isoleucine(I) | 1-4 | 1-5 | 0.5-3 | 2-6 | 0.1-1 | 4-10 |
| Tryptophan(W) | 2-6 | 1-5 | 4-10 | 0.1-1 | 0-0.001 | 0.01-0.05 |
| Aspartic acid(D) | 3-8 | 4-10 | 1-5 | 0.5-3 | 85-95 | 0.5-3 |
| Histidine(H) | 1-5 | 1-5 | 1-5 | 0.5-3 | 0.5-3 | 4-10 |
| Asparagine(N) | 3-9 | 4-10 | 1-5 | 0.5-3 | 0.1-1 | 1-4 |
| Arginine(R) | 1-4 | 0.5-3 | 0.5-3 | 0.01-0.05 | 0.1-1 | 0.01-0.1 |
| Glutamic acid(E) | 1-5 | 2-6 | 0.5-3 | 0.5-3 | 0.5-3 | 0.01-0.05 |

| Amino acid distribution ratio for each position of amino acid(%) - VH_CDR3_13AA | | | | | | |
|---|---|---|---|---|---|---|
| Cysteine(C) | 0.01-0.1 | 0.01-0.05 | 0.02-0.2 | 0.01-0.1 | 0-0.001 | 0.01-0.1 |
| Leucine(L) | 5-12 | 5-15 | 3-8 | 15-25 | 0.5-3 | 5-12 |
| Glutamine(Q) | 0.5-8 | 0.5-3 | 0.5-3 | 0-0.001 | 0.5-3 | 0.01-0.1, | when the heavy-chain complementarity-determining region 3 (CDRH3) in the heavy-chain variable region having the sequence of VH3-15 (SEQ ID NO: 1), VH3-23 (SEQ ID NO: 6) or VH1-69 (SEQ ID NO: 11) has 14 amino acids, the amino acid ratio for each position in CDRH3 has the following distribution ratio:

| Amino acid distribution ratio for each position of amino acid(%) - VH_CDR3_14AA | | | | | | | |
|---|---|---|---|---|---|---|---|
| Type of AA | 96 | 97 | 98 | 99 | 100 | 100a | 100b |
| Alanine(A) | 4-10 | 0.1-1 | 5-12 | 5-12 | 5-12 | 5-15 | 4-10 |
| Serine(S) | 2-6 | 2-6 | 5-15 | 10-20 | 10-20 | 5-15 | 5-15 |
| Glycine(G) | 5-15 | 0.05-0.5 | 10-20 | 10-20 | 5-15 | 10-20 | 5-15 |
| Phenylalanine(F) | 0.5-3 | 1-5 | 0.5-3 | 1-5 | 1-3 | 1-4 | 1-4 |
| Proline(P) | 0.5-3 | 3-8 | 1-4 | 1-4 | 1-4 | 1-5 | 1-4 |
| Valine(V) | 3-8 | 10-20 | 2-6 | 2-6 | 1-5 | 2-5 | 2-5 |
| Tyrosine(Y) | 0.1-1 | 40-50 | 4-10 | 5-15 | 5-15 | 5-15 | 10-20 |
| Methionine(M) | 0.1-1 | 0.5-3 | 1-4 | 0.5-3 | 0.1-1 | 0.01-0.05 | 0-0.001 |
| Threonine(T) | 0.5-3 | 0.05-0.5 | 3-8 | 2-6 | 3-9 | 3-8 | 3-8 |
| Lysine(K) | 0.5-3 | 0-0.001 | 1-4 | 1-4 | 0.5-3 | 0.5-3 | 1-4 |
| Isoleucine(I) | 0.5-3 | 4-10 | 1-4 | 1-5 | 1-4 | 2-5 | 1-4 |
| Tryptophan(W) | 0.1-1 | 0.05-0.5 | 1-4 | 1-5 | 3-8 | 3-8 | 3-8 |
| Aspartic acid(D) | 35-45 | 0.5-3 | 4-10 | 4-10 | 4-10 | 4-10 | 3-9 |
| Histidine(H) | 1-4 | 4-10 | 1-5 | 0.5-3 | 1-4 | 0.5-8 | 1-5 |
| Asparagine(N) | 1-4 | 1-4 | 1-5 | 2-6 | 3-8 | 3-8 | 3-9 |
| Arginine(R) | 0.5-3 | 0-0.001 | 1-4 | 1-4 | 0.5-3 | 0.5-3 | 1-5 |
| Glutamic acid(E) | 5-15 | 0.01-0.1 | 2-6 | 2-5 | 1-4 | 1-4 | 1-5 |
| Cysteine(C) | 0.01-0.1 | 0.05-0.5 | 0.01-0.05 | 0-0.001 | 0.01-0.1 | 0.01-0.05 | 0.01-0.05 |
| Leucine(L) | 3-8 | 4-10 | 5-15 | 3-9 | 5-12 | 5-15 | 5-15 |
| Glutamine(Q) | 0.5-3 | 0.01-0.1 | 1-4 | 1-4 | 1-3 | 0.5-3 | 1-5 |
| Type of AA | 100d | 100c | 100e | 100f | 100g | 101 | 102 |
| Alanine(A) | 2-6 | 4-10 | 1-4 | 5-15 | 1-4 | 0.5-3 | 0.5-3 |
| Serine(S) | 5-15 | 5-15 | 5-12 | 1-5 | 1-4 | 0.1-1 | 2-6 |
| Glycine(G) | 5-12 | 5-15 | 5-15 | 10-20 | 0.3-2 | 0.5-8 | 0-0.001 |
| Phenylalanine(F) | 1-5 | 1-4 | 1-4 | 1-4 | 30-40 | 0.1-1 | 0.5-3 |
| Proline(P) | 1-4 | 2-6 | 1-4 | 3-8 | 0.5-3 | 0.5-3 | 3-9 |
| Valine(V) | 1-4 | 1-4 | 0.5-3 | 1-4 | 0.5-3 | 0.1-1 | 15-25 |
| Tyrosine(Y) | 20-30 | 15-25 | 25-35 | 25-35 | 1-4 | 0.01-0.05 | 35-45 |
| Methionine(M) | 0-0.001 | 0.5-3 | 0.5-3 | 0.5-3 | 20-30 | 0.01-0.05 | 0-0.001 |
| Threonine(T) | 1-5 | 1-5 | 1-5 | 0.5-3 | 0.1-1 | 0.3-2 | 0.1-1 |
| Lysine(K) | 0.5-3 | 1-4 | 0.5-3 | 0-0.001 | 0-0.001 | 0-0.001 | 0-0.001 |
| Isoleucine(I) | 1-5 | 1-5 | 0.5-3 | 0.5-3 | 1-5 | 0.1-1 | 2-6 |
| Tryptophan(W) | 1-5 | 2-6 | 2-6 | 5-12 | 0.1-0.5 | 0-0.001 | 0.01-0.05 |
| Aspartic acid(D) | 3-9 | 3-8 | 4-10 | 0.5-3 | 0.1-1 | 80-90 | 0.5-3 |
| Histidine(H) | 1-5 | 1-4 | 2-6 | 1-5 | 0.5-3 | 0.5-3 | 4-10 |
| Asparagine(N) | 3-9 | 3-8 | 5-15 | 1-5 | 0.1-1 | 0.5-3 | 1-4 |
| Arginine(R) | 1-4 | 1-5 | 0.5-3 | 0.5-3 | 0.01-0.1 | 0.1-1 | 0.01-0.05 |
| Glutamic acid(E) | 2-5 | 1-4 | 1-4 | 0.5-3 | 0.1-1 | 1-4 | 0-0.001 |
| Cysteine(C) | 0-0.001 | 0.01-0.05 | 0.01-0.1 | 0.01-1 | 0.01-0.1 | 0-0.001 | 0.01-0.1 |
| Leucine(L) | 5-15 | 5-15 | 2-6 | 4-10 | 15-25 | 0.5-3 | 5-15 |
| Glutamine(Q) | 0.5-3 | 0.5-3 | 0.5-3 | 0.1-1 | 0-0.001 | 1-4 | 0-0.001, | the amino acid ratio for each position in the light-chain complementarity-determining region 1 (CDRL1) in the light-chain variable region having the sequence of VK1-39 (SEQ ID NO: 16) has the following distribution ratio:

| Amino acid distribution ratio for each position of amino acid(%) - Vx1-39_CDR1 | | | | | | |
|---|---|---|---|---|---|---|
| Type of AA | 24 | 25 | 26 | 27 | 28 | 29 |
| Alanine(A) | 0-0.001 | 95-99.99 | 0-0.01 | 0-0.001 | 3-6 | 0-0.1 |
| Serine(S) | 90-95 | 0-0.05 | 95-99.99 | 0-0.03 | 33-38 | 0-0.05 |
| Glycine(G) | 4-8 | 0-0.05 | 0-0.1 | 0-0.001 | 8-12 | 0-0.001 |
| Phenylalanine(F) | 0-0.001 | 0-0.001 | 0-0.001 | 0-0.001 | 0.5-1.5 | 0-0.001 |

-continued

| Amino acid distribution ratio for each position of amino acid(%) - Vx1-39_CDR1 | | | | | | |
|---|---|---|---|---|---|---|
| Proline(P) | 0-0.001 | 0-0.01 | 0-0.001 | 0-0.001 | 0.5-1.5 | 0-0.001 |
| Valine(V) | 0-0.01 | 0-0.3 | 0-0.1 | 0-0.001 | 0.5-1.5 | 80-90 |
| Tyrosine(Y) | 0-0.001 | 0-0.001 | 0-0.001 | 0-0.001 | 0.5-1.5 | 0-0.09 |
| Methionine(M) | 0-0.03 | 0-0.001 | 0-0.001 | 0-0.001 | 0-0.05 | 0-0.001 |
| Threonine(T) | 0-0.001 | 0-0.05 | 0-0.001 | 0-0.01 | 6-10 | 0-0.001 |
| Lysine(K) | 0-0.01 | 0-0.001 | 0-0.001 | 0-0.01 | 0.4-1.0 | 0-0.01 |
| Isoleucine(I) | 0-0.05 | 0-0.001 | 0-0.08 | 0-0.001 | 0.5-1.5 | 10-15 |
| Tryptophan(W) | 0-0.001 | 0-0.001 | 0-0.001 | 0-0.001 | 0-0.01 | 0-0.001 |
| Aspartic acid(D) | 0-0.01 | 0-0.001 | 0-0.001 | 0-0.05 | 29-33 | 0-0.01 |
| Histidine(H) | 0-0.001 | 0-0.001 | 0-0.001 | 0-0.3 | 1.0-2.0 | 0-0.001 |
| Asparagine(N) | 0-0.05 | 0-0.001 | 0-0.08 | 0-0.001 | 0-0.005 | 0-0.001 |
| Arginine(R) | 0-0.3 | 0-0.1 | 0-0.05 | 93-96 | 0-1.0 | 0-0.03 |
| Glutamic acid(E) | 0-0.01 | 0-0.05 | 0-0.03 | 0-0.1 | 0-0.03 | 0-0.01 |
| Cysteine(C) | 0-0.03 | 0-0.01 | 0-0.001 | 0-0.001 | 0-0.05 | 0-0.03 |
| Leucine(L) | 0-0.001 | 0-0.001 | 0-0.001 | 0-0.8 | 0-0.1 | 1-5 |
| Glutamine(Q) | 0-0.01 | 0-0.001 | 0-0.001 | 1-5 | 0-0.03 | 0-0.01 |

| Type of AA | 30 | 31 | 32 | 33 | 34 |
|---|---|---|---|---|---|
| Alanine(A) | 3-7 | 0.5-3 | 0.5-3 | 0-0.01 | 40-45 |
| Serine(S) | 30-40 | 10-20 | 5-10 | 0-0.03 | 1-4 |
| Glycine(G) | 4-10 | 0.5-3 | 0.5-3 | 0-0.01 | 1-4 |
| Phenylalanine(F) | 0-1 | 0.1-2 | 5-10 | 0-0.001 | 0-0.01 |
| Proline(P) | 0-0.05 | 0.5-3 | 0-0.07 | 0-0.1 | 0-0.01 |
| Valine(V) | 0-1 | 0.05-0.3 | 0-0.05 | 0-0.03 | 0.5-2 |
| Tyrosine(Y) | 1-4 | 0.5-3 | 35-45 | 0-0.03 | 0-0.03 |
| Methionine(M) | 0-0.001 | 0.1-0.8 | 0-0.001 | 0-0.001 | 0-0.001 |
| Threonine(T) | 3-7 | 5-15 | 0-0.1 | 0-0.01 | 0-0.1 |
| Lysine(K) | 1-5 | 5-15 | 0-0.03 | 0-0.01 | 0-0.05 |
| Isoleucine(I) | 1-5 | 1-5 | 0-0.001 | 3-8 | 0-0.1 |
| Tryptophan(W) | 0-0.001 | 0-0.001 | 10-20 | 0-0.001 | 0-0.001 |
| Aspartic acid(D) | 4-10 | 3-8 | 3-8 | 0-0.01 | 0.5-1.5 |
| Histidine(H) | 0.5-3 | 1-4 | 5-10 | 0-0.001 | 1-3 |
| Asparagine(N) | 20-25 | 35-45 | 3-8 | 0-0.001 | 40-50 |
| Arginine(R) | 2-6 | 1-4 | 0.5-3 | 0-0.001 | 0-0.03 |
| Glutamic acid(E) | 0.5-3 | 0.1-2 | 0.5-3 | 0-0.001 | 0-0.05 |
| Cysteine(C) | 0-0.01 | 0-0.01 | 0-0.1 | 0-0.001 | 0-0.001 |
| Leucine(L) | 1-3 | 0.1-1 | 2-6 | 90-99.99 | 0-0.001 |
| Glutamine(Q) | 0-0.01 | 0-0.01 | 0.5-3 | 0-0.001 | 0-0.001, | the amino acid ratio for each position in the light-chain complementarity-determining region 2 (CDRL2) in the light-chain variable region having the sequence of VK1-39 (SEQ ID NO: 16) has the following distribution ratio:

| Amino acid distribution ratio for each position of amino acid (%)-$V_K$1-39_CDR2 | | | | | | | |
|---|---|---|---|---|---|---|---|
| Type of AA | 50 | 51 | 52 | 53 | 54 | 55 | 56 |
| Alanine (A) | 20~30 | 75~85 | 0~0.001 | 1~5 | 0~0.001 | 1~3 | 1~5 |
| Serine (S) | 5~10 | 1~5 | 0.01~0.1 | 20~30 | 0~0.001 | 0~0.03 | 60~70 |
| Glycine (G) | 3~8 | 0.5~3 | 0~0.001 | 0.1~1 | 0~0.001 | 0.5~3 | 2~6 |
| Phenylalanine (F) | 0.1~0.8 | 0~0.01 | 0~0.01 | 0.5~3 | 0.01~0.3 | 0.1~2 | 0.5~2 |
| Proline (P) | 0.1~0.5 | 0.5~2 | 0~0.001 | 0~0.01 | 0.05~0.3 | 0.1~2 | 0.5~2 |
| Valine (V) | 0.5~3 | 2~6 | 0~0.001 | 0.5~3 | 0.01~0.03 | 0.1~2 | 0.5~2 |
| Tyrosine (Y) | 0.5~3 | 0~0.01 | 0~0.001 | 1~3 | 0.01~0.3 | 0.5~3 | 0.1~1.5 |
| Methionine (M) | 0.5~3 | 0~0.001 | 0~0.001 | 0~0.001 | 0~0.01 | 0~0.03 | 0~0.03 |
| Threonine (T) | 2~6 | 4~9 | 3~7 | 15~25 | 0~0.01 | 0~0.01 | 5~15 |
| Lysine (K) | 15~25 | 0~0.01 | 0.01~0.1 | 1~5 | 0~0.001 | 1~5 | 0.1~1.5 |
| Isoleucine (I) | 0.5~3 | 0.5~3 | 0~0.03 | 3~8 | 0~0.01 | 0~0.01 | 1~3 |
| Tryptophan (W) | 1~3 | 0~0.001 | 0~0.001 | 0~0.001 | 0~0.001 | 0~0.001 | 0~0.01 |
| Aspartic acid (D) | 10~20 | 0~0.03 | 0~0.05 | 1~5 | 0~0.001 | 1~4 | 3~7 |
| Histidine (H) | 0.1~0.8 | 0~0.001 | 0~0.001 | 0.1~1 | 5~15 | 5~8 | 0~0.01 |
| Asparagine (N) | 0.01~0.03 | 0~0.001 | 90~99 | 20~30 | 0~0.03 | 0.5~3 | 0.5~3 |
| Arginine (R) | 0.5~3 | 0~0.01 | 0~0.001 | 0.5~3 | 0~0.03 | 0.5~2 | 0.5~3 |
| Glutamic acid (E) | 5~10 | 1~3 | 0~0.001 | 0.01~0.05 | 0~0.001 | 35~45 | 0~0.05 |
| Cysteine (C) | 0.01~0.08 | 0~0.03 | 0~0.001 | 0~0.01 | 0~0.001 | 0~0.01 | 0.01~0.1 |
| Leucine (L) | 0.5~3 | 0~0.001 | 0~0.001 | 0.1~1 | 85~95 | 1~3 | 1~5 |
| Glutamine (Q) | 0.5~3 | 0~0.01 | 0~0.001 | 0.01~0.03 | 0~0.001 | 33~42 | 0~0.001, | the amino acid ratio for each position in the light-chain complementarity-determining region 3 (CDRL3) in the light-chain variable region having the sequence of VK1-39 (SEQ ID NO: 16) has the following distribution ratio:

| Amino acid distribution ratio for each position of amino acid (%)-V$_K$1-39_CDR3 | | | | | | | | |
|---|---|---|---|---|---|---|---|---|
| Type of AA | 89 | 90 | 91 | 92 | 93 | 94 | 95 | 96 |
| Alanine (A) | 0~0.001 | 0.01~0.03 | 2~6 | 0.5~1.5 | 1~5 | 8~15 | 0.01~00.5 | 0.1~1 |
| Serine (S) | 0~0.01 | 0.01~0.03 | 10~20 | 3~8 | 40~50 | 3~10 | 0.1~0.5 | 0.5~2 |
| Glycine (G) | 0.01~0.05 | 0~0.005 | 0.5~3 | 0.5~1.5 | 1~5 | 0.1~1.0 | 0~0.001 | 0.5~2 |
| Phenylalanine (F) | 0~0.001 | 0~0.001 | 1~4 | 2~6 | 0.5~1.5 | 5~13 | 0~0.001 | 3~9 |
| Proline (P) | 0.01~0.03 | 0.01~0.03 | 0.01~0.1 | 0.01~0.05 | 0.01~0.1 | 1~3 | 90~99.99 | 2~8 |
| Valine (V) | 0~0.001 | 0~0.001 | 0.5~2 | 0.1~0.5 | 0.5~1.5 | 1~4 | 0~0.001 | 0.5~3 |
| Tyrosine (Y) | 0~0.001 | 0~0.01 | 50~60 | 30~40 | 0.5~1.5 | 20~30 | 0~0.001 | 10~15 |
| Methionine (M) | 0~0.001 | 0~0.01 | 0~0.001 | 0~0.01 | 0~0.001 | 1~3 | 0~0.001 | 0.01~0.05 |
| Threonine (T) | 0~0.001 | 0~0.001 | 2~6 | 0.5~2 | 8~13 | 10~20 | 0.01~0.1 | 0.01~0.05 |
| Lysine (K) | 0~0.001 | 0.01~0.05 | 0.01~0.05 | 1~5 | 0.5~3 | 0~0.001 | 0~0.001 | 0.5~2 |
| Isoleucine (I) | 0~0.01 | 0~0.001 | 0.01~0.05 | 0.5~2 | 1~5 | 2~6 | 0~0.001 | 0.5~3 |
| Tryptophan (W) | 0.01~0.1 | 0~0.001 | 0~0.001 | 0~0.001 | 0~0.001 | 0.01~0.05 | 0~0.001 | 10~20 |
| Aspartic acid (D) | 0~0.001 | 0.1~0.5 | 1~4 | 5~15 | 3~8 | 0.5~2 | 0~0.001 | 0.1~1 |
| Histidine (H) | 0~0.001 | 6~12 | 6~10 | 3~9 | 0.5~2 | 1~3 | 0~0.001 | 1~4 |
| Asparagine (N) | 0~0.001 | 0~0.001 | 0.5~3 | 20~30 | 10~20 | 3~5 | 0~0.001 | 0.5~2 |
| Arginine (R) | 90~98 | 0.01~0.05 | 0.01~0.05 | 0.1~1.0 | 0.5~3 | 0.1~0.5 | 0.01~0.1 | 3~8 |
| Glutamic acid (E) | 0~0.001 | 1~4 | 0~0.01 | 0.5~3 | 0.5~3 | 0~0.001 | 0~0.001 | 0.1~1 |
| Cysteine (C) | 0~0.001 | 0~0.001 | 0.01~0.05 | 0.01~0.1 | 0.01~0.05 | 0.01~0.05 | 0~0.001 | 0.01~0.05 |
| Leucine (L) | 4~10 | 0.01~0.05 | 3~7 | 0.5~3 | 1~3 | 8~13 | 0.01~0.1 | 35~45 |
| Glutamine (Q) | 0.01~0.1 | 85~95 | 0~0.01 | 0.1~1.0 | 0.01~0.05 | 0~0.001 | 0.01~0.1 | 1~5, | the amino acid ratio for each position in the light-chain complementarity-determining region 1 (CDRL1) in the light-chain variable region having the sequence of VK3-20 (SEQ ID NO: 21) has the following distribution ratio:

| Amino acid distribution ratio for each position of amino acid (%)-V$_K$3-20_CDR1 | | | | | | |
|---|---|---|---|---|---|---|
| Type of AA | 3 | 4 | 5 | 6 | 7 | 8 |
| Alanine (A) | 0~0.001 | 95~99.99 | 0~0.001 | 0~0.001 | 0.5~2 | 0.5~2 |
| Serine (S) | 90~99.99 | 0.01~0.05 | 95~99.99 | 0.1~0.5 | 65~75 | 0.01~0.1 |
| Glycine (G) | 2~10 | 0.01~0.05 | 0.05~0.5 | 0~0.001 | 0.01~0.1 | 0~0.01 |
| Phenylalanine (F) | 0~0.001 | 0~0.001 | 0~0.001 | 0~0.001 | 0.5~2 | 1~3 |
| Proline (P) | 0~0.001 | 0~0.001 | 0~0.001 | 0.01~0.1 | 0.1~0.1 | 0.01~0.1 |
| Valine (V) | 0.01~0.05 | 0.01~0.1 | 0.01~0.1 | 0~0.01 | 0.05~0.5 | 50~60 |
| Tyrosine (Y) | 0.005~0.03 | 0~0.001 | 0.01~0.1 | 0~0.001 | 0.5~2 | 0.01~0.1 |
| Methionine (M) | 0.005~0.03 | 0~0.001 | 0~0.001 | 0~0.001 | 0~0.001 | 0.5~1.5 |
| Threonine (T) | 0~0.001 | 0.01~0.1 | 0~0.01 | 0~0.05 | 5~15 | 0.01~0.05 |
| Lysine (K) | 0.01~0.05 | 0~0.001 | 0~0.001 | 2~8 | 0~0.05 | 0~0.001 |
| Isoleucine (I) | 0~0.01 | 0~0.001 | 0.01~0.1 | 0~0.001 | 1~5 | 20~30 |
| Tryptophan (W) | 0~0.001 | 0~0.001 | 0~0.001 | 0~0.001 | 0~0.001 | 0~0.05 |
| Aspartic acid (D) | 0~0.001 | 0~0.001 | 0~0.001 | 0~0.001 | 0.5~2 | 0~0.01 |
| Histidine (H) | 0~0.001 | 0~0.001 | 0~0.001 | 2~8 | 0.3~1.5 | 0~0.001 |
| Asparagine (N) | 0.01~0.1 | 0~0.001 | 0.01~0.1 | 0.1~1.0 | 3~9 | 0~0.01 |
| Arginine (R) | 0.01~0.1 | 0.01~0.1 | 0.01~0.1 | 0.05~0.5 | 0.5~2 | 0.01~0.05 |
| Glutamic acid (E) | 0.01~0.1 | 0.01~0.1 | 0.01~0.1 | 0~0.05 | 0~0.05 | 0~0.001 |
| Cysteine (C) | 0.01~0.05 | 0.01~0.1 | 0.01~0.1 | 0~0.001 | 0~0.05 | 0.01~0.1 |
| Leucine (L) | 0~0.001 | 0~0.001 | 0~0.001 | 0~0.05 | 0.01~0.5 | 10~20 |
| Glutamine (Q) | 0~0.01 | 0~0.001 | 0~0.001 | 85~95 | 0~0.001 | 0~0.01 |
| Type of AA | 9 | 10 | 11 | 12 | 13 | 14 |
| Alanine (A) | 0~0.001 | 0~0.001 | 0~0.001 | 0~0.01 | 0~0.001 | 95~99.99 |
| Serine (S) | 0~0.001 | 0~0.001 | 0~0.001 | 5~15 | 0.05~0.5 | 0.01~0.1 |
| Glycine (G) | 0~0.001 | 0~0.001 | 0~0.001 | 0~0.05 | 80~90 | 0~0.01 |
| Phenylalanine (F) | 0~0.001 | 0~0.001 | 0~0.001 | 5~15 | 0~0.01 | 0~0.001 |
| Proline (P) | 0~0.001 | 0~0.001 | 0~0.001 | 0.01~0.1 | 0~0.001 | 0~0.05 |
| Valine (V) | 0~0.001 | 0~0.001 | 0~0.001 | 0~0.001 | 2~8 | 0.01~0.1 |
| Tyrosine (Y) | 0~0.001 | 0~0.001 | 0~0.001 | 55~65 | 0~0.001 | 0~0.001 |
| Methionine (M) | 0~0.001 | 0~0.001 | 0~0.001 | 0.01~0.1 | 0~0.05 | 0~0.001 |
| Threonine (T) | 0~0.001 | 0~0.001 | 0~0.001 | 0.01~0.1 | 0~0.001 | 0.01~0.1 |
| Lysine (K) | 0~0.001 | 0~0.001 | 0~0.001 | 0.5~2 | 0~0.001 | 0~0.001 |
| Isoleucine (I) | 0~0.001 | 0~0.001 | 0~0.001 | 0~0.001 | 0~0.01 | 0~0.001 |
| Tryptophan (W) | 0~0.001 | 0~0.001 | 0~0.001 | 0.5~1.5 | 0~0.001 | 0~0.001 |

-continued

| Amino acid distribution ratio for each position of amino acid (%)-V$_K$3-20_CDR1 | | | | | | |
|---|---|---|---|---|---|---|
| Aspartic acid (D) | 0~0.001 | 0~0.001 | 0~0.001 | 1~4 | 4~10 | 0~0.001 |
| Histidine (H) | 0~0.001 | 0~0.001 | 0~0.001 | 3~9 | 0~0.01 | 0~0.001 |
| Asparagine (N) | 0~0.001 | 0~0.001 | 0~0.001 | 3~9 | 0~0.05 | 0~0.001 |
| Arginine (R) | 0~0.001 | 0~0.001 | 0~0.001 | 0.1~1 | 0.05~0.5 | 0.01~0.1 |
| Glutamic acid (E) | 0~0.001 | 0~0.001 | 0~0.001 | 0~0.001 | 0~0.01 | 0.01~0.1 |
| Cysteine (C) | 0~0.001 | 0~0.001 | 0~0.001 | 0.01~0.1 | 0.01~0.1 | 0~0.01 |
| Leucine (L) | 0~0.001 | 0~0.001 | 0~0.001 | 0.5~3 | 0~0.05 | 0.01~0.1 |
| Glutamine (Q) | 0~0.001 | 0~0.001 | 0~0.001 | 0.5~3 | 0~0.001 | 0.01~0.1 , | the amino acid ratio for each position in the light-chain complementarity-determining region 2 (CDRL2) in the light-chain variable region having the sequence of VK3-20 (SEQ ID NO: 21) has the following distribution ratio:

| Amino acid distribution ratio for each position of amino acid (%)-V$_K$3-20 & 20-2_CDR2 | | | | | | | | | |
|---|---|---|---|---|---|---|---|---|---|
| Type of AA | 3 | 4 | 5 | 6 | 7 | 8 | 9 | 10 | 11 |
| Alanine (A) | 0~0.001 | 5~15 | 70~80 | 0.5~2 | 0.5~3 | 0~0.001 | 90~99.99 | 60~70 | 0.01~0.05 |
| Serine (S) | 3~9 | 3~8 | 2~7 | 80~90 | 20~30 | 0.01~0.1 | 0.01~0.5 | 5~10 | 0~0.01 |
| Glycine (G) | 0~0.01 | 25~35 | 0.5~2 | 0~0.01 | 0.5~2 | 0.01~0.1 | 0~0.01 | 0~0.001 | 3~8 |
| Phenylalanine (F) | 4~10 | 0.01~0.05 | 0.01~0.1 | 2~7 | 0.5~2 | 0~0.001 | 0~0.01 | 0~0.01 | 0~0.001 |
| Proline (P) | 0.01~0.1 | 0.01~0.05 | 0.1~1 | 0.1~1 | 0.01~0.05 | 0.01~0.1 | 0~0.01 | 5~15 | 0~0.001 |
| Valine (V) | 0~0.001 | 0.5~1.5 | 2~6 | 0.5~1.5 | 0.1~1 | 0.01~0.1 | 1~3 | 0.01~0.05 | 0~0.01 |
| Tyrosine (Y) | 65~75 | 0.1~1 | 0.01~0.1 | 1~3 | 0.5~2 | 0~0.001 | 0~0.001 | 0~0.001 | 0.01~0.05 |
| Methionine (M) | 0~0.001 | 0~0.001 | 0~0.001 | 0~0.001 | 0.1~2 | 0~0.001 | 0~0.001 | 0~0.001 | 0~0.001 |
| Threonine (T) | 0.01~0.1 | 0.5~3 | 5~15 | 1~4 | 10~20 | 0~0.01 | 0.01~0.1 | 10~20 | 0~0.01 |
| Lysine (K) | 0~0.01 | 0~0.01 | 0~0.001 | 0~0.001 | 4~10 | 0~0.001 | 0~0.001 | 0~0.001 | 0~0.001 |
| Isoleucine (I) | 0~0.001 | 0~0.01 | 1~4 | 0.5~1.5 | 2~7 | 0~0.001 | 0~0.001 | 0~0.01 | 0~0.001 |
| Tryptophan (W) | 0~0.001 | 0~0.01 | 0~0.001 | 0~0.001 | 0~0.001 | 0~0.001 | 0~0.001 | 0~0.001 | 0~0.001 |
| Aspartic acid (D) | 0~0.001 | 35~45 | 0.01~0.1 | 0~0.001 | 1~4 | 0~0.001 | 00.1~0.05 | 0.01~0.05 | 88~98 |
| Histidine (H) | 0~0.001 | 0.5~3 | 0.01~0.1 | 0.1~0.8 | 1~4 | 0.01~0.1 | 0~0.001 | 0~0.001 | 0~0.01 |
| Asparagine (N) | 0~0.001 | 1~4 | 0.01~0.1 | 0.1~0.8 | 30~40 | 0~0.001 | 0~0.001 | 0~0.001 | 0.01~0.05 |
| Arginine (R) | 0~0.001 | 0.5~2 | 0~0.01 | 0~0.01 | 1~4 | 95~99.99 | 0~0.01 | 0~0.001 | 0~0.001 |
| Glutamic acid (E) | 0~0.001 | 1~5 | 0.5~2 | 0~0.01 | 0~0.01 | 0~0.001 | 0~0.001 | 0~0.001 | 0.01~0.05 |
| Cysteine (C) | 0~0.001 | 0.01~0.1 | 0.01~0.1 | 0~0.05 | 0~0.01 | 0.01~0.2 | 0.01~0.05 | 0.01~0.05 | 0~0.001 |
| Leucine (L) | 0~0.001 | 0.5~2 | 0.5~1.5 | 0.5~2 | 0.5~2 | 0.01~0.2 | 0.01~0.05 | 0.01~0.05 | 0~0.001 |
| Glutamine (Q) | 0~0.001 | 0.01~0.1 | 0.10~0.1 | 0~0.001 | 0~0.001 | 0~0.001 | 0~0.001 | 0~0.001 | 0~0.001, | the amino acid ratio for each position in the light-chain complementarity-determining region 3 (CDRL3) in the light-chain variable region having the sequence of VK3-20 (SEQ ID NO: 21) has the following distribution ratio:

| Amino acid distribution ratio for each position of amino acid (%)-V$_K$3-20 & 20-2_CDR3 | | | | | | | | |
|---|---|---|---|---|---|---|---|---|
| Type of AA | 4 | 5 | 6 | 7 | 8 | 9 | 10 | 11 |
| Alanine (A) | 0~0.001 | 0.01~0.05 | 4~10 | 2~6 | 1~3 | 3~8 | 0.01~0.05 | 0.1~0.5 |
| Serine (S) | 0~0.01 | 0.01~0.05 | 4~10 | 8~18 | 20~30 | 30~40 | 0.05~0.3 | 0.5~2 |
| Glycine (G) | 0~0.01 | 0~0.001 | 1~4 | 10~20 | 2~4 | 0.1~1 | 0~0.001 | 0.5~2 |
| Phenylalanine (F) | 0~0.001 | 0~0.001 | 2~5 | 0.5~2 | 0.1~1 | 0.5~3 | 0~0.001 | 2~7 |
| Proline (P) | 0~0.001 | 0~0.001 | 0.01~0.1 | 0.01~0.1 | 0.01~0.1 | 1~4 | 95~99.99 | 2~7 |
| Valine (V) | 0~0.001 | 0~0.001 | 0.1~0.5 | 0.5~2 | 0.1~1 | 0.1~1 | 0~0.001 | 0.5~3 |
| Tyrosine (Y) | 0~0.001 | 0~0.01 | 55~65 | 10~20 | 0.5~3 | 1~5 | 0~0.001 | 5~15 |
| Methionine (M) | 0~0.001 | 0~0.001 | 0~0.001 | 0~0.001 | 0~0.001 | 0~0.001 | 0~0.001 | 0~0.01 |
| Threonine (T) | 0~0.001 | 0~0.001 | 0.5~2 | 2~6 | 4~10 | 6~15 | 0.01~0.05 | 0.01~0.05 |
| Lysine (K) | 0~0.001 | 0~0.02 | 0.01~0.05 | 0.5~2 | 1~4 | 0~0.001 | 0~0.001 | 0.1~1 |
| Isoleucine (I) | 0~0.001 | 0~0.001 | 0.01~0.05 | 1~3 | 1~4 | 0.5~3 | 0~0.001 | 0.5~2 |
| Tryptophan (W) | 0.05~0.5 | 0~0.001 | 0.1~0.5 | 0~0.02 | 0~0.001 | 20~30 | 0~0.001 | 10~20 |
| Aspartic acid (D) | 0~0.001 | 0~0.001 | 0.5~2 | 4~10 | 3~10 | 0.01~0.05 | 0~0.001 | 0.1~1 |
| Histidine (H) | 0~0.001 | 5~15 | 2~6 | 1~5 | 3~8 | 0~0.01 | 0~0.001 | 1~5 |
| Asparagine (N) | 0~0.001 | 0~0.001 | 0.5~2 | 10~20 | 20~30 | 0.5~3 | 0~0.001 | 0.1~1 |
| Arginine (R) | 88~98 | 0.03~0.3 | 4~8 | 0.1~1 | 0.5~3 | 0.1~1 | 0.02~0.1 | 3~9 |

-continued

| Amino acid distribution ratio for each position of amino acid (%)-$V_K$3-20 & 20-2_CDR3 | | | | | | | | |
|---|---|---|---|---|---|---|---|---|
| Type of AA | 4 | 5 | 6 | 7 | 8 | 9 | 10 | 11 |
| Glutamic acid (E) | 0~0.001 | 0~0.01 | 0~0.02 | 0.5~3 | 0.5~3 | 0~0.001 | 0~0.001 | 0.1~1 |
| Cysteine (C) | 0~0.001 | 0~0.001 | 0.1~0.5 | 0.01~0.05 | 0.01~0.05 | 0~0.01 | 0~0.001 | 0.01~0.1 |
| Leucine (L) | 2~5 | 0~0.05 | 0.5~2 | 5~15 | 1~3 | 5~10 | 0.05~0.5 | 38~48 |
| Glutamine (Q) | 0.01~0.1 | 85~95 | 0.01~0.1 | 0~0.01 | 6~10 | 0~0.001 | 0.05~0.5 | 1~6, | the amino acid ratio for each position in the light-chain complementarity-determining region 1 (CDRL1) in the light-chain variable region having the sequence of VK3-20-2 (SEQ ID NO: 26) has the following distribution ratio:

| Amino acid distribution ratio for each position of amino acid (%)-$V_K$3-20-2_CDR1 | | | | | |
|---|---|---|---|---|---|
| Type of AA | 3 | 4 | 5 | 6 | 7 |
| Alanine (A) | 0~0.001 | 95~99.99 | 0~0.001 | 0~0.001 | 0.5~3 |
| Serine (S) | 90~99.99 | 0.01~0.1 | 95~99.99 | 0.01~0.1 | 60~70 |
| Glycine (G) | 3~9 | 0.01~0.1 | 0.01~0.1 | 0~0.01 | 1~4 |
| Phenylalanine (F) | 0~0.001 | 0~0.001 | 0~0.001 | 0~0.001 | 0.01~0.1 |
| Proline (P) | 0~0.001 | 0~0.01 | 0~0.001 | 0.01~0.1 | 0.1~1 |
| Valine (V) | 0.01~0.05 | 0.01~0.1 | 0.01~0.1 | 0~0.01 | 0.01~0.1 |
| Tyrosine (Y) | 0~0.001 | 0~0.001 | 0~0.001 | 0~0.01 | 0.5~3 |
| Methionine (M) | 0.01~0.05 | 0~0.001 | 0~0.001 | 0~0.001 | 0~0.001 |
| Threonine (T) | 0~0.01 | 0.01~0.1 | 0~0.01 | 0~0.01 | 3~8 |
| Lysine (K) | 0~0.01 | 0~0.001 | 0~0.01 | 0~0.01 | 0.01~0.05 |
| Isoleucine (I) | 0.01~0.05 | 0~0.001 | 0.01~0.1 | 0~0.01 | 0.5~2 |
| Tryptophan (W) | 0~0.001 | 0~0.01 | 0~0.001 | 0~0.001 | 0~0.001 |
| Aspartic acid (D) | 0~0.01 | 0~0.001 | 0~0.001 | 0.01~0.1 | 1~4 |
| Histidine (H) | 0~0.001 | 0~0.001 | 0~0.001 | 0~0.001 | 0~0.01 |
| Asparagine (N) | 0.05~0.1 | 0~0.001 | 0.01~0.1 | 0~0.01 | 10~20 |
| Arginine (R) | 0.01~0.1 | 0.01~0.1 | 0.01~0.1 | 90~99.99 | 0.5~3 |
| Glutamic acid (E) | 0.01~0.1 | 0.01~0.1 | 0.01~0.1 | 0.01~0.1 | 0~0.01 |
| Cysteine (C) | 0~0.01 | 0.01~0.1 | 0~0.01 | 0~0.01 | 0.01~0.1 |
| Leucine (L) | 0~0.001 | 0~0.001 | 0~0.001 | 0.01~0.1 | 0.1~0.5 |
| Glutamine (Q) | 0~0.01 | 0~0.001 | 0~0.001 | 2~7 | 0~0.01 |
| Type of AA | 8 | 9 | 10 | 11 | 12 |
| Alanine (A) | 0.5~3 | 2~6 | 0.5~2 | 0.1~1 | 0.01~0.1 |
| Serine (S) | 0.1~1 | 30~40 | 25~35 | 4~10 | 0.01~0.1 |
| Glycine (G) | 0~0.01 | 6~15 | 1~4 | 0.1~0.5 | 80~90 |
| Phenylalanine (F) | 0.5~3 | 0.1~1 | 0.5~2 | 3~6 | 0~0.01 |
| Proline (P) | 0~0.01 | 0.01~0.1 | 0.1~1 | 0.01~0.05 | 0~0.001 |
| Valine (V) | 40~50 | 0.5~2 | 0.5~2 | 0~0.001 | 2~7 |
| Tyrosine (Y) | 0.01~0.1 | 0.5~3 | 1~4 | 20~30 | 0~0.01 |
| Methionine (M) | 0~0.01 | 0~0.01 | 0~0.01 | 0~0.01 | 0~0.01 |
| Threonine (T) | 0.01~0.1 | 3~8 | 10~20 | 0.5~2 | 0~0.01 |
| Lysine (K) | 0~0.001 | 0.5~3 | 2~5 | 2~6 | 0~0.001 |
| Isoleucine (I) | 30~40 | 1~4 | 3~7 | 0.01~0.05 | 0~00.1 |
| Tryptophan (W) | 0~0.01 | 0~0.01 | 0~0.01 | 0.5~2 | 0~0.001 |
| Aspartic acid (D) | 0~0.01 | 3~10 | 2~5 | 2~6 | 4~10 |
| Histidine (H) | 0.01~0.1 | 0.5~2 | 0.5~2 | 3~7 | 0~0.001 |
| Asparagine (N) | 0.01~0.1 | 15~25 | 25~35 | 35~45 | 0~0.01 |
| Arginine (R) | 0.01~0.1 | 2~5 | 1~5 | 0.1~1 | 0.01~0.1 |
| Glutamic acid (E) | 0~0.01 | 0.5~3 | 0~0.01 | 0.5~2 | 0.01~0.1 |

-continued

| Amino acid distribution ratio for each position of amino acid (%)-V$_K$3-20-2_CDR1 | | | | | |
|---|---|---|---|---|---|
| Cysteine (C) | 0.01~0.1 | 0.01~0.05 | 0.01~0.05 | 0.01~0.1 | 0.01~0.1 |
| Leucine (L) | 10~20 | 1~4 | 0.05~0.1 | 1~4 | 0.1~1 |
| Glutamine (Q) | 0~0.01 | 0.01~0.05 | 0.01~0.05 | 0.5~2 | 0~0.001, | the amino acid ratio for each position in the light-chain complementarity-determining region 2 (CDRL2) in the light-chain variable region having the sequence of VK3-20-2 (SEQ ID NO: 26) has the following distribution ratio:

| Amino acid distribution ratio for each position of amino acid (%)-V$_K$3-20 & 20-2_CDR2 | | | | | | | | | |
|---|---|---|---|---|---|---|---|---|---|
| Type of AA | 3 | 4 | 5 | 6 | 7 | 8 | 9 | 10 | 11 |
| Alanine (A) | 0~0.001 | 5~15 | 70~80 | 0.5~2 | 0.5~3 | 0~0.001 | 90~99.99 | 60~70 | 0.01~0.05 |
| Serine (S) | 3~9 | 3~8 | 2~7 | 80~90 | 20~30 | 0.01~0.1 | 0.01~0.5 | 5~10 | 0~0.01 |
| Glycine (G) | 0~0.01 | 25~35 | 0.5~2 | 0~0.01 | 0.5~2 | 0.01~0.1 | 0~0.01 | 0~0.001 | 3~8 |
| Phenylalanine (F) | 4~10 | 0.01~0.05 | 0.01~0.1 | 2~7 | 0.5~2 | 0~0.001 | 0~0.01 | 0~0.01 | 0~0.001 |
| Proline (P) | 0.01~0.1 | 0.01~0.05 | 0.1~1 | 0.1~1 | 0.01~0.05 | 0.01~0.1 | 0~0.01 | 5~15 | 0~0.001 |
| Valine (V) | 0~0.001 | 0.5~1.5 | 2~6 | 0.5~1.5 | 0.1~1 | 0.01~0.1 | 1~3 | 0.01~0.05 | 0~0.01 |
| Tyrosine (Y) | 65~75 | 0.1~1 | 0.01~0.1 | 1~3 | 0.5~2 | 0~0.001 | 0~0.001 | 0~0.001 | 0.01~0.05 |
| Methionine (M) | 0~0.001 | 0~0.001 | 0~0.001 | 0~0.001 | 0.1~2 | 0~0.001 | 0~0.001 | 0~0.001 | 0~0.001 |
| Threonine (T) | 0.01~0.1 | 0.5~3 | 5~15 | 1~4 | 10~20 | 0~0.01 | 0.01~0.1 | 10~20 | 0~0.01 |
| Lysine (K) | 0~0.01 | 0~0.01 | 0~0.001 | 0~0.001 | 4~10 | 0~0.001 | 0~0.001 | 0~0.001 | 0~0.001 |
| Isoleucine (I) | 0~0.001 | 0~0.01 | 1~4 | 0.5~1.5 | 2~7 | 0~0.001 | 0~0.001 | 0~0.01 | 0~0.001 |
| Tryptophan (W) | 0~0.001 | 0~0.01 | 0~0.001 | 0~0.001 | 0~0.001 | 0~0.001 | 0~0.001 | 0~0.001 | 0~0.001 |
| Aspartic acid (D) | 0~0.001 | 35~45 | 0.01~0.1 | 0~0.001 | 1~4 | 0~0.001 | 00.1~0.05 | 0.01~0.05 | 88~98 |
| Histidine (H) | 0~0.001 | 0.5~3 | 0.01~0.1 | 0.1~0.8 | 1~4 | 0.01~0.1 | 0~0.001 | 0~0.001 | 0~0.01 |
| Asparagine (N) | 0~0.001 | 1~4 | 0.01~0.1 | 0.1~0.8 | 30~40 | 0~0.001 | 0~0.001 | 0~0.001 | 0.01~0.05 |
| Arginine (R) | 0~0.001 | 0.5~2 | 0~0.01 | 0~0.01 | 1~4 | 95~99.99 | 0~0.01 | 0~0.001 | 0~0.001 |
| Glutamic acid (E) | 0~0.001 | 1~5 | 0.5~2 | 0~0.01 | 0~0.01 | 0~0.001 | 0~0.001 | 0~0.001 | 0.01~0.05 |
| Cysteine (C) | 0~0.001 | 0.01~0.1 | 0.01~0.1 | 0~0.05 | 0~0.01 | 0.01~0.2 | 0.01~0.05 | 0.01~0.05 | 0~0.001 |
| Leucine (L) | 0~0.001 | 0.5~2 | 0.5~1.5 | 0.5~2 | 0.5~2 | 0.01~0.2 | 0.01~0.05 | 0.01~0.05 | 0~0.001 |
| Glutamine (Q) | 0~0.001 | 0.01~0.1 | 0.10~0.1 | 0~0.001 | 0~0.001 | 0~0.001 | 0~0.001 | 0~0.001 | 0~0.001, | the amino acid ratio for each position in the light-chain complementarity-determining region 3 (CDRL3) in the light-chain variable region having the sequence of VK3-20-2 (SEQ ID NO: 26) has the following distribution ratio:

| Amino acid distribution ratio for each position of amino acid (%)-V$_K$3-20 & 20-2_CDR3 | | | | | | | | |
|---|---|---|---|---|---|---|---|---|
| Type of AA | 4 | 5 | 6 | 7 | 8 | 9 | 10 | 11 |
| Alanine (A) | 0~0.001 | 0.01~0.05 | 4~10 | 2~6 | 1~3 | 3~8 | 0.01~0.05 | 0.1~0.5 |
| Serine (S) | 0~0.01 | 0.01~0.05 | 4~10 | 8~18 | 20~30 | 30~40 | 0.05~0.3 | 0.5~2 |
| Glycine (G) | 0~0.01 | 0~0.001 | 1~4 | 10~20 | 2~4 | 0.1~1 | 0~0.001 | 0.5~2 |
| Phenylalanine (F) | 0~0.001 | 0~0.001 | 2~5 | 0.5~2 | 0.1~1 | 0.5~3 | 0~0.001 | 2~7 |
| Proline (P) | 0~0.001 | 0~0.001 | 0.01~0.1 | 0.01~0.1 | 0.01~0.1 | 1~4 | 95~99.99 | 2~7 |
| Valine (V) | 0~0.001 | 0~0.001 | 0.1~0.5 | 0.5~2 | 0.1~1 | 0.1~1 | 0~0.001 | 0.5~3 |
| Tyrosine (Y) | 0~0.001 | 0~0.01 | 55~65 | 10~20 | 0.5~3 | 1~5 | 0~0.001 | 5~15 |
| Methionine (M) | 0~0.001 | 0~0.001 | 0~0.001 | 0~0.001 | 0~0.001 | 0~0.001 | 0~0.001 | 0~0.01 |
| Threonine (T) | 0~0.001 | 0~0.001 | 0.5~2 | 2~6 | 4~10 | 6~15 | 0.01~0.05 | 0.01~0.05 |
| Lysine (K) | 0~0.001 | 0~0.02 | 0.01~0.05 | 0.5~2 | 1~4 | 0~0.001 | 0~0.001 | 0.1~1 |
| Isoleucine (I) | 0~0.001 | 0~0.001 | 0.01~0.05 | 1~3 | 1~4 | 0.5~3 | 0~0.001 | 0.5~2 |
| Tryptophan (W) | 0.05~0.5 | 0~0.001 | 0.1~0.5 | 0~0.02 | 0~0.001 | 20~30 | 0~0.001 | 10~20 |
| Aspartic acid (D) | 0~0.001 | 0~0.001 | 0.5~2 | 4~10 | 3~10 | 0.01~0.05 | 0~0.001 | 0.1~1 |
| Histidine (H) | 0~0.001 | 5~15 | 2~6 | 1~5 | 3~8 | 0~0.01 | 0~0.001 | 1~5 |
| Asparagine (N) | 0~0.001 | 0~0.001 | 0.5~2 | 10~20 | 20~30 | 0.5~3 | 0~0.001 | 0.1~1 |
| Arginine (R) | 88~98 | 0.03~0.3 | 4~8 | 0.1~1 | 0.5~3 | 0.1~1 | 0.02~0.1 | 3~9 |
| Glutamic acid (E) | 0~0.001 | 0~0.01 | 0~0.02 | 0.5~3 | 0.5~3 | 0~0.001 | 0~0.001 | 0.1~1 |
| Cysteine (C) | 0~0.001 | 0~0.001 | 0.1~0.5 | 0.01~0.05 | 0.01~0.05 | 0~0.01 | 0~0.001 | 0.01~0.1 |
| Leucine (L) | 2~5 | 0~0.05 | 0.5~2 | 5~15 | 1~3 | 5~10 | 0.05~0.5 | 38~48 |
| Glutamine (Q) | 0.01~0.1 | 85~95 | 0.01~0.1 | 0~0.01 | 6~10 | 0~0.001 | 0.05~0.5 | 1~6, | the amino acid ratio for each position in the light-chain complementarity-determining region 1 (CDRL1) in the light-chain variable region having the sequence of VA1-51 (SEQ ID NO: 31) has the following distribution ratio:

TABLE 20

| Amino acid distribution ratio for each position of amino acid (%)-Vλ1-51_CDR1 | | | | | | | |
|---|---|---|---|---|---|---|---|
| Type of AA | 3 | 4 | 5 | 6 | 7 | 8 | 9 |
| Alanine (A) | 0~0.01 | 0.01~0.1 | 0.5~3 | 1~3 | 0.01~0.1 | 0~0.001 | 0.1~0.5 |
| Serine (S) | 95~99.99 | 0.01~0.1 | 75~85 | 45~55 | 95~99.99 | 0.01~0.1 | 0.01~0.1 |
| Glycine (G) | 0~0.001 | 95~99.99 | 4~10 | 2~7 | 0~0.001 | 0~0.001 | 0.01~0.1 |
| Phenylalanine (F) | 0.1~0.1 | 0~0.001 | 0.01~0.1 | 0.1~1.5 | 0.1~0.5 | 0~0.001 | 0.01~0.1 |
| Proline (P) | 0.~0.5 | 0~0.001 | 0.1~0.5 | 0.01~0.1 | 0.01~0.1 | 0~0.001 | 0~0.001 |
| Valine (V) | 0~0.001 | 0.01~0.1 | 0.01~0.1 | 0.01~0.1 | 0~0.001 | 0~0.001 | 85~95 |
| Tyrosine (Y) | 0.01~0.05 | 0~0.001 | 0.01~0.1 | 0.5~2 | 0.01~0.1 | 0~0.01 | 0.01~0.1 |
| Methionine (M) | 0~0.001 | 0~0.001 | 0~0.001 | 0~0.001 | 0~0.001 | 0.1~0.5 | 0~0.001 |
| Threonine (T) | 0.01~0.05 | 0~0.001 | 3~9 | 6~15 | 0~0.01 | 0.01~0.1 | 0~0.001 |
| Lysine (K) | 0~0.001 | 0~0.001 | 0~0.01 | 0.5~3 | 0~0.001 | 0.01~0.1 | 0~0.001 |
| Isoleucine (I) | 0~0.001 | 0~0.001 | 0.5~3 | 0.5~3 | 0~0.01 | 0.01~0.1 | 5~15 |
| Tryptophan (W) | 0~0.001 | 0.01~0.1 | 0~0.001 | 0~0.01 | 0~0.001 | 0~0.001 | 0~0.001 |
| Aspartic acid (D) | 0~0.001 | 0.01~0.1 | 0.5~3 | 1~4 | 0~0.001 | 0~0.01 | 0~0.001 |
| Histidine (H) | 0~0.001 | 0~0.001 | 0~0.01 | 0.5~3 | 0~0.001 | 0~0.001 | 0~0.001 |
| Asparagine (N) | 0~0.001 | 0~0.001 | 0.5~3 | 15~25 | 0~0.001 | 95~99.99 | 0~0.001 |
| Arginine (R) | 0~0.001 | 0.01~0.1 | 0.5~3 | 1~4 | 0~0.001 | 0~0.001 | 0~0.001 |
| Glutamic acid (E) | 0~0.001 | 0~0.001 | 0~0.001 | 0~0.001 | 0~0.001 | 0~0.001 | 0~0.001 |
| Cysteine (C) | 0.01~0.1 | 0.01~0.1 | 0~0.01 | 0~0.01 | 0.01~0.1 | 0~0.01 | 0.1~0.5 |
| Leucine (L) | 0.01~0.1 | 0~0.001 | 0.1~0.5 | 0.01~0.5 | 0.1~0.5 | 0~0.001 | 0.1~0.5 |
| Glutamine (Q) | 0~0.001 | 0~0.001 | 0~0.001 | 0~0.001 | 0~0.001 | 0~0.001 | 0~0.001 |

| Type of AA | 10 | 11 | 12 | 13 | 14 | 15 |
|---|---|---|---|---|---|---|
| Alanine (A) | 3~8 | 0.5~3 | 0~0.001 | 4~10 | 0.01~0.5 | 1~4 |
| Serine (S) | 0~0.01 | 25~35 | 1~5 | 5~15 | 0~0.001 | 30~40 |
| Glycine (G) | 2~5 | 1~4 | 0.1~1 | 0.1~1 | 0~0.001 | 0~0.001 |
| Phenylalanine (F) | 0~0.001 | 0.01~0.1 | 0.5~2 | 5~15 | 0~0.001 | 0.5~3 |
| Proline (P) | 0~0.001 | 0.1~0.5 | 0.01~0.1 | 1~6 | 0~0.001 | 0.01~0.1 |
| Valine (V) | 0~0.001 | 0.3~1 | 0~0.001 | 0.5~3 | 95~99.99 | 0~0.01 |
| Tyrosine (Y) | 0~0.001 | 1~3 | 2~6 | 25~35 | 0~0.001 | 10~20 |
| Methionine (M) | 0~0.001 | 0~0.001 | 0~0.001 | 0~0.001 | 0.01~0.5 | 0~0.001 |
| Threonine (T) | 0~0.001 | 4~10 | 0.5~3 | 10~20 | 0~0.001 | 0.5~3 |
| Lysine (K) | 0.05~0.5 | 2~6 | 2~5 | 0~0.001 | 0~0.001 | 0.1~2 |
| Isoleucine (I) | 0~0.01 | 2~6 | 0.1~3 | 1~5 | 0~0.001 | 0~0.001 |
| Tryptophan (W) | 0~0.001 | 0~0.001 | 0~0.001 | 0~0.001 | 0~0.001 | 0~0.001 |
| Aspartic acid (D) | 0.01~0.1 | 4~10 | 0.5~3 | 2~6 | 0~0.001 | 0.5~3 |
| Histidine (H) | 0~0.001 | 0.5~3 | 3~7 | 3~7 | 0~0.001 | 2~6 |
| Asparagine (N) | 0.01~0.1 | 30~40 | 70~80 | 2~6 | 0~0.001 | 30~40 |
| Arginine (R) | 0~0.001 | 1~5 | 0.3~2 | 0.1~1 | 0.01~0.1 | 0.01~0.05 |
| Glutamic acid (E) | 85~95 | 0.5~1.5 | 0.5~3 | 0~0.01 | 0~0.001 | 0.01~0.05 |
| Cysteine (C) | 0.01~0.1 | 0~0.001 | 0~0.001 | 0.01~0.1 | 0.01~0.1 | 0.01~0.05 |
| Leucine (L) | 0~0.001 | 0.5~3 | 0~0.001 | 1~4 | 0.01~0.1 | 0.1~1 |
| Glutamine (Q) | 0~0.001 | 0~0.001 | 0.3~2 | 0~0.01 | 0~0.001 | 0.5~2 , | the amino acid ratio for each position in the light-chain complementarity-determining region 2 (CDRL2) in the light-chain variable region having the sequence of VA1-51 (SEQ ID NO: 31) has the following distribution ratio:

| Amino acid distribution ratio for each position of amino acid (%)-Vλ1-51_CDR2 | | | | | | | | |
|---|---|---|---|---|---|---|---|---|
| Type of AA | 49 | 50 | 51 | 52 | 53 | 54 | 55 | 56 |
| Alanine (A) | 0~0.001 | 4~10 | 0~0.001 | 0.1~1 | 0~0.001 | 0~0.001 | 0~0.001 | 0~0.001 |
| Serine (S) | 1~5 | 5~15 | 2~6 | 4~12 | 0.5~3 | 0~0.001 | 0~0.001 | 95~100 |
| Glycine (G) | 0~0.001 | 5~15 | 0.1~1 | 0.5~2 | 0~0.001 | 0~0.001 | 0~0.001 | 0~0.001 |
| Phenylalanine (F) | 5~15 | 0.1~1.5 | 0.1~2 | 0.5~2 | 0~0.001 | 0~0.001 | 0~0.001 | 0~0.001 |
| Proline (P) | 0~0.001 | 0~0.001 | 0~0.001 | 0~0.001 | 0~0.001 | 0~0.001 | 95~100 | 0~0.001 |
| Valine (V) | 0~0.001 | 0.1~1.5 | 0.5~4 | 0.1~2 | 0.1~1 | 0~0.001 | 0~0.001 | 0~0.001 |
| Tyrosine (Y) | 70~80 | 1~4 | 0.5~3 | 1~5 | 0.5~3 | 0~0.001 | 0~0.001 | 0~0.001 |
| Methionine (M) | 0~0.001 | 0.5~2 | 0~0.001 | 0~0.001 | 0.5~3 | 0~0.001 | 0~0.001 | 0~0.001 |
| Threonine (T) | 0~0.001 | 1~5 | 2~7 | 5~12 | 0~0.001 | 0~0.001 | 0~0.001 | 0~0.001 |
| Lysine (K) | 0~0.001 | 1~5 | 0.1~2 | 1~4 | 15~25 | 0~0.001 | 0~0.001 | 0~0.001 |

| Amino acid distribution ratio for each position of amino acid (%)-Vλ1-51_CDR2 | | | | | | | | |
|---|---|---|---|---|---|---|---|---|
| Type of AA | 49 | 50 | 51 | 52 | 53 | 54 | 55 | 56 |
| Isoleucine (I) | 0~0.001 | 0.5~3 | 0.5~2 | 2~5 | 1~3 | 0~0.001 | 0~0.001 | 0~0.001 |
| Tryptophan (W) | 0~0.001 | 0.1~2 | 0~0.001 | 0~0.001 | 0~0.001 | 0~0.001 | 0~0.001 | 0~0.001 |
| Aspartic acid (D) | 0.1~2 | 20~30 | 10~20 | 10~20 | 0.5~4 | 0~0.001 | 0~0.001 | 0~0.001 |
| Histidine (H) | 2~7 | 0.5~2 | 0.5~2 | 1~5 | 1~7 | 0~0.001 | 0~0.001 | 0~0.001 |
| Asparagine (N) | 0.5~2 | 10~15 | 60~70 | 45~55 | 15~25 | 0~0.001 | 0~0.001 | 0~0.001 |
| Arginine (R) | 0.1~2 | 1~5 | 0.1~1 | 0.5~2 | 1~4 | 95~100 | 0~0.001 | 0~0.001 |
| Glutamic acid (E) | 0~0.001 | 5~15 | 0~0.001 | 0.5~2 | 2~8 | 0~0.001 | 0~0.001 | 0~0.001 |
| Cysteine (C) | 0.05~0.5 | 0~0.001 | 0~0.001 | 0~0.001 | 0~0.001 | 0~0.001 | 0~0.001 | 0~0.001 |
| Leucine (L) | 0.5~2 | 0.5~3 | 0~0.001 | 0~0.001 | 3~9 | 0~0.001 | 0~0.001 | 0~0.001 |
| Glutamine (Q) | 0.5~2 | 0.1~2 | 0~0.001 | 0~0.001 | 25~35 | 0~0.001 | 0~0.001 | 0~0.001, | and the amino acid ratio for each position in the light-chain complementarity-determining region 3 (CDRL3) in the light-chain variable region having the sequence of VA1-51 (SEQ ID NO: 31) has the following distribution ratio:

| Amino acid distribution ratio for each position of amino acid (%)-Vλ1-51_CDR3 | | | | | | |
|---|---|---|---|---|---|---|
| Type of AA | 4 | 5 | 6 | 7 | 8 | 9 |
| Alanine (A) | 40~50 | 25~35 | 0.1~1 | 0~0.001 | 2~5 | 0.5~3 |
| Serine (S) | 3~7 | 25~35 | 0~0.001 | 0~0.001 | 25~35 | 58~75 |
| Glycine (G) | 10~20 | 0.1~1 | 0.01~0.1 | 0.1~0.5 | 2~8 | 1~5 |
| Phenylalanine (F) | 0~0.001 | 0.01~0.1 | 0.5~3 | 0~0.001 | 0.01~0.1 | 0.05~0.5 |
| Proline (P) | 0.01~0.1 | 0.01~0.1 | 0~0.001 | 0~0.001 | 0.01~0.1 | 0.5~2 |
| Valine (V) | 0.5~3 | 10~20 | 0~0.01 | 0.01~0.05 | 0.5~2 | 0.5~2 |
| Tyrosine (Y) | 0.01~0.1 | 0.01~0.1 | 10~20 | 0~0.01 | 0.5~2 | 0.5~2 |
| Methionine (M) | 0~0.001 | 0~0.001 | 0.01~0.1 | 0.01~0.05 | 0~0.01 | 0~0.001 |
| Threonine (T) | 0.5~3 | 20~30 | 0.01~0.1 | 0~0.001 | 3~8 | 3~7 |
| Lysine (K) | 0~0.01 | 0~0.001 | 0~0.001 | 0~0.001 | 0.5~3 | 0.5~2 |
| Isoleucine (I) | 0~0.001 | 0.5~3 | 0~0.01 | 0.01~0.05 | 1~4 | 1~4 |
| Tryptophan (W) | 0~0.001 | 0.01~0.1 | 75~85 | 0~0.001 | 0.01~0.1 | 0~0.001 |
| Aspartic acid (D) | 0~0.01 | 0~0.001 | 0~0.001 | 95~99.999 | 25~35 | 1~4 |
| Histidine (H) | 0.5~3 | 0.01~0.1 | 0.5~3 | 0~0.001 | 0.5~3 | 0.01~0.5 |
| Asparagine (N) | 0~0.001 | 0.01~0.1 | 0~0.001 | 0.01~0.1 | 8~18 | 5~15 |
| Arginine (R) | 0.01~0.1 | 0~0.001 | 0.1~1 | 0.01~0.1 | 0.5~3 | 1~4 |
| Glutamic acid (E) | 0.5~3 | 0.01~0.1 | 0~0.001 | 0.01~0.1 | 0.5~3 | 0~0.01 |
| Cysteine (C) | 0~0.001 | 0~0.01 | 0.0~0.1 | 0~0.001 | 0.01~0.1 | 0.01~0.05 |
| Leucine (L) | 0.5~3 | 1~4 | 0.01~0.1 | 0~0.001 | 0.01~0.1 | 0.5~3 |
| Glutamine (Q) | 25~35 | 0~0.001 | 0~0.001 | 0~0.001 | 0~0.001 | 0~0.001 |
| Type of AA | 10 | 11 | 12 | 13 | 14 | |
| Alanine (A) | 0.01~0.1 | 0.5~3 | 25~35 | 1~7 | 1~4 | |
| Serine (S) | 5~15 | 25~35 | 2~4 | 1~7 | 0.01~0.1 | |
| Glycine (G) | 0.1~1 | 1~4 | 15~25 | 3~10 | 0.01~0.1 | |
| Phenylalanine (F) | 0~0.01 | 0.01~0.1 | 0.5~3 | 0.5~3 | 0.5~3 | |
| Proline (P) | 0.5~2 | 0.05~0.5 | 0.5~3 | 2~7 | 0.01~0.1 | |
| Valine (V) | 0.5~2 | 0.1~1 | 2~6 | 15~25 | 55~65 | |
| Tyrosine (Y) | 0.01~0.05 | 0.5~3 | 0.5~3 | 20~30 | 0~0.01 | |
| Methionine (M) | 0.01~0.05 | 0~0.001 | 0~0.01 | 0.5~3 | 2~6 | |
| Threonine (T) | 1~4 | 3~9 | 1~4 | 0.01~0.1 | 0~0.001 | |
| Lysine (K) | 0~0.001 | 2~6 | 0~0.01 | 0~0.01 | 0~0.001 | |
| Isoleucine (I) | 0.5~3 | 0.5~3 | 1~4 | 0.01~0.1 | 5~10 | |
| Tryptophan (W) | 0.01~0.05 | 0~0.001 | 0.01~0.1 | 15~25 | 0.01~0.1 | |
| Aspartic acid (D) | 0.5~2 | 10~20 | 1~5 | 0~0.01 | 0.01~0.1 | |
| Histidine (H) | 0~0.01 | 1~4 | 10~20 | 1~4 | 0~0.001 | |
| Asparagine (N) | 1~4 | 25~35 | 0.5~3 | 0~0.01 | 0~0.001 | |
| Arginine (R) | 0.1~1 | 1~4 | 0.5~3 | 1~4 | 0.01~0.1 | |
| Glutamic acid (E) | 0~0.1 | 0.5~3 | 0.5~3 | 0.5~3 | 0~0.001 | |
| Cysteine (C) | 0.01~0.05 | 0~0.01 | 0.01~0.1 | 0.01~0.1 | 0.01~0.1 | |
| Leucine (L) | 75~85 | 0.01~0.1 | 2~7 | 5~15 | 20~30 | |
| Glutamine (Q) | 0.01~0.1 | 0~0.01 | 1~4 | 0.5~3 | 0~0.001. | |

5. The set of antibodies or fragments thereof according to claim 1, wherein the fragment of the antibody has one or more forms selected from the group consisting of Fab, Fab', F(ab')$_2$, scFv (scFv)$_2$, scFv-Fc, and Fv.

6. The set of antibodies or fragments thereof according to claim 1, wherein the set of antibodies or fragments thereof has one or more characteristics selected from the following i) to iv):
  i) redundancy (percentage of repetitive sequences) of 10% or less;
  ii) p-value of CDR composition >0.05;
  iii) thermal stability of 70° C. or higher; and
  iv) diversity (library size) of 107 or more.

7. The set of antibodies or fragments thereof according to claim 1, wherein the set of antibodies or fragments thereof is expressed on a surface of a phage or host cell introduced with a nucleic acid encoding the set of antibodies or fragments thereof.

8. The set of antibodies or fragments thereof according to claim 7, wherein the host cell is *E. coli* or yeast.

9. A method of identifying an antibody or fragment thereof specific for an antigen comprising:
  (a) contacting an antigen with the set of antibodies or fragments thereof according to claim 1; and
  (b) selecting one or more antibodies or antibody fragments that bind to the antigen.

10. The method according to claim 9, wherein the set of antibodies or fragments thereof is expressed on a surface of a phage or host cell introduced with the nucleic acid encoding the set of antibodies or fragments thereof.

* * * * *

UNITED STATES PATENT AND TRADEMARK OFFICE
CERTIFICATE OF CORRECTION

PATENT NO. : 12,071,710 B2
APPLICATION NO. : 17/058124
DATED : August 27, 2024
INVENTOR(S) : Dong-Sik Kim et al.

Page 1 of 1

It is certified that error appears in the above-identified patent and that said Letters Patent is hereby corrected as shown below:

In the Specification

Column 69, Lines 19-20, "SEQ ID NO: (Vk3-20-F1)" should be -- SEQ ID NO: 98 (Vk3-20-F1) --.
Column 76, Line 34, "(0/N)" should be -- (O/N) --.
Column 76, Line 38, "(0/N)" should be -- (O/N) --.
Column 85, Lines 8-9, "VH3-_F3_CDR9" should be -- VH3-15_F3_CDR9 --.
Column 88, Line 25, "(0/N)" should be -- (O/N) --.

In the Claims

Column 151, Line 32, "VK1-39" should be -- Vκ1-39 --.
Column 151, Line 46, "VK1-39" should be -- Vκ1-39 --.
Column 168, Line 57, "VK1-39" should be -- Vκ1-39 --.
Column 169, Line 41, "VK1-39" should be -- Vκ1-39 --.
Column 171, Line 4, "VK1-39" should be -- Vκ1-39 --.
Column 171, Line 32, "VK3-20" should be -- Vκ3-20 --.
Column 173, Line 16, "VK3-20" should be -- Vκ3-20 --.
Column 173, Line 44, "VK3-20" should be -- Vκ3-20 --.
Column 175, Line 10, "VK3-20-2" should be -- Vκ3-20-2 --.
Column 177, Line 12, "VK3-20-2" should be -- Vκ3-20-2 --.
Column 177, Line 40, "VK3-20-2" should be -- Vκ3-20-2 --.
Column 179, Line 4, "VA1-51" should be -- Vλ1-51 --.
Column 179, Line 52, "VA1-51" should be -- Vλ1-51 --.
Column 181, Line 16, "VA1-51" should be -- Vλ1-51 --.
Column 183, Line 13, "107" should be -- $10^7$ --.

Signed and Sealed this
Eleventh Day of March, 2025

Coke Morgan Stewart
*Acting Director of the United States Patent and Trademark Office*